US010561739B2

(12) United States Patent
Howard et al.

(10) Patent No.: US 10,561,739 B2
(45) Date of Patent: Feb. 18, 2020

(54) TARGETED PYRROLOBENZODIAZAPINE CONJUGATES

(71) Applicants: SEATTLE GENETICS INC., Bothell, WA (US); MEDIMMUNE LIMITED, Cambridge (GB)

(72) Inventors: Philip Wilson Howard, Cambridge (GB); Scott Jeffrey, Bothell, WA (US); Patrick Burke, Bothell, WA (US); Peter Senter, Bothell, WA (US)

(73) Assignees: SEATTLE GENETICS INC., Bothell, WA (US); MEDIMMUNE LIMITED, Cambridge (GB)

( * ) Notice: Subject to any disclaimer, the term of this patent is extended or adjusted under 35 U.S.C. 154(b) by 0 days.

(21) Appl. No.: 16/381,448

(22) Filed: Apr. 11, 2019

(65) Prior Publication Data
US 2019/0336614 A1  Nov. 7, 2019

Related U.S. Application Data

(63) Continuation of application No. 15/951,753, filed on Apr. 12, 2018, now abandoned, which is a continuation of application No. 15/422,000, filed on Feb. 1, 2017, now abandoned, which is a continuation of application No. 14/995,944, filed on Jan. 14, 2016, now Pat. No. 9,592,240, which is a continuation of application No. 13/641,219, filed as application No. PCT/US2011/032664 on Apr. 15, 2011, now Pat. No. 9,242,013.

(60) Provisional application No. 61/324,623, filed on Apr. 15, 2010.

(51) Int. Cl.
| C07D 487/04 | (2006.01) |
| C07D 519/00 | (2006.01) |
| A61K 47/68 | (2017.01) |
| C07K 16/30 | (2006.01) |
| C07K 16/28 | (2006.01) |
| A61K 31/5517 | (2006.01) |
| A61K 39/00 | (2006.01) |

(52) U.S. Cl.
CPC ...... *A61K 47/6851* (2017.08); *A61K 31/5517* (2013.01); *A61K 47/6803* (2017.08); *A61K 47/6849* (2017.08); *A61K 47/6861* (2017.08); *A61K 47/6867* (2017.08); *A61K 47/6871* (2017.08); *A61K 47/6889* (2017.08); *C07K 16/2812* (2013.01); *C07K 16/2875* (2013.01); *C07K 16/2878* (2013.01); *C07K 16/30* (2013.01); *C07K 16/3038* (2013.01); *C07K 16/3061* (2013.01); *A61K 2039/505* (2013.01); *C07K 2317/21* (2013.01); *C07K 2317/24* (2013.01); *Y02A 50/385* (2018.01); *Y02A 50/414* (2018.01); *Y02A 50/423* (2018.01)

(58) Field of Classification Search
CPC .......................... C07D 487/04; C07D 519/00
See application file for complete search history.

(56) References Cited

U.S. PATENT DOCUMENTS

| 3,361,742 A | 1/1968 | Julius et al. |
| 3,523,941 A | 8/1970 | Leimgruber et al. |
| 3,524,849 A | 8/1970 | Batcho et al. |
| 3,794,644 A | 2/1974 | Karlyone et al. |
| 4,185,016 A | 1/1980 | Takanabe et al. |
| 4,239,683 A | 12/1980 | Takanabe et al. |
| 4,309,437 A | 1/1982 | Ueda et al. |
| 4,353,827 A | 10/1982 | Hunkeler et al. |
| 4,382,032 A | 5/1983 | Hunkeler et al. |
| 4,386,028 A | 5/1983 | Hunkeler et al. |
| 4,405,516 A | 9/1983 | Hunkeler et al. |
| 4,405,517 A | 9/1983 | Hunkeler et al. |
| 4,407,752 A | 10/1983 | Hunkeler et al. |
| 4,427,587 A | 1/1984 | Kaneko et al. |
| 4,427,588 A | 1/1984 | Kaneko et al. |
| 4,701,325 A | 10/1987 | Ueda et al. |
| 4,923,984 A | 5/1990 | Matsumura et al. |
| 5,418,241 A | 5/1995 | Jegham et al. |
| 6,362,331 B1 | 3/2002 | Kamal et al. |
| 6,562,806 B1 | 3/2003 | Thurston et al. |
| 6,608,192 B1 | 8/2003 | Thurston et al. |
| 6,660,742 B2 | 12/2003 | Lee |
| 6,660,856 B2 | 12/2003 | Wang |
| 6,747,144 B1 | 6/2004 | Thurston et al. |
| 6,884,799 B2 | 4/2005 | Kamal et al. |
| 6,909,006 B1 | 6/2005 | Thurston et al. |
| 7,067,511 B2 | 6/2006 | Thurston et al. |
| 7,049,311 B1 | 8/2006 | Thurston et al. |
| 7,244,724 B2 | 7/2007 | Liu et al. |
| 7,265,105 B2 | 9/2007 | Thurston et al. |
| 7,407,951 B2 | 5/2008 | Thurston et al. |
| 7,429,658 B2 | 9/2008 | Howard et al. |
| 7,612,062 B2 | 3/2009 | Gregson et al. |

(Continued)

FOREIGN PATENT DOCUMENTS

| CN | 101171257 | 4/2008 |
| EP | 1813614 | 8/2007 |

(Continued)

OTHER PUBLICATIONS

Adair, J.R. et al., "Antibody-drug conjugates—a perfect synergy," Exp. Opin. Biol. Ther. (2012) 16 pages.

(Continued)

*Primary Examiner* — Bruce Kifle

(74) *Attorney, Agent, or Firm* — Casimir Jones, S.C.; Melissa E. Kolom

(57) ABSTRACT

Provided are Conjugate comprising PBDs conjugated to a targeting agent and methods of using such PBDs.

22 Claims, 5 Drawing Sheets

(56) References Cited

U.S. PATENT DOCUMENTS

| | | |
|---|---|---|
| 7,528,126 B2 | 5/2009 | Howard et al. |
| 7,557,099 B2 | 7/2009 | Howard et al. |
| 7,704,924 B2 | 4/2010 | Thurston et al. |
| 7,741,319 B2 | 6/2010 | Howard et al. |
| 8,034,808 B2 | 11/2011 | Delavault et al. |
| 8,163,736 B2 | 4/2012 | Gauzy et al. |
| 8,501,934 B2 | 6/2013 | Howard et al. |
| 8,487,092 B2 | 7/2013 | Howard et al. |
| 8,592,576 B2 | 11/2013 | Howard et al. |
| 8,633,185 B2 | 1/2014 | Howard et al. |
| 8,637,664 B2 | 1/2014 | Howard et al. |
| 8,697,688 B2 | 4/2014 | Howard et al. |
| 8,829,184 B2 | 9/2014 | Howard et al. |
| 8,940,733 B2 | 1/2015 | Howard et al. |
| 9,102,704 B2 | 8/2015 | Howard |
| 9,242,013 B2 | 1/2016 | Howard et al. |
| 9,321,774 B2 | 4/2016 | Howard et al. |
| 9,376,440 B2 | 6/2016 | Howard et al. |
| 9,387,259 B2 | 7/2016 | Jeffrey et al. |
| 9,388,187 B2 | 7/2016 | Howard et al. |
| 9,399,073 B2 | 7/2016 | Howard et al. |
| 9,399,641 B2 | 7/2016 | Howard |
| 9,415,117 B2 | 8/2016 | Howard |
| 9,526,798 B2 | 12/2016 | Jeffrey et al. |
| 9,562,049 B2 | 2/2017 | Howard |
| 9,567,340 B2 | 2/2017 | Howard |
| 9,592,240 B2 | 3/2017 | Howard et al. |
| 9,624,227 B2 | 4/2017 | Howard et al. |
| 9,649,390 B2 | 5/2017 | Howard et al. |
| 9,707,301 B2 | 7/2017 | Jeffrey et al. |
| 9,713,647 B2 | 7/2017 | Jeffrey et al. |
| 9,732,084 B2 | 8/2017 | Howard et al. |
| 9,745,303 B2 | 8/2017 | Howard |
| 9,821,074 B2 | 11/2017 | Howard et al. |
| 9,889,207 B2 | 2/2018 | Howard |
| 9,956,298 B2 | 5/2018 | Howard et al. |
| 2003/0195196 A1 | 10/2003 | Thurston et al. |
| 2004/0138269 A1 | 7/2004 | Sun et al. |
| 2004/0198722 A1 | 10/2004 | Thurston et al. |
| 2007/0154906 A1 | 7/2007 | Liu et al. |
| 2007/0191349 A1 | 8/2007 | Howard et al. |
| 2007/0185336 A1 | 9/2007 | Thurston et al. |
| 2007/0232592 A1 | 10/2007 | Delavault et al. |
| 2007/0249591 A1 | 10/2007 | Howard et al. |
| 2008/0090812 A1 | 4/2008 | Pepper et al. |
| 2008/0092940 A1 | 4/2008 | Nakajima |
| 2008/0213289 A1 | 9/2008 | Francisco et al. |
| 2009/0148942 A1 | 6/2009 | McDonagh et al. |
| 2011/0256157 A1 | 10/2011 | Howard et al. |
| 2011/0160192 A1 | 11/2011 | Delavault et al. |
| 2013/0266595 A1 | 6/2013 | Howard et al. |
| 2013/0028917 A1 | 7/2013 | Howard et al. |
| 2014/0030279 A1 | 1/2014 | Polakis et al. |
| 2014/0030280 A1 | 1/2014 | Howard et al. |
| 2014/0066435 A1 | 3/2014 | Howard et al. |
| 2014/0120118 A1 | 5/2014 | Howard |
| 2014/0127239 A1 | 5/2014 | Howard |
| 2014/0274907 A1 | 9/2014 | Howard et al. |
| 2014/0286970 A1 | 9/2014 | Jeffrey et al. |
| 2014/0294868 A1 | 10/2014 | Howard et al. |
| 2015/0111880 A1 | 4/2015 | Howard et al. |
| 2015/0126495 A1 | 5/2015 | Howard et al. |
| 2015/0158869 A1 | 6/2015 | Howard |
| 2015/0183883 A1 | 7/2015 | Asundi |
| 2015/0265722 A1 | 9/2015 | Van Berkel |
| 2015/0273077 A1 | 10/2015 | Van Berkel |
| 2015/0273078 A1 | 10/2015 | Van Berkel |
| 2015/0274737 A1 | 10/2015 | Howard et al. |
| 2015/0283258 A1 | 10/2015 | Van Berkel |
| 2015/0283262 A1 | 10/2015 | Van Berkel |
| 2015/0283263 A1 | 10/2015 | Van Berkel |
| 2015/0297746 A1 | 10/2015 | Van Berkel |
| 2015/0315196 A1 | 11/2015 | Howard et al. |
| 2015/0344482 A1 | 12/2015 | Howard et al. |
| 2016/0015828 A1 | 1/2016 | Torgor |
| 2016/0031887 A1 | 2/2016 | Howard et al. |
| 2016/0250345 A1 | 9/2016 | Howard et al. |
| 2016/0310611 A1 | 10/2016 | Flygare et al. |
| 2017/0239365 A1 | 8/2017 | Howard et al. |
| 2017/0290924 A1 | 10/2017 | Jeffrey et al. |
| 2017/0298137 A1 | 10/2017 | Jeffrey et al. |
| 2017/0340752 A1 | 11/2017 | Howard |
| 2018/0125997 A1 | 5/2018 | Howard et al. |
| 2018/0134717 A1 | 5/2018 | Howard et al. |

FOREIGN PATENT DOCUMENTS

| | | |
|---|---|---|
| FR | 2027356 | 12/1969 |
| FR | 2586683 | 3/1987 |
| GB | 1299198 | 12/1972 |
| GB | 2053894 | 2/1981 |
| JP | 53-82792 | 7/1978 |
| JP | 57131791 | 8/1982 |
| JP | 58180487 | 10/1983 |
| WO | WO 92/19620 | 11/1992 |
| WO | WO 93/18045 | 9/1993 |
| WO | WO 95/04718 | 2/1995 |
| WO | WO 00/03291 | 1/2000 |
| WO | WO 00/12506 | 3/2000 |
| WO | WO 00/12507 | 3/2000 |
| WO | WO 00/12508 | 3/2000 |
| WO | WO 00/12509 | 3/2000 |
| WO | WO 01/16104 | 3/2001 |
| WO | WO 2004/043963 | 5/2004 |
| WO | WO 2005/023814 | 3/2005 |
| WO | WO 2005/040170 | 5/2005 |
| WO | WO 2005/042535 | 5/2005 |
| WO | WO 2005/082023 | 9/2005 |
| WO | WO 2005/085177 | 9/2005 |
| WO | WO 2005/085250 | 9/2005 |
| WO | WO 2005/085251 | 9/2005 |
| WO | WO 2005/085259 | 9/2005 |
| WO | WO 2005/085260 | 9/2005 |
| WO | WO 2005/105113 | 11/2005 |
| WO | WO 2005/110423 | 11/2005 |
| WO | WO 2006/111759 | 10/2006 |
| WO | WO 2007/039752 | 4/2007 |
| WO | WO 2007/085930 | 8/2007 |
| WO | WO 2008/010101 | 1/2008 |
| WO | WO 2008/047242 | 4/2008 |
| WO | WO 2008/050140 | 5/2008 |
| WO | WO 2008/070593 | 6/2008 |
| WO | WO 2009/016516 | 2/2009 |
| WO | WO 2009/060208 | 5/2009 |
| WO | WO 2009/060215 | 5/2009 |
| WO | WO 2010/010347 | 1/2010 |
| WO | WO 2010/043877 | 4/2010 |
| WO | WO 2010/043880 | 4/2010 |
| WO | WO 2010/091150 | 8/2010 |
| WO | WO 2011/023883 | 3/2011 |
| WO | WO 2011/100227 | 8/2011 |
| WO | WO 2011/128650 | 10/2011 |
| WO | WO 2011/130598 | 10/2011 |
| WO | WO 2011/130613 | 10/2011 |
| WO | WO 2011/130616 | 10/2011 |
| WO | WO 2012/112708 | 8/2012 |
| WO | WO 2012/128868 | 9/2012 |
| WO | WO 2013/041606 | 3/2013 |
| WO | WO 2013/053871 | 4/2013 |
| WO | WO 2013/053872 | 4/2013 |
| WO | WO 2013/053873 | 4/2013 |
| WO | WO 2013/055987 | 4/2013 |
| WO | WO 2013/055990 | 4/2013 |
| WO | WO 2013/055993 | 4/2013 |
| WO | WO 2013/164592 | 11/2013 |
| WO | WO 2013/164593 | 11/2013 |
| WO | WO 2014/011518 | 1/2014 |
| WO | WO 2014/011519 | 1/2014 |
| WO | WO 2014/057072 | 4/2014 |
| WO | WO 2014/057073 | 4/2014 |
| WO | WO 2014/057074 | 4/2014 |
| WO | WO 2014/057113 | 4/2014 |
| WO | WO 2014/057114 | 4/2014 |
| WO | WO 2014/057115 | 4/2014 |

(56) References Cited

FOREIGN PATENT DOCUMENTS

| WO | WO 2014/057117 | 4/2014 |
|---|---|---|
| WO | WO 2014/057118 | 4/2014 |
| WO | WO 2014/057119 | 4/2014 |
| WO | WO 2014/057120 | 4/2014 |
| WO | WO 2014/057122 | 4/2014 |
| WO | WO 2014/022679 | 6/2014 |
| WO | WO 2014/096365 | 6/2014 |
| WO | WO 2014/096368 | 6/2014 |
| WO | WO 2014/130879 | 8/2014 |
| WO | WO 2014/140174 | 9/2014 |
| WO | WO 2014/140862 | 9/2014 |
| WO | WO 2014/159981 | 10/2014 |
| WO | WO 2014/174111 | 10/2014 |
| WO | WO 2015/052321 | 4/2015 |
| WO | WO 2015/052322 | 4/2015 |
| WO | WO 2015/052532 | 4/2015 |
| WO | WO 2015/052533 | 4/2015 |
| WO | WO 2015/052534 | 4/2015 |
| WO | WO 2015/052535 | 4/2015 |
| WO | WO 2015/095124 | 6/2015 |
| WO | WO 2015/159076 | 10/2015 |

OTHER PUBLICATIONS

Adams et al., "Molecular modelling of a sequence-specific DNA-binding agent based on the pyrrolo [2,1-c][1,4]benzodiazepines," Pharm. Pharmacol. Commun. (1999) 5:555-560.
Aird, R.E. et al., "ABCB1 genetic polymorphism influences the pharmacology of the new pyrrolobenzodiazepine derivative SJG-136," Pharmacogenomics Journal (2008) 8(4):289-296.
Alley, M.C. et al., "SJG-136 (NSC 694501), a novel rationally designed DNA minor groove interstrand cross-linking agent with potent and broad spectrum antitumor activity. Part 2: Efficacy evaluations," Cancer Res. (2004) 64:6700-6706.
Alley, M.C., "Efficacy evaluations of SJG-136 (NSC 694501), a novel pyrrolobenzodiazepine dimer with broad spectrum antitumor activity," Proceedings of the American Association for Cancer Research Annual Meeting (Mar. 2002) 43:63.
Althius, T. H. and Hess, H. J., "Synthesis and Identification of the Major Metabolites of Prazosin Formed in Dog and Rat," J. Medicinal Chem. (1977) 20(1):146-148.
Antonow, D. et al.,"Parallel synthesis of a novel C2-aryl pyrrolo [2,1-c] [1,4]benzodiazepine (PBD) library," J. Comb. Chem. (2007) 9:437-445.
Arima et al., "Studies on Tomaymycin, a New Antibiotic. I. Isolation and Properties of Tomaymycin," J. Antibiotics (1972) 25:437-444.
Arnould, S., "Impact on the cell cycle and involvement of ATM, ATR, chk1 and chk2 kinases in the cytotoxicity of SJG-136, a new pyrrolobenzodiazepine dimer," Proceedings of the American Association for Cancer Research Annual Meeting (Mar. 2004) 45:1298, Abstract No. 5618.
Arnould, S., "Time-dependent cytotoxicity induced by SJG-136 (NSC 694501): influence of the rate of interstrand cross-link formation on DNA damage signaling," Mol. Canc. Therap. (2006) 5(6):1602-1609.
Banker, G.S. et al., Modern Pharmaceutics, Third edition, Marcel Dekker, New York (1996) 451 and 596.
Berge et al., "Pharmaceutical Salts," J. Pharm. Sci. (1977) 66:1-19.
Berry, J. M. et al., "Solid-phase synthesis of DNA-interactive pyrrolo [2,1-c][1,4]benzodiazepines," Tetrahedron Letters (2000) 41:6171-6174.
Bose et al., "New Approaches to Pyrrolo[2,1-c][1,4]benzodiazepines: Synthesis, DNA-binding and cytotoxicity of DC-81," Tetrahedron, 48, 751-758 (1992).
Bose, D.S. et al., "Effect of linker length on DNA-binding affinity, cross-linking efficiency and cytotoxicity of C8 linked pyrrolobenzodiazepine dimers," J. Chem. Soc. Chem. Commun. (1992) 20:1518-1520.
Bose, D.S. et al., "Rational Design of a Highly Efficient Irreversible DNA Interstrand Cross-Linking Agent Based on the Pyrrolobenzodiazepine Ring System," J. Am. Chem. Soc., 114, 4939-4941 (1992).
Buhrow, S.A., "LC-MS/MS assay and dog pharmacokinetics of the dimeric pyrrolobenzodiazepine SJG-136 (NSC 694501)," J. Chromat. B: Anal. Tech. Biomed. Life Sci. (2006) 840(1):56-62.
Burke, P.J. et al., "Anti-CD70 antibody-drug conjugates containing pyrrolobenzodiazepine dimers demonstrate robust antitumor activity," AACR National Meeting, Apr. 2012, Chicago, Illinois, Abstract No. 4631.
Burke, P.J. et al., "Novel immunoconjugates comprised of streptonigrin and 17-amino-geldanamycin attached via a dipeptide-p-aminobenzylamine linker system," Bioorg. Med. Chem. Lett., Apr. 2009, 19(10):2650-2653.
Calcutt, M.W., "Determination of chemically reduced pyrrolobenzodiazepine SJG-136 in human plasma by HPLC-MS/MS: application to an anticancer phase I dose escalation study," J. Mass Spectrom. (2008) 43(1):42-52.
Chen, Z. et al., "A novel approach to the synthesis of cytotoxic C2-C3 unsaturated pyrrolo [2,1-c][1,4]benzodiazepines (PBDs) with conjugated acrylyl C2-substituents," Biorg. Med. Chem. Lett. (2004) 14:1547-1549.
Cheung, A., "Direct liquid chromatography determination of the reactive imine SJG-136 (NSC 694501)," J. Chromat. B: Anal. Techn. Biomed. Life Sci. (2005) 822(1-2):10-20.
Cipolla, L., "Pyrrolo[2,1-c][1,4]benzodiazepine as a scaffold for the design and synthesis of anti-tumour drugs," Anti-Cancer Agents in Medicinal Chemistry (Jan. 2009) 9(1):1-31.
Clingen, P.H., "The role of nucleotide excision repair and homologous recomination in the sensitivity of mammalian cells to the minor groove crosslinking pyrrolo [2,1-c] [1,4]benzodiazepine dimer SJG-136 (NSC694501)," Proceedings of the American Association for Cancer Research Annual Meeting (Jul. 2003) 44:524.
Clingen, P.H., "The XPF-ERCC1 endonuclease and homologous recombination contribute to the repair of minor groove DNA interstrand crosslinks in mammalian cells produced by the pyrrolo [2,1-c][1,4]benzodiazepine dimer SJG-136," Nucl. Acids Res. (2005) 33(10):3283-3291.
Cooper, N. et al., "Synthesis of novel PBDs as anti-tumour agents," Chem. Commun. (2002) 16:1764-1765.
Cooper, N., "Design, Synthesis and Evaluation of Novel C2-Aryl Pyrrolobenzodiazepines as Potential Anticancer Agents," Thesis submitted to School of Pharmacy, University of London, Dated Oct. 5, 2006.
Courtney, S. M. et al., "A new convenient procedure for the synthesis of pyrrolo[2,1-c][1,4]benzodiazepines", Tetrahedron Letters, vol. 34, No. 33, 5327-28 (1993).
Dattolo, G. et al., "Polycondensed nitrogen heterocycles. IX. 5,6-dihydro-7H-pyrrolo[1,2-d][1,4]benzodiazepin-6-one," J. Heterocyclic. Chem. (1980) 17:701-703.
Dong, Q. et al., "Reductive cleavage of TROC groups under neutral conditions with cadmium-lead couple," Tetrahedron Lett. (1995) 36(32):5681-5682.
Doronina, S.O. et al., "Development of potent monoclonal antibody auristatin conjugates for cancer therapy," Nature Biotech (2003) 21:778-784.
Dorwald, F.Z., Side Reactions in Organic Synthesis: a Guide to Successful Synthesis Design, Weinheim: Wiley-VCH Verlag GmbH & Co., KGaA (2005) Preface.
Doyle, M., "Response of Staphylococcus aureus to subinhibitory concentrations of a sequence-selective, DNA minor groove crosslinking pyrrolobenzodiazepine dimer," J. Antimicrob. Chemo., Aug. 2009, 64(5):949-959.
Dupont, C. et al., "Synthesis of rhazinilam analogue acting as an inhibitor of tubulin assembly," Tetrahedron Lett. (2000) 41:5853-5856.
Farmer, J.D. et al., "Synthesis and DNA crosslinking ability of a dimeric anthramycin analog," Tetrahedron Letters (1988) 29(40):5105-5108, Abstract only.
Farmer, J.D. et al., "DNA binding properties of a new class of linked anthramycin analogs,", Chemical Abstracts, Abstract No. 239940r, vol. 114, No. 25, 25 899-903 (1991).

(56) References Cited

OTHER PUBLICATIONS

Fey, T. et al., "Silica-supported TEMPO catalyst: synthesis and application in the anelli oxidation of alcohols," J. Org. Chem. (2001) 66:8154-8159.
Firsching, A. et al., "Antiproliferative and angiostatic activity of suramin analogues," Cancer Res. (1995) 55:4957-4961.
Foloppe, M.P. et al., "DNA-binding properties of pyrrolo [2,1-c][1,4]benzodiazephine N10-C11 amidines," Eur. J. Med. Chem., 31, 407-410 (1996).
Fujisawa Pharmaceutical Co., Ltd., Abstract No. 139983k, "Benzodiazepine derivatives", Chemical Abstracts, vol. 99, No. 17, 603 (1983).
Fujisawa Pharmaceutical Co., Ltd., Abstract No. 72145x, "Benzodiazepine derivatives", Chemical Abstracts, vol. 98, No. 9, 638 (1983).
Fukuyama, T. et al., "Total Synthesis of (+)-Porothramycin B," Tetrahedron Letters, vol. 34, 16, 2577-2580 (1993).
Gallmeier, E., "Targeted disruption of FANCC and FANCG in human cancer provides a preclinical model for specific therapeutic options," Gastroenterology (2006) 130(7):2145-2154.
Gavezzotti, A., "Are crystal structures predictable?" Acc. Chem. Res. (1994) 27:309-314.
Greene, T.W. and Wuts, P.G.M., Protective Groups in Organic Synthesis, John Wiley & Sons, 2nd ed., Ch 7, 315-345 (1991).
Greene, T.W. et al., Protective Groups in Organic Synthesis, John Wiley & Sons (1999) 3rd Edition, 23-200, 503-549, 633-647.
Gregson, S. et al., "Synthesis of a novel C2/C2'-exo unsaturated pyrrolobenzodiazepine cross-linking agent with remarkable DNA binding affinity and cytotoxicity," Chemical Communications, 797-798 (1999).
Gregson, S.J. et al., "Effect of C2/C3-endo unsaturation on the cytotoxicity and DNA-binding reactivity of pyrrolo-[2,1-c][1,4]-benzodiazepines," Bioorg. Med. Chem. Lett. (2000) 10(16):1849-1851.
Gregson, S.J. et al., "Linker length modulates DNA cross-linking reactivity and cytotoxic potency of C8/C8' ether-linked C2-exo-unsaturated pyrrolo [2,1-c][1,4]benzodiazepine (PBD) dimers," J. Med. Chem. (2004) 1161-1174.
Gregson, S.J. et al., "Synthesis of the first example of a C2-C3/C2'-C3'-endo unsaturated pyrrolo [2,1-c][1,4]benzodiazepine dimer," Biorg. Med. Chem. Lett. (2001) 11:2859-2862.
Gregson, S.J. et al., "Synthesis of the first examples of A-C8/C-C2 amide-linked pyrrolo [2,1-c][1,4]benzodiazepine dimers," Biorg. Med. Chem. Lett. (2003) 13:2277-2280.
Gregson, S.J. et al., "Design, Synthesis and Evaluation of a Novel Pyrrolobenzodiazepine DNA-Interactive Agent with Highly Efficient Cross-Linking Ability and Potent Cytotoxicity", J. Med. Chem., 44: 737-748 (2001).
Gregson, S.J. et al., "Effect of C2-exo Unsaturation on the Cytotoxicity and DNA-Binding Reactivity of Pyrrolo[2,1-c]1,4]benzodiazepines", Bioorganic & Medicinal Chemistry Letters, 10: 1845-1847 (2000).
Guichard, S.M., "Influence of P-glycoprotein expression on in vitro cytotoxicity and in vivo antitumour activity of the novel pyrrolobenzodiazepine dimer SJG-136," Eur. J. Cancer (2005) 41(12):1811-1818.
Guiotto, A. et al., "Synthesis of novel C7-aryl substituted pyrrolo [2,1-c][1,4]benzodiazepines (PBDs) via Pro-N10-troc protection and suzuki coupling," Bioorganic & Medicinal Chemistry Letters, 8, No. 21, 3017-3018 (1998).
Hadjivassileva, T., "Antibacterial activity of pyrrolobenzodiazepine dimers, a novel group of DNA-binding compounds," Abstracts of the Interscience Conference on Antimicrobial Agents and Chemotherapy (Oct.-Nov. 2004).
Hadjivassileva, T., "Interactions of pyrrolobenzodiazepine dimers and duplex DNA from methicillin-resistant Staphylococcus aureus," Int. J. Antimicrob. Agents (2007) 29(6):672-678.
Hadjivassileva, T., "Pyrrolobenzodiazepine dimers: novel sequence-selective, DNA-interactive, cross-linking agents with activity against Gram-positive bacteria," J. Antimicrob. Chemo. (2005) 56(3):513-518.
Hamaguchi, A., "DNA cross-linking and in vivo antitumour activity of the extended pyrrolo [2,1-c][1,4]benzodiazepine dimer SG2057 (DRG-16)," EJC Supplements (Nov. 2006) 4(12):96.
Hara et al., "DC 102, a new glycosidic pyrrolo(1,4)benzodiazepine antibiotic produced by Streptomyces sp.", J. Antibiotics, 41, 702-704 (1988).
Hartley, J.A. et al., "SG2285, a novel C2-aryl-substituted pyrrolobenzodiazepine dimer prodrug that cross-links DNA and exerts highly potent antitumor activity," Cancer Res., Sep. 2010, 70(17):6849-6858.
Hartley, J.A. et al., "SJG-136 (NSC 694501), a novel rationally designed DNA minor groove interstrand cross-linking agent with potent and broad spectrum antitumor activity. Part 1: Cellular pharmacology, in vitro and initial in vivo antitumor activity," Cancer Res. (2004) 64:6693-6699.
Hartley, J.A., "In vitro antitumor activity and in vivo DNA interstrand crosslinking by the novel pyrrolobenzodiazepine dimer SJG-136 (NSC 694501)," Proceedings of the American Association for Cancer Research Annual Meeting (Mar. 2002) 43:489.
Hartley, J.A., "SJG-136 (NSC-D694501)—a novel DNA sequence specific minor groove crosslinking agent with significant antitumor activity," Proceedings of the American Association for Cancer Research Annual Meeting (Mar. 2000) 41:425.
Hochhauser, D., "Phase I study of sequence-selective minor groove DNA binding agent SJG-136 in patients with advanced solid tumors," Clin. Cancer Res., Mar. 2009, 15(6):2140-2147.
Hochlowski, J. et al., "Abbeymycin, a new anthramycin-type antibiotic produced by a streptomycete," J. Antibiotics, 40, 145-148 (1987).
Howard, P.W. et al., "Design, synthesis and biological evaluation of ZC-423, a novel C2-aryl substituted pyrrolobenzodiazepine (PBD) dimer," Clinical Cancer Research (2005) 11(23):9015S-9016S (A205).
Howard, P.W. et al., "Synthesis of a novel C2/C2'-aryl-substituted pyrrolo[2,1-c][1,4]benzodiazepine dimer prodrug with improved water solubility and reduced DNA reaction rate," Bioorg. Med. Chem., Sep. 2009, In Press, 4 pages now: Sep. 2009, 19:6463-6466.
Howard, P.W. et al., "The design, synthesis and biological evaluation of a set of C2-aryl substituted pyrrolo [2,1-c][1,4]benzodiazepine dimers," EJC Supplements (2006) 4(12):95—Poster Abstract 301.
Howard, P.W., "Design, synthesis and biological evaluation of novel C2-aryl-substituted pyrrolo [2,1-c][1,4]benzodiazepine monomers," Proceedings of the American Association for Cancer Research Annual Meeting (Apr. 2006) 47:132.
Hurley, L. and Needham-Vandevanier, D., "Covalent Binding of Antitumor Antibiotics in the Minor Groove of DNA. Mechanism of Action of CC-1065 and the Pyrrolo(1,4)benzodiazepines," Acc. Chem. Res., 19,.230-237 (1986).
Itoh et al., "Sibanomicin, a new pyrrolo(1,4)benzodiazepine antitumor antibiotic produced by a micromonospora sp." J. Antibiotics, 41, 1281-1284 (1988).
Janjigian, Y.Y., "A phase I trial of SJG-136 (NSC#694501) in advanced solid tumors," Cancer Chemotherapy and Pharmacology, Aug. 2009, 65(5):833-838.
Jeffrey, S.C. et al., "Development of Pyrrolobenzodiazepine-Based Antibody-Drug Conjugates for Cancer," AACR Annual Meeting 2013, Abstract No. 4321.
Jeffrey, S.C., "Design, synthesis, and in vitro evaluation of dipeptide-based antibody minor groove binder conjugates," J. Med. Chem. (2005) 48(5):1344-1358.
Jia, L., "Interspecies differences in pharmacokinetics and time-dissociated toxicokinetics of SJG-136," Proceedings of the American Association for Cancer Research Annual Meeting (Mar. 2004) 45:487.
Jia, L., "Use of the comet assay as a surrogate biomarker for the in vivo measurement of DNA damage to lymphocytes," Proceedings of the American Association for Cancer Research Annual Meeting (Mar. 2004) 45:452-453.
Jordan, V.C., "Tamoxifen: a most unlikely pioneering medicine," Nature Reviews: Drug Discovery (2003).
Kamal et al., "Synthesis and DNA-binding affinity of A-C8/C-C2 alkoxyamido-linked pyrrolo [2,1-c][1,4]benzodiazepine dimers" Biorg. Med. Chem. Lett. (2003) 13(22):3955-3958.

(56) References Cited

OTHER PUBLICATIONS

Kamal, A. et al., "Design, synthesis and evaluation of new noncross-linking pyrrolobenzodiazepine dimers with efficient DNA binding ability and potent antitumor activity," J. Med. Chem. (2002) 45:4679-4688.
Kamal, A., "Development of pyrrolo [2,1-c][1,4]benzodiazepine beta-galactoside prodrugs for selective therapy of cancer by ADEPT and PMT," Chemmedchem (2008) 3:794-802.
Kamal, A., "Remarkable DNA binding affinity and potential anticancer activity of pyrrolo[2,1-c][1,4]benzodiazepine-naphthalamide conjugates linked through piperazine side-armed alkane spacers," Bioorg. Med. Chem. (2008) 16(15):7218-7224.
Kamal, A., "Remarkable enhancement in the DNA-binding ability of C2-fluoro substituted pyrrolo[2,1-c][1,4]benzodiazepines and their anticancer potential," Bioorg. Med. Chem., Jan. 2009, 17(4):1557-1572.
Kamal, A., "Synthesis of fluorinated analogues of SJG-136 and their DNA-binding potential," Bioorg. Med. Chem. Lett (2004) 14(22):5699-5702.
Kamal, A., et al., "An Efficient Synthesis of Pyrrolo[2,1-c][1,4] Benzodiazepine Antibiotics via Reductive Cyclization," Bioorg. Med. Chem. Ltrs, 7, No. 14, 1825-1828 (1997).
Kamal, A., et al., "Synthesis of Pyrrolo [2,1-c][1,4]-Benzodiazepene Antibiotics: Oxidation of Cyclic Secondary Amine with TPAP", Tetrahedron, v. 53, No. 9, 3223-3230 (1997).
Kamal, et al., "Synthesis of pyrrolo[2,1-c][1,4]benzodiazepines via reductive cyclization of w-azido carbonyl compounds by TMSI: an efficient preparation of antibiotic DC-81 and its dimers," Biorg. Med. Chem. Lett. (2000) 10:2311-2313.
Kaneko, T. et al., "Bicyclic and tricyclic analogues of anthramycin," J. Med. Chem. (1985) 28:388-392.
Kang, G.-D. et al., "Synthesis of a novel C2-aryl substituted 1,2-unsaturated pyrrolobenzodiazepine," Chem. Commun. (2003) 1688-1689.
Kohn, K., "Anthramycin," *Antibiotics III*, Springer-Verlag, NY, 3-11 (1975).
Konishi, M. et al., "Chicamycin, a new antitumor antibiotic II. Structure determination of chicamycins A and B,"*J. Antibiotics*, 37, 200-206 (1984).
Kunimoto et al., "Mazethramycin, a new member of anthramycin group antibiotics," *J. Antibiotics*, 33, 665-667.
Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," *J. Org. Chem.*, 52, 91-97 (1987).
Langlois, N. et al., "Synthesis and cytotoxicity on sensitive and doxorubicin-resistant cell lines of new pyrrolo[2,1-c][1,4]benzodiazepines related to anthramycin," J. Med. Chem. (2001) 44:3754-3757.
Leber, J.D. et al., "A revised structure for sibiromycin," *J. Am. Chem. Soc.*, 110, 2992-2993 (1988).
Leimgruber, W. et al., "Isolation and characterization of anthramycin, a new antitumor antibiotic," *J. Am. Chem. Soc.*, 87, 5791-5793 (1965).
Leimgruber, W. et al., "The structure of anthramycin,"*J. Am. Chem. Soc.*, 87, 5793-5795 (1965).
Leimgruber, W. et al., "Total synthesis of anthramycin," *J. Am. Chem. Soc.*, 90, 5641-5643 (1968).
Lown et al., "Molecular Mechanism of Binding of Pyrrolo(1,4)benzodiazepine antitumour agents to deoxyribonucleic—anthramycin and tomaymycin," Biochem. Pharmacol. (1979), 28 (13), 2017-2026.
Marin, D., "Voltammetric studies of the interaction of pyrrolo[2,1-c][1,4]benzodiazepine (PBD) monomers and dimers with DNA," J. Electroanal. Chem. (2006) 593(1-2):241-246.
Martin, C. et al., "Sequence-selective interaction of the minor-groove interstrand cross-linking agent SJG-136 with naked and cellular DNA: footprinting and enzyme inhibition studies," Biochem. (2005) 44(11):4135-4147.

Mori, M. et al., "Total syntheses of prothracarcin and tomaymycin by use of palladium catalyzed carbonylation," Tetrahedron (1986) 42(14):3793-3806.
Mountzouris, J.A. et al., "Comparison of a DSB-120 DNA interstrand cross-linked adduct with the corresponding bis-Tomamycin adduct," J. Med. Chem. (1994) 37:3132-3140.
Nagasaka, T. and Koseki, Y, "Stereoselective Synthesis of Tilivalline," *Journal of Organic Chemistry*, vol. 63, No. 20, 6797-6801 (1998).
Nagasaka, T. et al., "Stereoselective Synthesis of Tilivalline," *Tetrahedron Letters*, 30:14, 1871-1872 (1989).
Narayanaswamy, M., "A novel HPLC/MS assay to measure DNA interstrand cross-linking efficacy in oligonucleotides of varying sequence," EJC Supplements (Nov. 2006) 4(12):92-93.
Narayanaswamy, M., "An assay combining high-performance liquid chromatography and mass spectrometry to measure DNA interstrand cross-linking efficiency in oligonucleotides of varying sequences," Anal. Biochem. (2008) 374(1):173-181.
Narayanaswamy, M., "Use of HPLC-MS to characterize novel mono and intrastrand cross-linked DNA adducts formed by the sequence-selective DNA-interactive agent SJG-136," Proceedings of the American Association for Cancer Research Annual Meeting (Apr. 2007) 48:760-761.
Narukawa, Y., "General and efficient synthesis of 2-alkylcarbapenems synthesis of dethia carba analogs of clinically useful carbapenems via palladium-catalyzed cross-coupling reaction," Tetrahedron (1997) 53:539-556.
O'Neil, Chemical Abstract No. 171573p, "The synthesis of Functionalized Pyrrolo-[2,1-c][1,4]-Benzodiazepines", *Chemical Abstracts*, vol. 126, No. 13, 618 (1997).
O'Neil, I.A., et al., "The Synthesis of Functionalized Pyrrolo-[2,1-c][1,4]-Benzodiazepines," *Synlett*, 75-78 (1997).
O'Neil, I.A. et al., "DPPE: A Convenient Replacement for Triphenylphosphine in the Staudinger and Mitsunobu Reactions", *Tetrahedron Letters*, vol. 39, No. 42, 7787-7790 (1998).
Pepper, C., "Fludarabine-mediated suppression of the excision repair enzyme ERCC1 contributes to the cytotoxic synergy with the DNA minor groove crosslinking agent SJG-136 (NSC 694501) in chronic lymphocytic leukaemia cells," Br. J. Cancer (2007) 97(2):253-259.
Pepper, C.J. et al., "The novel sequence-specific DNA cross-linking agent SJG-136 (NSC 694501) has potent and selective in vitro cytotoxicity in human B-cell chronic lymphocytic leukemia cells with evidence of a p53-independent mechanism of cell kill," Cancer Res. (2004) 64:6750-6755.
Puzanov, I., "Phase I and pharmacokinetic trial of SJG-136 administered on a daily x5 schedule," EJC Supplements (Nov. 2006) 4(12):93.
Quintas-Cardama, A., "Sequencing of subcloned PCR products facilitates earlier detetction of BCR-ABL 1 and other mutants compared to direct sequencing of the ABL 1 kinase domain," Leukemia (2008) 22(4):877-878.
Rahman, K.M., "Effect of microwave irradiation on covalent ligand-DNA interactions," Chem. Commun. (Cambridge, UK), Apr. 2009, 20:2875-2877.
Rahman, K.M., "Rules of DNA adduct formation for pyrrolobenzodiazepine (PBD) dimers," Proceedings of the American Association for Cancer Research Annual Meeting (Apr. 2010) 51:851.
Rahman, K.M., "The pyrrolobenzodiazepine dimer SJG-136 forms sequence-dependent intrastrand DNA cross-lins and monoalkylated adducts in addition to interstrand cross-links," J. Am. Chem. Soc., Sep. 2009, 131(38):13756-13766.
Reid, J.M., "LC-MS/MS assay and rat pharmacokinetics and metabolism of the dimeric pyrrolobenzodiazepine SJG-136," Proceedings of the American Association for Cancer Research Annual Meeting (Mar. 2004) 45:1248.
Rich, I.N., "Validation and development of a predictive paradigm for hemotoxicology using a multifunctional bioluminescence colony-forming proliferation assay," Toxicological Sci. (2005) 87(2):427-441.

(56) References Cited

OTHER PUBLICATIONS

Sagnou, M.J. et al., "Design and Synthesis of Novel Pyrrolobenzodiazepine (PDB) Prodrugs for ADEPT and GDEPT,"*Bioorganic & Medicinal Chemistry Letters*, 10, 2083-2086 (2000).
Schweikart, K., "In vitro myelosuppression of SJG-136, a pyrrolobenzodiazepine dimer: comparison to bizelesin," Proceedings of the American Association for Cancer Research Annual Meeting (Mar. 2004) 45:486.
Shimizu, K et al., "Prothracarcin, a Novel Antitumor Antibiotic," *J. Antibiotics*, 35, 972-978 (1982).
Smellie, M. et al., "Cellular pharmacology of novel C8-linked anthramycin-based sequence-selective DNA minor groove cross-linking agents," Br. J. Cancer (1994) 70:48-53.
Smellie, M. et al., "Sequence selective recognition of duplex DNA through covalent interstrand cross-linking," Biochem. (2003) 42:8232-8239.
Souillac, P. et al., "Chracterization of delivery systems, differential scanning calorimetry," Encyclopedia of Controlled Drug Delivery (1999) 212-227 (pp. 217-218).
Suggitt, M., "The hollow fibre model—facilitating anti-cancer pre-clinical pharmacodynamics and improving animal welfare," Int. J. Oncol. (2006) 29(6):1493-1499.
Suggs, J.W. et al., "Synthesis and structure of anthramycin analogs via hydride reduction of dilactams," *Tetrahedron Letters*, 26, No. 40, 4871-4874 (1985).
Sutherland, M.S.K. et al., "SGN-CD33A: a novel CD33-directed antibody-drug conjugate, utilizing pyrrolobenzodiazepine dimers, demonstrates preclinical anti-tumor activity against multi-drug resistant human AML," American Society of Hematology (Dec. 8-12, 2012) Atlanta, Georgia, Abstract No. 3589.
Takeuchi, T. et al., "Neothramycins A and B, New Antitumor Antibiotics," *J. Antibiotics*, 29, 93-96 (1976).
Tercel, M. et al., "Unsymmetrical DNA cross-linking agents: combination of the CBI and PBD pharmacophores," J. Med. Chem. (2003) 46:2132-2151.
Thurston, D. E., "Advances in the study of Pyrrolo[2,1-c][1,4] benzodiazepine (PBD) Antitumour Antibiotics", *Molecular Aspects of Anticancer Drug-DNA Interaction*, Neidle, S. and Waring, M.J., Eds.; Macmillan Press Ltd, 1:54-88 (1993).
Thurston, D.E. and Bose, D.S., "Synthesis of DNA-Interactive Pyrrolo[2,1-c][1,4]benzodiazepines," *Chem. Rev.*, 94:433-465 (1994).
Thurston, D.E. and Thompson, A.S., "The molecular recognition of DNA," *Chem. Brit.*, 26, 767-772 (1990).
Thurston, D.E. et al., "Effect of A-ring modifications on the DNA-binding behavior and cytotoxicity of pyrrolo [2,1-c][1,4]benzodiazepines", *Journal of Medicinal Chemistry*, 42:1951-1964 (1999).
Thurston, D.E. et al., "Synthesis of Sequence-selective C8-linked Pyrrolo [2,1-c][1,4] Benzodiazepine DNA Interstrand Cross-linking Agent," *J. Org. Chem.*, 61:8141-8147 (1996).
Thurston, D.E. et al., "Synthesis of a novel GC-specific covalent-binding DNA affinity-cleavage agent based on pyrrolobenzodiazepines (PBDs)," Chemical Communications, 563-565 (1996).
Thurston, D.E., "Nucleic acid targeting: therapeutic strategies for the 21st century," Brit. J. Cancer (1999) 80(1):65-85.
Tiberghien, A.C. et al., "Application of the stille coupling reaction to the synthesis of C2-substituted endo-exo unsaturated pyrrolo [2,1-c][1,4]benzodiazepines (PBDs)," Biorg. Med. Chem. Lett. (2004) 14:5041-5044.
Tiberghien, A.C., "Application of the stille coupling reaction to the synthesis of C2-substituted endo-exo unsaturated pyrrolo[2,1-c][1,4]benzodiazepines (PBDs)," Bioorg. Med. Chem. Lett. (2008) 18(6):2073-2077.
Tozuka et al., "Studies on tomaymycin. II. Total synthesis of the antitumor antibiotics, E-and Z-tomaymycins," J. Antibiotics (Tokyo) (1983) 36:276-282.
Tsunakawa, M. et al., "Porothramycin, a new antibiotic of the anthramycin group: Production, isolation, structure and biological activity," *J. Antibiotics*, 41:1366-1373 (1988).
Umezawa, H. et al., Chemical Abstract No. 4427a, "Mazethramycins" *Chemical Abstracts*, vol. 90, No. 1, 428 (1979).
Vippagunta, S.R. et al., "Crystalline solids," Adv. Drug Delivery Rev. (2001) 48:3-26.
Wang, J.H., "Determination of antitumor agent AJG-136 in human serum by HPLC with tandem mass spectrometric detection (HPLC-MS/MS)," Abstracts of Papers American Chemical Society (Mar. 13, 2005) 229(1):U119.
Weidner-Wells, M.A. et al., "Photochemical approach to the synthesis of the pyrrolo[1,4]benzodiazepine antibiotics," J. Org. Chem. (1989) 54:5746-5758.
Wells, G. et al., "Design, synthesis and biophysical and biological evaluation of a series of pyrrolobenzodiazepine-poly(N-methylpyrrole) conjugates," J. Med. Chem. (2006) 49:5442-5461.
Wilkinson, G.P., "Pharmacokinetics and intracellular pharmacological characteristics of the novel pyrrolobenzodiazepine (PBD) dimer SJG-136," Proceedings of the American Association for Cancer Research Annual Meeting (Jul. 2003) 44:320.
Wilkinson, G.P., "Pharmacokinetics, metabolism and glutathione reactivity of SJG-136," Br. J. Cancer (2003) 88(Supp. 1):S29.
Wilkinson, G.P., "Preliminary pharmacokinetic and bioanalytical studies of SJG-136 (NSC 694501), a sequence-selective pyrrolobenzodiazepine dimer DNA-cross-linking agent," Investigational New Drugs (2004) 22(3):231-240.
Wilson, S.C. et al., "Design and Synthesis of a Novel Epoxide-Containing Pyrrolo[2,1-c][1,4]benzodiazepine (PBD) via a New Cyclization Procedure," *Tetrahedron Letters*, 36, No. 35, 6333-6336 (1995).
Wilson, S.C. et al., "Design, Synthesis, and Evaluation of a Novel Sequence-Selective Epoxide-Containing DNA Cross-Linking Agent Based on the Pyrrolo[2,1-c][1,4]benzodiazepine System", J. Med. Chem. 42:4028-4041 (1999).
Wolff, M.E., Burger's Medicinal Chemistry, 4th Edition, Part I, Wiley: New York (1979) 336-337.
Wolff, M.E., Burger's Medicinal Chemistry, 5th Edition, Part I, John Wiley & Sons (1995) 975-977.
Workman, P. et al., "United Kingdom Co-ordinating Committee on Cancer Research (UKCCCR) guidelines for the welfare of animals in experimental neoplasia (second edition)," Br. J. Cancer (1998) 77(1):1-10.
Xie, G. et al., "Bisindolylmaleimides linked to DNA minor groove binding lexitropsins: synthesis, inhibitory activity against topoisomerasel, and biological evaluation," J. Med. Chem. (1996) 39:1049-1055.
International Search Report and Written Opinion for Application No. PCT/US2011/032664 dated Aug. 19, 2011 (13 pages).

Figure 4: Efficacy of h1F6-1910(2) on Caki1 (RCC) Tumors in Nude Female Mice

TARGETED PYRROLOBENZODIAZAPINE CONJUGATES

CROSS-REFERENCE TO RELATED APPLICATIONS

This application is a continuation of copending U.S. application Ser. No. 15/951,753, filed on Apr. 12, 2018, which is a continuation of U.S. application Ser. No. 15/422,000, filed on Feb. 1, 2017, now abandoned, which is a continuation of U.S. application Ser. No. 14/995,944, filed on Jan. 14, 2016, now U.S. Pat. No. 9,592,240, which is a continuation of U.S. application Ser. No. 13/641,219, filed on Oct. 15, 2012, now U.S. Pat. No. 9,242,013, which claims the benefit of U.S. Provisional Application No. 61/324,623, filed on Apr. 15, 2010, the entire contents of which are fully incorporated herein by reference.

The present invention relates to targeted pyrrolobenzodiazepine (PBD) conjugates, in particular pyrrolobenzodiazepine dimers that are conjugated to a targeting agent via the C2 position of one of the monomers.

BACKGROUND TO THE INVENTION

Some pyrrolobenzodiazepines (PBDs) have the ability to recognise and bond to specific sequences of DNA; the preferred sequence is PuGPu. The first PBD antitumour antibiotic, anthramycin, was discovered in 1965 (Leimgruber, et al., *J. Am. Chem. Soc.*, 87, 5793-5795 (1965); Leimgruber, et al., *J. Am. Chem. Soc.*, 87, 5791-5793 (1965)). Since then, a number of naturally occurring PBDs have been reported, and over 10 synthetic routes have been developed to a variety of analogues (Thurston, et al., *Chem. Rev.* 1994, 433-465 (1994)). Family members include abbeymycin (Hochlowski, et al., *J. Antibiotics*, 40, 145-148 (1987)), chicamycin (Konishi, et al., *J. Antibiotics*, 37, 200-206 (1984)), DC-81 (Japanese Patent 58-180 487; Thurston, et al., *Chem. Brit.*, 26, 767-772 (1990); Bose, et al., *Tetrahedron*, 48, 751-758 (1992)), mazethramycin (Kuminoto, et al., *J. Antibiotics*, 33, 665-667 (1980)), neothramycins A and B (Takeuchi, et al., *J. Antibiotics*, 29, 93-96 (1976)), porothramycin (Tsunakawa, et al., *J. Antibiotics*, 41, 1366-1373 (1988)), prothracarcin (Shimizu, et al, *J. Antibiotics*, 29, 2492-2503 (1982); Langley and Thurston, *J. Org. Chem.*, 52, 91-97 (1987)), sibanomicin (DC-102)(Hara, et al., *J. Antibiotics*, 41, 702-704 (1988); Itoh, et al., *J. Antibiotics*, 41, 1281-1284 (1988)), sibiromycin (Leber, et al., *J. Am. Chem. Soc.*, 110, 2992-2993 (1988)) and tomamycin (Arima, et al., *J. Antibiotics*, 25, 437-444 (1972)). PBDs are of the general structure:

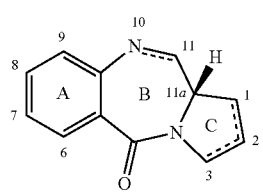

They differ in the number, type and position of substituents, in both their aromatic A rings and pyrrolo C rings, and in the degree of saturation of the C ring. In the B-ring there is either an imine (N=C), a carbinolamine(NH—CH(OH)), or a carbinolamine methyl ether (NH—CH(OMe)) at the N10-C11 position, which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In *Antibiotics III*. Springer-Verlag. New York, pp. 3-11 (1975); Hurley and Needham-VanDevanter, *Acc. Chem. Res.*, 19, 230-237 (1986)). The ability of PBDs to form an adduct in the minor groove enables them to interfere with DNA processing, hence their use as antitumour agents.

The biological activity of these molecules can be potentiated by joining two PBD units together through their C8/C'-hydroxyl functionalities via a flexible alkylene linker (Bose, D. S., et al., *J. Am. Chem. Soc.*, 114, 4939-4941 (1992); Thurston, D. E., et al., *J. Org. Chem.*, 61, 8141-8147 (1996)). The PBD dimers are thought to form sequence-selective DNA lesions such as the palindromic 5'-Pu-GATC-Py-3' interstrand cross-link (Smellie, M., et al., *Biochemistry*, 42, 8232-8239 (2003); Martin, C., et al., *Biochemistry*, 44, 4135-4147) which is thought to be mainly responsible for their biological activity. One example of a PBD dimer is SG2000 (SJG-136):

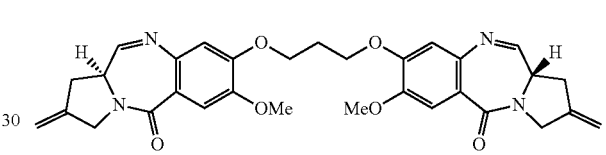

(Gregson, S., et al., *J. Med. Chem.*, 44, 737-748 (2001); Alley, M. C., et al., *Cancer Research*, 64, 6700-6706 (2004); Hartley, J. A., et al., *Cancer Research*, 64, 6693-6699 (2004)).

Due to the manner in which these highly potent compounds act in cross-linking DNA, PBD dimers have been made symmetrically, i.e., both monomers of the dimer are the same. This synthetic route provides for straightforward synthesis, either by constructing the PBD dimer moiety simultaneously having already formed the dimer linkage, or by reacting already constructed PBD monomer moieties with the dimer linking group. These synthetic approaches have limited the options for preparation of targeted conjugates containing PBDs. Due to the observed potency of PBD dimers, however, there exists a need for PBD dimers that are conjugatable to targeting agents for use in targeted therapy.

DISCLOSURE OF THE INVENTION

The present invention relates to Conjugates comprising dimers of PBDs linked to a targeting agent, wherein a PBD monomer has a substituent in the C2 position that provides an anchor for linking the compound to the targeting agent. The present invention also relates to Conjugates comprising dimers of PBDs conjugated to a targeting agent, wherein the PBD monomers of the dimer are different. One of PBD monomers has a substituent in the C2 position that provides an anchor for linking the compound to the targeting agent. The Conjugates described herein have potent cytotoxic and/or cytostatic activity against cells expressing a target molecule, such as cancer cells or immune cells. These conjugates exhibit good potency with reduced toxicity, as compared with the corresponding PBD dimer free drug compounds.

In some embodiments, the Conjugates have the following formula I:

wherein L is a Ligand unit (i.e., a targeting agent), LU is a Linker unit and D is a Drug unit comprising a PBD dimer. The subscript p is an integer of from 1 to 20. Accordingly, the Conjugates comprise a Ligand unit covalently linked to at least one Drug unit by a Linker unit. The Ligand unit, described more fully below, is a targeting agent that binds to a target moiety. The Ligand unit can, for example, specifically bind to a cell component (a Cell Binding Agent) or to other target molecules of interest. Accordingly, the present invention also provides methods for the treatment of, for example, various cancers and autoimmune disease. These methods encompass the use of the Conjugates wherein the Ligand unit is a targeting agent that specifically binds to a target molecule. The Ligand unit can be, for example, a protein, polypeptide or peptide, such as an antibody, an antigen-binding fragment of an antibody, or other binding agent, such as an Fc fusion protein.

In a first aspect, the Conjugates comprise a Conjugate of formula I (supra), wherein the Drug unit comprises a PBD dimer of the following formula II:

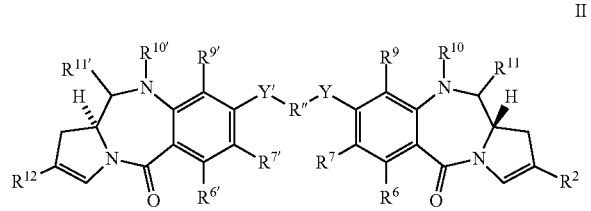

wherein:
$R^2$ is of formula III:

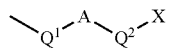

where A is a $C_{5-7}$ aryl group, X is an activatable group for conjugation to the Linker unit, wherein X is selected from the group comprising: —O—, —S—, —C(O)O—, —C(O)—, —NHC(O)—, and —N($R^N$)—, wherein $R^N$ is selected from the group comprising H. $C_{1-4}$ alkyl and $(C_2H_4O)_mCH_3$, where m is 1 to 3, and either:
 (i) $Q^1$ is a single bond, and $Q^2$ is selected from a single bond and —Z—$(CH_2)_n$—, where Z is selected from a single bond, O, S and NH and n is from 1 to 3; or
 (ii) $Q^1$ is —CH=CH—, and $Q^2$ is a single bond;
$R^{12}$ is a $C_{5-10}$ aryl group, optionally substituted by one or more substituents selected from the group comprising: halo, nitro, cyano, ether, $C_{1-7}$ alkyl, $C_{3-7}$ heterocyclyl and bis-oxy-$C_{1-3}$ alkylene:
$R^6$ and $R^9$ are independently selected from H, R, OH, OR, SH, SR, $NH_2$, NHR, NRR', nitro, $Me_3Sn$ and halo;
 where R and R' are independently selected from optionally substituted $C_{1-12}$ alkyl, optionally substituted $C_{3-20}$ heterocyclyl and optionally substituted $C_{5-20}$ aryl groups;
$R^7$ is selected from H, R, OH, OR, SH, SR, $NH_2$, NHR, NHRR', nitro, $Me_3Sn$ and halo; either:

(a) $R^{10}$ is H, and $R^{11}$ is OH or $OR^A$, where $R^A$ is $C_{1-4}$ alkyl;
 (b) $R^{10}$ and $R^{11}$ form a nitrogen-carbon double bond between the nitrogen and carbon atoms to which they are bound; or
 (c) $R^{10}$ is H and $R^{11}$ is $SO_zM$, where z is 2 or 3 and M is a monovalent pharmaceutically acceptable cation;
R" is a $C_{3-12}$ alkylene group, which chain may be interrupted by one or more heteroatoms, e.g. O, S, $NR^{N2}$ (where $R^{N2}$ is H or $C_{1-4}$ alkyl), and/or aromatic rings, e.g. benzene or pyridine;
Y and Y' are selected from O, S, or NH;
$R^{6'}$, $R^{7'}$, $R^{9'}$ are selected from the same groups as $R^6$, $R^7$ and $R^9$ respectively and $R^{10'}$ and
$R^{11'}$ are the same as $R^{10}$ and $R^{11}$, wherein if $R^{11}$ and $R^{11'}$ are $SO_zM$, M may represent a divalent pharmaceutically acceptable cation.

In a second aspect, the use of the Conjugate of formula I is provided for the manufacture of a medicament for treating a proliferative disease or autoimmune disease. In a related third aspect, the use of the Conjugate of formula I is provided for the treatment of a proliferative disease or an autoimmune disease.

In another aspect there is provided the use of a Conjugate of formula I to provide a PBD dimer, or a salt or solvate thereof, at a target location.

One of ordinary skill in the art is readily able to determine whether or not a candidate conjugate treats a proliferative condition for any particular cell type. For example, assays which may conveniently be used to assess the activity offered by a particular compound are described in the examples below.

The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g., histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreatic cancer, brain cancer, sarcoma, osteosarcoma, Kaposi's sarcoma, melanoma), leukemias, psoriasis, bone diseases, fibroproliferative disorders (e.g. of connective tissues), and atherosclerosis. Other cancers of interest include, but are not limited to, haematological; malignancies such as leukemias and lymphomas, such as non-Hodgkin lymphoma, and subtypes such as DLBCL, marginal zone, mantle zone, and follicular, Hodgkin lymphoma, AML, and other cancers of B or T cell origin.

Examples of autoimmune disease include the following: rheumatoid arthritis, autoimmune demyelinative diseases (e.g., multiple sclerosis, allergic encephalomyelitis), psoriatic arthritis, endocrine ophthalmopathy, uveoretinitis, systemic lupus erythematosus, myasthenia gravis, Graves' disease, glomerulonephritis, autoimmune hepatological disorder, inflammatory bowel disease (e.g., Crohn's disease), anaphylaxis, allergic reaction, Sjögren's syndrome, type I diabetes mellitus, primary biliary cirrhosis, Wegener's granulomatosis, fibromyalgia, polymyositis, dermatomyositis, multiple endocrine failure, Schmidt's syndrome, autoimmune uveitis, Addison's disease, adrenalitis, thyroiditis, Hashimoto's thyroiditis, autoimmune thyroid disease, pernicious anemia, gastric atrophy, chronic hepatitis, lupoid hepatitis, atherosclerosis, subacute cutaneous lupus erythematosus, hypoparathyroidism. Dressler's syndrome, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyly, and telangiectasia), male and female autoimmune infertility, ankylosing spondolytis, ulcerative colitis, mixed connective tissue disease, polyarteritis nedosa, systemic necrotizing vasculitis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, toxic epidermal necrolysis, Alport's syndrome, alveolitis, allergic alveolitis, fibrosing alveolitis, interstitial lung disease, erythema nodosum, pyoderma gangrenosum, transfusion reaction, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, cardiomyopathy, Eaton-Lambert syndrome, relapsing polychondritis, cryoglobulinemia, Waldenstrom's macroglobulemia, Evan's syndrome, and autoimmune gonadal failure.

In some embodiments, the autoimmune disease is a disorder of B lymphocytes (e.g., systemic lupus erythematosus, Goodpasture's syndrome, rheumatoid arthritis, and type I diabetes), Th1-lymphocytes (e.g., rheumatoid arthritis, multiple sclerosis, psoriasis, Sjögren's syndrome, Hashimoto's thyroiditis, Graves' disease, primary biliary cirrhosis, Wegener's granulomatosis, tuberculosis, or graft versus host disease), or Th2-lymphocytes (e.g., atopic dermatitis, systemic lupus erythematosus, atopic asthma, rhinoconjunctivitis, allergic rhinitis, Omenn's syndrome, systemic sclerosis, or chronic graft versus host disease). Generally, disorders involving dendritic cells involve disorders of Th1-lymphocytes or Th2-lymphocytes. In some embodiments, the autoimmune disorder is a T cell-mediated immunological disorder.

In a fourth aspect of the present invention comprises a method of making the Conjugates formula I.

The dimeric PBD compounds for use in the present invention are made by different strategies to those previously employed in making symmetrical dimeric PBD compounds. In particular, the present inventors have developed a method which involves adding each C2 aryl substituent to a symmetrical PBD dimer core in separate method steps. Accordingly, a sixth aspect of the present invention provides a method of making a Conjugate of formula I, comprising at least one of the method steps described herein.

DEFINITIONS

Figure 1:
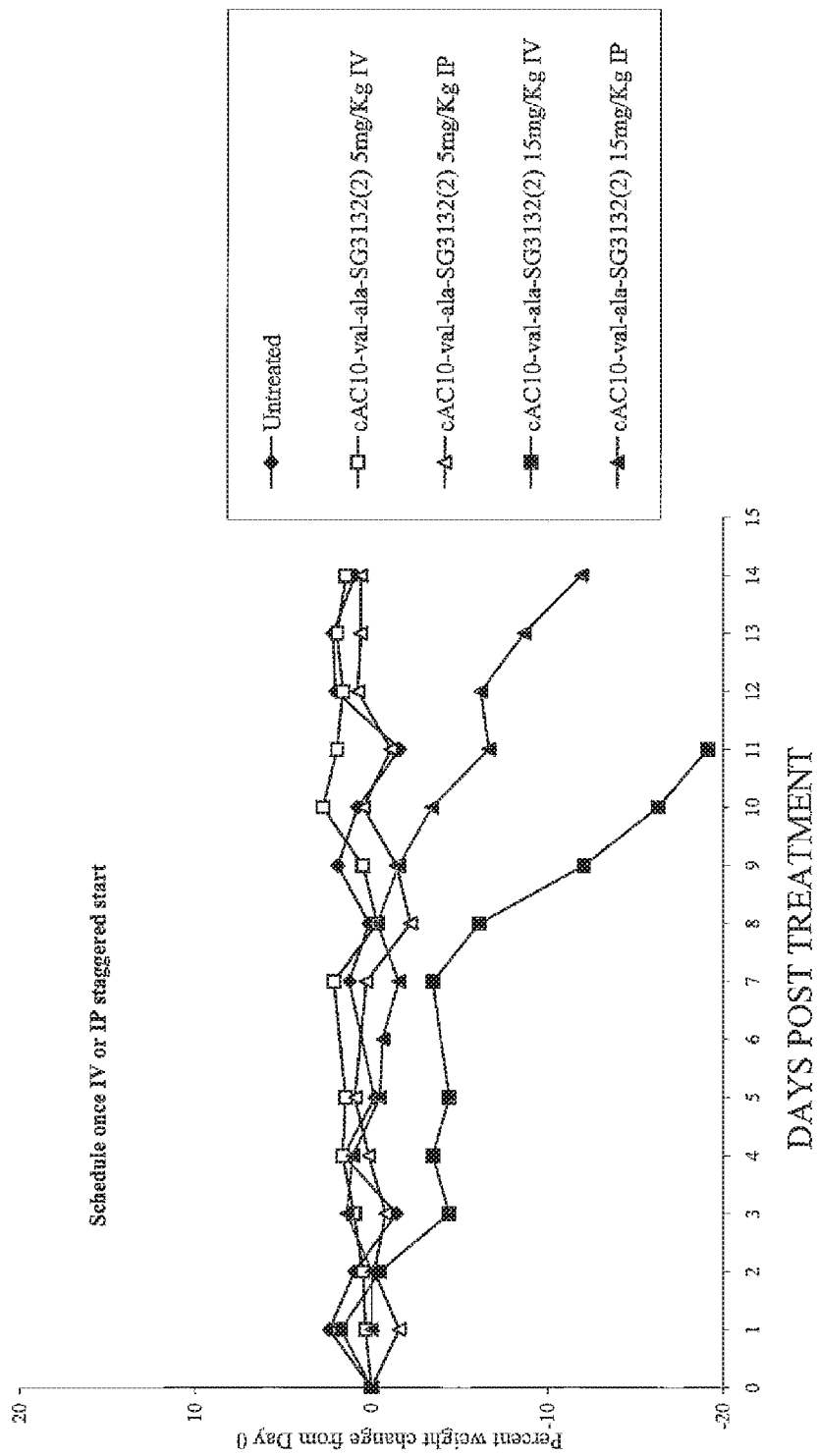
FIGS. 1 to 6 show the effect of conjugates of the present invention in tumours.

When a trade name is used herein, reference to the trade name also refers to the product formulation, the generic drug, and the active pharmaceutical ingredient(s) of the trade name product, unless otherwise indicated by context.

Binding Agent and Targeting Agent

The terms "binding agent" and "targeting agent as used herein refer to a molecule, e.g., protein, polypeptide or peptide, that specifically binds to a target molecule. Examples can include a full length antibody, an antigen binding fragment of a full length antibody, other agent (protein, polypeptide or peptide) that includes an antibody heavy and/or light chain variable region that specifically bind to the target molecule, or an Fc fusion protein comprising an extracellular domain of a protein, peptide polypeptide that binds to the target molecule and that is joined to an Fc region, domain or portion thereof, of an antibody.

Specifically Binds

The terms "specifically binds" and "specific binding" refer to the binding of an antibody or other protein, polypeptide or peptide to a predetermined molecule (e.g., an antigen). Typically, the antibody or other molecule binds with an affinity of at least about $1 \times 10^7$ $M^{-1}$, and binds to the predetermined molecule with an affinity that is at least two-fold greater than its affinity for binding to a non-specific molecule (e.g., BSA, casein) other than the predetermined molecule or a closely-related molecule.

Pharmaceutically Acceptable Cations

Examples of pharmaceutically acceptable monovalent and divalent cations are discussed in Berge, et al., *J. Pharm. Sci.*, 66, 1-19 (1977), which is incorporated herein by reference.

The pharmaceutically acceptable cation may be inorganic or organic.

Examples of pharmaceutically acceptable monovalent inorganic cations include, but are not limited to, alkali metal ions such as $Na^+$ and $K^+$. Examples of pharmaceutically acceptable divalent inorganic cations include, but are not limited to, alkaline earth cations such as $Ca^{2+}$ and $Mg^{2+}$. Examples of pharmaceutically acceptable organic cations include, but are not limited to, ammonium ion (i.e. $NH_4^+$) and substituted ammonium ions (e.g. $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Substituents

The phrase "optionally substituted" as used herein, pertains to a parent group which may be unsubstituted or which may be substituted.

Unless otherwise specified, the term "substituted" as used herein, pertains to a parent group which bears one or more substituents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Examples of substituents are described in more detail below.

$C_{1-12}$ alkyl: The term "$C_{1-12}$ alkyl" as used herein, pertains to a monovalent moiety obtained by removing a hydrogen atom from a carbon atom of a hydrocarbon compound having from 1 to 12 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{2-12}$ Alkenyl: The term "$C_{2-12}$ alkenyl" as used herein, pertains to an alkyl group having one or more carbon-carbon double bonds.

Examples of unsaturated alkenyl groups include, but are not limited to, ethenyl (vinyl, —CH=$CH_2$), 1-propenyl (—CH=CH—$CH_3$), 2-propenyl (allyl, —CH—CH=$CH_2$), isopropenyl (1-methylvinyl, —C($CH_3$)=$CH_2$), butenyl ($C_4$), pentenyl ($C_5$), and hexenyl ($C_6$).

$C_{2-12}$ alkynyl: The term "$C_{2-12}$ alkynyl" as used herein, pertains to an alkyl group having one or more carbon-carbon triple bonds.

Examples of unsaturated alkynyl groups include, but are not limited to, ethynyl (—C≡CH) and 2-propynyl (propargyl, —$CH_2$—C≡CH).

$C_{3-12}$ cycloalkyl: The term "$C_{3-12}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:

Saturated Monocyclic Hydrocarbon Compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$) and methylcyclohexane ($C_7$);

Unsaturated Monocyclic Hydrocarbon Compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$) and methylcyclohexene ($C_7$); and Saturated Polycyclic Hydrocarbon Compounds:
norcarane ($C_7$), norpinane ($C_7$), norbomane ($C_7$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:
$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);
$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);
$S_1$: thiirane ($C_3$), thietane ($C_4$), thiolane (tetrahydrothiophene) ($C_5$), thiane (tetrahydrothiopyran) ($C_6$), thiepane ($C_7$);
$O_2$: dioxolane ($C_5$), dioxane ($C_6$), and dioxepane ($C_7$);
$O_3$: trioxane (C6);
$N_2$: imidazolidine ($C_5$), pyrazolidine (diazolidine) ($C_5$), imidazoline ($C_5$), pyrazoline (dihydropyrazole) ($C_5$), piperazine ($C_6$);
$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);
$N_1S_1$: thiazoline ($C_5$), thiazolidine ($C_5$), thiomorpholine ($C_6$);
$N_2O_1$: oxadiazine ($C_6$);
$O_1S_1$: oxathiole ($C_5$) and oxathiane (thioxane) ($C_6$); and,
$N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of an aromatic compound, which moiety has from 3 to 20 ring atoms. Preferably, each ring has from 5 to 7 ring atoms.

In this context, the prefixes (e.g. $C_{3-20}$, $C_{5-7}$, $C_{5-6}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

The ring atoms may be all carbon atoms, as in "carboaryl groups".

Examples of carboaryl groups include, but are not limited to, those derived from benzene (i.e. phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of monocyclic heteroaryl groups include, but are not limited to, those derived from:
$N_1$: pyrrole (azole) ($C_5$), pyridine (azine) ($C_6$);
$O_1$: furan (oxole) ($C_5$);
$S_1$: thiophene (thiole) ($C_5$);
$N_1O_1$: oxazole ($C_5$), isoxazole ($C_5$), isoxazine ($C_6$);
$N_2O_1$: oxadiazole (furazan) ($C_5$);
$N_3O_1$: oxatriazole ($C_5$):
$N_1S_1$: thiazole ($C_5$), isothiazole ($C_5$);
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);
$N_3$: triazole ($C_5$), triazine ($C_6$); and,
$N_4$: tetrazole ($C_5$).

Examples of heteroaryl which comprise fused rings, include, but are not limited to:

$C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$ (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$ (with 2 fused rings) derived from benzodiazepine ($N_2$);

$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$ (with 3 fused rings) derived from acridine ($N_1$), xanthene ($O_1$), thioxanthene ($S_1$), oxanthrene ($O_2$), phenoxathiin ($O_1S$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

The above groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

Alkoxy: —OR, wherein R is an alkyl group, for example, a $C_{1-7}$ alkyl group. Examples of $C_{1-7}$ alkoxy groups include, but are not limited to, —OMe (methoxy), -OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH($OR^1$)($OR^2$), wherein $R^1$ and $R^2$ are independently acetal substituents, for example, a $C_{1-7}$ alkyl group, a $C_{3-20}$ heterocyclyl group, or a $C_{5-20}$ aryl group, preferably a $C_{1-7}$ alkyl group, or, in the case of a "cyclic" acetal group, $R^1$ and $R^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)($OR^1$), wherein $R^1$ is a hemiacetal substituent, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —CH(OH)(OMe) and —CH(OH)(OEt).

Ketal: —CR($OR^1$)($OR^2$), where $R^1$ and $R^2$ are as defined for acetals, and R is a ketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)($OR^1$), where $R^1$ is as defined for hemiacetals, and R is a hemiketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —OC(=O)OCH$_3$, —OC(=O)OCH$_2$CH$_3$, —OC(=O)OC(CHa)$_3$, and —OC(=O)OPh.

Amino: —NR$^1$R$^2$, wherein $R^1$ and $R^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, $R^1$ and $R^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Acylamido (acylamino): —NR$^1$C(=O)R$^2$, wherein R$^1$ is an amide substituent, for example, hydrogen, a C$_{1-7}$ alkyl group, a C$_{3-20}$ heterocyclyl group, or a C$_{5-20}$ aryl group, preferably hydrogen or a C$_{1-7}$ alkyl group, and R$^2$ is an acyl substituent, for example, a C$_{1-7}$ alkyl group, a C$_{3-20}$ heterocyclyl group, or a C$_{5-20}$aryl group, preferably hydrogen or a C$_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

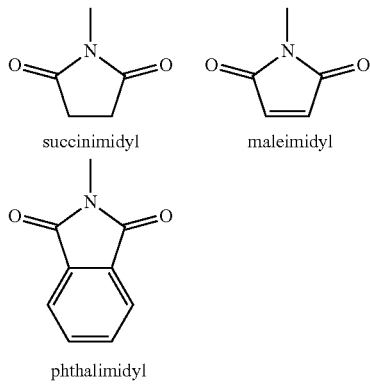

succinimidyl   maleimidyl phthalimidyl

Aminocarbonyloxy: —OC(=O)NR$^1$R$^2$, wherein R$^1$ and R$^2$ are independently amino substituents, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.

Ureido: —N(R$^1$)CONR$^2$R$^3$ wherein R$^2$ and R$^3$ are independently amino substituents, as defined for amino groups, and R$^1$ is a ureido substituent, for example, hydrogen, a C$_{1-7}$ alkyl group, a C$_{3-20}$ heterocyclyl group, or a C$_{5-20}$ aryl group, preferably hydrogen or a C$_{1-7}$ alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom,

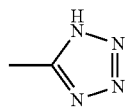

Imino: =NR, wherein R is an imino substituent, for example, for example, hydrogen, a C$_{1-7}$ alkyl group, a C$_{3-20}$ heterocyclyl group, or a C$_{5-20}$ aryl group, preferably H or a C$_{1-7}$alkyl group. Examples of imino groups include, but are not limited to, =NH, =NMe, and =NEt.

Amidine (amidino): —C(=NR)NR$_2$, wherein each R is an amidine substituent, for example, hydrogen, a C$_{1-7}$ alkyl group, a C$_{3-20}$ heterocyclyl group, or a C$_{5-20}$ aryl group, preferably H or a C$_{1-7}$ alkyl group. Examples of amidine groups include, but are not limited to, —C(=NH)NH$_2$, —C(=NH)NMe$_2$, and —C(=NMe)NMe$_2$.

Nitro: —NO$_2$.

Nitroso: —NO.

Azido: —N$_3$.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a C$_{1-7}$ alkyl group (also referred to as a C$_{1-7}$alkylthio group), a C$_{3-20}$ heterocyclyl group, or a C$_{5-20}$ aryl group, preferably a C$_{1-7}$ alkyl group. Examples of C$_{1-7}$ alkylthio groups include, but are not limited to, —SCH$_3$ and —SCH$_2$CH$_3$.

Disulfide: —SS—R, wherein R is a disulfide substituent, for example, a C$_{1-7}$ alkyl group, a C$_{3-20}$ heterocyclyl group, or a C$_{5-20}$ aryl group, preferably a C$_{1-7}$ alkyl group (also referred to herein as C$_{1-7}$ alkyl disulfide). Examples of C$_{1-7}$ alkyl disulfide groups include, but are not limited to, —SSCH$_3$ and —SSCH$_2$CH$_3$.

Sulfine (sulfinyl, sulfoxide): —S(=O)R, wherein R is a sulfine substituent, for example, a C$_{1-7}$ alkyl group, a C$_{3-20}$ heterocyclyl group, or a C$_{5-20}$ aryl group, preferably a C$_{1-7}$ alkyl group. Examples of sulfine groups include, but are not limited to, —S(=O)CH$_3$ and —S(=O)CH$_2$CH$_3$.

Sulfone (sulfonyl): —S(=O)$_2$R, wherein R is a sulfone substituent, for example, a C$_{1-7}$ alkyl group, a C$_{3-20}$ heterocyclyl group, or a C$_{5-20}$ aryl group, preferably a C$_{1-7}$ alkyl group, including, for example, a fluorinated or perfluorinated C$_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$C$_4$F$_9$ (nonaflyl), —S(=O)$_2$CH$_2$CF$_3$ (tresyl), —S(=O)$_2$CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO$_2$H.

Sulfonic acid (sulfo): —S(=O)$_2$OH, —SO$_3$H.

Sulfinate (sulfinic acid ester): —S(=O)OR; wherein R is a sulfinate substituent, for example, a C$_{1-7}$ alkyl group, a C$_{3-20}$ heterocyclyl group, or a C$_{5-20}$ aryl group, preferably a C$_{1-7}$ alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(=O)$_2$OR, wherein R is a sulfonate substituent, for example, a C$_{1-7}$ alkyl group, a C$_{3-20}$ heterocyclyl group, or a C$_{5-20}$ aryl group, preferably a C$_{1-7}$ alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a C$_{1-7}$ alkyl group, a C$_{3-20}$ heterocyclyl group, or a C$_{5-20}$ aryl group, preferably a C$_{1-7}$ alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a C$_{1-7}$ alkyl group, a C$_{3-20}$ heterocyclyl group, or a C$_{5-20}$ aryl group, preferably a C$_{1-7}$ alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a C$_{1-7}$ alkyl group, a C$_{3-20}$ heterocyclyl group, or a C$_{5-20}$ aryl group, preferably a C$_{1-7}$ alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)h, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to. —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfonamino groups include, but are not limited to, —NHS(=O)$_2$CH$_3$ and —N(CH$_3$)S(=O)$_2$ C$_6$H$_5$.

Sulfinamino: —NR$^1$S(=O)R, wherein R$^1$ is an amino substituent, as defined for amino groups, and R is a sulfinamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfinamino groups include, but are not limited to, —NHS(=O)CH$_3$ and —N(CH$_3$)S(=O) C$_6$H$_5$.

Phosphino (phosphine): —PR$_2$, wherein R is a phosphino substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substituent, for example, a C$_{1-7}$ alkyl group, a C$_{3-20}$ heterocyclyl group, or a C$_{5-20}$ aryl group, preferably a C$_{1-7}$ alkyl group or a C$_{5-20}$ aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphate groups include, but are not limited to, —OP(=O)(OCH$_3$)$_2$, —OP(=O)(OCH$_2$CH$_3$)$_2$, —OP(=OXO-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR$^1$)—NR$^2$$_2$, where R$^1$ and R$^2$ are phosphoramidite substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^2$$_2$, where R$^1$ and R$^2$ are phosphoramidate substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

Alkylene

C$_{3-12}$ alkylene: The term "C$_{3-12}$ alkylene", as used herein, pertains to a bidentate moiety obtained by removing two hydrogen atoms, either both from the same carbon atom, or one from each of two different carbon atoms, of a hydrocarbon compound having from 3 to 12 carbon atoms (unless otherwise specified), which may be aliphatic or alicyclic, and which may be saturated, partially unsaturated, or fully unsaturated. Thus, the term "alkylene" includes the subclasses alkenylene, alkynylene, cycloalkylene, etc., discussed below.

Examples of linear saturated C$_{3-12}$ alkylene groups include, but are not limited to, —(CH$_2$)$_n$—where n is an integer from 3 to 12, for example, —CH$_2$CH$_2$CH$_2$— (propylene), —CH$_2$CH$_2$CH$_2$CH$_2$— (butylene), —CH$_2$CH$_2$CH$_2$CH$_2$CH$_2$— (pentylene) and —CH$_2$CH$_2$CH$_2$CH$_2$CH$_2$CH$_2$CH$_2$— (heptylene).

Examples of branched saturated C$_{3-12}$ alkylene groups include, but are not limited to, —CH(CH$_3$)CH—, —CH(CH$_3$)CH$_2$CH—, —CH(CH$_3$)CH$_2$CH$_2$CH$_2$—, —CH$_2$CH(CH$_3$)CH$_2$—, —CH$_2$CH(CH$_3$)CH$_2$CH$_2$—, —CH(CH$_2$CH$_3$)—, —CH(CH$_2$CH$_3$)CH$_2$—, and —CH$_2$CH(CH$_2$CH$_3$)CH$_2$.

Examples of linear partially unsaturated C$_{3-12}$ alkylene groups (C$_{3-12}$ alkenylene, and alkynylene groups) include, but are not limited to, —CH=CH—CH$_2$—, —CH$_2$—CH=CH$_2$—, —CH=CH—CH$_2$—CH$_2$—, —CH=CH—CH$_2$—CH$_2$—CH$_2$—, —CH=CH—CH=CH—, —CH=CH—CH=CH—CH$_2$—, —CH=CH—CH$_2$—CH=CH—, —CH=CH—CH$_2$—CH$_2$—, —CH=CH—CH$_2$—CH=CH—, and —CH$_2$—C≡C—CH$_2$—.

Examples of branched partially unsaturated C$_{3-12}$ alkylene groups (C$_{3-12}$ alkenylene and alkynylene groups) include, but are not limited to, —C(CH$_3$)=CH—, —C(CH$_3$)=CH—CH$_2$—, —CH=CH—CH(CH$_3$)— and —C≡C—CH(CH$_3$)—.

Examples of alicyclic saturated C$_{3-12}$ alkylene groups (C$_{3-12}$ cycloalkylenes) include, but are not limited to, cyclopentylene (e.g. cyclopent-1,3-ylene), and cyclohexylene (e.g. cyclohex-1,4-ylene).

Examples of alicyclic partially unsaturated C$_{3-12}$ alkylene groups (C$_{3-12}$ cycloalkylenes) include, but are not limited to, cyclopentenylene (e.g. 4-cyclopenten-1,3-ylene), cyclohexenylene (e.g. 2-cyclohexen-1,4-ylene; 3-cyclohexen-1,2-ylene; 2,5-cyclohexadien-1,4-ylene).

Oxygen protecting group: the term "oxygen protecting group" refers to a moiety which masks a hydroxy group, and these are well known in the art. A large number of suitable groups are described on pages 23 to 200 of Greene, T. W. and Wuts, G. M., Protective Groups in Organic Synthesis, 3$^{rd}$ Edition, John Wiley & Sons. Inc., 1999, which is incorporated herein by reference. Classes of particular interest include silyl ethers (e.g. TMS, TBDMS), substituted methyl ethers (e.g. THP) and esters (e.g. acetate).

Carbamate nitrogen protecting group: the term "carbamate nitrogen protecting group" pertains to a moiety which masks the nitrogen in the imine bond, and these are well known in the art. These groups have the following structure:

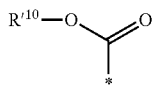

wherein R'$^{10}$ is R as defined above. A large number of suitable groups are described on pages 503 to 549 of Greene, T. W. and Wuts, G. M., Protective Groups in Organic Synthesis, 3$^{rd}$ Edition, John Wiley & Sons, Inc., 1999, which is incorporated herein by reference.

Hemi-aminal nitrogen protecting group: the term "hemi-aminal nitrogen protecting group" pertains to a group having the following structure:

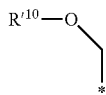

wherein R'$^{10}$ is R as defined above. A large number of suitable groups are described on pages 633 to 647 as amide protecting groups of Greene, T. W. and Wuts, G. M., Protective Groups in Organic Synthesis, 3$^{rd}$ Edition, John Wiley & Sons, Inc., 1999, which is incorporated herein by reference.

DETAILED DESCRIPTION OF THE INVENTION

The present invention provides Conjugates comprising a PBD dimer connected to a Ligand unit via a Linker Unit. In one embodiment, the Linker unit includes a Stretcher unit (A), a Specificity unit (L$^1$), and a Spacer unit (L$^2$). The Linker unit is connected at one end to the Ligand unit and at the other end to the PBD dimer compound.

In one aspect, such a Conjugate is shown below in formula Ia:

(Ia)

wherein:
L is the Ligand unit; and
-A$^1_a$-L$^1_s$-L$^2_y$- is a Linker unit (LU), wherein:
-A$^1$- is a Stretcher unit,
a is 1 or 2.
L$^1$- is a Specificity unit,
s is an integer ranging from 1 to 12,
-L$^2$- is a Spacer unit,
y is 0, 1 or 2;
-D is an PBD dimer; and
p is from 1 to 20.

The drug loading is represented by p, the number of drug molecules per Ligand unit (e.g., an antibody). Drug loading may range from 1 to 20 Drug units (D) per Ligand unit (e.g., Ab or mAb). For compositions, p represents the average drug loading of the Conjugates in the composition, and p ranges from 1 to 20.

In some embodiments, p is from about 1 to about 8 Drug units per Ligand unit. In some embodiments, p is 1. In some embodiments, p is 2. In some embodiments, p is from about 2 to about 8 Drug units per Ligand unit. In some embodiments, p is from about 2 to about 6, 2 to about 5, or 2 to about 4 Drug units per Ligand unit. In some embodiments, p is about 2, about 4, about 6 or about 8 Drug units per Ligand unit.

The average number of Drugs units per Ligand unit in a preparation from a conjugation reaction may be characterized by conventional means such as mass spectroscopy, ELISA assay, and HPLC. The quantitative distribution of Conjugates in terms of p may also be determined. In some instances, separation, purification, and characterization of homogeneous Conjugates, where p is a certain value, from Conjugates with other drug loadings may be achieved by means such as reverse phase HPLC or electrophoresis.

In another aspect, such a Conjugate is shown below in formula Ib:

(Ib)

Also illustrated as:

(Ib)

wherein:
L is the Ligand unit; and
-A$^1_a$-L$^1_s$(L$^2_y$)- is a Linker unit (LU), wherein:
-A$^1$- is a Stretcher unit linked to a Stretcher unit (L$^2$),
a is 1 or 2,
L$^1$- is a Specificity unit linked to a Stretcher unit (L$^2$),
s is an integer ranging from 0 to 12,
-L$^2$- is a Spacer unit,
y is 0, 1 or 2;
-D is a PBD dimer; and
p is from 1 to 20.

Preferences

The following preferences may apply to all aspects of the invention as described above, or may relate to a single aspect. The preferences may be combined together in any combination.

In one embodiment, the Conjugate has the formula:

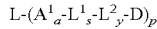

wherein L, $A^1$, a, $L^1$, s, $L^2$, D and p are as described above.

In one embodiment, the Ligand unit (L) is a Cell Binding Agent (CBA) that specifically binds to a target molecule on the surface of a target cell. An exemplary formula is illustrated below:

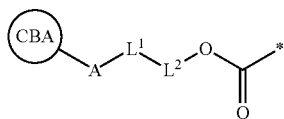

where the asterisk indicates the point of attachment to the Drug unit (D), CBA is the Cell Binding Agent, $L^1$ is a Specificity unit, $A^1$ is a Stretcher unit connecting $L^1$ to the Cell Binding Agent, $L^2$ is a Spacer unit, which is a covalent bond, a self-immolative group or together with —OC(=O)— forms a self-immolative group, and $L^2$ optional.

In another embodiment, the Ligand unit (L) is a Cell Binding Agent (CBA) that specifically binds to a target molecule on the surface of a target cell. An exemplary formula is illustrated below:

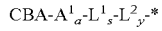

where the asterisk indicates the point of attachment to the Drug unit (D), CBA is the Cell Binding Agent, $L^1$ is a Specificity unit, $A^1$ is a Stretcher unit connecting $L^1$ to the Cell Binding Agent, $L^2$ is a Spacer unit which is a covalent bond or a self-immolative group, and a is 1 or 2, s is 0, 1 or 2, and y is 0 or 1 or 2.

In the embodiments illustrated above, $L^1$ can be a cleavable Specificity unit, and may be referred to as a "trigger" that when cleaved activates a self-immolative group (or self-immolative groups) $L^2$, when a self-immolative group(s) is present. When the Specificity unit $L^1$ is cleaved, or the linkage (i.e., the covalent bond) between $L^1$ and $L^2$ is cleaved, the self-immolative group releases the Drug unit (D).

In another embodiment, the Ligand unit (L) is a Cell Binding Agent (CBA) that specifically binds to a target molecule on the surface of a target cell. An exemplary formula is illustrated below:

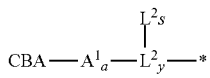

where the asterisk indicates the point of attachment to the Drug (D), CBA is the Cell Binding Agent, $L^1$ is a Specificity unit connected to $L^2$, $A^1$ is a Stretcher unit connecting $L^2$ to the Cell Binding Agent, $L^2$ is a self-immolative group, and a is 1 or 2, s is 1 or 2, and y is 1 or 2.

In the various embodiments discussed herein, the nature of $L^1$ and $L^2$ can vary widely. These groups are chosen on the basis of their characteristics, which may be dictated in part, by the conditions at the site to which the conjugate is delivered. Where the Specificity unit $L^1$ is cleavable, the structure and/or sequence of $L^1$ is selected such that it is cleaved by the action of enzymes present at the target site (e.g., the target cell). $L^1$ units that are cleavable by changes in pH (e.g. acid or base labile), temperature or upon irradiation (e.g. photolabile) may also be used. $L^1$ units that are cleavable under reducing or oxidising conditions may also find use in the Conjugates.

In some embodiments, $L^1$ may comprise one amino acid or a contiguous sequence of amino acids. The amino acid sequence may be the target substrate for an enzyme.

In one embodiment, $L^1$ is cleavable by the action of an enzyme. In one embodiment, the enzyme is an esterase or a peptidase. For example, $L^1$ may be cleaved by a lysosomal protease, such as a cathepsin.

In one embodiment, $L^2$ is present and together with —C(=O)O— forms a self-immolative group or self-immolative groups. In some embodiments, —C(=O)O— also is a self-immolative group.

In one embodiment, where $L^1$ is cleavable by the action of an enzyme and $L^2$ is present, the enzyme cleaves the bond between $L^1$ and $L^2$, whereby the self-immolative group(s) release the Drug unit.

$L^1$ and $L^2$, where present, may be connected by a bond selected from:
—C(=O)NH—,
—C(=O)O—,
—NHC(=O)—,
—OC(=O)O—,
—NHC(=O)O—,
—OC(=O)NH—,
—NHC(=O)NH, and
—O— (a glycosidic bond).

An amino group of $L^1$ that connects to $L^2$ may be the N-terminus of an amino acid or may be derived from an amino group of an amino acid side chain, for example a lysine amino acid side chain.

A carboxyl group of $L^1$ that connects to $L^2$ may be the C-terminus of an amino acid or may be derived from a carboxyl group of an amino acid side chain, for example a glutamic acid amino acid side chain.

A hydroxy group of $L^1$ that connects to $L^2$ may be derived from a hydroxy group of an amino acid side chain, for example a serine amino acid side chain.

In one embodiment, —C(=O)O— and $L^2$ together form the group:

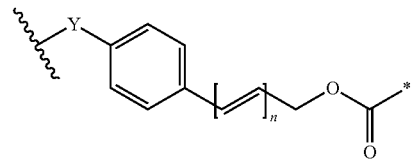

where the asterisk indicates the point of attachment to the Drug unit, the wavy line indicates the point of attachment to the $L^1$, Y is —N(H)—, —O—, —C(=O)N(H)— or —C(=O)O—, and n is 0 to 3. The phenylene ring is optionally substituted with one, two or three substituents as described herein.

In one embodiment, Y is NH.

In one embodiment, n is 0 or 1. Preferably, n is 0.

Where Y is NH and n is 0, the self-immolative group may be referred to as a p-aminobenzylcarbonyl linker (PABC).

The self-immolative group will allow for release of the Drug unit (i.e., the asymmetric PBD) when a remote site in the linker is activated, proceeding along the lines shown below (for n=0):

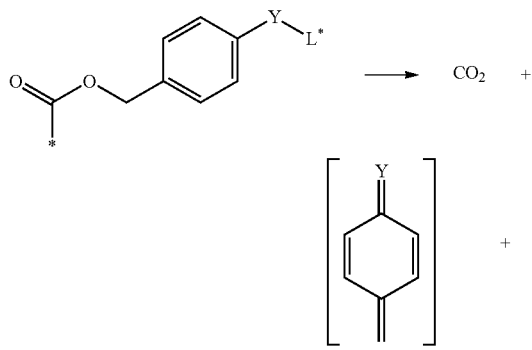

where the asterisk indicates the attachment to the Drug, L* is the activated form of the remaining portion of the linker and the released Drug unit is not shown. These groups have the advantage of separating the site of activation from the Drug.

In another embodiment, —C(=O)O— and $L^2$ together form a group selected from:

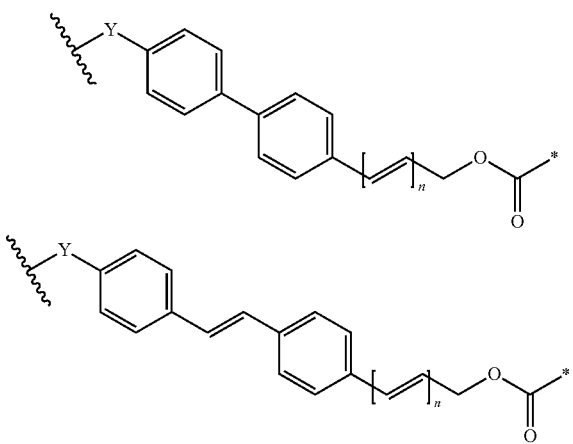

where the asterisk, the wavy line, Y, and n are as defined above. Each phenylene ring is optionally substituted with one, two or three substituents as described herein. In one embodiment, the phenylene ring having the Y substituent is optionally substituted and the phenylene ring not having the Y substituent is unsubstituted.

In another embodiment, —C(=O)O— and $L^2$ together form a group selected from:

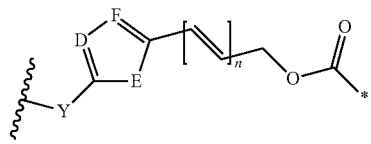

where the asterisk, the wavy line, Y, and n are as defined above, E is O, S or NR, D is N, CH, or CR, and F is N, CH, or CR.

In one embodiment, D is N.
In one embodiment, D is CH.
In one embodiment, E is O or S.
In one embodiment, F is CH.

In a preferred embodiment, the covalent bond between $L^1$ and $L^2$ is a cathepsin labile (e.g., cleavable) bond.

In one embodiment, $L^1$ comprises a dipeptide. The amino acids in the dipeptide may be any combination of natural amino acids and non-natural amino acids. In some embodiments, the dipeptide comprises natural amino acids. Where the linker is a cathepsin labile linker, the dipeptide is the site of action for cathepsin-mediated cleavage. The dipeptide then is a recognition site for cathepsin.

In one embodiment, the group —$X_1$—$X_2$ in dipeptide, —NH—$X_1$—$X_2$—CO—, is selected from:
-Phe-Lys-,
-Val-Ala-,
-Val-Lys-,
-Ala-Lys-,
-Val-Cit-,
-Phe-Cit-,
-Leu-Cit-,
-Ile-Cit-,
-Phe-Arg-, and
-Trp-Cit-;
where Cit is citrulline. In such a dipeptide, —NH— is the amino group of $X_1$, and CO is the carbonyl group of $X_2$.

Preferably, the group —$X_1$—$X_2$— in dipeptide, —NH—$X_1$—$X_2$—CO—, is selected from:
-Phe-Lys-,
-Val-Ala-,
-Val-Lys-,
-Ala-Lys-, and
-Val-Cit-.

Most preferably, the group —$X_1$—$X_2$— in dipeptide, —NH—$X_1$—$X_2$—CO—, is -Phe-Lys-, Val-Cit or -Val-Ala-.

Other dipeptide combinations of interest include:
-Gly-Gly-,
-Pro-Pro-, and
-Val-Glu-.

Other dipeptide combinations may be used, including those described by Dubowchik et al., which is incorporated herein by reference.

In one embodiment, the amino acid side chain is chemically protected, where appropriate. The side chain protecting group may be a group as discussed below. Protected amino acid sequences are cleavable by enzymes. For example, a dipeptide sequence comprising a Boc side chain-protected Lys residue is cleavable by cathepsin.

Protecting groups for the side chains of amino acids are well known in the art and are described in the Novabiochem Catalog. Additional protecting group strategies are set out in Protective groups in Organic Synthesis, Greene and Wuts.

Possible side chain protecting groups are shown below for those amino acids having reactive side chain functionality:
Arg: Z, Mtr, Tos;
Asn: Trt, Xan;
Asp: Bzl, t-Bu;
Cys: Acm, Bzl, Bzl-OMe, Bzl-Me, Trt;
Glu: Bzl, t-Bu;
Gln: Trt, Xan;
His: Boc, Dnp, Tos, Trt;
Lys: Boc, Z—Cl, Fmoc, Z;
Ser: Bzl, TBDMS, TBDPS;
Thr: Bz;
Trp: Boc;
Tyr: Bzl, Z, Z—Br.

In one embodiment, —X$_2$— is connected indirectly to the Drug unit. In such an embodiment, the Spacer unit L$^2$ is present.

In one embodiment, the dipeptide is used in combination with a self-immolative group(s) (the Spacer unit). The self-immolative group(s) may be connected to —X$_2$—.

Where a self-immolative group is present, —X$_2$— is connected directly to the self-immolative group. In one embodiment, —X$_2$— is connected to the group Y of the self-immolative group. Preferably the group —X$_2$—CO— is connected to Y, where Y is NH.

—X$_1$— is connected directly to A$^1$. In one embodiment, —X$_1$— is connected directly to A$^1$. Preferably the group NH—X$_1$— (the amino terminus of X$_1$) is connected to A$^1$. A$^1$ may comprise the functionality —CO— thereby to form an amide link with —X$_1$—.

In one embodiment, L$^1$ and L$^2$ together with —OC(=O)— comprise the group —X$_1$—X$_2$— PABC-. The PABC group is connected directly to the Drug unit. In one example, the self-immolative group and the dipeptide together form the group -Phe-Lys-PABC-, which is illustrated below:

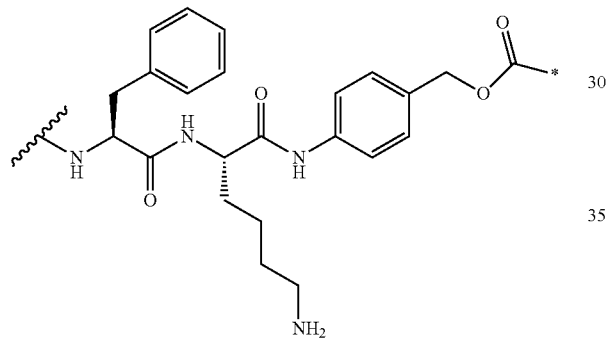

where the asterisk indicates the point of attachment to the Drug unit, and the wavy line indicates the point of attachment to the remaining portion of L$^1$ or the point of attachment to A$^1$. Preferably, the wavy line indicates the point of attachment to A$^1$.

Alternatively, the self-immolative group and the dipeptide together form the group -Val-Ala-PABC-, which is illustrated below:

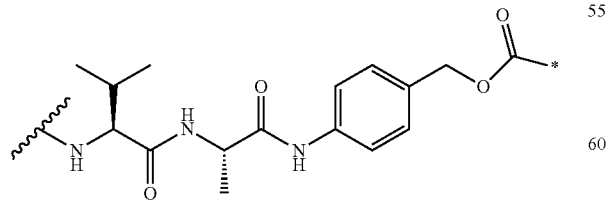

where the asterisk and the wavy line are as defined above.

In another embodiment, L$^1$ and L$^2$ together with —OC(=O)— represent:

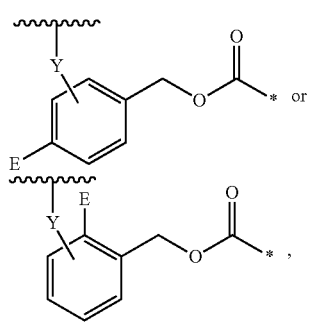

where the asterisk indicates the point of attachment to the Drug unit, the wavy line indicates the point of attachment to A$^1$, Y is a covalent bond or a functional group, and E is a group that is susceptible to cleavage thereby to activate a self-immolative group.

E is selected such that the group is susceptible to cleavage, e.g., by light or by the action of an enzyme. E may be —NO$_2$ or glucuronic acid (e.g., β-glucuronic acid). The former may be susceptible to the action of a nitroreductase, the latter to the action of a 3-glucuronidase.

The group Y may be a covalent bond.

The group Y may be a functional group selected from:
—C(=O)—
—NH—
—O—
—C(=O)NH—,
—C(=O)O—,
—NHC(=O)—,
—OC(=O),
—OC(=O)O—,
—NHC(=O)O—,
—OC(=O)NH—,
—NHC(=O)NH—,
—NHC(=O)NH.
—C(=O)NHC(=O)—,
SO$_2$, and
—S—.

The group Y is preferably —NH—, —CH$_2$—, —O—, and —S—.

In some embodiments, L$^1$ and L$^2$ together with —OC(=O)— represent:

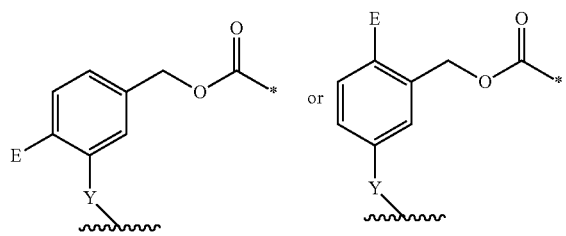

where the asterisk indicates the point of attachment to the Drug unit, the wavy line indicates the point of attachment to A, Y is a covalent bond or a functional group and E is glucuronic acid (e.g., β-glucuronic acid). Y is preferably a functional group selected from —NH—.

In some embodiments, L¹ and L² together represent:

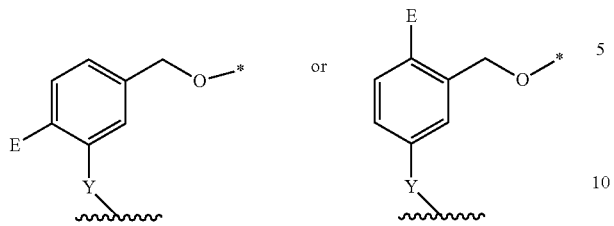

where the asterisk indicates the point of attachment to the remainder of L² or the Drug unit, the wavy line indicates the point of attachment to A¹, Y is a covalent bond or a functional group and E is glucuronic acid (e.g., β-glucuronic acid). Y is preferably a functional group selected from —NH—, —CH$_2$—, —O—, and —S—.

In some further embodiments, Y is a functional group as set forth above, the functional group is linked to an amino acid, and the amino acid is linked to the Stretcher unit A¹. In some embodiments, amino acid is β-alanine. In such an embodiment, the amino acid is equivalently considered part of the Stretcher unit.

The Specificity unit L¹ and the Ligand unit are indirectly connected via the Stretcher unit.

L¹ and A¹ may be connected by a bond selected from:
—C(=O)NH—,
—C(=O)O—,
—NHC(=O)—,
—OC(=O)O—,
—NHC(=O)O—,
—OC(=O)NH—, and
—NHC(=O)NH—.

In one embodiment, the group A¹ is:

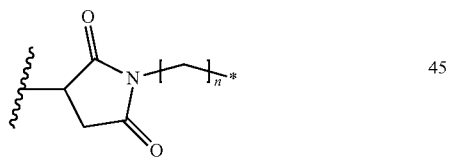

where the asterisk indicates the point of attachment to L¹, the wavy line indicates the point of attachment to the Ligand unit, and n is 0 to 6. In one embodiment, n is 5.

In one embodiment, the group A¹ is:

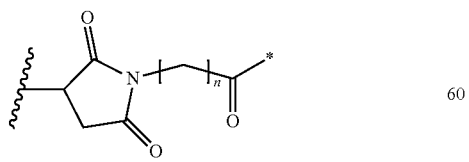

where the asterisk indicates the point of attachment to L¹, the wavy line indicates the point of attachment to the Ligand unit, and n is 0 to 6. In one embodiment, n is 5.

In one embodiment, the group A¹ is:

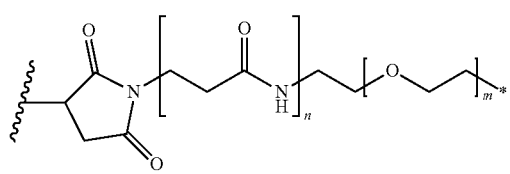

where the asterisk indicates the point of attachment to L¹, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the group A¹ is:

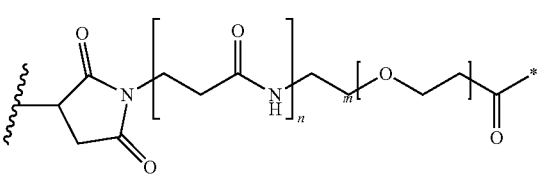

where the asterisk indicates the point of attachment to L¹, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the group A¹ is:

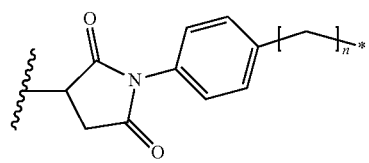

where the asterisk indicates the point of attachment to L¹, the wavy line indicates the point of attachment to the Ligand unit, and n is 0 to 6. In one embodiment, n is 5.

In one embodiment, the group A¹ is:

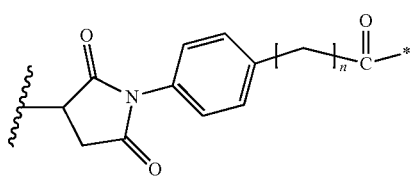

where the asterisk indicates the point of attachment to L¹, the wavy line indicates the point of attachment to the Ligand unit, and n is 0 to 6. In one embodiment, n is 5.

In one embodiment, the group $A^1$ is:

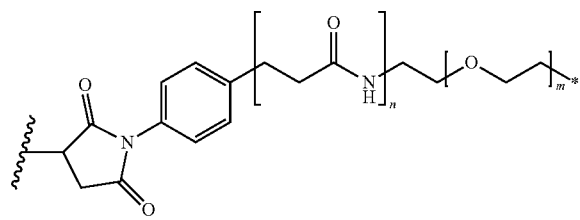

where the asterisk indicates the point of attachment to $L^1$, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the group $A^1$ is:

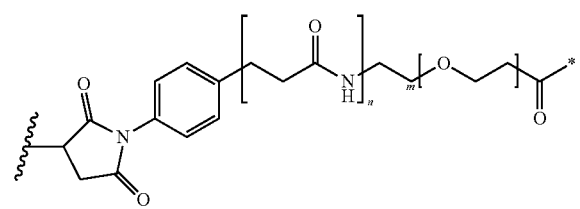

where the asterisk indicates the point of attachment to $L^1$, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the connection between the Ligand unit and $A^1$ is through a thiol residue of the Ligand unit and a maleimide group of $A^1$.

In one embodiment, the connection between the Ligand unit and $A^1$ is:

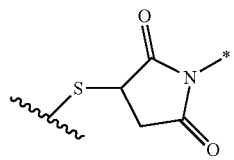

where the asterisk indicates the point of attachment to the remaining portion of $A^1$, $L^1$, $L^2$ or D, and the wavy line indicates the point of attachment to the remaining portion of the Ligand unit. In this embodiment, the S atom is typically derived from the Ligand unit.

In each of the embodiments above, an alternative functionality may be used in place of the malemide-derived group shown below:

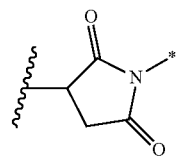

where the wavy line indicates the point of attachment to the Ligand unit as before, and the asterisk indicates the bond to the remaining portion of the $A^1$ group, or to $L^1$, $L^2$ or D.

In one embodiment, the maleimide-derived group is replaced with the group:

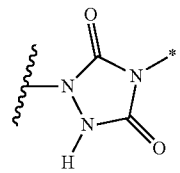

where the wavy line indicates point of attachment to the Ligand unit, and the asterisk indicates the bond to the remaining portion of the $A^1$ group, or to $L^1$, $L^2$ or D.

In one embodiment, the maleimide-derived group is replaced with a group, which optionally together with a Ligand unit (e.g., a Cell Binding Agent), is selected from:
—C(=O)NH—,
—C(=O)O—,
—NHC(=O)—,
—OC(=O)—,
—OC(=O)O—,
—NHC(=O)O—,
—OC(=O)NH—,
—NHC(=O)NH—,
—NHC(=O)NH,
—C(=O)NHC(=O)—,
—S—,
—S—S—,
—CH$_2$C(=O)—
—C(=O)CH$_2$—,
=N—NH—, and
—NH—N=.

In one embodiment, the maleimide-derived group is replaced with a group, which optionally together with the Ligand unit, is selected from:

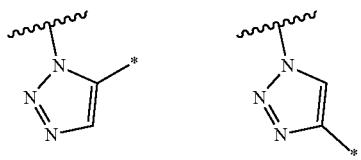

where the wavy line indicates either the point of attachment to the Ligand unit or the bond to the remaining portion of the $A^1$ group, and the asterisk indicates the other of the point of attachment to the Ligand unit or the bond to the remaining portion of the $A^1$ group.

Other groups suitable for connecting $L^1$ to the Cell Binding Agent are described in WO 2005/082023.

In one embodiment, the Stretcher unit $A^1$ is present, the Specificity unit $L^1$ is present and Spacer unit $L^2$ is absent. Thus, $L^1$ and the Drug unit are directly connected via a bond. Equivalently in this embodiment, $L^2$ is a bond.

$L^1$ and D may be connected by a bond selected from:
—C(=O)NH—,
—C(=O)O—,
—NHC(=O)—,
—OC(=O), —OC(=O)O—,
—NHC(=O)O—,
—OC(=O)NH—, and
—NHC(=O)NH—.

In one embodiment, $L^1$ and D are preferably connected by a bond selected from:
—C(=O)NH—, and
—NHC(=O)—.

In one embodiment, $L^1$ comprises a dipeptide and one end of the dipeptide is linked to D. As described above, the amino acids in the dipeptide may be any combination of natural amino acids and non-natural amino acids. In some embodiments, the dipeptide comprises natural amino acids. Where the linker is a cathepsin labile linker, the dipeptide is the site of action for cathepsin-mediated cleavage. The dipeptide then is a recognition site for cathepsin.

In one embodiment, the group —$X_1$—$X_2$— in dipeptide, —NH—$X_1$—$X_2$—CO—, is selected from:
-Phe-Lys-,
-Val-Ala-,
-Val-Lys-,
-Ala-Lys-,
-Val-Cit-,
-Phe-Cit-,
-Leu-Cit-,
-Ile-Cit-,
-Phe-Arg-, and
-Trp-Cit-;

where Cit is citrulline. In such a dipeptide, —NH— is the amino group of $X_1$, and CO is the carbonyl group of $X_2$.

Preferably, the group —$X_1$—$X_2$— in dipeptide, —NH—$X_1$—$X_2$—CO—, is selected from:
-Phe-Lys-,
-Val-Ala-,
-Val-Lys-,
-Ala-Lys-, and
-Val-Cit-.

Most preferably, the group —$X_1$—$X_2$ in dipeptide, —NH—$X_1$—$X_2$CO—, is -Phe-Lys- or -Val-Ala-.

Other dipeptide combinations of interest include:
-Gly-Gly-,
-Pro-Pro-, and
-Val-Glu-.

Other dipeptide combinations may be used, including those described above.

In one embodiment, $L^1$-D is:

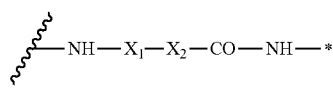

where —NH—$X_1$—$X_2$—CO is the dipeptide, —NH— is part of the Drug unit, the asterisk indicates the point of attachment to the remainder of the Drug unit, and the wavy line indicates the point of attachment to the remaining portion of $L^1$ or the point of attachment to $A^1$. Preferably, the wavy line indicates the point of attachment to $A^1$.

In one embodiment, the dipeptide is valine-alanine and $L^1$-D is:

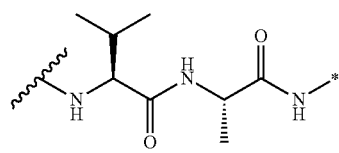

where the asterisk, —NH— and the wavy line are as defined above.

In one embodiment, the dipeptide is phenylalanine-lysine and $L^1$-D is:

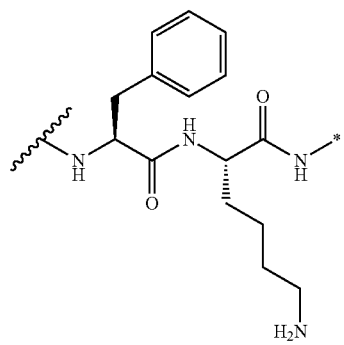

where the asterisk, —NH— and the wavy line are as defined above.

In one embodiment, the dipeptide is valine-citrulline.

In one embodiment, the groups $A^1$-$L^2$ are:

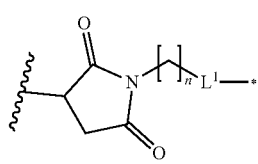

where the asterisk indicates the point of attachment to $L^2$ or D, the wavy line indicates the point of attachment to the Ligand unit, and n is 0 to 6. In one embodiment, n is 5.

In one embodiment, the groups $A^1$-$L^1$ are:

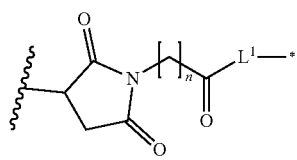

where the asterisk indicates the point of attachment to D, the wavy line indicates the point of attachment to the Ligand unit, and n is 0 to 6. In one embodiment, n is 5.

In one embodiment, the groups $A^1$-$L^1$ are:

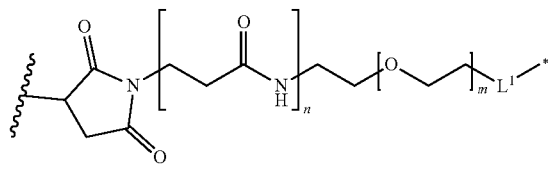

where the asterisk indicates the point of attachment to D, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups $A^1$-$L^1$ are:

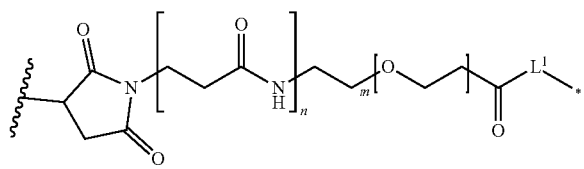

where the asterisk indicates the point of attachment to D, the wavy line indicates the point of attachment to the Ligand unit, n is 0 or 1, and m is 0 to 30. In a preferred embodiment, n is 1 and m is 0 to 10, 1 to 7, preferably 3 to 7, most preferably 3 or 7.

In one embodiment, the groups $A^1$-$L^1$ are:

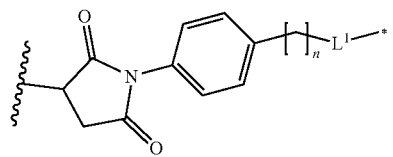

where the asterisk indicates the point of attachment to $L^2$ or D, the wavy line indicates the point of attachment to the Ligand unit, and n is 0 to 6. In one embodiment, n is 5.

In one embodiment, the groups $A^1$-$L^1$ are:

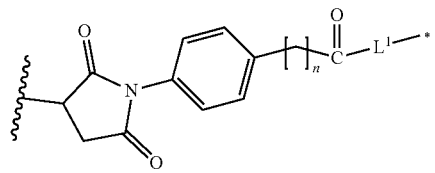

where the asterisk indicates the point of attachment to $L^2$ or D, the wavy line indicates the point of attachment to the Ligand unit, and n is 0 to 6. In one embodiment, n is 5.

In one embodiment, the groups $A^1$-$L^1$ are:

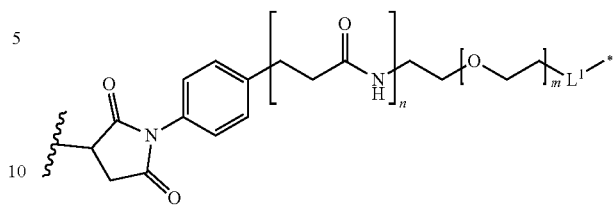

where the asterisk indicates the point of attachment to $L^2$ or D, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups $A^1$-$L^1$ is:

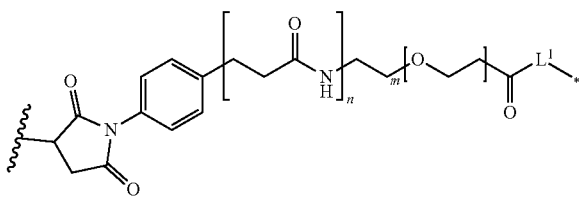

where the asterisk indicates the point of attachment to $L^2$ or D, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups L-$A^1$-$L^1$ are:

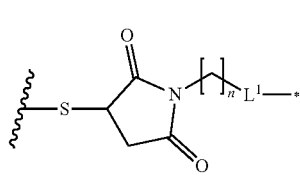

where the asterisk indicates the point of attachment to D, S is a sulphur group of the Ligand unit, the wavy line indicates the point of attachment to the rest of the Ligand unit, and n is 0 to 6. In one embodiment, n is 5.

In one embodiment, the group L-$A^1$-$L^1$ are:

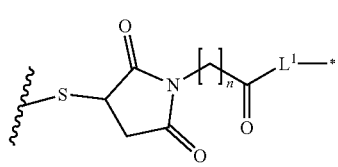

where the asterisk indicates the point of attachment to D, S is a sulphur group of the Ligand unit, the wavy line indicates the point of attachment to the remainder of the Ligand unit, and n is 0 to 6. In one embodiment, n is 5.

In one embodiment, the groups L-A$^1$-L$^1$ are:

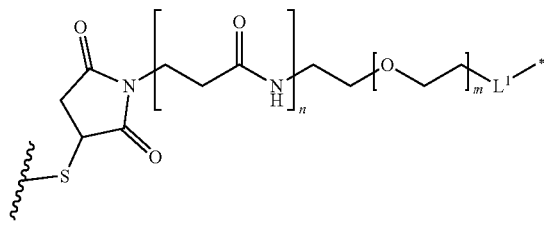

where the asterisk indicates the point of attachment to D, S is a sulphur group of the Ligand unit, the wavy line indicates the point of attachment to the remainder of the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups L-A$^1$-L$^1$ are:

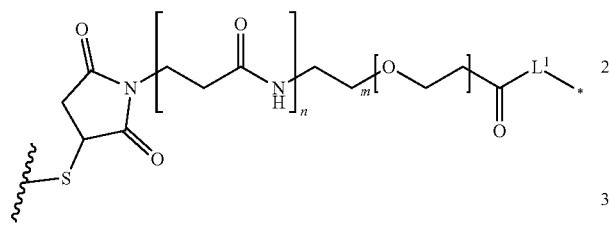

where the asterisk indicates the point of attachment to D, the wavy line indicates the point of attachment to the Ligand unit, n is 0 or 1, and m is 0 to 30. In a preferred embodiment, n is 1 and m is 0 to 10, 1 to 7, preferably 4 to 8, most preferably 4 or 8. In one embodiment, the groups L-A$^1$-L$^1$ are:

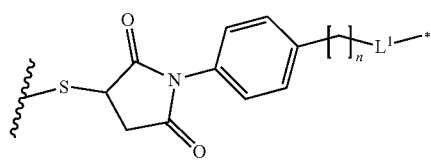

where the asterisk indicates the point of attachment to L$^2$ or D, the wavy line indicates the point of attachment to the remainder of the Ligand unit, and n is 0 to 6. In one embodiment, n is 5.

In one embodiment, the groups L-A$^1$-L$^1$ are:

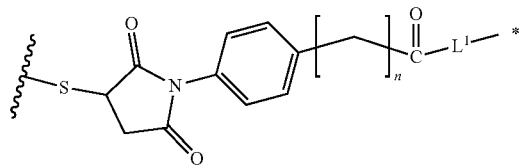

where the asterisk indicates the point of attachment to L$^2$ or D, the wavy line indicates the point of attachment to the remainder of the Ligand unit, and n is 0 to 6. In one embodiment, n is 5.

In one embodiment, the groups L-A$^1$-L$^1$ are:

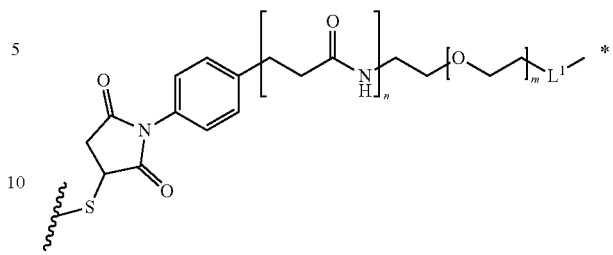

where the asterisk indicates the point of attachment to L$^2$ or D, the wavy line indicates the point of attachment to the remainder of the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups L-A$^1$-L$^1$ are:

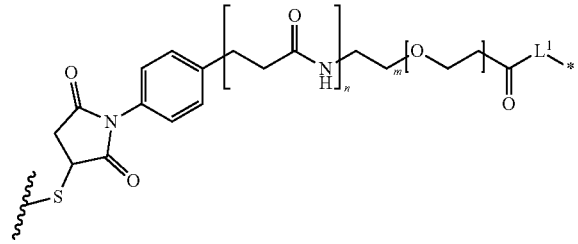

where the asterisk indicates the point of attachment to L$^2$ or D, the wavy line indicates the point of attachment to the remainder of the Ligand unit, n is 0 or 1, and m is 0 to 30. In a preferred embodiment, n is 1 and m is 0 to 10, 1 to 8, preferably 4 to 8, most preferably 4 or 8.

In one embodiment, the Stretcher unit is an acetamide unit, having the formula:

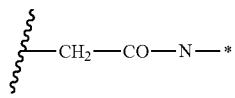

where the asterisk indicates the point of attachment to the remainder of the Stretcher unit, L$^1$ or D, and the wavy line indicates the point of attachment to the Ligand unit.

In other embodiments, Linker-Drug compounds are provided for conjugation to a Ligand unit. In one embodiment, the Linker-Drug compounds are designed for connection to a Cell Binding Agent.

In one embodiment, the Drug Linker compound has the formula:

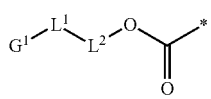

where the asterisk indicates the point of attachment to the Drug unit, G$^1$ is a Stretcher group (A') to form a connection to a Ligand unit, L$^1$ is a Specificity unit, L$^2$ (a Spacer unit) is a covalent bond or together with —OC(=O)— forms a self-immolative group(s).

In another embodiment, the Drug Linker compound has the formula:

where the asterisk indicates the point of attachment to the Drug unit. $G^1$ is a Stretcher unit ($A^1$) to form a connection to a Ligand unit, $L^1$ is a Specificity unit, $L^2$ (a Spacer unit) is a covalent bond or a self-immolative group(s).

$L^1$ and $L^2$ are as defined above. References to connection to $A^1$ can be construed here as referring to a connection to $G^1$.

In one embodiment, where $L^1$ comprises an amino acid, the side chain of that amino acid may be protected. Any suitable protecting group may be used. In one embodiment, the side chain protecting groups are removable with other protecting groups in the compound, where present. In other embodiments, the protecting groups may be orthogonal to other protecting groups in the molecule, where present.

Suitable protecting groups for amino acid side chains include those groups described in the Novabiochem Catalog 2006/2007. Protecting groups for use in a cathepsin labile linker are also discussed in Dubowchik et al.

In certain embodiments of the invention, the group $L^1$ includes a Lys amino acid residue. The side chain of this amino acid may be protected with a Boc or Alloc protected group. A Boc protecting group is most preferred.

The functional group $G^1$ forms a connecting group upon reaction with a Ligand unit (e.g., a cell binding agent).

In one embodiment, the functional group $G^1$ is or comprises an amino, carboxylic acid, hydroxy, thiol, or maleimide group for reaction with an appropriate group on the Ligand unit. In a preferred embodiment, $G^1$ comprises a maleimide group.

In one embodiment, the group $G^1$ is an alkyl maleimide group. This group is suitable for reaction with thiol groups, particularly cysteine thiol groups, present in the cell binding agent, for example present in an antibody.

In one embodiment, the group $G^1$ is:

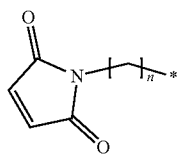

where the asterisk indicates the point of attachment to $L^1$, $L^2$ or D, and n is 0 to 6. In one embodiment, n is 5.
In one embodiment, the group $G^1$ is:

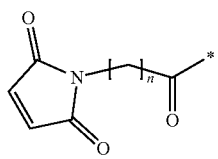

where the asterisk indicates the point of attachment to $L^1$, $L^2$ or D, and n is 0 to 6. In one embodiment, n is 5.

In one embodiment, the group $G^1$ is:

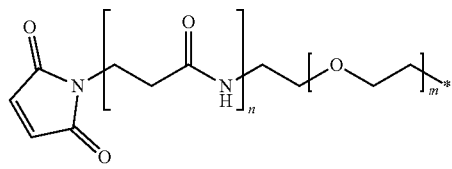

where the asterisk indicates the point of attachment to $L^1$, n is 0 or 1, and m is 0 to 30. In a preferred embodiment, n is 1 and m is 0 to 10, 1 to 2, preferably 4 to 8, and most preferably 4 or 8.

In one embodiment, the group $G^1$ is:

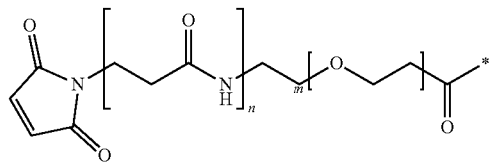

where the asterisk indicates the point of attachment to $L^1$, n is 0 or 1, and m is 0 to 30. In a preferred embodiment, n is 1 and m is 0 to 10, 1 to 8, preferably 4 to 8, and most preferably 4 or 8.

In one embodiment, the group $G^1$ is:

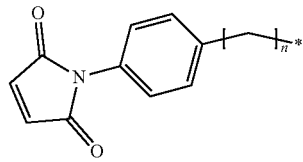

where the asterisk indicates the point of attachment to $L^1$, $L^2$ or D, and n is 0 to 6. In one embodiment, n is 5.
In one embodiment, the group $G^1$ is:

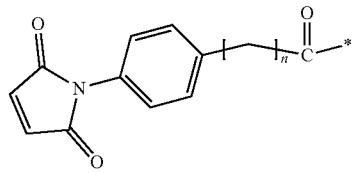

where the asterisk indicates the point of attachment to $L^1$, $L^2$ or D, and n is 0 to 6. In one embodiment, n is 5.
In one embodiment, the group $G^1$ is:

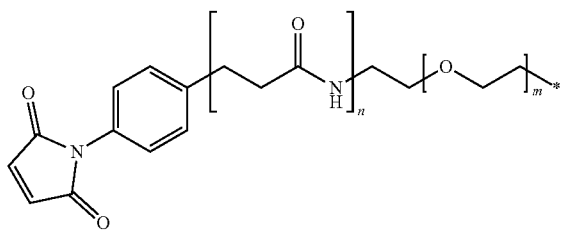

where the asterisk indicates the point of attachment to $L^1$, n is 0 or 1, and m is 0 to 30. In a preferred embodiment, n is 1 and m is 0 to 10, 1 to 2, preferably 4 to 8, and most preferably 4 or 8.

In one embodiment, the group $G^1$ is:

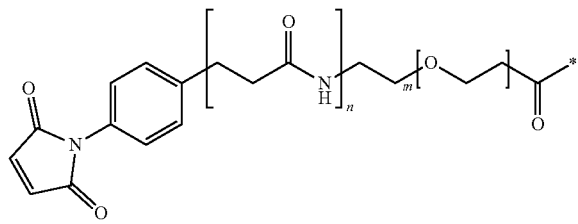

where the asterisk indicates the point of attachment to $L^1$, n is 0 or 1, and m is 0 to 30. In a preferred embodiment, n is 1 and m is 0 to 10, 1 to 8, preferably 4 to 8, and most preferably 4 or 8.

In each of the embodiments above, an alternative functionality may be used in place of the malemide group shown below:

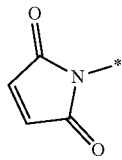

where the asterisk indicates the bond to the remaining portion of the G group.

In one embodiment, the maleimide-derived group is replaced with the group:

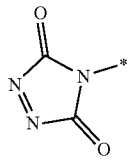

where the asterisk indicates the bond to the remaining portion of the G group.

In one embodiment, the maleimide group is replaced with a group selected from:
—C(=O)OH,
—OH,
—NH$_2$,
—SH,
—C(=O)CH$_2$X, where X is Cl, Br or I,
—CHO,
—NHNH$_2$
—C≡CH, and
—N$_3$ (azide).

In one embodiment, $L^1$ is present, and $G^1$ is —NH$_2$, —NHMe, —COOH, —OH or —SH.

In one embodiment, where $L^1$ is present, $G^1$ is —NH$_2$ or —NHMe. Either group may be the N-terminal of an $L^1$ amino acid sequence.

In one embodiment, $L^1$ is present and $G^1$ is —NH$_2$, and $L^1$ is an amino acid sequence —$X_1$—$X_2$—, as defined above.

In one embodiment, $L^1$ is present and $G^1$ is COOH. This group may be the C-terminal of an $L^1$ amino acid sequence.

In one embodiment, $L^1$ is present and $G^1$ is OH.

In one embodiment, $L^1$ is present and $G^1$ is SH.

The group $G^1$ may be convertable from one functional group to another. In one embodiment, $L^1$ is present and $G^1$ is —NH$_2$. This group is convertable to another group $G^1$ comprising a maleimide group. For example, the group —NH$_2$ may be reacted with an acids or an activated acid (e.g., N-succinimide forms) of those $G^1$ groups comprising maleimide shown above.

The group $G^1$ may therefore be converted to a functional group that is more appropriate for reaction with a Ligand unit.

As noted above, in one embodiment, $L^1$ is present and $G^1$ is —NH$_2$, —NHMe, —COOH, —OH or —SH. In a further embodiment, these groups are provided in a chemically protected form. The chemically protected form is therefore a precursor to the linker that is provided with a functional group.

In one embodiment, $G^1$ is —NH$_2$ in a chemically protected form. The group may be protected with a carbamate protecting group. The carbamate protecting group may be selected from the group consisting of:

Alloc, Fmoc, Boc, Troc, Teoc, Cbz and PNZ.

Preferably, where $G^1$ is —NH$_2$, it is protected with an Alloc or Fmoc group.

In one embodiment, where $G^1$ is —NH$_2$, it is protected with an Fmoc group.

In one embodiment, the protecting group is the same as the carbamate protecting group of the capping group.

In one embodiment, the protecting group is not the same as the carbamate protecting group of the capping group. In this embodiment, it is preferred that the protecting group is removable under conditions that do not remove the carbamate protecting group of the capping group.

The chemical protecting group may be removed to provide a functional group to form a connection to a Ligand unit. Optionally, this functional group may then be converted to another functional group as described above.

In one embodiment, the active group is an amine. This amine is preferably the N-terminal amine of a peptide, and may be the N-terminal amine of the preferred dipeptides of the invention.

The active group may be reacted to yield the functional group that is intended to form a connection to a Ligand unit.

In other embodiments, the Linker unit is a precursor to the Linker unit having an active group. In this embodiment, the Linker unit comprises the active group, which is protected by way of a protecting group. The protecting group may be removed to provide the Linker unit having an active group.

Where the active group is an amine, the protecting group may be an amine protecting group, such as those described in Green and Wuts.

The protecting group is preferably orthogonal to other protecting groups, where present, in the Linker unit.

In one embodiment, the protecting group is orthogonal to the capping group. Thus, the active group protecting group is removable whilst retaining the capping group. In other embodiments, the protecting group and the capping group is removable under the same conditions as those used to remove the capping group.

In one embodiment, the Linker unit is:

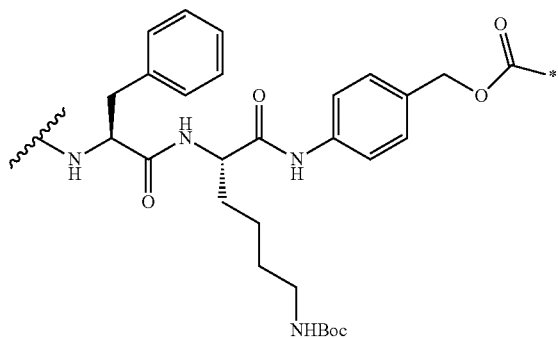 [SMILES: *N[C@@H](Cc1ccccc1)C(=O)N[C@@H](CCCCNC(=O)OC(C)(C)C)C(=O)Nc1ccc(COC(*)=O)cc1]

where the asterisk indicates the point of attachment to the Drug unit, and the wavy line indicates the point of attachment to the remaining portion of the Linker unit, as applicable or the point of attachment to $G^1$. Preferably, the wavy line indicates the point of attachment to $G^1$.

In one embodiment, the Linker unit is:

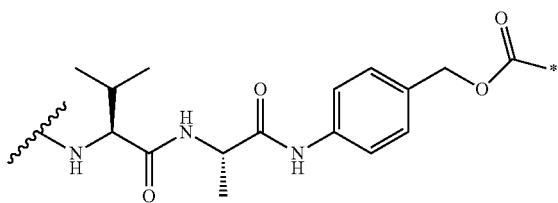 [SMILES: *N[C@H](C(=O)N[C@@H](C)C(=O)Nc1ccc(COC(*)=O)cc1)C(C)C]

where the asterisk and the wavy line are as defined above.

Other functional groups suitable for use in forming a connection between $L^1$ and the Cell Binding Agent are described in WO 2005/082023.

Ligand Unit

The Ligand Unit may be of any kind, and include a protein, polypeptide, peptide and a non-peptidic agent that specifically binds to a target molecule. In some embodiments, the Ligand unit may be a protein, polypeptide or peptide. In some embodiments, the Ligand unit may be a cyclic polypeptide. These Ligand units can include antibodies or a fragment of an antibody that contains at least one target molecule-binding site, lymphokines, hormones, growth factors, or any other cell binding molecule or substance that can specifically bind to a target.

Examples of Ligand units include those agents described for use in WO 2007/085930, which is incorporated herein.

In some embodiments, the Ligand unit is a Cell Binding Agent that binds to an extracellular target on a cell. Such a Cell Binding Agent can be a protein, polypeptide, peptide or a non-peptidic agent. In some embodiments, the Cell Binding Agent may be a protein, polypeptide or peptide. In some embodiments, the Cell Binding Agent may be a cyclic polypeptide. The Cell Binding Agent also may be antibody or an antigen-binding fragment of an antibody. Thus, in one embodiment, the present invention provides an antibody-drug conjugate (ADC).

In one embodiment the antibody is a monoclonal antibody; chimeric antibody; humanized antibody; fully human antibody; or a single chain antibody. One embodiment the antibody is a fragment of one of these antibodies having biological activity. Examples of such fragments include Fab, Fab', F(ab')$_2$ and Fv fragments.

The antibody may be a diabody, a domain antibody (DAB) or a single chain antibody.

In one embodiment, the antibody is a monoclonal antibody.

Antibodies for use in the present invention include those antibodies described in WO 2005/082023 which is incorporated herein. Particularly preferred are those antibodies for tumour-associated antigens. Examples of those antigens known in the art include, but are not limited to, those tumour-associated antigens set out in WO 2005/082023. See, for instance, pages 41-55.

In some embodiments, the conjugates are designed to target tumour cells via their cell surface antigens. The antigens may be cell surface antigens which are either over-expressed or expressed at abnormal times or cell types. Preferably, the target antigen is expressed only on proliferative cells (preferably tumour cells); however this is rarely observed in practice. As a result, target antigens are usually selected on the basis of differential expression between proliferative and healthy tissue.

Antibodies have been raised to target specific tumour related antigens including:

Cripto, CD19, CD20, CD22, CD30, CD33, Glycoprotein NMB, CanAg, Her2 (ErbB2/Neu), CD56 (NCAM), CD70, CD79, CD138, PSCA, PSMA (prostate specific membrane antigen), BCMA, E-selectin, EphB2, Melanotransferin, Muc16 and TMEFF2.

The Ligand unit is connected to the Linker unit. In one embodiment, the Ligand unit is connected to A, where present, of the Linker unit.

In one embodiment, the connection between the Ligand unit and the Linker unit is through a thioether bond.

In one embodiment, the connection between the Ligand unit and the Linker unit is through a disulfide bond.

In one embodiment, the connection between the Ligand unit and the Linker unit is through an amide bond.

In one embodiment, the connection between the Ligand unit and the Linker unit is through an ester bond.

In one embodiment, the connection between the Ligand unit and the Linker is formed between a thiol group of a cysteine residue of the Ligand unit and a maleimide group of the Linker unit.

The cysteine residues of the Ligand unit may be available for reaction with the functional group of the Linker unit to form a connection. In other embodiments, for example where the Ligand unit is an antibody, the thiol groups of the antibody may participate in interchain disulfide bonds. These interchain bonds may be converted to free thiol groups by e.g. treatment of the antibody with DTT prior to reaction with the functional group of the Linker unit.

In some embodiments, the cysteine residue is an introduced into the heavy or light chain of an antibody. Positions for cysteine insertion by substitution in antibody heavy or light chains include those described in Published U.S. Application No. 2007-0092940 and International Patent Publication WO2008070593, which are incorporated herein.

Methods of Treatment

The Conjugates of the present invention may be used in a method of therapy. Also provided is a method of treatment, comprising administering to a subject in need of treatment a therapeutically-effective amount of a Conjugate of formula I. The term "therapeutically effective amount" is an amount sufficient to show benefit to a patient. Such benefit may be at least amelioration of at least one symptom. The actual amount of a Conjugate administered, and rate and timecourse of administration, will depend on the nature and severity of what is being treated. Prescription of treatment, e.g. decisions on dosage, is within the responsibility of general practitioners and other medical doctors.

In some embodiments, the amount of the Conjugate administered ranges from about 0.01 to about 10 mg/kg per dose. In some embodiments, the amount of the Conjugate administered ranges from about 0.01 to about 5 mg/kg per dose. In some embodiments, the amount of the Conjugate administered ranges from about 0.05 to about 5 mg/kg per dose. In some embodiments, the amount of the Conjugate administered ranges from about 0.1 to about 5 mg/kg per dose. In some embodiments, the amount of the Conjugate administered ranges from about 0.1 to about 4 mg/kg per dose. In some embodiments, the amount of the Conjugate administered ranges from about 0.05 to about 3 mg/kg per dose.

In some embodiments, the amount of the Conjugate administered ranges from about 0.1 to about 3 mg/kg per dose. In some embodiments, the amount of the Conjugate administered ranges from about 0.1 to about 2 mg/kg per dose. In some embodiments, the amount of the Conjugate administered ranges from about 0.01 to about 1 mg/kg per dose.

A conjugate may be administered alone or in combination with other treatments, either simultaneously or sequentially dependent upon the condition to be treated. Examples of treatments and therapies include, but are not limited to, chemotherapy (the administration of active agents, including, e.g. drugs; surgery; and radiation therapy).

Pharmaceutical compositions according to the present invention, and for use in accordance with the present invention, may comprise, in addition to the active ingredient, i.e. a Conjugate of formula I, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO⁻), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O⁻), a salt or solvate thereof, as well as conventional protected forms.

Salts

It may be convenient or desirable to prepare, purify, and/or handle a corresponding salt of the active compound (the Conjugate), for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —COO⁻), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e. NH$_4^+$) and substituted ammonium ions (e.g. NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the Conjugate is cationic, or has a functional group which may be cationic (e.g. —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the Conjugate(s). The term "solvate" is used herein in the conventional sense to refer to a complex of solute (e.g. active Conjugate, salt of active Conjugate) and solvent. If the solvent is water, the solvate may be conveniently referred to as a hydrate, for example, a mono-hydrate, a di-hydrate, a tri-hydrate, etc.

Carbinolamines

The invention includes Conjugate where a solvent adds across the imine bond of the PBD moiety, which is illustrated below for a PBD monomer where the solvent is water or an alcohol (R$^A$OH, where R$^A$ is C$_{1-4}$ alkyl):

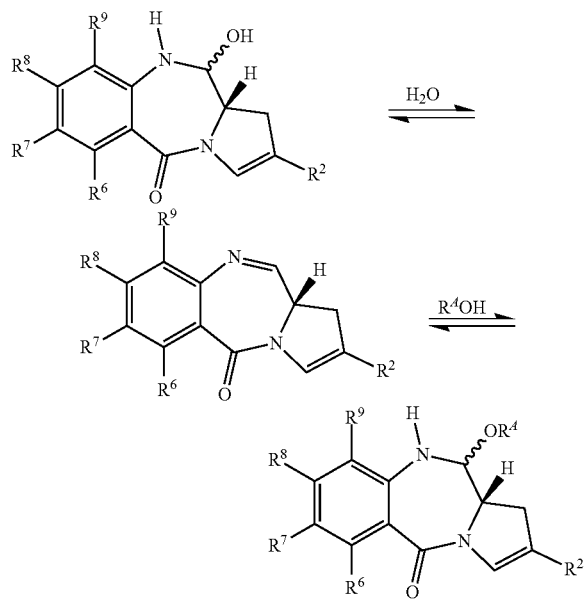

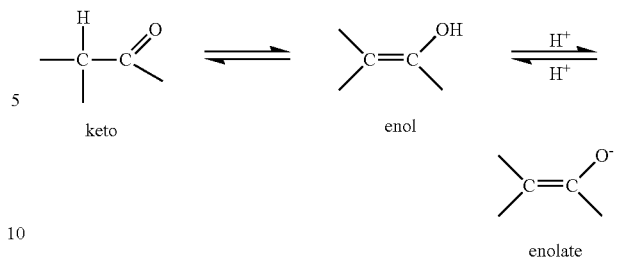

These forms can be called the carbinolamine and carbinolamine ether forms of the PBD.

The balance of these equilibria depend on the conditions in which the compounds are found, as well as the nature of the moiety itself.

These particular compounds may be isolated in solid form, for example, by lyophilisation.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g. C$_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including 16O and $^{18}$O; and the like.

Unless otherwise specified, a reference to a particular compound or Conjugate includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

General Synthetic Routes

The synthesis of PBD dimer compounds is extensively discussed in the following references, which discussions are incorporated herein by reference:

a) WO 00/12508 (pages 14 to 30);
b) WO 2005/023814 (pages 3 to 10);
c) WO 2004/043963 (pages 28 to 29); and
d) WO 2005/085251 (pages 30 to 39).

Synthesis Route

The Conjugates of the present invention, where R$^{10}$ and R$^{11}$ form a nitrogen-carbon double bond between the nitrogen and carbon atoms to which they are bound, can be synthesised from a compound of Compound formula 2:

Formula 2

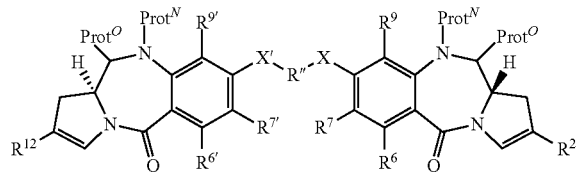

where R$^2$, R$^6$, R$^7$, R$^9$, R$^{6'}$, R$^{7'}$, R$^{9'}$, R$^{12}$, X, X' and R$^{11}$ are as defined for compounds of formula II, Prot$^N$ is a nitrogen protecting group for synthesis and Prot$^O$ is a protected oxygen group for synthesis or an oxo group, by deprotecting the imine bond by standard methods.

The compound produced may be in its carbinolamine or carbinolamine ether form depending on the solvents used. For example if Prot$^N$ is Alloc and Prot$^O$ is an oxygen protecting group for synthesis, then the deprotection is carried using palladium to remove the N10 protecting group, followed by the elimination of the oxygen protecting group for synthesis. If Prot$^N$ is Troc and Prot$^O$ is an oxygen protecting group for synthesis, then the deprotection is carried out using a Cd/Pb couple to yield the compound of formula (I). If Prot$^N$ is SEM, or an analogous group, and Prot$^O$ is an oxo group, then the oxo group can be removed by reduction, which leads to a protected carbinolamine intermediate, which can then be treated to remove the SEM protecting group, followed by the elimination of water. The reduction of the compound of Compound formula 2 can be accomplished by, for example, lithium tetraborohydride, whilst a suitable means for removing the SEM protecting group is treatment with silica gel.

Compounds of Compound formula 2 can be synthesised from a compound of Compound formula 3a:

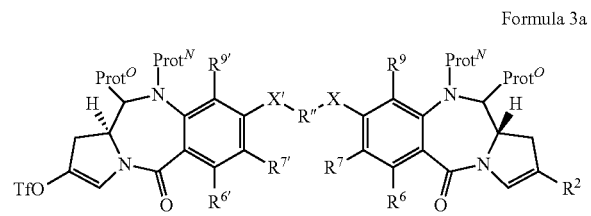

Formula 3a where $R^2$, $R^6$, $R^7$, $R^9$, $R^{6'}$, $R^{7'}$, $R^{9'}$, X, X' and R'' are as defined for compounds of Compound formula 2, by coupling an organometallic derivative comprising $R^{12}$, such as an organoboron derivative. The organoboron derivative may be a boronate or boronic acid.

Compounds of Compound formula 2 can be synthesised from a compound of Compound formula 3b:

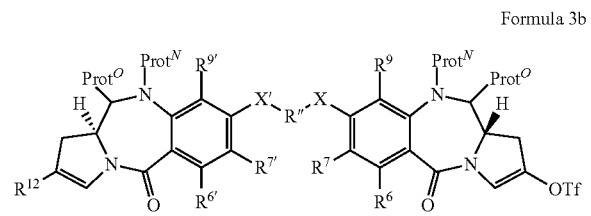

Formula 3b where $R^{12}$, $R^6$, $R^7$, $R^9$, $R^{6'}$, $R^{7'}$, $R^{9'}$, X, X' and R'' are as defined for compounds of Compound formula 2, by coupling an organometallic derivative comprising $R^2$, such as an organoboron derivative. The organoboron derivative may be a boronate or boronic acid.

Compounds of Compound formulae 3a and 3b can be synthesised from a compound of formula 4:

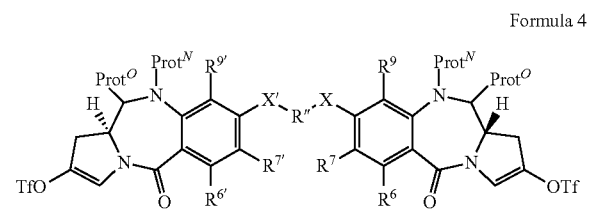

Formula 4 where $R^2$, $R^6$, $R^7$, $R^9$, $R^{6'}$, $R^{7'}$, $R^{9'}$, X, X' and R'' are as defined for compounds of Compound formula 2, by coupling about a single equivalent (e.g. 0.9 or 1 to 1.1 or 1.2) of an organometallic derivative, such as an organoboron derivative, comprising $R^2$ or $R^{12}$.

The couplings described above are usually carried out in the presence of a palladium catalyst, for example Pd(PPh$_3$)$_4$, Pd(OCOCH$_3$)$_2$, PdCl$_2$, or Pd$_2$(dba)$_3$. The coupling may be carried out under standard conditions, or may also be carried out under microwave conditions.

The two coupling steps are usually carried out sequentially. They may be carried out with or without purification between the two steps. If no purification is carried out, then the two steps may be carried out in the same reaction vessel. Purification is usually required after the second coupling step. Purification of the compound from the undesired by-products may be carried out by column chromatography or ion-exchange separation.

The synthesis of compounds of Compound formula 4 where Prot$^O$ is an oxo group and Prot$^N$ is SEM are described in detail in WO 00/12508, which is incorporated herein by reference. In particular, reference is made to scheme 7 on page 24, where the above compound is designated as intermediate P. This method of synthesis is also described in WO 2004/043963.

The synthesis of compounds of Compound formula 4 where Prot$^O$ is a protected oxygen group for synthesis are described in WO 2005/085251, which synthesis is herein incorporated by reference.

Compounds of formula I where $R^{10}$ and $R^{10'}$ are H and $R^{11}$ and $R^{11'}$ are SO$_z$M, can be synthesised from compounds of formula I where $R^{10}$ and $R^{11}$ form a nitrogen-carbon double bond between the nitrogen and carbon atoms to which they are bound, by the addition of the appropriate bisulphite salt or sulphinate salt, followed by an appropriate purification step. Further methods are described in GB 2 053 894, which is herein incorporated by reference.

Nitrogen Protecting Groups for Synthesis

Nitrogen protecting groups for synthesis are well known in the art. In the present invention, the protecting groups of particular interest are carbamate nitrogen protecting groups and hemi-aminal nitrogen protecting groups.

Carbamate nitrogen protecting groups have the following structure:

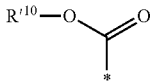

wherein $R'^{10}$ is R as defined above. A large number of suitable groups are described on pages 503 to 549 of Greene, T. W. and Wuts, G. M., *Protective Groups in Organic Synthesis*, 3$^{rd}$ Edition, John Wiley & Sons, Inc., 1999, which is incorporated herein by reference.

Particularly preferred protecting groups include Troc, Teoc, Fmoc, BOC, Doc, Hoc, TcBOC, 1-Adoc and 2-Adoc.

Other possible groups are nitrobenzyloxycarbonyl (e.g. 4-nitrobenzyloxycarbonyl) and 2-(phenylsulphonyl)ethoxycarbonyl.

Those protecting groups which can be removed with palladium catalysis are not preferred, e.g. Alloc.

Hemi-aminal nitrogen protecting groups have the following structure:

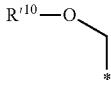

wherein $R'^{10}$ is R as defined above. A large number of suitable groups are described on pages 633 to 647 as amide protecting groups of Greene, T. W. and Wuts, G. M., Protective Groups in Organic Synthesis, 3$^{rd}$ Edition, John Wiley & Sons, Inc., 1999, which is incorporated herein by reference. The groups disclosed herein can be applied to compounds for use in the present invention. Such groups include, but are not limited to, SEM, MOM, MTM, MEM, BOM, nitro or methoxy substituted BOM, and Cl$_3$CCH$_2$OCH$_2$—.

Protected Oxygen Group for Synthesis

Protected oxygen group for synthesis are well known in the art. A large number of suitable oxygen protecting groups are described on pages 23 to 200 of Greene. T. W. and Wuts, G. M., Protective Groups in Organic Synthesis, 3$^{rd}$ Edition, John Wiley & Sons, Inc., 1999, which is incorporated herein by reference.

Classes of particular interest include silyl ethers, methyl ethers, alkyl ethers, benzyl ethers, esters, acetates, benzoates, carbonates, and sulfonates.

Preferred oxygen protecting groups include acetates, TBS and THP.

Further Preferences

The following preferences may apply to all aspects of the invention as described above, or may relate to a single aspect. The preferences may be combined together in any combination.

In some embodiments, R$^{6'}$, R$^{7'}$, R$^{9'}$, R$^{10'}$, R$^{11'}$ and Y' are preferably the same as R$^6$, R$^7$, R$^9$, R$^{10}$, R$^{11}$ and Y respectively.

Dimer Link

Y and Y' are preferably O.

R" is preferably a C$_{3-7}$ alkylene group with no substituents. More preferably R" is a C$_3$, C$_5$ or C$_7$ alkylene.

R$^6$ to R$^9$

R$^9$ is preferably H.

R$^6$ is preferably selected from H, OH, OR, SH, NH$_2$, nitro and halo, and is more preferably H or halo, and most preferably is H.

R$^7$ is preferably selected from H, OH, OR, SH, SR, NH$_2$, NHR, NRR', and halo, and more preferably independently selected from H, OH and OR, where R is preferably selected from optionally substituted C$_{1-7}$ alkyl, C$_{3-10}$ heterocyclyl and C$_{5-10}$ aryl groups. R may be more preferably a C$_{1-4}$ alkyl group, which may or may not be substituted. A substituent of interest is a C$_{5-6}$ aryl group (e.g. phenyl). Particularly preferred substituents at the 7-positions are OMe and OCH$_2$Ph.

These preferences apply to R$^{9'}$, R$^{6'}$, and R$^{7'}$ respectively.

R$^2$

A in R$^2$ may be phenyl group or a C$_{5-7}$ heteroaryl group, for example furanyl, thiophenyl and pyridyl. In some embodiments, A is preferably phenyl. In other embodiments, A is preferably thiophenyl, for example, thiophen-2-yl and thiophen-3-yl.

X is a group selected from the list comprising: —O—, —S—, —C(O)O—, —C(O)—, —NH(C═O)— and —N(R$^N$)—, wherein R$^N$ is selected from the group comprising H and C$_{1-4}$ alkyl. X may preferably be: —O—, —S—, —C(O)O—, —NH(C═O)— or —NH—, and may more preferably be: —O—, —S—, or —NH—, and most preferably is —NH—.

Q$^2$-X may be on any of the available ring atoms of the C$_{5-7}$ aryl group, but is preferably on a ring atom that is not adjacent the bond to the remainder of the compound, i.e. it is preferably β or γ to the bond to the remainder of the compound. Therefore, where the C$_{5-7}$ aryl group (A) is phenyl, the substituent (Q$^2$-X) is preferably in the meta- or para-positions, and more preferably is in the para-position, In some embodiments, Q$^1$ is a single bond. In these embodiments, Q$^2$ is selected from a single bond and —Z—(CH$_2$)$_n$—, where Z is selected from a single bond, O, S and NH and is from 1 to 3. In some of these embodiments, Q$^2$ is a single bond. In other embodiments, Q$^2$ is —Z—(CH$_2$)$_n$—. In these embodiments. Z may be O or S and n may be 1 or n may be 2. In other of these embodiments, Z may be a single bond and n may be 1.

In other embodiments, Q$^1$ is —CH═CH—.

In some embodiments, R$^2$ may be -A-CH$_2$—X and -A-X. In these embodiments, X may be —O—, —S—, —C(O)O—, —C(O)— and —NH—. In particularly preferred embodiments, X may be —NH—.

R$^{12}$

R$^{12}$ may be a C$_{5-7}$ aryl group. A C$_{5-7}$ aryl group may be a phenyl group or a C$_{5-7}$ heteroaryl group, for example furanyl, thiophenyl and pyridyl. In some embodiments, R$^{12}$ is preferably phenyl. In other embodiments, R$^{12}$ is preferably thiophenyl, for example, thiophen-2-yl and thiophen-3-yl.

R$^{12}$ may be a C$_{8-10}$ aryl, for example a quinolinyl or isoquinolinyl group. The quinolinyl or isoquinolinyl group may be bound to the PBD core through any available ring position. For example, the quinolinyl may be quinolin-2-yl, quinolin-3-yl, quinolin-4yl, quinolin-5-yl, quinolin-6-yl, quinolin-7-yl and quinolin-8-yl. Of these quinolin-3-yl and quinolin-6-yl may be preferred. The isoquinolinyl may be isoquinolin-1-yl, isoquinolin-3-yl, isoquinolin-4yl, isoquinolin-5-yl, isoquinolin-6-yl, isoquinolin-7-yl and isoquinolin-8-yl. Of these isoquinolin-3-yl and isoquinolin-6-yl may be preferred.

R$^{12}$ may bear any number of substituent groups. It preferably bears from 1 to 3 substituent groups, with 1 and 2 being more preferred, and singly substituted groups being most preferred. The substituents may be any position.

Where R$^{12}$ is C$_{5-7}$ aryl group, a single substituent is preferably on a ring atom that is not adjacent the bond to the remainder of the compound, i.e. it is preferably β or γ to the bond to the remainder of the compound. Therefore, where the C$_{5-7}$ aryl group is phenyl, the substituent is preferably in the meta- or para-positions, and more preferably is in the para-position.

Where R$^{12}$ is a C$_{8-10}$ aryl group, for example quinolinyl or isoquinolinyl, it may bear any number of substituents at any position of the quinoline or isoquinoline rings. In some embodiments, it bears one, two or three substituents, and these may be on either the proximal and distal rings or both (if more than one substituent).

R$^{12}$ Substituents

If a substituent on R$^{12}$ is halo, it is preferably F or Cl, more preferably Cl.

If a substituent on R$^{12}$ is ether, it may in some embodiments be an alkoxy group, for example, a C$_{1-7}$ alkoxy group (e.g. methoxy, ethoxy) or it may in some embodiments be a C$_{5-7}$ aryloxy group (e.g. phenoxy, pyridyloxy, furanyloxy). The alkoxy group may itself be further substituted, for example by an amino group (e.g. dimethylamino).

If a substituent on R$^{12}$ is C$_{1-7}$ alkyl, it may preferably be a C$_{1-4}$ alkyl group (e.g. methyl, ethyl, propyl, butyl).

If a substituent on R$^{12}$ is C$_{3-7}$ heterocyclyl, it may in some embodiments be C$_6$ nitrogen containing heterocyclyl group, e.g. morpholino, thiomorpholino, piperidinyl, piperazinyl. These groups may be bound to the rest of the PBD moiety via the nitrogen atom. These groups may be further substituted, for example, by $C_{1-4}$ alkyl groups. If the $C_6$ nitrogen containing heterocyclyl group is piperazinyl, the said further substituent may be on the second nitrogen ring atom.

If a substituent on $R^{12}$ is bis-oxy-$C_{1-3}$ alkylene, this is preferably bis-oxy-methylene or bis-oxy-ethylene.

Particularly preferred substituents for $R^{12}$ include methoxy, ethoxy, fluoro, chloro, cyano, bis-oxy-methylene, methyl-piperazinyl, morpholino and methyl-thiophenyl. Another particularly preferred substituent for $R^{12}$ is dimethylaminopropyloxy.

$R^{12}$ Groups

Particularly preferred substituted $R^{12}$ groups include, but are not limited to, 4-methoxyphenyl, 3-methoxyphenyl, 4-ethoxy-phenyl, 3-ethoxy-phenyl, 4-fluoro-phenyl, 4-chloro-phenyl, 3,4-bisoxymethylene-phenyl, 4-methylthiophenyl, 4-cyanophenyl, 4-phenoxyphenyl, quinolin-3-yl and quinolin-6-yl, isoquinolin-3-yl and isoquinolin-6-yl, 2-thienyl, 2-furanyl, methoxynaphthyl, and naphthyl. Another possible substituted $R^{12}$ group is 4-nitrophenyl.

M and Z

It is preferred that M and M' are monovalent pharmaceutically acceptable cations, and are more preferably $Na^+$.

z is preferably 3.

EXAMPLES

General Experimental Methods

Optical rotations were measured on an ADP 220 polarimeter (Bellingham Stanley Ltd.) and concentrations (c) are given in g/100 mL. Melting points were measured using a digital melting point apparatus (Electrothermal). IR spectra were recorded on a Perkin-Elmer Spectrum 1000 FT IR Spectrometer. $^1H$ and $^{13}C$ NMR spectra were acquired at 300 K using a Bruker Avance NMR spectrometer at 400 and 100 MHz, respectively. Chemical shifts are reported relative to TMS ($\delta$=0.0 ppm), and signals are designated as s (singlet), d (doublet), t (triplet), dt (double triplet), dd (doublet of doublets), ddd (double doublet of doublets) or m (multiplet), with coupling constants given in Hertz (Hz). Mass spectroscopy (MS) data were collected using a Waters Micromass ZQ instrument coupled to a Waters 2695 HPLC with a Waters 2996 PDA. Waters Micromass ZQ parameters used were: Capillary (kV), 3.38; Cone (V), 35; Extractor (V), 3.0; Source temperature (° C.), 100; Desolvation Temperature (° C.), 200; Cone flow rate (L/h), 50; De-solvation flow rate (L/h), 250. High-resolution mass spectroscopy (HRMS) data were recorded on a Waters Micromass QTOF Global in positive W-mode using metal-coated borosilicate glass tips to introduce the samples into the instrument. Thin Layer Chromatography (TLC) was performed on silica gel aluminium plates (Merck 60, $F_{254}$), and flash chromatography utilised silica gel (Merck 60, 230-400 mesh ASTM). Except for the HOBt (NovaBiochem) and solid-supported reagents (Argonaut), all other chemicals and solvents were purchased from Sigma-Aldrich and were used as supplied without further purification. Anhydrous solvents were prepared by distillation under a dry nitrogen atmosphere in the presence of an appropriate drying agent, and were stored over 4 Å molecular sieves or sodium wire. Petroleum ether refers to the fraction boiling at 40-60° C.

Compound 1b was synthesised as described in WO 00/012508 (compound 210), which is herein incorporated by reference.

General LC/MS conditions: The HPLC (Waters Alliance 2695) was run using a mobile phase of water (A) (formic acid 0.1%) and acetonitrile (B) (formic acid 0.1%). Gradient: initial composition 5% B over 1.0 min then 5% B to 95% B within 3 min. The composition was held for 0.5 min at 95% B, and then returned to 5% B in 0.3 minutes. Total gradient run time equals 5 min. Flow rate 3.0 mL/min, 400 μL was split via a zero dead volume tee piece which passes into the mass spectrometer. Wavelength detection range: 220 to 400 nm. Function type: diode array (535 scans). Column: Phenomenex® Onyx Monolithic C18 50×4.60 mm LC/MS conditions specific for compounds protected by both a Troc and a TBDMs group: Chromatographic separation of Troc and TBDMS protected compounds was performed on a Waters Alliance 2695 HPLC system utilizing a Onyx Monolitic reversed-phase column (3 μm particles, 50×4.6 mm) from Phenomenex Corp. Mobile-phase A consisted of 5% acetonitrile—95% water containing 0.1% formic acid, and mobile phase B consisted of 95% acetonitrile—5% water containing 0.1% formic acid. After 1 min at 5% B, the proportion of B was raised to 95% B over the next 2.5 min and maintained at 95% B for a further 1 min, before returning to 95% A in 10 s and re-equilibration for a further 50 sec, giving a total run time of 5.0 min. The flow rate was maintained at 3.0 mL/min.

LC/MS conditions specific for compound 33: LC was run on a Waters 2767 sample Manager coupled with a Waters 2996 photodiode array detector and a Waters ZQ single quadruple mass Spectrometer. The column used was Luna Phenyl-Hexyl 150×4.60 mm, 5 μm, Part no. 00F-4257-E0 (Phenomenex). The mobile phases employed were: Mobile phase A: 100% of HPLC grade water (0.05% triethylamine), pH=7 Mobile phase B: 20% of HPLC grade water and 80% of HPLC grade acetonitrile (0.05% triethylamine), pH=7

The gradients used were:

| Time (min) | Flow Rate (ml/mm) | % A | % B |
| --- | --- | --- | --- |
| Initial | 1.50 | 90 | 10 |
| 1.0 | 1.50 | 90 | 10 |
| 16.0 | 1.50 | 64 | 36 |
| 30.0 | 1.50 | 5 | 95 |
| 31.0 | 1.50 | 90 | 10 |
| 32.0 | 1.50 | 90 | 10 |

Mass Spectrometry was carried out in positive ion mode and SIR (selective ion monitor) and the ion monitored was m/z=727.2.

Synthesis of key intermediates

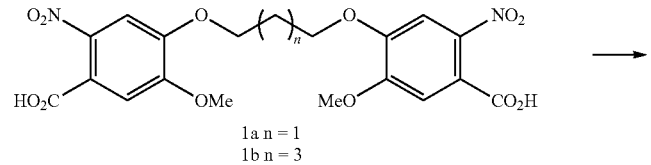

1a n = 1
1b n = 3

-continued
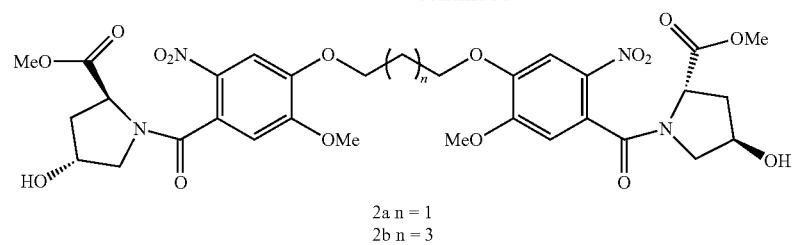
2a n = 1
2b n = 3
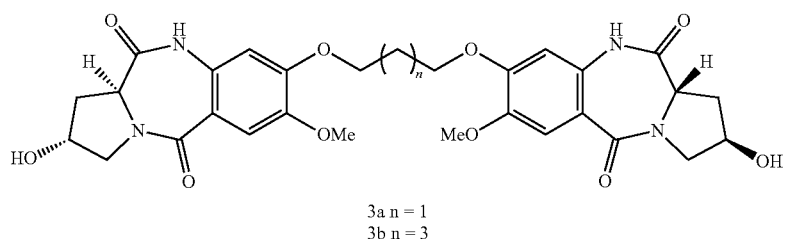
3a n = 1
3b n = 3
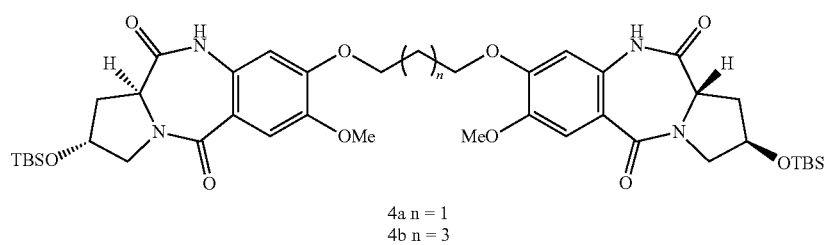
4a n = 1
4b n = 3
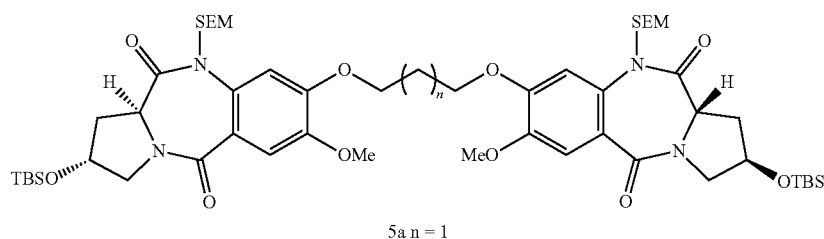
5a n = 1
5b n = 3
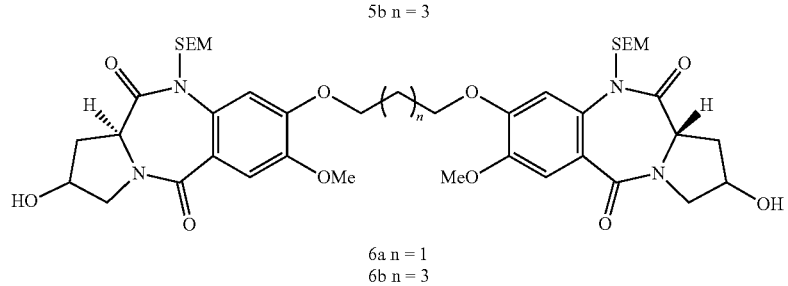
6a n = 1
6b n = 3
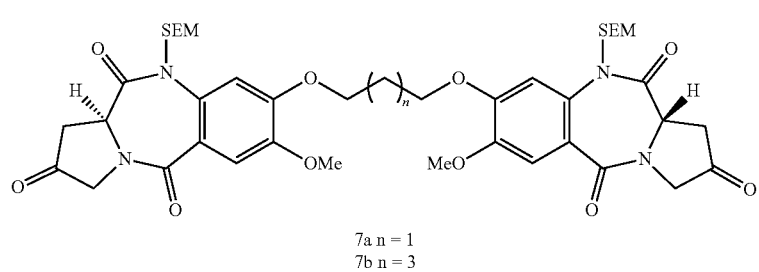
7a n = 1
7b n = 3

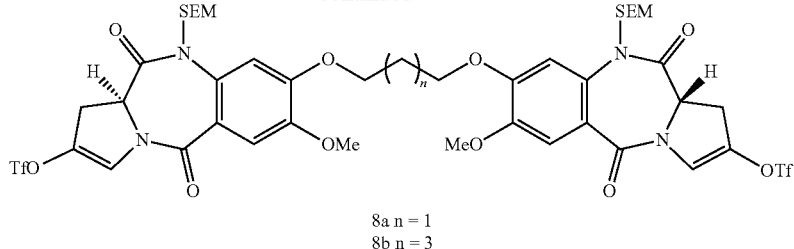

8a n = 1
8b n = 3

(a) 1,1'-[[(Propane-1,3-diyl)dioxy]bis[(5-methoxy-2-nitro-1,4-phenylene)carbonyl]]bis[(2S,4R)-methyl-4-hydroxypyrrolidine-2-carboxylate] (2a)

Method A: A catalytic amount of DMF (2 drops) was added to a stirred solution of the nitro-acid 1a (1.0 g, 2.15 mmol) and oxalyl chloride (0.95 mL, 1.36 g, 10.7 mmol) in dry THF (20 mL). The reaction mixture was allowed to stir for 16 hours at room temperature and the solvent was removed by evaporation in vacuo. The resulting residue was re-dissolved in dry THF (20 mL) and the acid chloride solution was added dropwise to a stirred mixture of (2S,4R)-methyl-4-hydroxypyrrolidine-2-carboxylate hydrochloride (859 mg, 4.73 mmol) and TEA (6.6 mL, 4.79 g, 47.3 mmol) in THF (10 mL) at −30° C. (dry ice/ethylene glycol) under a nitrogen atmosphere. The reaction mixture was allowed to warm to room temperature and stirred for a further 3 hours after which time TLC (95:5 v/v CHCl$_3$/MeOH) and LC/MS (2.45 min (ES+) m/z (relative intensity) 721 ([M+H]$^+$, 20)) revealed formation of product. Excess THF was removed by rotary evaporation and the resulting residue was dissolved in DCM (50 mL). The organic layer was washed with 1N HCl (2×15 mL), saturated NaHCO$_3$ (2×15 mL), H$_2$O (20 mL), brine (30 mL) and dried (MgSO$_4$). Filtration and evaporation of the solvent gave the crude product as a dark coloured oil. Purification by flash chromatography (gradient elution: 100% CHCl$_3$a to 96:4 v/v CHCl$_3$/MeOH) isolated the pure amide 2a as an orange coloured glass (840 mg, 54%).

Method B: Oxalyl chloride (9.75 mL, 14.2 g, 111 mmol) was added to a stirred suspension of the nitro-acid 1a (17.3 g, 37.1 mmol) and DMF (2 mL) in anhydrous DCM (200 mL). Following initial effervescence the reaction suspension became a solution and the mixture was allowed to stir at room temperature for 16 hours. Conversion to the acid chloride was confirmed by treating a sample of the reaction mixture with MeOH and the resulting bis-methyl ester was observed by LC/MS. The majority of solvent was removed by evaporation in vacuo, the resulting concentrated solution was re-dissolved in a minimum amount of dry DCM and triturated with diethyl ether. The resulting yellow precipitate was collected by filtration, washed with cold diethyl ether and dried for 1 hour in a vacuum oven at 40° C. The solid acid chloride was added portionwise over a period of 25 minutes to a stirred suspension of (2S,4R)-methyl-4-hydroxypyrrolidine-2-carboxylate hydrochloride (15.2 g, 84.0 mmol) and TEA (25.7 mL, 18.7 g, 185 mmol) in DCM (150 mL) at −40° C. (dry ice/CH$_3$CN). Immediately, the reaction was complete as judged by LC/MS (2.47 min (ES+) m/z (relative intensity) 721 ([M+H]$^+$, 100)). The mixture was diluted with DCM (150 mL) and washed with 1N HCl (300 mL), saturated NaHCO$_3$ (300 mL), brine (300 mL), filtered (through a phase separator) and the solvent evaporated in vacuo to give the pure product 2a as an orange solid (21.8 g, 82%).

Analytical Data: [α]$^{22}_D$=−46.1° (c=0.47, CHCl$_3$); $^1$H NMR (400 MHz, CDCl$_3$) (rotamers) δ 7.63 (s, 2H), 6.82 (s, 2H), 4.79-4.72 (m, 2H), 4.49-4.28 (m, 6H), 3.96 (s, 6H), 3.79 (s, 6H), 3.46-3.38 (m, 2H), 3.02 (d, 2H, J=11.1 Hz), 2.48-2.30 (m, 4H), 2.29-2.04 (m, 4H); $^{13}$C NMR (100 MHz, CDCl$_3$) (rotamers) δ 172.4, 166.7, 154.6, 148.4, 137.2, 127.0, 109.7, 108.2, 69.7, 65.1, 57.4, 57.0, 56.7, 52.4, 37.8, 29.0; IR (ATR, CHCl$_3$) 3410 (br), 3010, 2953, 1741, 1622, 1577, 1519, 1455, 1429, 1334, 1274, 1211, 1177, 1072, 1050, 1008, 871 cm$^{-1}$; MS (ES$^+$) m/z (relative intensity) 721 ([M+H]$^+$, 47), 388 (80); HRMS [M+H]$^+$ theoretical C$_{31}$H$_{36}$N$_4$O$_{16}$ m/z 721.2199, found (ES$^+$) m/z 721.2227.

(a) 1,1'-[[(Pentane-1,5-diyl)dioxy]bis[(5-methoxy-2-nitro-1,4-phenylene)carbonyl]]bis[(2S,4R)-methyl-4-hydroxypyrrolidine-2-carboxylate] (2b)

Preparation from 1b according to Method B gave the pure product as an orange foam (75.5 g, 82%).

Analytical Data: (ES$^+$) m/z (relative intensity) 749 ([M+H]$^+$, 100).

(b) 1,1'-[[(Propane-1,3-diyl)dioxy]bis(11aS,2R)-2-(hydroxy)-7-methoxy-1,2,3,10,11,11a-hexahydro-5H-pyrrolo[2,1-c][1,4]-benzodiazepin-5,11-dione] (3a)

Method A: A suspension of 10% Pd/C (7.5 g, 10% w/w) in DMF (40 mL) was added to a solution of the nitro-ester 2a (75 g, 104 mmol) in DMF (360 mL). The suspension was hydrogenated in a Parr hydrogenation apparatus over 8 hours. Progress of the reaction was monitored by LC/MS (2.12 min (ES+) m/z (relative intensity) 597 ([M+H]J, 100), (ES−) m/z (relative intensity) 595 ([M+H]$^+$, 100) after the hydrogen uptake had stopped. Solid Pd/C was removed by filtration and the filtrate was concentrated by rotary evaporation under vacuum (below 10 mbar) at 40° C. to afford a dark oil containing traces of DMF and residual charcoal. The residue was digested in EtOH (500 mL) at 40° C. on a water bath (rotary evaporator bath) and the resulting suspension was filtered through celite and washed with ethanol (500 mL) to give a clear filtrate. Hydrazine hydrate (10 mL, 321 mmol) was added to the solution and the reaction mixture was heated at reflux. After 20 minutes the formation of a white precipitate was observed and reflux was allowed to continue for a further 30 minutes. The mixture was allowed to cool down to room temperature and the precipitate was retrieved by filtration, washed with diethyl ether (2*1 volume of precipitate) and dried in a vacuum desiccator to provide 3a (50 g, 81%).

Method B: A solution of the nitro-ester 2a (6.80 g, 9.44 mmol) in MeOH (300 mL) was added to Raney™ nickel (4 large spatula ends of a ~50% slurry in H$_2$O) and anti-bumping granules in a 3-neck round bottomed flask. The mixture was heated at reflux and then treated dropwise with a solution of hydrazine hydrate (5.88 mL, 6.05 g, 188 mmol) in MeOH (50 mL) at which point vigorous effervescence was observed. When the addition was complete (~30 minutes) additional Raney™ nickel was added carefully until effervescence had ceased and the initial yellow colour of the reaction mixture was discharged. The mixture was heated at reflux for a further 30 minutes at which point the reaction was deemed complete by TLC (90:10 v/v CHCl$_3$/MeOH) and LC/MS (2.12 min (ES+) m/z (relative intensity) 597 ([M+H], 100)). The reaction mixture was allowed to cool to around 40° C. and then excess nickel removed by filtration through a sinter funnel without vacuum suction. The filtrate was reduced in volume by evaporation in vacuo at which point a colourless precipitate formed which was collected by filtration and dried in a vacuum desiccator to provide 3a (5.40 g, 96%).

Analytical Data: $[\alpha]^{27}_D$=+404° (c=0.10, DMF); $^1$H NMR (400 MHz, DMSO-d$_6$) δ 10.2 (s, 2H, NH), 7.26 (s, 2H), 6.73 (s, 2H), 5.11 (d, 2H, J=3.98 Hz, OH), 4.32-4.27 (m, 2H), 4.19-4.07 (m, 6H), 3.78 (s, 6H), 3.62 (dd, 2H, J=12.1, 3.60 Hz), 3.43 (dd, 2H, J=12.0, 4.72 Hz), 2.67-2.57 (m, 2H), 2.26 (p, 2H, J=5.90 Hz), 1.99-1.89 (m, 2H); $^{13}$C NMR (100 MHz, DMSO-d$_6$) δ 169.1, 164.0, 149.9, 144.5, 129.8, 117.1, 111.3, 104.5, 54.8, 54.4, 53.1, 33.5, 27.5; IR (ATR, neat) 3438, 1680, 1654, 1610, 1605, 1516, 1490, 1434, 1379, 1263, 1234, 1216, 1177, 1156, 1115, 1089, 1038, 1018, 952, 870 cm$^{-1}$; MS (ES$^+$) m/z (relative intensity) 619 ([M+Na]$^+$, 10), 597 ([M+H]$^+$, 52), 445 (12), 326 (11); HRMS [M+H]$^+$ theoretical C$_{29}$H$_{32}$N$_4$O$_{10}$ m/z 597.2191, found (ES$^+$) m/z 597.2205.

(b) 1,1'-[[(Pentane-1,5-diyl)dioxy]bis(11aS,2R)-2-(hydroxy)-7-methoxy-1,2,3,10,11,11a-hexahydro-5H-pyrrolo[2,1-c][1,4]-benzodiazepin-5,11-dione] (36)

Preparation from 2b according to Method A gave the product as a white solid (22.1 g, 86%).

Analytical Data: MS (ES$^-$) m/z (relative intensity) 623.3 ([M–H]$^-$, 100);

(c) 1,1'-[[(Propane-1,3-diyl)dioxy]bis(11aS,2R)-2-(tert-butyldimethylsilyloxy)-7-methoxy-1,2,3,10,11,11a-hexahydro-5H-pyrrolo[2,1-c][1,4]-benzodiazepin-5,11-dione] (4a)

TBSCl (317 mg, 2.1 mmol) and imidazole (342 mg, 5.03 mmol) were added to a cloudy solution of the tetralactam 3a (250 mg, 0.42 mmol) in anhydrous DMF (6 mL). The mixture was allowed to stir under a nitrogen atmosphere for 3 hours after which time the reaction was deemed complete as judged by LC/MS (3.90 min (ES+) m/z (relative intensity) 825 ([M+H]$^+$, 100)). The reaction mixture was poured onto ice (~25 mL) and allowed to warm to room temperature with stirring. The resulting white precipitate was collected by vacuum filtration, washed with H$_2$O, diethyl ether and dried in the vacuum desiccator to provide pure 4a (252 mg, 73%).

Analytical Data: $[\alpha]^{23}_D$=+2340 (c=0.41, CHCl$_3$); $^1$H NMR (400 MHz, CDCl$_3$) δ 8.65 (s, 2H, NH), 7.44 (s, 2H), 6.54 (s, 2H), 4.50 (p, 2H, J=5.38 Hz), 4.21-4.10 (m, 6H), 3.87 (s, 6H), 3.73-3.63 (m, 4H), 2.85-2.79 (m, 2H), 2.36-2.29 (m, 2H), 2.07-1.99 (m, 2H), 0.86 (s, 18H), 0.08 (s, 12H); $^{13}$C NMR (100 MHz, CDCl$_3$) δ 170.4, 165.7, 151.4, 146.6, 129.7, 118.9, 112.8, 105.3, 69.2, 65.4, 56.3, 55.7, 54.2, 35.2, 28.7, 25.7, 18.0, −4.82 and −4.86; IR (ATR, CHCl$_3$) 3235, 2955, 2926, 2855, 1698, 1695, 1603, 1518, 1491, 1446, 1380, 1356, 1251, 1220, 1120, 1099, 1033 cm$^{-1}$; MS (ES$^+$) n/z (relative intensity) 825 ([M+H]$^+$, 62), 721 (14), 440 (38); HRMS [M+H]$^+$ theoretical C$_{41}$H$_{60}$N$_4$O$_{10}$Si$_2$ n/z 825.3921, found (ES$^+$) m/z 825.3948.

(c) 1,1'-[[(Pentane-1,5-diyl)dioxy]bis(11aS,2R)-2-(tert-butyldimethylsilyloxy)-7-methoxy-1,2,3,10,11,11a-hexahydro-5H-pyrrolo[2,1-c][1,4]-benzodiazepin-5,11-dione] (4b)

Preparation from 3b according to the above method gave the product as a white solid (27.3 g, 93%).

Analytical Data: MS (ES$^+$) m/z (relative intensity) 853.8 ([M+H]$^+$, 100), (ES$^-$) m/z (relative intensity) 851.6 ([M–H]$^-$, 100.

(d) 1,1'-[[(Propane-1,3-diyl)dioxy]bis(11aS,2R)-2-(tert-butyldimethylsilyloxy)-7-methoxy-10-((2-(trimethylsilyl)ethoxy)methyl)-1,2,3,10,11,11a-hexahydro-5H-pyrrolo[2,1-c][1,4]-benzodiazepin-5,11-dione] (5a)

A solution of n-BuLi (4.17 mL of a 1.6 M solution in hexane, 6.67 mmol) in anhydrous THF (10 mL) was added dropwise to a stirred suspension of the tetralactam 4a (2.20 g, 2.67 mmol) in anhydrous THF (30 mL) at −30° C. (dry ice/ethylene glycol) under a nitrogen atmosphere. The reaction mixture was allowed to stir at this temperature for 1 hour (now a reddish orange colour) at which point a solution of SEMCl (1.18 mL, 1.11 g, 6.67 mmol) in anhydrous THF (10 mL) was added dropwise. The reaction mixture was allowed to slowly warm to room temperature and was stirred for 16 hours under a nitrogen atmosphere. The reaction was deemed complete as judged by TLC (EtOAc) and LC/MS (4.77 min (ES+) m/z (relative intensity) 1085 ([M+H]$^+$, 100)). The THF was removed by evaporation in vacuo and the resulting residue dissolved in EtOAc (60 mL), washed with H$_2$O (20 mL), brine (20 mL), dried (MgSO$_4$) filtered and evaporated in vacuo to provide the crude product. Purification by flash chromatography (80:20 v/v Hexane/EtOAc) gave the pure N10-SEM-protected tetralactam 5a as an oil (2.37 g, 82%).

Analytical Data: $[\alpha]^{23}_D$=+163° (c=0.41, CHCl$_3$); $^1$H NMR (400 MHz, CDCl$_3$) δ 7.33 (s, 2H), 7.22 (s, 2H), 5.47 (d, 2H, J=9.98 Hz), 4.68 (d, 2H. J=9.99 Hz), 4.57 (p, 2H, J=5.77 Hz), 4.29-4.19 (m, 6H), 3.89 (s, 6H), 3.79-3.51 (m, 8H), 2.87-2.81 (m, 2H), 2.41 (p, 2H, J=5.81 Hz), 2.03-1.90 (m, 2H), 1.02-0.81 (m, 22H), 0.09 (s, 12H), 0.01 (s, 18H); $^{13}$C NMR (100 MHz, CDCl$_3$) δ 170.0, 165.7, 151.2, 147.5, 133.8, 121.8, 111.6, 106.9, 78.1, 69.6, 67.1, 65.5, 56.6, 56.3, 53.7, 35.6, 30.0, 25.8, 18.4, 18.1, −1.24, −4.73; IR (ATR, CHCl$_3$) 2951, 1685, 1640, 1606, 1517, 1462, 1433, 1360, 1247, 1127, 1065 cm$^{-1}$; MS (ES$^+$) m/z (relative intensity) 1113 ([M+Na]$^+$, 48), 1085 ([M+H]$^+$, 100), 1009 (5), 813 (6); HRMS [M+H]$^+$ theoretical C$_{53}$H$_{88}$N$_4$O$_{12}$Si$_4$ m/z 1085.5548, found (ES$^+$) m/z 1085.5542.

(d) 1,1'-[[(Pentane1,5-diyl)dioxy]bis(11aS,2R)-2-(tert-butyldimethylsilyloxy)-7-methoxy-10-((2-(trimethylsilyl)ethoxy)methyl)-1,2,3,10,11,11a-hexahydro-5H-pyrrolo[2,1-c][1,4]-benzodiazepin-5,11-dione] (5b)

Preparation from 4b according to the above method gave the product as a pale orange foam (46.9 g, 100%), used without further purification.

Analytical Data: MS (ES+) m/z (relative intensity) 1114 ([M+H]+, 90), (ES−) m/z (relative intensity) 1158 ([M+2Na]−, 100).

(e) 1,1'-[[(Propane-1,3-diyl)dioxy]bis(11aS,2R)-2-hydroxy-7-methoxy-10-((2-(trimethylsilyl)ethoxy)methyl)-1,2,3,10,11,11a-hexahydro-5H-pyrrolo[2,1-c][1,4]-benzodiazepin-5,11-dione] (6a)

A solution of TBAF (5.24 mL of a 1.0 M solution in THF, 5.24 mmol) was added to a stirred solution of the bis-silyl ether 5a (2.58 g, 2.38 mmol) in THF (40 mL) at room temperature.

After stirring for 3.5 hours, analysis of the reaction mixture by TLC (95:5 v/v CHCl$_3$/MeOH) revealed completion of reaction. The reaction mixture was poured into a solution of saturated NH$_4$Cl (100 mL) and extracted with EtOAc (3×30 mL). The combined organic layers were washed with brine (60 mL), dried (MgSO$_4$), filtered and evaporated in vacuo to provide the crude product. Purification by flash chromatography (gradient elution: 100% CHCl$_3$ to 96:4 v/v CHCl$_3$/MeOH) gave the pure tetralactam 6a as a white foam (1.78 g, 87%).

Analytical Data: $[\alpha]^{23}_D$=+202° (c=0.34, CHCl$_3$); $^1$H NMR (400 MHz, CDCl$_3$) δ 7.28 (s, 2H), 7.20 (s, 2H), 5.44 (d, 2H, J=10.0 Hz), 4.72 (d, 2H, J=10.0 Hz), 4.61-4.58 (m, 2H), 4.25 (t, 4H, J=5.83 Hz), 4.20-4.16 (m, 2H), 3.91-3.85 (m, 8H), 3.77-3.54 (m, 6H), 3.01 (br s, 2H, OH), 2.96-2.90 (m, 2H), 2.38 (p, 2H, J=5.77 Hz), 2.11-2.05 (m, 2H), 1.00-0.91 (m, 4H), 0.00 (s, 18H); $^{13}$C NMR (100 MHz, CDCl$_3$) δ 169.5, 165.9, 151.3, 147.4, 133.7, 121.5, 111.6, 106.9, 79.4, 69.3, 67.2, 65.2, 56.5, 56.2, 54.1, 35.2, 29.1, 18.4, −1.23; IR (ATR, CHCl$_3$) 2956, 1684, 1625, 1604, 1518, 1464, 1434, 1361, 1238, 1058, 1021 cm$^{-1}$; MS (ES+) m/z (relative intensity) 885 ([M+29]+, 70), 857 ([M+H]+, 100), 711 (8), 448 (17); HRMS [M+H]+ theoretical C$_{41}$H$_{60}$N$_4$O$_{12}$Si$_2$ m/z 857.3819, found (ES+) m/z 857.3826.

(e) 1,1'-[[(Pentane-1,5-diyl)dioxy]bis(11aS,2R)-2-hydroxy-7-methoxy-10-((2-(trimethylsilyl)ethoxy)methyl)-1,2,3,10,11,11a-hexahydro-5H-pyrrolo[2,1-c][1,4]-benzodiazepin-5,11-dione] (6b)

Preparation from 5b according to the above method gave the product as a white foam (15.02 g).

Analytical Data: MS (ES+) m/z (relative intensity) 886 ([M+H]+, 10), 739.6 (100), (ES−) m/z (relative intensity) 884 ([M−H]−, 40).

(f) 1,1'-[[(Propane-1,3-diyl)dioxy]bis[((11aS)-11-sulpho-7-methoxy-2-oxo-10-((2-(trimethylsilyl)ethoxy)methyl)1,2,3,10,11,11a-hexahydro-5H-pyrrolo[2,1-c][1,4]benzodiazepin-5,11-dione]] (7a)

Method A: A 0.37 M sodium hypochlorite solution (142.5 mL, 52.71 mmol, 2.4 eq) was added dropwise to a vigorously stirred mixture of the diol 6a (18.8 g, 21.96 mmol, 1 eq), TEMPO (0.069 g, 0.44 mmol, 0.02 eq) and 0.5 M potassium bromide solution (8.9 mL, 4.4 mmol, 0.2 eq) in DCM (115 mL) at 0° C. The temperature was maintained between 0° C. and 5° C. by adjusting the rate of addition. The resultant yellow emulsion was stirred at 0° C. to 5° C. for 1 hour. TLC (EtOAc) and LC/MS [3.53 min. (ES+) m/z (relative intensity) 875 ([M+Na]+, 50), (ES−) m/z (relative intensity) 852 ([M−H]−, 100)] indicated that reaction was complete.

The reaction mixture was filtered, the organic layer separated and the aqueous layer was backwashed with DCM (×2). The combined organic portions were washed with brine (×1), dried (MgSO$_4$) and evaporated to give a yellow foam. Purification by flash column chromatography (gradient elution 35/65 v/v n-hexane/EtOAC, 30/70 to 25/75 v/v n-hexane/EtOAC) afforded the bis-ketone 7a as a white foam (14.1 g, 75%).

Sodium hypochlorite solution, reagent grade, available at chlorine 10-13%, was used. This was assumed to be 10% (10 g NaClO in 100 g) and calculated to be 1.34 M in NaClO. A stock solution was prepared from this by diluting it to 0.37 M with water. This gave a solution of approximately pH 14. The pH was adjusted to 9.3 to 9.4 by the addition of solid NaHCO$_3$. An aliquot of this stock was then used so as to give 2.4 mol eq. for the reaction. On addition of the bleach solution an initial increase in temperature was observed. The rate of addition was controlled, to maintain the temperature between 0° C. to 5° C. The reaction mixture formed a thick, lemon yellow coloured, emulsion.

The oxidation was an adaptation of the procedure described in Thomas Fey et al, *J. Org. Chem.*, 2001, 66, 8154-8159.

Method B: Solid TCCA (10.6 g, 45.6 mmol) was added portionwise to a stirred solution of the alcohol 6a (18.05 g, 21.1 mmol) and TEMPO (123 mg, 0.78 mmol) in anhydrous DCM (700 mL) at 0° C. (ice/acetone). The reaction mixture was stirred at 0° C. under a nitrogen atmosphere for 15 minutes after which time TLC (EtOAc) and LC/MS [3.57 min (ES+) m/z (relative intensity) 875 ([M+Na]+, 50)] revealed completion of reaction. The reaction mixture was filtered through celite and the filtrate was washed with saturated aqueous NaHCO$_3$ (400 mL), brine (400 mL), dried (MgSO$_4$), filtered and evaporated in vacuo to provide the crude product. Purification by flash column chromatography (80:20 v/v EtOAc/Hexane) afforded the bis-ketone 7a as a foam (11.7 g, 65%).

Method C: A solution of anhydrous DMSO (0.72 mL, 0.84 g, 10.5 mmol) in dry DCM (18 mL) was added dropwise over a period of 25 min to a stirred solution of oxalyl chloride (2.63 mL of a 2.0 M solution in DCM, 5.26 mmol) under a nitrogen atmosphere at −60° C. (liq N$_2$/CHCl$_3$). After stirring at −55° C. for 20 minutes, a slurry of the substrate 6a (1.5 g, 1.75 mmol) in dry DCM (36 mL) was added dropwise over a period of 30 min to the reaction mixture. After stirring for a further 50 minutes at −55° C., a solution of TEA (3.42 mL, 2.49 g; 24.6 mmol) in dry DCM (18 mL) was added dropwise over a period of 20 min to the reaction mixture. The stirred reaction mixture was allowed to warm to room temperature (~1.5 h) and then diluted with DCM (50 mL). The organic solution was washed with 1 N HCl (2×25 mL), H$_2$O (30 mL), brine (30 mL) and dried (MgSO$_4$). Filtration and evaporation of the solvent in vacuo afforded the crude product which was purified by flash column chromatography (80:20 v/v EtOAc/Hexane) to afford bis-ketone 7a as a foam (835 mg, 56%)

Analytical Data: $[\alpha]^{20}_D$=+291 (c=0.26, CHCl$_3$); $^1$H NMR (400 MHz, CDCl$_3$) δ 7.32 (s, 2H), 7.25 (s, 2H), 5.50 (d, 2H, J=10.1 Hz), 4.75 (d, 2H, J=10.1 Hz), 4.60 (dd, 2H, J=9.85, 3.07 Hz), 4.31-4.18 (m, 6H), 3.89-3.84 (m, 8H), 3.78-3.62 (m, 4H), 3.55 (dd, 2H, J=19.2, 2.85 Hz), 2.76 (dd, 2H, J=19.2, 9.90 Hz), 2.42 (p, 2H, J=5.77 Hz), 0.98-0.91 (m, 4H), 0.00 (s, 18H); $^{13}$C NMR (100 MHz, CDCl$_3$) δ 206.8, 168.8, 165.9, 151.8, 148.0, 133.9, 120.9, 111.6, 107.2, 78.2, 67.3, 65.6, 56.3, 54.9, 52.4, 37.4, 29.0, 18.4, −1.24; IR (ATR, CHCl$_3$) 2957, 1763, 1685, 1644, 1606, 1516, 1457, 1434, 1360, 1247, 1209, 1098, 1066, 1023 cm$^{-1}$; MS (ES+)

m/z (relative intensity) 881 ([M+29]⁺, 38), 853 ([M+H]⁺, 100), 707 (8), 542 (12); HRMS [M+H]⁺ theoretical $C_{41}H_{56}N_4O_{12}Si_2$ m/z 853.3506, found (ES⁺) m/z 853.3502.

(f) 1,1'-[[(Pentane-1,5-diyl)dioxy]bis[(11aS)-11-sulpho-7-methoxy-2-oxo-10-((2-(trimethylsilyl)ethoxy)methyl) 1,2,3,10,11,11a-hexahydro-5H-pyrrolo[2,1-c][1,4]benzodiazepin-5,11-dione]] (7b)

Preparation from 6b according to Method C gave the product as a white foam (10.5 g, 76%).

Analytical Data: MS (ES⁺) m/z (relative intensity) 882 ([M+H]⁺, 30), 735 (100), (ES⁻) m/z (relative intensity) 925 ([M+45]⁻, 100), 880 ([M−H]⁻, 70).

(g) 1,1'-[[(Propane-1,3-diyl)dioxy]bis(11 aS)-7-methoxy-2-[[(trifluoromethyl)sulfonyl]oxy-10-((2-(trimethylsilyl)ethoxy)methyl)-1,10,11,11a-tetrahydro-5H-pyrrolo[2,1-c][1,4]-benzodiazepin-5,11-dione] (8a)

Anhydrous 2,6-lutidine (5.15 mL, 4.74 g, 44.2 mmol) was injected in one portion to a vigorously stirred solution of bis-ketone 7a (6.08 g, 7.1 mmol) in dry DCM (180 mL) at −45° C. (dry ice/acetonitrile cooling bath) under a nitrogen atmosphere. Anhydrous triflic anhydride, taken from a freshly opened ampoule (7.2 mL, 12.08 g, 42.8 mmol), was injected rapidly dropwise, while maintaining the temperature at −40° C. or below. The reaction mixture was allowed to stir at −45° C. for 1 hour at which point TLC (50/50 v/v n-hexane/EtOAc) revealed the complete consumption of starting material. The cold reaction mixture was immediately diluted with DCM (200 mL) and, with vigorous shaking, washed with water (1×100 mL), 5% citric acid solution (1×200 mL) saturated NaHCO₃ (200 mL), brine (100 mL) and dried (MgSO₄). Filtration and evaporation of the solvent in vacuo afforded the crude product which was purified by flash column chromatography (gradient elution: 90:10 v/v n-hexane/EtOAc to 70:30 v/v n-hexane/EtOAc) to afford bis-enol triflate 8a as a yellow foam (5.5 g, 70%).

Analytical Data: $[\alpha]^{24}_D$=+271° (c=0.18, CHCl₃); ¹H NMR (400 MHz, CDCl₃) δ 7.33 (s, 2H), 7.26 (s, 2H), 7.14 (t, 2H, J=1.97 Hz), 5.51 (d, 2H, J=10.1 Hz), 4.76 (d, 2H, J=10.1 Hz), 4.62 (dd, 2H, J=11.0, 3.69 Hz), 4.32-4.23 (m, 4H), 3.94-3.90 (m, 8H), 3.81-3.64 (m, 4H), 3.16 (ddd, 2H, J=16.3, 11.0, 2.36 Hz), 2.43 (p, 2H, J=5.85 Hz), 1.23-0.92 (m, 4H), 0.02 (s, 18H); ¹³C NMR (100 MHz, CDCl₃) δ 167.1, 162.7, 151.9, 148.0, 138.4, 133.6, 120.2, 118.8, 111.9, 107.4, 78.6, 67.5, 65.6, 56.7, 56.3, 30.8, 29.0, 18.4, −1.25; IR (ATR, CHCl₃) 2958, 1690, 1646, 1605, 1517, 1456, 1428, 1360, 1327, 1207, 1136, 1096, 1060, 1022, 938, 913 cm⁻¹; MS (ES⁺) m/z (relative intensity) 1144 ([M+28]⁺, 100), 1117 ([M+H]⁺, 48), 1041 (40), 578 (8); HRMS [M+H]⁺ theoretical $C_{43}H_{54}N_4O_{16}Si_2S_2F_6$ m/z 1117.2491, found (ES⁺) m/z 1117.2465.

(g) 1,1'-[[(Pentane-1,5-diyl)dioxy]bis(11aS)-7-methoxy-2-[[(trifluoromethyl)sulfonyl]oxy]-10-((2-(trimethylsilyl)ethoxy)methyl)-1,10,11,11a-tetrahydro-5H-pyrrolo[2,1-c][1,4]-benzodiazepin-5,11-dione] (8b)

Preparation from 7b according to the above method gave the bis-enol triflate as a pale yellow foam (6.14 g, 82%).

Analytical Data: (ES+) m/z (relative intensity) 1146 ([M+H]⁺, 85).

Example 1

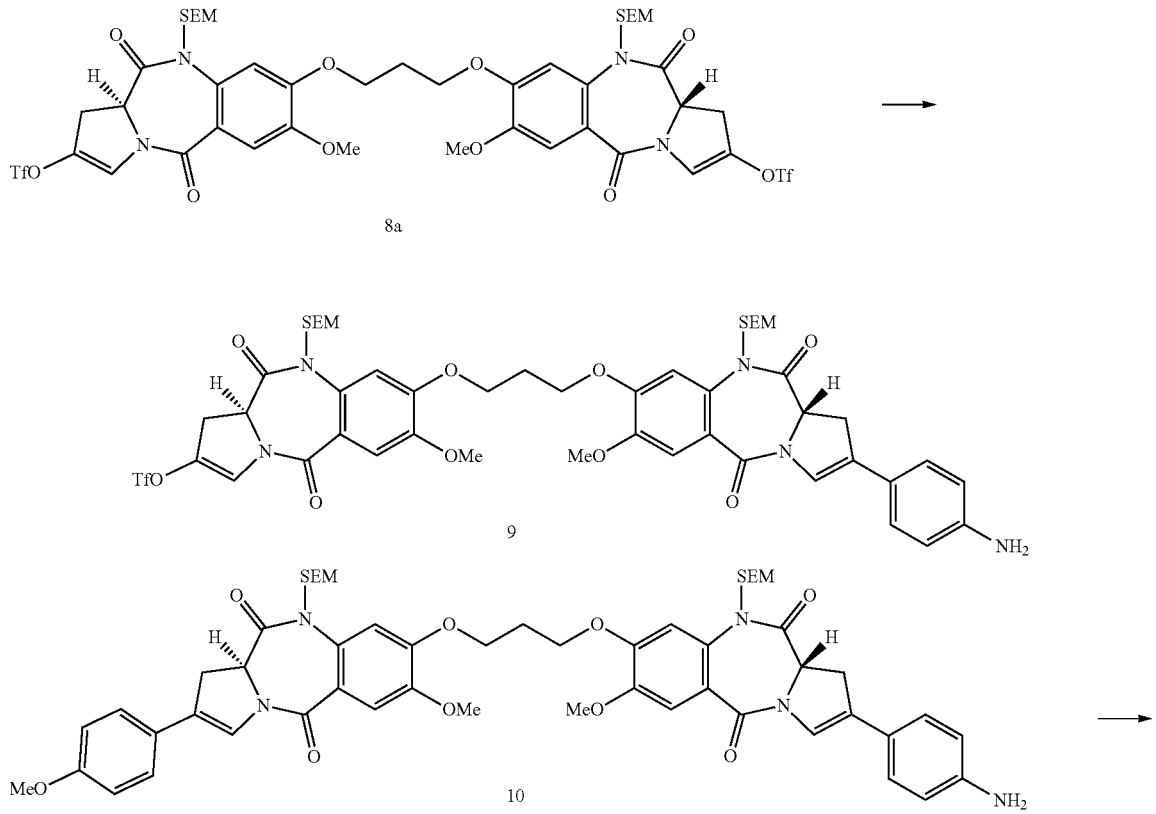

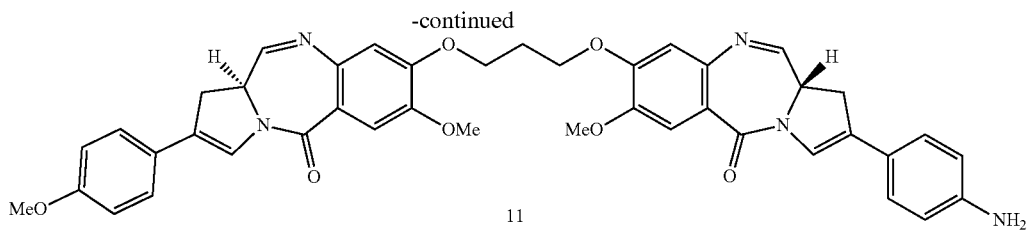

(a) (S)-2-(4-aminophenyl)-7-methoxy-8-(3-((S)-7-methoxy-2-(trifluoromethylsulfonyl)-5,11-dioxo-10-((2-(trimethylsilyl)ethoxy)methyl)-5,10,11,11a-tetrahydro-1H-pyrrolo[2,1-c][1,4]benzodiazepin-8-yloxy)propoxy)-10-((2-(trimethylsilyl)ethoxy)methyl)-1H-pyrrolo[2,1-c][1,4]benzodiazepine-5,1(10H,11aH)-dione (9)

Solid Pd(PPh$_3$)$_4$ (20.18 mg, 17.46 mmol) was added to a stirred solution of the triflate 8a (975 mg, 0.87 mmol), 4-(4,4,5,5-tetramethyl-1,3,2-dioxaboralane-2-yl)aniline (172 mg, 0.79 mmol) and Na$_2$CO$_3$ (138 mg, 3.98 mol) in toluene (13 mL) EtOH (6.5 mL) and H$_2$O (6.5 mL). The dark solution was allowed to stir under a nitrogen atmosphere for 24 hours, after which time analysis by TLC (EtOAc) and LC/MS revealed the formation of the desired mono-coupled product and as well as the presence of unreacted starting material. The solvent was removed by rotary evaporation under reduced pressure and the resulting residue partitioned between H$_2$O (100 mL) and EtOAc (100 mL), after eventual separation of the layers the aqueous phase was extracted again with EtOAc (2×25 mL). The combined organic layers were washed with H$_2$O (50 mL), brine (60 mL), dried (MgSO$_4$), filtered and evaporated in vacuo to provide the crude Suzuki product. The crude Suzuki product was subjected to flash chromatography (40% EtOAc/60% Hexane→70% EtOAc, 30% Hexane). Removal of the excess eluent by rotary evaporation under reduced pressure afforded the desired product 9 (399 mg) in 43% yield.

$^1$H-NMR: (CDCl$_3$, 400 MHz) δ 7.40 (s, 1H), 7.33 (s, 1H), 7.27 (bs, 3H), 7.24 (d, 2H, J=8.5 Hz), 7.15 (t, 1H, J=2.0 Hz), 6.66 (d, 2H, J=8.5 Hz), 5.52 (d, 2H. J=10.0 Hz), 4.77 (d, 1H, J=10.0 Hz), 4.76 (d, 1H, J=10.0 Hz), 4.62 (dd, 1H, J=3.7, 11.0 Hz), 4.58 (dd, 1H, J=3.4, 10.6 Hz), 4.29 (t, 4H, J=5.6 Hz), 4.00-3.85 (m, 8H), 3.80-3.60 (m, 4H), 3.16 (ddd, 1H, J=2.4, 11.0, 16.3 Hz), 3.11 (ddd, 1H, J=2.2, 10.5, 16.1 Hz), 2.43 (p, 2H, J=5.9 Hz), 1.1-0.9 (m, 4H), 0.2 (s, 18H). $^{13}$C-NMR: (CDCl$_3$, 100 MHz) δ 169.8, 168.3, 164.0, 162.7, 153.3, 152.6, 149.28, 149.0, 147.6, 139.6, 134.8, 134.5, 127.9 (methine), 127.5, 125.1, 123.21, 121.5, 120.5 (methine), 120.1 (methine), 116.4 (methine), 113.2 (methine), 108.7 (methine), 79.8 (methylene), 79.6 (methylene), 68.7 (methylene), 68.5 (methylene), 67.0 (methylene), 66.8 (methylene), 58.8 (methine), 58.0 (methine), 57.6 (methoxy), 32.8 (methylene), 32.0 (methylene), 30.3 (methylene), 19.7 (methylene), 0.25 (methyl).

(b) (S)-2-(4-aminophenyl)-7-methoxy-8-(3-((S)-7-methoxy-2-(4-methoxyphenyl)-5,11-dioxo-10-((2-(trimethylsilyl)ethoxy)methyl)-5,10,11,11a-tetrahydro-1H-pyrrolo[2,1-c][1,4]benzodiazepin-8-yloxy)propoxy)-10-((2-(trimethylsilyl)ethoxy)methyl)-1H-pyrrolo[2,1-c][1,4]benzodiazepine-5,11(10H,11aH)-dione (10)

Solid Pd(PPh$_3$)$_4$ (10 mg, 8.69 μmol) was added to a stirred solution of the mono-triflate 9 (230 mg, 0.22 mmol) in toluene (3 mL), EtOH (10 mL), with 4-methoxyphenyl boronic acid (43 mg, 0.28 mmol), Na$_2$CO$_3$ (37 mg, 0.35 mmol), in H$_2$O (1.5 mL) at room temperature. The reaction mixture was allowed to stir under a nitrogen atmosphere for 20 h, at which point the reaction was deemed complete as judged by LC/MS and TLC (EtOAc). The solvent was removed by rotary evaporation under reduced pressure in vacuo and the resulting residue partitioned between EtOAc (75 mL) and H$_2$O (75 mL). The aqueous phase was extracted with EtOAc (3×30 mL) and the combined organic layers washed with H$_2$O (30 mL), brine (40 mL), dried (MgSO$_4$), filtered and evaporated to provide the crude product. The crude product was purified by flash chromatography (60% Hexane: 40% EtOAc→80% EtOAc: 20% Hexane) to provide the pure dimer as an orange foam. Removal of the excess eluent under reduced pressure afforded the desired product 10 (434 mg) in 74% yield.

$^1$H-NMR: (CDCl$_3$, 400 MHz) δ7.38 (s, 2H), 7.34 (d, 2H, J=8.8 Hz), 7.30 (bs, 1H), 7.26-7.24 (m, 3H), 7.22 (d, 2H, J=8.5 Hz), 6.86 (d, 2H, J=8.8 Hz), 6.63 (d, 2H, J=8.5 Hz), 5.50 (d, 2H, J=10.0 Hz), 4.75 (d, 1H, J=10.0 Hz), 4.74 (d, 1H, J=10.0 Hz), 4.56 (td, 2H, J=3.3, 10.1 Hz), 4.27 (t, 2H, J=5.7 Hz), 4.00-3.85 (m, 8H), 3.80 (s, 3H), 3.77-3.60 (m, 4H), 3.20-3.00 (m, 2H), 2.42 (p, 2H, J=5.7 Hz), 0.96 (t, 4H, J=8.3 Hz), 0.00 (s, 18H). $^{13}$C-NMR: (CDCl$_3$, 100 MHz) δ 169.8, 169.7, 162.9, 162.7, 160.6, 152.7, 152.6, 149.0, 147.5, 134.8, 127.8 (methine), 127.4, 126.8, 125.1, 123.1, 123.0, 121.5 (methine), 120.4 (methine), 116.4 (methine), 115.5 (methine), 113.1 (methine), 108.6 (methine), 79.6 (methylene), 68.5 (methylene), 66.9 (methylene), 58.8 (methine), 57.6 (methoxy), 56.7 (methoxy), 32.8 (methylene), 30.3 (methylene), 19.7 (methylene), 0.0 (methyl).

(c) (S)-2-(4-aminophenyl)-7-methoxy-8-(3-((S)-7-methoxy-2-(4-methoxyphenyl)-5-oxo-5,11a-dihydro-1H-pyrrolo[2,1-c][1,4]benzodiazepin-8-yloxy)propoxy)-1H-pyrrolo[2,1-c][1,4]benzodiazepine-5 (11aH)-one (11)

Fresh LiBH$_4$ (183 mg, 8.42 mmol) was added to a stirred solution of the SEM-dilactam 10 (428 mg, 0.42 mmol) in THF (5 mL) and EtOH (5 mL) at room temperature. After 10 minutes, delayed vigorous effervescence was observed requiring the reaction vessel to be placed in an ice bath. After removal of the ice bath the mixture was allowed to stir at room temperature for 1 hour. LC/MS analysis at this point revealed total consumption of starting material with very little mono-reduced product. The reaction mixture was poured onto ice (100 mL) and allowed to warm to room temperature with stirring. The aqueous mixture was extracted with DCM (3×30 mL) and the combined organic layers washed with H$_2$O (20 mL), brine (30 mL) and concentrated in vacuo. The resulting residue was treated with DCM (5 mL), EtOH (14 mL), H$_2$O (7 mL) and silica gel (10 g). The viscous mixture was allowed to stir at room temperature for 3 days. The mixture was filtered slowly through a sinter funnel and the silica residue washed with 90% CHCl$_3$: 10% MeOH (~250 mL) until UV activity faded completely from the eluent. The organic phase was washed with H$_2$O (50 mL), brine 60 mL), dried (MgSO$_4$) filtered and evaporated in vacuo to provide the crude material. The crude product was purified by flash chromatography (97% CHCl$_3$: 3% MeOH) to provide the pure C$_2$/C$_2$' aryl PBD dimer 11 (185 mg) 61% yield.

$^1$H-NMR: (CDCl$_3$, 400 MHz) δ7.88 (d, 1H, J=4.0 Hz), 7.87 (d, 1H, J=4.0 Hz), 7.52 (s, 2H), 7.39 (bs, 1H), 7.37-7.28 (m, 3H), 7.20 (d, 2H, J=8.5 Hz), 6.89 (d, 2H, J=8.8 Hz), 6.87 (s, 1H), 6.86 (s, 1H), 6.67 (d, 2H, J=8.5 Hz), 4.40-4.20 (m, 6H), 3.94 (s, 6H), 3.82 (s, 3H), 3.61-3.50 (m, 2H), 3.40-3.30 (m, 2H), 2.47-2.40 (m, 2H). $^{13}$C-NMR: (CDCl$_3$, 100 MHz) δ 162.5 (imine methine), 161.3, 161.1, 159.3, 156.0, 151.1, 148.1, 146.2, 140.3, 126.2 (methine), 123.2, 122.0, 120.5 (methine), 119.4, 115.2 (methine), 114.3 (methine), 111.9 (methine), 111.2 (methine), 65.5 (methylene), 56.2 (methoxy), 55.4 (methoxy), 53.9 (methine), 35.6 (methylene), 28.9 (methylene).

Example 2

4-(4,4,5,5-tetramethyl-1,3,2-dioxaboralan-2-yl)aniline (0.203 g, 0.93 mmol) and Na$_2$CO$_3$ (0.056 g, 0.53 mmol) were added followed by solid Pd(PPh$_3$)$_4$ (10 mg, 8.6 µmol). The reaction mixture was allowed to stir under a nitrogen atmosphere for a further 20 hours. LC/MS indicated the formation of desired product. EtOAc (100 mL) and H$_2$O (100 mL) were added, the aqueous was separated and extracted with EtOAc (3×30 mL). The combined organic layers were washed with H$_2$O (100 mL), brine (100 mL), dried (MgSO$_4$), filtered and evaporated to provide a dark brown oil. The oil was dissolved in DCM and loaded onto a 10 g SCX-2 cartridge pre-equilibrated with DCM (1 vol). The cartridge was washed with DCM (3 vol), MeOH (3 vol) and the crude product eluted with 2M NH$_3$ in MeOH (2 vol). Flash chromatography (50% n-hexane: 50% EtOAc—20% n-hexane: 80% EtOAc) provided the pure dimer 12 as a yellow foam (0.16 g, 34%).

Analytical Data: $[\alpha]^{23}_D$=+3880 (C=0.22, CHCl$_3$); $^1$H-NMR: (CDCl$_3$, 400 MHz) δ 7.39 (s, 2H), 7.35 (d, 2H, J=12.8 Hz), 7.32 (bs, 1H), 7.26-7.23 (m, 5H), 6.89 (d, 2H, J=8.8 Hz), 6.66 (d, 2H, J=8.5 Hz), 5.55 (d, 2H, J=10.0 Hz), 4.73 (d, 1H, J=10.0 Hz), 4.72 (d, 1H, J=10.0 Hz), 4.62 (td,

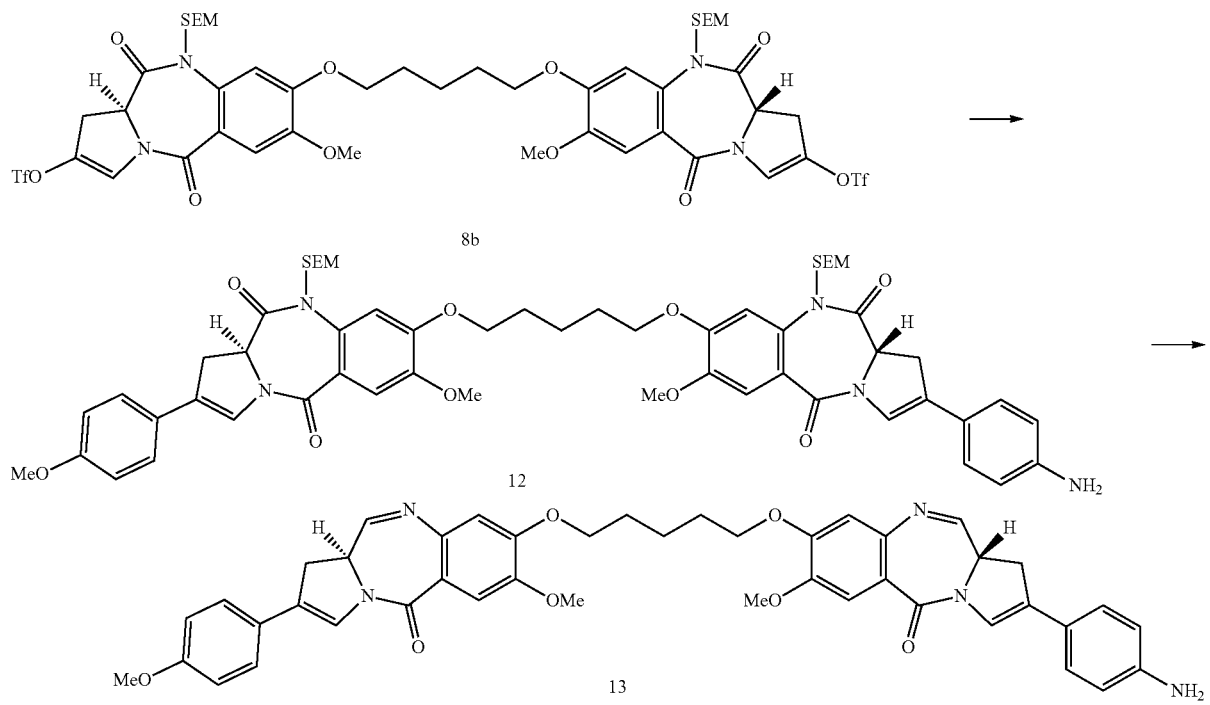

(a) (S)-2-(4-aminophenyl)-7-methoxy-8-(5-((S)-7-methoxy-2-(4-methoxyphenyl)-5,11-dioxo-10-((2-(trimethylsilyl)ethoxy)methyl)-5,10,11,11a-tetrahydro-1H-pyrrolo[2,1-c][1,4]benzodiazepin-8-yloxy)pentyloxy)-10-((2-(trimethylsilyl)ethoxy)methyl)-1H-pyrrolo[2,1-c][1,4]benzodiazepine-5,11(10H,11aH)-dione (12)

Solid Pd(PPh$_3$)$_4$ (32 mg, 27.7 µmol) was added to a stirred solution of the bis-triflate 8b (1.04 g, 0.91 mmol) in toluene (10 mL), EtOH (5 mL), with 4-methoxyphenyl boronic acid (0.202 g, 1.32 mmol), Na$_2$CO$_3$ (0.169 g, 1.6 mmol), in H$_2$O (5 mL) at 30° C. The reaction mixture was allowed to stir under a nitrogen atmosphere for 20 hours. Additional solid 2H, J=3.2, 10.4 Hz), 4.15-4.05 (m, 4H), 4.00-3.85 (m, 8H), 3.82 (s, 3H), 3.77-3.63 (m, 4H), 3.20-3.05 (m, 2H), 2.05-1.95 (m, 4H), 1.75-1.67 (m, 2H) 1.01-0.95 (m, 4H), 0.03 (s, 18H); MS (ES$^+$) m/z (relative intensity) 1047 ([M+H]$^+$, 45).

(b) (S)-2-(4-aminophenyl)-7-methoxy-8-(5-((S)-7-methoxy-2-(4-methoxyphenyl)-5-oxo-5,11a-dihydro-1H-pyrrolo[2,1-c][1,4]benzodiazepin-8-yloxy)pentyloxy)-H-pyrrolo[2,1-c][1,4]benzodiazepine-5(11aH)-one (13)

Fresh LiBH$_4$ (66 mg, 3.04 mmol) was added to a stirred solution of the SEM-dilactam 12 (428 mg, 0.42 mmol) in THF (3 mL) and EtOH (3 mL) at 0° C. (ice bath). The ice bath was removed and the reaction mixture was allowed to reach room temperature (vigorous effervescence). After 2 hours LC/MS analysis indicated the complete consumption of starting material. The reaction mixture was poured onto ice (50 mL) and allowed to warm to room temperature with stirring. The aqueous mixture was extracted with DCM 3.50 (m, 2H), 3.45-3.3 (m, 2H), 2.05-1.9 (m, 4H), 1.75-1.65 (m, 2H); MS (ES$^+$) (relative intensity) 754.6 ([M+H]$^+$, 100), (ES$^+$) (relative intensity) 752.5 ([M−H]$^−$, 100).

Example 3

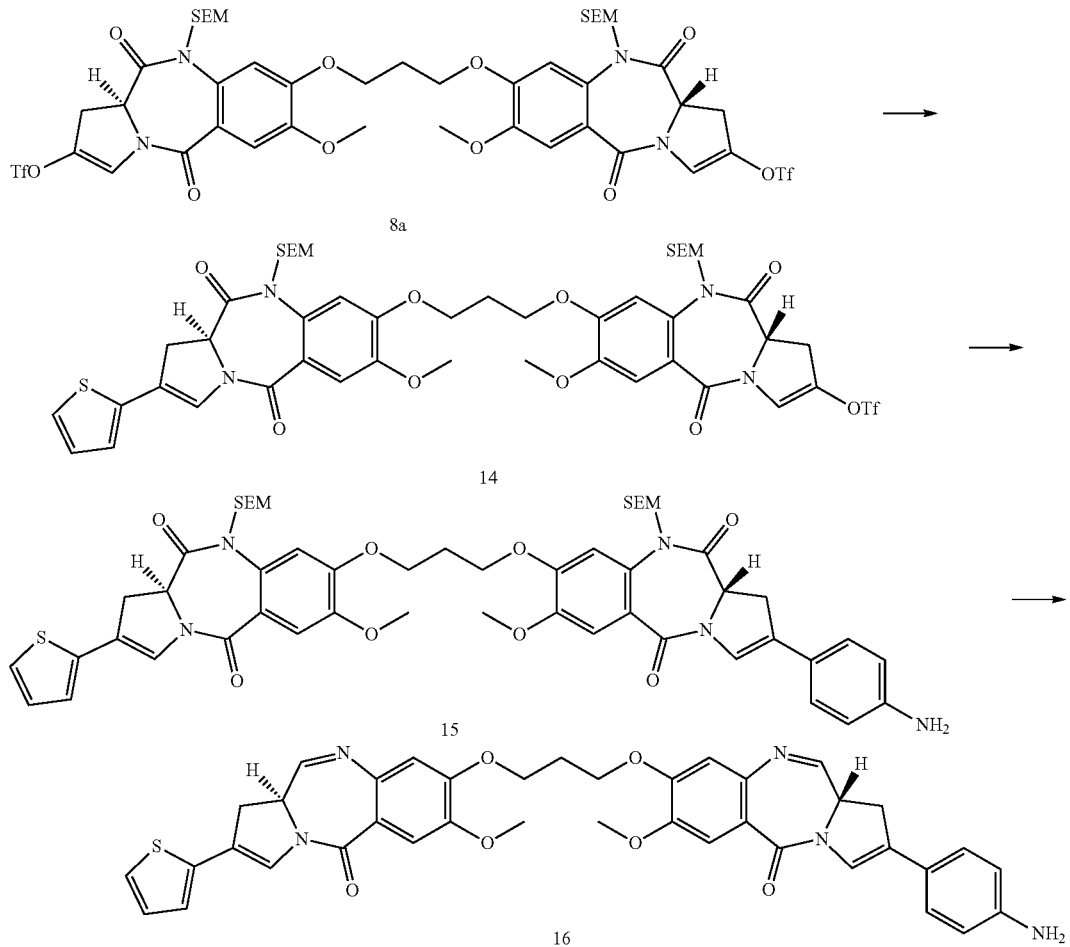

(3×50 mL) and the combined organic layers washed with H$_2$O (50 mL), brine (50 mL), dried (MgSO$_4$) and concentrated in vacuo. The resulting residue was treated with DCM (2 mL), EtOH (5 mL), H$_2$O (2.5 mL) and silica gel (3.7 g). The viscous mixture was allowed to stir at room temperature for 3 days. The mixture was filtered through a sinter funnel and the silica residue washed with 90% CHCl$_3$: 10% MeOH (~250 mL) until UV activity faded completely from the eluent. The organic phase was dried (MgSO$_4$) filtered and evaporated in vacuo to provide the crude material. The crude product was purified by flash chromatography (99.5% CHCl$_3$: 0.5% MeOH to 97.5% CHCl$_3$: 2.5% MeOH in 0.5% increments)) to provide the pure C$_2$/C$_2$' aryl PBD dimer 13 (59 mg, 52%).

Analytical Data: [α]$^{28}_D$=+760° (c=0.14, CHCl$_3$); $^1$H NMR (400 MHz, CDCl$_3$) δ 7.89 (d, 1H, J=4.0 Hz), 7.87 (d, 1H, J=4.0 Hz), 7.52 (s, 2H), 7.39 (bs, 1H), 7.37-7.28 (m, 3H), 7.22 (d, 2H, J=8.4 Hz), 6.91 (d, 2H, J=8.8 Hz), 6.815 (s, 1H), 6.81 (s, 1H), 6.68 (d, 2H, J=8.4 Hz), 4.45-4.35 (m, 2H), 4.2-4.0 (m, 4H), 3.94 (s, 6H), 3.85-3.7 (s, 3H), 3.65-

(a)(S)-2-(thien-2-yl)-7-methoxy-8-(3-((S)-7-methoxy-2-(trifluoromethanesulfonyloxy)-5,11-dioxo-10-((2-(trimethylsilyl)ethoxy)methyl)-5,10,11,11a-tetrahydro-1H-pyrrolo[2,1-c][1,4] benzodiazepin-8-yloxy)propyloxy)-10-((2-(trimethylsilyl)ethoxy)methyl)-1H-pyrrolo[2,1-c][1,4]benzodiazepine-5,11(10H,11aH)-dione (14)

Solid Pd(PPh$_3$)$_4$ (41 mg, 0.036 mmol) was added to a stirred solution of the bis-triflate 8a (1 g, 0.9 mmol) in toluene (10 mL), EtOH (5 mL), with thien-2-yl boronic acid (149 mg, 1.16 mmol), Na$_2$CO$_3$ (152 mg, 1.43 mmol), in H$_2$O (5 mL). The reaction mixture was allowed to stir under a nitrogen atmosphere overnight at room temperature. The solvent was removed by evaporation in vacuo and the resulting residue partitioned between H$_2$O (100 mL) and EtOAc (100 mL). The aqueous layer was extracted with EtOAc (2×30 mL) and the combined organic layers washed with H$_2$O (50 mL), brine (50 mL) dried (MgSO$_4$), filtered and evaporated in vacuo to provide the crude product which was purified by flash chromatography (80 hexane: 20 EtOAc→50 hexane: 50 EtOAc) to provide the dimer 14 (188 mg, 20%) yield Analytical data: LC-MS RT 4.27 mins, 1051 (M+H); $^1$H-NMR (400 MHZ, CDCl$_3$) δ 7.36 (s, 1H), 7.31 (bs, 1H), 7.27 (bs, 1H), 7.26-7.23 (m, 2H), 7.22-7.17 (m, 1H), 7.12 (bs, 1H), 7.02-6.96 (m, 2H), 5.50 (d, J=10.0 Hz, 2H), 7.75 (d, J=10.0 Hz, 2H), 4.65-4.55 (m, 2H), 4.37-4.13 (m, 4H), 4.00-3.85 (m, 8H), 3.8-3.6 (m, 4H), 3.20-3.10 (m, 2H), 2.50-2.35 (m, 2H), 1.0-0.9 (m, 4H), 0 (s, 18H).

(b) (S)-2-(thien-2-yl)-7-methoxy-8-(3-((S)-7-methoxy-2-(trifluoromethanesulfonyloxy)-5,11-dioxo-10-((2-(trimethylsilyl)ethoxy)methyl)-5,10,11,11a-tetrahydro-1H-pyrrolo[2,1-c][1,4]benzodiazepin-8-yloxy)pentyloxy)-10-((2-(trimethylsilyl)ethoxy)methyl)-1H-pyrrolo[2,1-c][1,4]benzodiazepine-5,11(10H,11aH)-dione (15)

Solid Pd(PPh$_3$)$_4$ (7.66 mg, 6.63 μmol) was added to a stirred, cloudy solution of 14 (174 mg, 0.17 mmol), Na$_2$CO$_3$ (28 mg, 0.22 mmol) and 4-(4,4,5,5-tetramethyl-1,3,2-dioxaborolan-2-yl)aniline (47 mg, 0.22 mmol) in toluene (2-5 mL), EtOH (1.25 mL) and H$_2$O (125 mL) at room temperature. The reaction mixture was allowed to stir under a N$_2$ atmosphere for 24 hours at which point the reaction was deemed complete by LC/MS major peak (@ 3.97 min, FW=1016, M+Na) and TLC (EtOAc). The solvent was removed by evaporation in vacuo and the resulting residue partitioned between EtOAc (60 mL) and H$_2$O (30 mL). The layers were separated and the organic phase was washed with H$_2$O) (20 mL), brine (30 mL) dried (MgSO$_4$) filtered and evaporated in vacuo to provide the crude product 123 mg, 75% yield.

Analytical data: LC-MS RT 3.98 mins, 100% area, 994 (M+H); $^1$H-NMR (400 MHZ, CDCl$_3$) δ 7.40 (d, J=5.3 Hz, 2H), 7.30 (t, J=1.70 Hz, 1H), 7.29-7.27 (m, 3H), 7.25 (d, J=8.5 Hz, 2H), 7.21 (dd, J=1.4, 4.73 Hz, 1H), 7.03-6.97 (m, 2H), 6.66 (d, J=8.5 Hz, 2H), 5.52 (d, J=10.0 Hz, 2H), 4.78 (d, J=10.0 Hz, 1H), 4.77 (d, J=10.0 Hz, 1H), 4.62 (dd, J=3.4, 10.5 Hz, 1H), 4.59 (dd, J=3.40, 10.6 Hz, 1H), 4.30 (t, J=5.85 Hz, 4H), 3.85-4.03 (m, 8H), 3.84-3.64 (m, 6H), 3.18 (ddd, J=2.2, 10.5, 16.0 Hz, 1H), 3.11 (ddd, J=2.2, 10.5, 16.0 Hz, 1H), 2.44 (p, J=5.85 Hz, 2H), 0.98 (t, J=1.5 Hz, 4H), 0 (s, 18H).

(c) (S)-2-(thien-2-yl)-7-methoxy-8-(3-((S)-7-methoxy-2-(4-aminophenyl)-5-oxo-5,11a-dihydro-1H-pyrrolo[2,1-c][1,4]benzodiazepine-8-yloxy)propyloxy)-1H-pyrrolo[2,1-c][1,4]benzodiazepine-5(11aH)-one (16)

Fresh LiBH$_4$ (47 mg, 2.22 mmol) was added to a stirred solution of the SEM-dilactam 15 (110 mg, 0.11 mmol) in dry THF (3 mL) and EtOH (3 mL) at 0° C. (ice bath). The ice bath was removed and the reaction mixture stirred under a N$_2$ atmosphere for 1 hour. Analysis of the reaction by LC/MS analysis revealed significant formation of the desired product (Pk @ 2.57 min) (1=69.32), FW=702, M+H) and half-imine. The reaction mixture was allowed to stir for a further 1 hour after which time no further reaction progress was observed by LC/MS. The reaction mixture was poured onto ice, stirred and allowed to warm to room temperature. Following partition between DCM (50 mL) and water (50 mL), the aqueous phase was extracted with DCM (3×20 mL). The combined organic layers were washed with H$_2$O (50 mL), brine (50 mL) and the solvent removed by evaporation in vacuo under reduced pressure.

The resulting residue was dissolved in DCM (5 mL), EtOH (15 mL) and H$_2$O (7 mL) then treated with silica gel (5 g). The reaction was allowed to stir at room temperature for 48 h. The silica was removed by filtration through a sinter funnel and the residue rinsed with 90:10 CHCl$_3$: MeOH (100 mL). H$_2$O (50 mL) was added to the filtrate and the layers were separated (after shaking). The aqueous layer was extracted with CHCl$_3$ (2×30 mL) and H$_2$O (50 mL), brine (50 mL), dried (MgSO$_4$) filtered and evaporated in vacuo to provide the crude product. Flash chromatography (CHCl$_3$→98% CHCl$_3$: 2% MeOH) afforded the product (41 mg, 53%).

Analytical data: LC-MS RT 2.55 mins, 702 (M+H)

Example 4

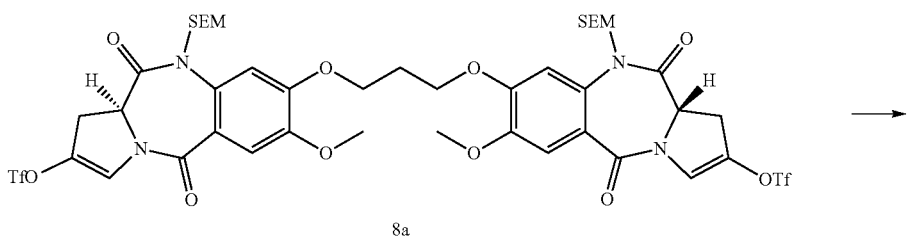

8a

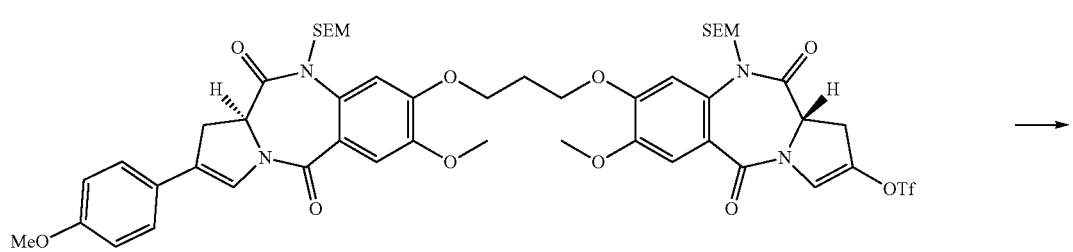

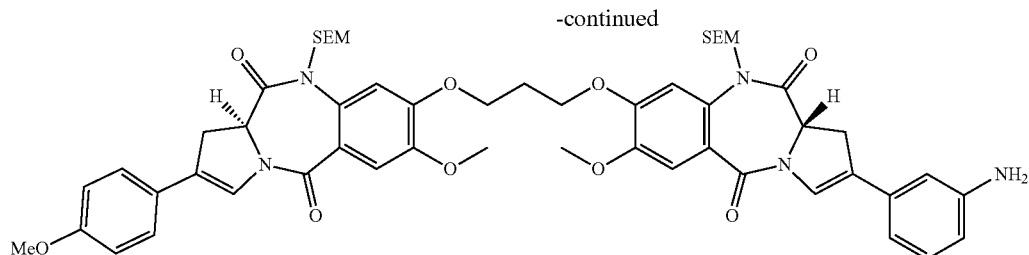
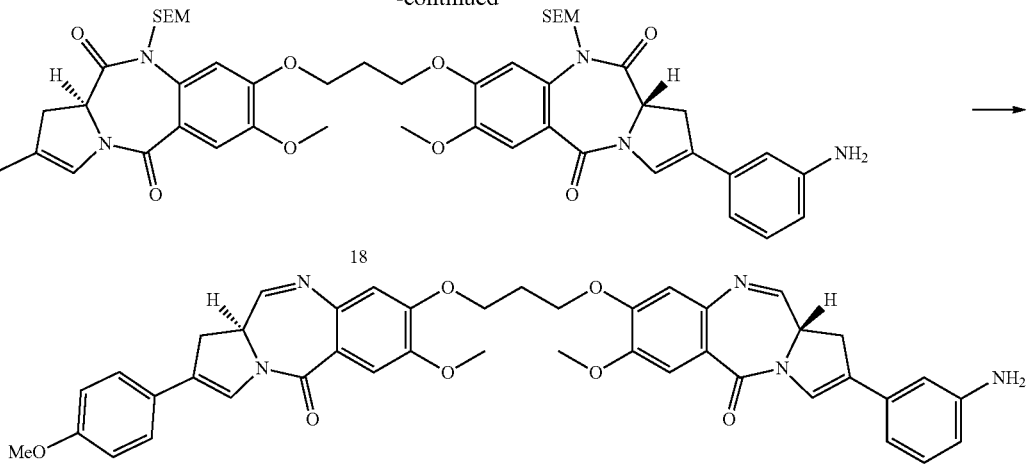

(a) (S)-2-(4-methoxyphenyl)-7-methoxy-8-(3-((S)-7-methoxy-2-(trifluoromethylsulphonyl)-5,11-dioxo-10-((2-(trimethylsilyl)ethoxy)methyl)-5,10,11,11a-tetrahydro-1H-pyrrolo[2,1-c][1,4]benzodiazepin-8-yloxy)propyloxy)-10-((2-(trimethylsilyl)ethoxy)methyl)-1H-pyrrolo[2,1-c][1,4]benzodiazepine-5,11(10H,11aH)-dione (17)

Solid 4-methoxybenzeneboronic acid (0.388 g, 2.55 mmol) was added to a solution of the SEM protected bis triflate (8a)(3.0 g, 2.69 mmol), sodium carbonate (426 mg, 4.02 mmol) and palladium tetrakis triphenylphosphine (0.08 mmol) in toluene (54.8 mL), ethanol (27 mL) and water (27 mL). The reaction mixture was allowed to stir at room temperature for 3 hours. The reaction mixture was then partitioned between ethyl acetate and water. The organic layer was washed with water and brine and dried over magnesium sulphate. Excess solvent was removed by rotary evaporation under reduced pressure and the resulting residue was subjected to flash column chromatography (silica gel; gradient elution EtOAc/hexane 30/70→35/65→40/60→45/55) to remove unreacted bis-triflate (0.6 g). Removal of excess eluent from selected fractions afforded the 4-methoxyphenyl coupled product (1.27 g, 1.18 mmol, 41%).

LC-MS RT 4.30 mins, 1076 (M+H); $^1$H-NMR (400 MHZ, CDCl$_3$) δ 7.41 (s, 1H), 7.39 (d, J=8.8 Hz, 2H), 7.35 (s, 1H), 7.34 (bs, 1H), 7.29 (s, 1H), 7.16 (t, J=1.9 Hz, 1H), 6.90 (d, J=8.8 Hz, 2H), 5.53 (d, J=10.0 Hz, 2H), 4.79 (d, J=10.0 Hz, 1H), 4.78 (d, J=10.0 Hz, 1H), 4.66-4.60 (m, 2H), 4.30 (t, J=5.7 Hz, 4H), 4.0-3.94 (m, 2H), 3.93 (s, 3H), 3.92 (s, 3H), 3.84 (s, 3H), 3.83-3.60 (m, 4H), 3.22-3.10 (m, 2H), 2.45 (t, J=5.9 Hz, 2H), 1.05-0.94 (m, 4H), 0 (s, 18H).

(b) (S)-2-(3-aminophenyl)-7-methoxy-8-(3-((S)-7-methoxy-2-(4-methoxyphenyl)-5,11-dioxo-10-((2-(trimethylsilyl)ethoxy)methyl)-5,10,11,11a-tetrahydro-1H-pyrrolo[2,1-c][1,4]benzodiazepin-8-yloxy)propyloxy)-10-((2-(trimethylsilyl)ethoxy)methyl)-1H-pyrrolo[2,1-c][1,4]benzodiazepine-5,11(10H,11aH)-dione (18)

Solid 3-aminobenzeneboronic acid (0.143 g, 0.92 mmol) was added to a solution of the mono triflate (17)(0.619 g, 0.58 mmol), sodium carbonate (195 mg, 1.84 mmol) and palladium tetrakis triphenylphosphine (26.6 mg, 0.023 mmol) in toluene (10 mL), ethanol (5 mL) and water (5 mL). The reaction mixture was allowed to stir at room temperature for overnight at 30° C. The reaction mixture was then partitioned between ethyl acetate and water. The organic layer was washed with water and brine and dried over magnesium sulphate. Excess solvent was removed by rotary evaporation under reduced pressure and the resulting residue was subjected to flash column chromatography (silica gel; gradient elution EtOAc/hexane 70/30→85/15). Removal of excess eluent from selected fractions afforded the desired product (0.502 g, 0.49 mmol, 85%).

LC-MS RT 4.02 mins, 1019 (M+H); $^1$H-NMR (400 MHZ, CDCl$_3$) δ 7.38-7.35 (m, 4H), 7.33 (bs, 1H), 7.30 (bs, 1H), 7.25 (s, 2H), 7.10 (t, J=7.8 Hz, 1H), 6.88-6.80 (m, 3H), 6.72 (bs, 1H), 6.57 (dd, J=7.9, 1.8 Hz, 1H), 5.50 (d, J=10.0 Hz, 2H), 4.75 (d, 10.0 Hz, 2H), 4.58 (dd, J=10.6, 3.3 Hz, 2H), 4.27 (t, J=5.8 Hz, 4H), 3.95-3.91 (m, 2H), 3.90 (s, 6H), 3.80 (s, 3H), 3.77-3.60 (m, 6H), 3.15-3.05 (m, 2H), 2.41 (p, J=5.8 Hz, 2H), 0.95 (t, =8.25 Hz, 4H), 0 (s, 18H).

(c) (S)-2-(3-aminophenyl)-7-methoxy-8-(3-((S)-7-methoxy-2-(4-methoxyphenyl)-5-oxo-5,11a-dihydro-1H-pyrrolo[2,1-c][1,4]benzodiazepin-8-yloxy)propyloxy)-1H-pyrrolo[2,1-c][1,4]benzodiazepine-5(11aH)-one (19)

A solution of superhydride (0.56 mL, 0.56 mmol, 1.0 M in THF) was added dropwise to a solution of the SEM dilactam (18)(0.271 g, 0.27 mmol) in dry THF (10 mL) at −78° C. under a nitrogen atmosphere. After 1 hr a further aliquot of superhydride solution (0.13 ml, 0.13 mmol) was added and the reaction mixture was allowed to stir for another 0.5 hr, at which time LC-MS indicated that reduction was complete. The reaction mixture was diluted with water and allowed to warm to room temperature. The reaction mixture was partitioned between chloroform and water, the layers were separated and the aqueous layer extracted with additional chloroform (emulsions). Finally the combined organic phase was washed with brine and dried over magnesium sulphate. The reduced product was dissolved in methanol, chloroform and water and allowed to stir in the presence of silica gel for 72 hours. The crude product was subjected to flash column chromatography (methanol/chloroform gradient) to afford the desired imine product (150 mg, 0.21 mmol, 77%) after removal of excess eluent from selected fractions.
LC-MS RT 2.63 mins, 97% area, 726 (M+H); ¹H-NMR (400 MHZ, CDCl₃) δ 7.85 (d, J=3.9 Hz, 1H), 7.84 (d, J=3.9 Hz, 1H), 7.50 (s, 1H), 7.49 (s, 1H), 7.42 (s, 1H), 7.36 (s, 1H), 7.32 (d, J=7.3 Hz, 2H), 7.11 (t, (d, J=7.8 Hz, 1H), 6.90-6.80 (m, 4H), 6.77 (d, J=7.9 Hz, 1H), 4.40-4.20 (m, 6H), 3.92 (s, 6H), 3.80 (s, 3H), 3.60-3.27 (m, 6H), 2.48-2.29 (m, 2H)
Example 5
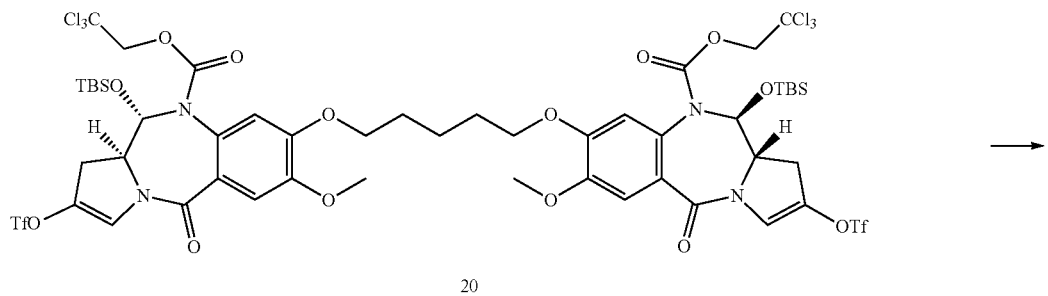
20
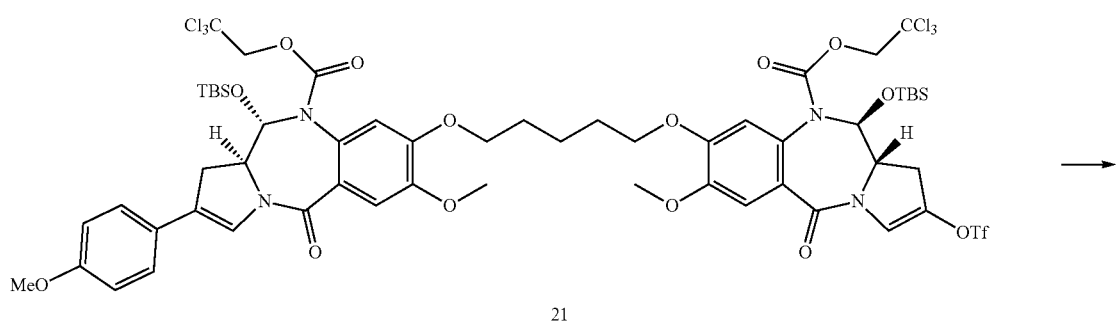
21
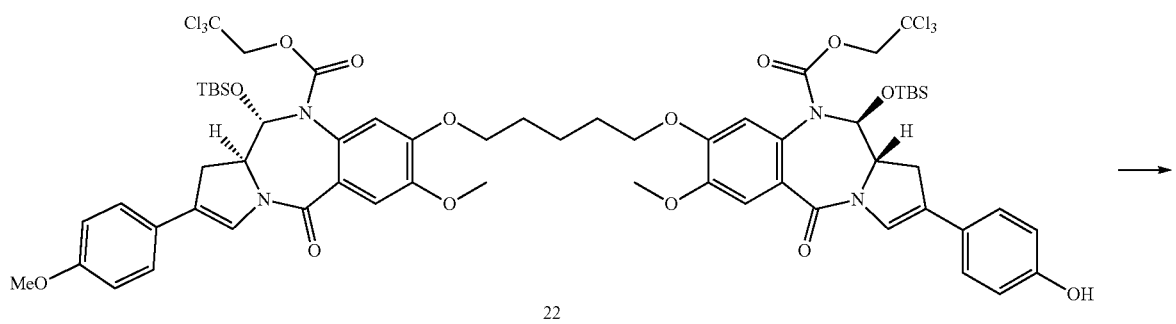
22
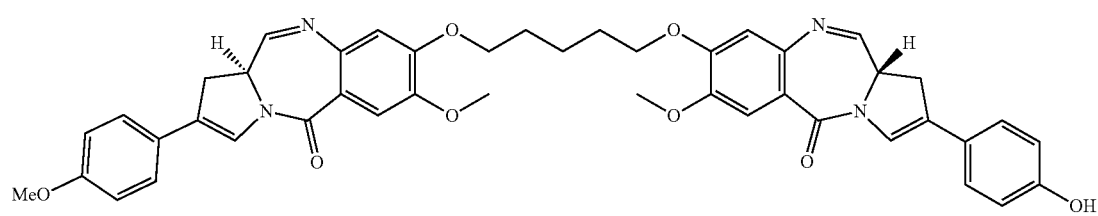
23

(a) (11S,11aS)-2,2,2-trichloroethyl 11-(tert-butyldimethylsilyloxy)-8-(5-((11S,11aS)-11-(tert-butyldimethylsilyloxy)-7-methoxy-2-(4-methoxyphenyl)-5-oxo-10-((2,2,2-trichloroethoxy)carbonyl)-5,10,11,11a-tetrahydro-1H-pyrrolo [2,1-c][1,4]benzodiazepin-8-yloxy)pentyloxy)-7-methoxy-5-oxo-2-(trifluoromethylsulfonyloxy)-11,11a-dihydropyrrolo[2,1-c][1,4]benzodiazepine-10(5H)-carboxylate 21

Solid 4-methoxybenzeneboronic acid (59 mg, 0.39 mmol) was added to a solution of the Troc protected bis triflate (Compound 44, WO 2006/111759) (600 mg, 0.41 mmol), sodium carbonate (65 mg, 0.61 mmoml) and palladium tetrakis triphenylphosphine (0.012 mmol) in toluene (10.8 mL), ethanol (5.4 mL) and water (5.4 mL). The reaction mixture was allowed to stir at room temperature overnight. The reaction mixture was then partitioned between ethylacetate and water. The organic layer was washed with water and brine and dried over magnesium sulphate. Excess solvent was removed by rotary evaporation under reduced pressure and the resulting residue was subjected to flash column chromatography (silica gel; gradient elution EtOAc/hexane 20/80→30/70→40/60→60/40) to remove unreacted bis-triflate. Removal of excess eluent from selected fractions afforded the 4-methoxyphenyl coupled product (261 mg, 0.18 mmol, 46%).

LC-MS RT 4.17 mins, 1427 (M+H); $^1$H-NMR (400 MHZ, CDCl$_3$) δ 7.38 (s, 1H), 7.33 (s, 1H), 7.31 (s, 1H), 7.30 (s, 1H), 7.25 (s, 1H), 7.20 (bs, 1H), 6.92 (d, J=8.6 Hz, 2H), 6.77 (d, J=8.7 Hz, 2H), 6.0-5.90 (m, 2H), 5.25 (d, J=12.0 Hz, 1H), 5.24 (d, J=12.0 Hz, 1H), 4.24 (d, J=12.0 Hz, 1H), 4.22 (d, J=12.0 Hz, 1H), 4.18-4.08 (m, 2H), 4.07-3.89 (m, 10H), 3.81 (s, 3H), 3.44-3.25 (m, 2H), 2.85 (d, J=16.6 Hz, 2H), 2.05-1.90 (m, 4H), 1.76-1.64 (m, 2H), 0.93 (s, 9H), 0.90 (s, 9H), 0.30 (s, 6H), 0.26 (s, 6H).

(b) (11S,11aS)-2,2,2-trichloroethyl 11-(tert-butyldimethylsilyloxy)-8-(5-((11S,11aS)-11-(tert-butyldimethylsilyloxy)-2-(4-hydroxyphenyl)-7-methoxy-5-oxo-10-((2,2,2-trichloroethoxy)carbonyl)-5,10,11,11a-tetrahydro-1H-pyrrolo [2,1-c][1,4]benzodiazepin-8-yloxy)pentyloxy)-7-methoxy-2-(4-methoxyphenyl)-5-oxo-11,11a-dihydro-1H-pyrrolo[2,1-c][1,4]benzodiazepine-10(5H)-carboxylate 22

The Suzuki coupling procedure described in step (a) was applied to the synthesis of Compound 21. Compound 20 (62.5 mg 0.044 mmol,) was treated with 1 equivalent of 4-hydroxybenzeneboronic acid (10 mg) at 30° C. overnight to afford the desired compound after filtration through a pad of silica gel. (40 mg, 0.029 mmol, 66% yield). The compound was used directly in the subsequent step LC-MS RT 4.27 mins, 1371 (M+H)

(c) (S)-2-(4-hydroxyphenyl)-7-methoxy-8-(5-((S)-7-methoxy-2-(4-methoxyphenyl)-5-oxo-5,11a-dihydro-1H-pyrrolo[2,1-c][1,4]benzodiazepin-8-yloxy)pentyloxy)-1H-pyrrolo[2,1-c][1,4]benzodiazepine-5(11aH)-one 23

Cadmium/lead couple (100 mg, Q Dong et al. Tetrahedron Letters vol 36, issue 32, 5681-5682, 1995) was added to a solution of 21 (40 mg, 0.029 mmol) in THF (1 mL) and ammonium acetate (1N, 1 mL) and the reaction mixture was allowed to stir for 1 hour. The reaction mixture was partitioned between chloroform and water, the phases separated and the aqueous phase extracted with chloroform. The combined organic layers were washed with brine and dried over magnesium sulphate. Rotary evaporation under reduced pressure yielded the crude product which was subjected to column chromatography (silica gel, 0→4% MeOH/CHCl$_3$). Removal of excess eluent by rotary evaporation under reduced pressure afforded the desired imine product (17 mg 0.023 mmol 79%).

LC-MS RT 2.20 mins, 755 (M+H); $^1$H-NMR (400 MHZ, CDCl$_3$) δ 7.89 (d, J=3.94 Hz, 1H), 7.89 (d, J=4.00 Hz, 1H), 7.53 (s, 1H), 7.52 (s, 1H), 7.38 (d, J=8.7 Hz, 2H), 7.33 (d, J=8.6 Hz, 2H), 7.28 (s, 1H), 6.90 (d, J=8.7 Hz, 2H), 6.84 (d, J=8.6 Hz, 2H), 6.82 (s, 1H), 6.81 (s, 1H), 5.68 (bs, 1H), 4.50-4.30 (m, 2H), 4.22-4.00 (m, 4H), 3.93 (s, 6H), 3.82 (s, 3H), 3.69-3.45 (m, 2H), 3.44-3.28 (m, 2H), 2.64-1.88 (m, 4H), 1.77-1.62 (m, 2H).

Example 6

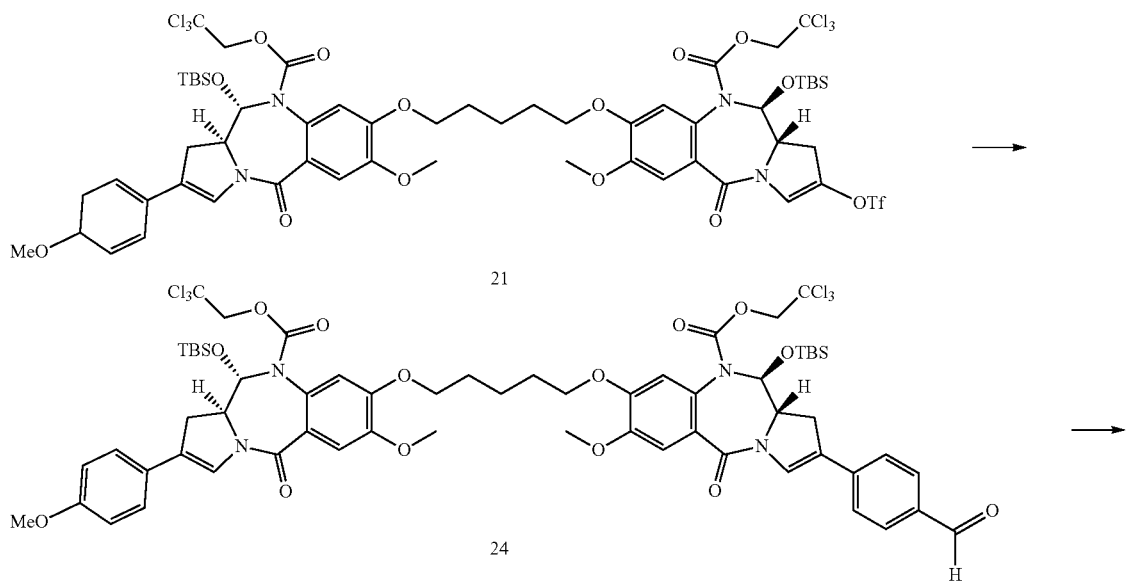

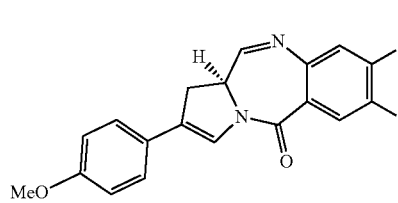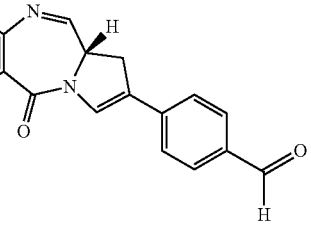

25

(a) (11S,11aS)-2,2,2-trichloroethyl 11-(tert-butyldimethylsilyloxy)-8-(5-((11S,11aS)-11-(tert-butyldimethylsilyloxy)-2-(4-formylphenyl)-7-methoxy-5-oxo-10-((2,2,2-trichloroethoxy)carbonyl)-5,10,11,11a-tetrahydro-1H-pyrrolo[2,1-c][1,4]benzodiazepin-8-yloxy)pentyloxy)-7-methoxy-2-(4-methoxyphenyl)-5-oxo-11,11a-dihydro-1H-pyrrolo[2,1-c][1,4]benzodiazepine-10(5H)-carboxylate 24

The Suzuki coupling procedure described in Example 5, step (a), was applied to the synthesis of Compound 24. Compound 21 (62.5 mg, 0.044 mmol) was treated with 1 equivalent of 4-formylbenzeneboronic acid (10.5 mg) at room temperature overnight to afford the desired compound after filtration through a pad of silica gel (45 mg, 0.033 mmol, 75% yield). The compound was used directly in the subsequent step.
LC-MS RT 4.42 mins, 1383 (M+H)

(b) 4-((S)-7-methoxy-8-(5-((S)-7-methoxy-2-(4-methoxyphenyl)-5-oxo-5,11a-dihydro-1H-pyrrolo[2,1-c][1,4]benzodiazepin-8-yloxy)pentyloxy)-5-oxo-5,11a-dihydro-1H-pyrrolo[2,1-c][1,4]benzodiazepine-2-yl)benzaldehyde 25

Compound 24 was deprotected by the method described in Example 5, step (c), to yield the desired compound (18 mg, 0.023 mmol, 79%).
LC-MS RT 3.18 mins, 768 (M+H); $^1$H-NMR (400 MHZ, CDCl$_3$) δ 9.98 (s, 1H), 7.91 (d, J=3.90 Hz, 1H), 7.90-7.80 (m, 3H), 7.68 (s, 1H), 7.60-7.45 (m, 4H), 7.39 (s, 1H), 7.33 (d, J=8.7 Hz, 1H), 6.90 (d, J=8.7 Hz, 2H), 6.83 (s, 1H), 6.82 (s, 1H), 4.55-4.44 (m, 1H), 4.43-4.36 (m, 1H), 4.23-4.00 (m, 4H), 3.95 (s, 3H), 3.94 (s, 3H), 3.82 (s, 3H), 3.66-3.51 (m, 2H), 3.50-3.34 (m, 2H), 2.05-1.87 (m, 4H), 1.76-164 (m, 2H).

Example 7

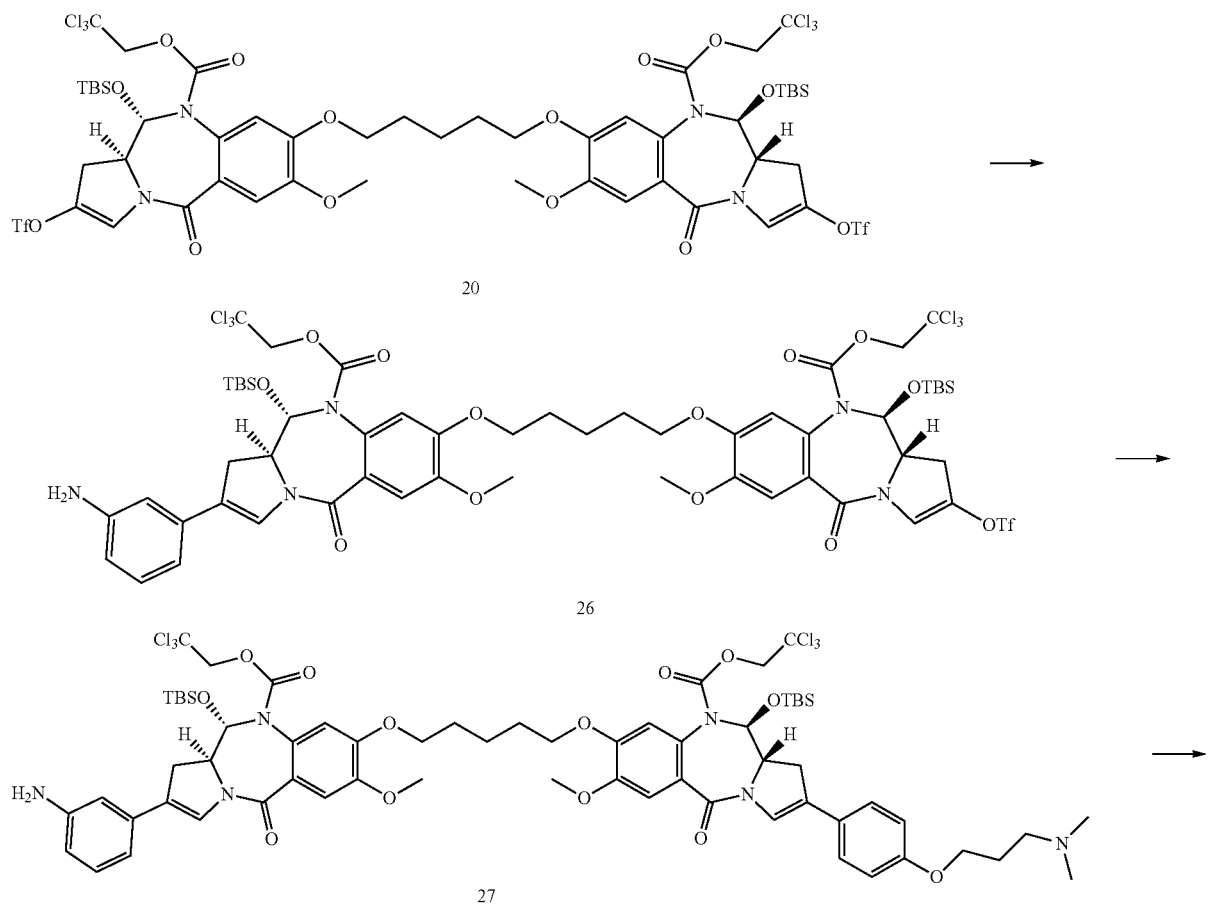

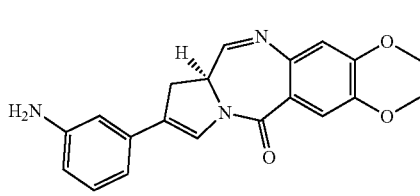
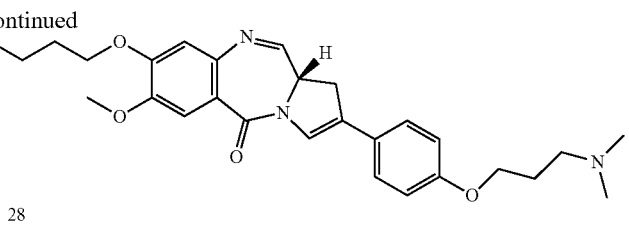

28

(a) (11S,11aS)-2,2,2-trichloroethyl 2-(3-aminophenyl)-11-(tert-butyldimethylsiloxy)-8-(5-((11S,11aS)-11-(tert-butyldimethylsilyloxy)-7-methoxy-5-oxo-10-((2,2,2-trichloroethoxy)carbonyl)-2-(trifluoromethylsulphonyloxy)-5,10,11,11a-tetrahydro-1H-pyrrolo[2,1-c][1,4]benzodiazepin-8-yloxy)pentyloxy)-7-methoxy-5-oxo-11,11a-dihydro-1H-pyrrolo[2,1-c][1,4]benzodiazepine-10(5H)-carboxylate 26

The Suzuki coupling procedure described in Example 5, step (a), was applied to the synthesis of Compound 26, using 3-aminobenzeneboronic acid to afford the desired compound in 41% yield (230 mg, 0.163 mmol)

LC-MS RT 4.28 mins, 1411 (M+H); $^1$H-NMR (400 MHZ, CDCl$_3$) δ 7.44 (bs, 1H), 7.29 (s, 1H), 7.25 (s, 1H), 7.20 (s, 1H), 7.16 (t, J=7.9 Hz, 1H), 6.84-6.73 (m, 3H), 6.70 (bs, 1H), 6.62 (dd, J=7.9, 1.7 Hz, 1H), 6.66-6.58 (m, 2H), 5.25 (d, J=12.0 Hz, 1H), 5.24 (d, J=12.0 Hz, 1H), 4.24 (d, J=12.0 Hz, 1H), 4.22 (d, J=12.0 Hz, 1H), 4.17-4.07 (m, 2H), 4.08-3.89 (m, 10H), 3.43-3.28 (m, 2H), 2.85 (d, J=1.65 Hz, 2H), 2.07-1.90 (m, 4H), 1.78-1.63 (m, 2H), 0.94 (s, 9H), 0.90 (s, 9H), 0.30 (s, 6H), 0.27 (s, 6H).

(b) (11S,11aS)-2,2,2-trichloroethyl 2-(3-aminophenyl)-11-(tert-butyldimethylsilyloxy)-8-(5-((11S,11aS)-11-(tert-butyldimethylsilyloxy)-2-(4-(3-(dimethylamino)propoxy)phenyl)-7-methoxy-5-oxo-10-((2,2,2-trichloroethoxy)carbonyl)-5,10,11,11a-tetrahydro-1H-pyrrolo[2,1-c][1,4]benzodiazepin-8-yloxy)pentyloxy)-7-methoxy-5-oxo-11,11a-dihydro-1H-pyrrolo[2,1-c][1,4]benzodiazepine-10(5H)-carboxylate 27

Solid 4-[3-(dimethylamino)propoxybenzeneboronic acid pinacol ester (25 mg, 0.082 mmol) was added to a solution of 26 (73 mg, 0.052 mmol), sodium carbonate (18 mg, 0.17 mmol) and palladium tetrakis triphenylphosphine (3 mg) in toluene (1 mL), ethanol (0.5 mL) and water (0.5 mL). The reaction mixture was allowed to stir at room temperature over night. The reaction mixture was then partitioned between ethyl acetate and water. The organic layer was washed with water and brine and dried over magnesium sulphate. Excess solvent was removed by rotary evaporation under reduced pressure and the resulting residue was eluted through a plug of silica gel with chloroform/methanol. Removal of excess eluent from selected fractions afforded the 4-methoxyphenyl coupled product (50 mg, 0.035 mmol, 67%).

LC-MS RT 4.12 mins, 1440 (M+H)

(c) (S)-2-(3-aminophenyl)-8-(5-((S)-2-(4-(3-(dimethylamino)propoxy)phenyl)-7-methoxy-5-oxo-5,11a-dihydro-1H-pyrrolo[2,1-c][1,4]benzodiazepine-8-yloxy)pentyloxy)-7-methoxy-1H-pyrrolo[2,1-c][1,4]benzodiazepine-5(11aH)-one 28

Compound 27 was deprotected by the method described in Example 5, step (c), to yield the desired compound. The reaction mixture was partitioned between DCM and aqueous sodium hydrogen carbonate (emulsion) and the crude product purified by gradient column chromatography on silica gel (5% methanol chloroform→35% methanol/chloroform) to afford the desired unsymmetrical PBD imine (50 mg, 0.018 mmol, 58%) LC-MS RT 2.55 mins, 826 (M+H); $^1$H-NMR (400 MHZ, CDCl$_3$) δ 7.92-7.82 (m, 2H), 7.52 (bs, 2H), 7.45 (bs, 1H), 7.39 (bs, 1H), 7.31 (d, J=8.6 Hz, 2H), 7.14 (t, J=7.8 Hz, 1H), 6.89 (d, J=8.6 Hz, 2H), 6.85-6.75 (m, 3H), 6.72 (bs, 1H), 6.60 (d, J=8.0 Hz, 1H), 4.46-4.33 (m, 2H), 4.21-3.98 (m, 6H), 3.94 (s, 6H), 3.63-3.50 (m, 2H), 3.43-3.29 (m, 2H), 2.64-2.48 (m, 2H), 2.34 (s, 6H), 2.10-1.89 (m, 6H), 1.57 (m, 2H).

Example 8

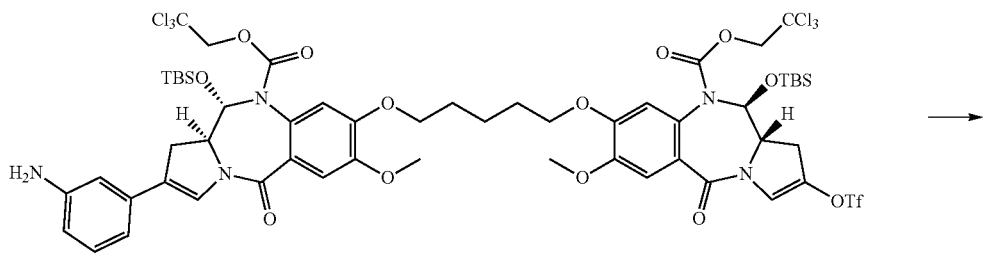

26

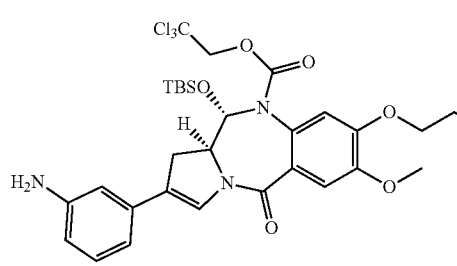
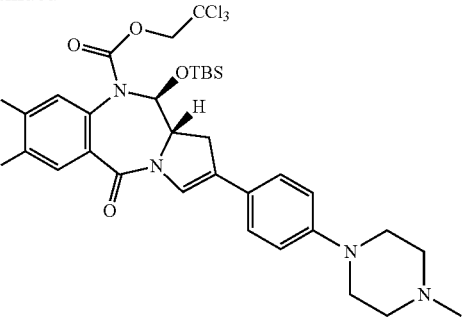

29

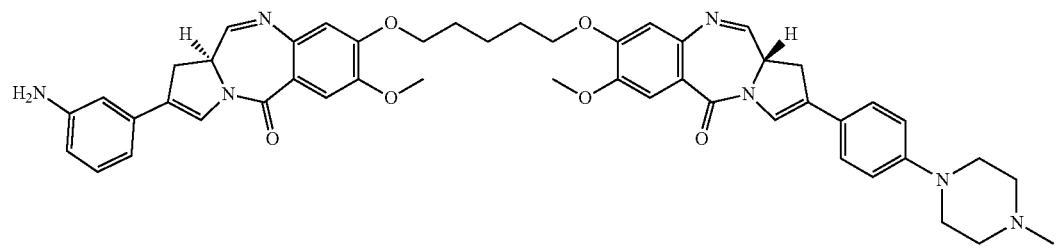

30

(a) (11S,11aS)-2,2,2-trichloroethyl 2-(3-aminophenyl)-11-(tert-butyldimethylsilyloxy)-8-(5-((11S,11aS)-11-(tert-butyldimethylsilyloxy)-7-methoxy-2-(4-(4-methylpiperazin-1-yl)phenyl)-5-oxo-10-((2,2,2-trichloroethoxy)carbonyl)-5,10,11,11a-tetrahydro-1H-pyrrolo[2,1-c][1,4]benzodiazepin-8-yloxy)pentyloxy)-7-methoxy-5-oxo-11,11a-dihydro-1H-pyrrolo[2,1-c][1,4]benzodiazepine-10(5H)-carboxylate 29

The method of Example 7, step (b), was performed to afford the desired product (58 mg, 0.0.040 mmol, 78%) after filtration through a plug of silica gel (with 1/3 methanol/chloroform) and removal of excess solvent by rotary evaporation under reduced pressure.

LC-MS RT 4.08 mins, 1439 (M+H)

(b) (S)-2-(3-aminophenyl)-7-methoxy-8-(5-((S)-7-methoxy-2-(4-(4-methylpiperazin-1-yl)phenyl)-5-oxo-5,11a-dihydro-H-pyrrolo[2,1-c][1,4]benzodiazepin-8-yloxy)pentyloxy)-1H-pyrrolo[2,1-c][1,4]benzodiazepine-5(11aH)-one 30

The method for Example 7, step (c) was used to deprotect compound 29. The crude product was purified by silica gel gradient chromatography (2% methanol chloroform-35% methanol/chloroform) to afford the desired unsymmetrical PBD imine (18 mg, 0.022 mmol, 59%)

LC-MS RT 2.52 mins, 823 (M+H); ¹H-NMR (400 MHZ, CDCl₃) δ 7.80 (d, J=3.8 Hz, 2H), 7.45 (s, 2H), 7.38 (s, 1H), 7.30 (s, 1H), 7.23 (d, J=8.6 Hz, 2H), 7.07 (t, J=7.8 Hz, 1H), 6.83 (d, J=8.6 Hz, 2H), 6.79-6.89 (m, 3H), 6.65 (s, 1H), 6.54 (d, J=7.9 Hz, 1H), 4.40-4.24 (m, 2H), 4.15-3.93 (m, 4H), 3.87 (s, 6H), 3.56-3.42 (m, 2H), 3.37-3.23 (m, 2H), 3.22-3.08 (m, 4H), 2.61-2.41 (m, 4H), 2.29 (s, 3H), 1.98-1.80 (m, 4H), 1.67-1.54 (m, 2H).

Example 9

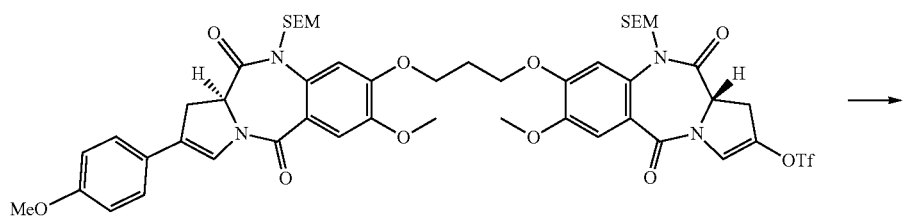

17

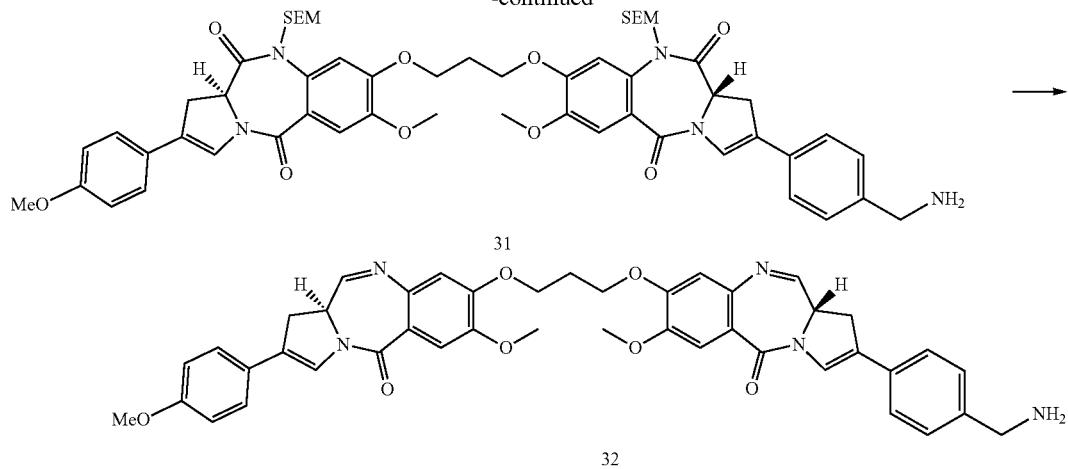

31

32

(a) (S)-2-(4-(aminomethyl)phenyl)-7-methoxy-8-(3-((S)-7-methoxy-2-(4-methoxyphenyl)-5,11-dioxo-10-((2-(trimethylsilyl)ethoxy)methyl)-5,10,11,11a-tetrahydro-1H-pyrrolo[2,1-c][1,4]benzodiazepin-8-yloxy)propyloxy)-10-((2-(trimethylsilyl)ethoxy)methyl)-1H-pyrrolo[2,1-c][1,4]benzodiazepine-5,11(10H,11aH)-dione 31

Solid 4-aminomethylbenzeneboronic acid hydrochloride (0.111 g, 0.59 mmol) was added to a solution of 17 (0.394 g, 0.37 mmol), sodium carbonate (175 mg, 1.654 mmol) and palladium tetrakis triphenylphosphine (28.0 mg, 0.024 mmol) in toluene (10 mL), ethanol (5 mL) and water (5 mL). The reaction mixture was allowed to stir overnight at 30° C. The following day the reaction mixture was heated for a further 3 hours at 70° C. The reaction mixture was then partitioned between ethyl acetate and water. The organic layer was washed with water and brine and dried over magnesium sulphate. Excess solvent was removed by rotary evaporation under reduced pressure and the resulting residue was subjected to flash column chromatography (silica gel; gradient elution EtOAc/hexane 2/98→15/85). Removal of excess eluent from selected fractions afforded the desired product (0.230 mg, 0.22 mmol, 61%).

LC-MS RT 3.63 mins, 1034 (M+2H); $^1$H-NMR (400 MHz, DMSO $d_6$) δ 11.7 (s, 2H), 7.52 (d, J=8.2 Hz, 2H), 7.48 (d, J=8.7 Hz, 2H), 7.40 (s, 1H), 7.50 (d, J=8.1 Hz, 2H), 7.38-7.19 (m, 5H) 6.93 (d, J=8.7 Hz, 2H), 5.40 (d, J=2.13 Hz, 1H), 5.38 (d, J=2.12 Hz, 1H), 5.32 (d, J=10.6 Hz, 2H), 5.25 (d, J=10.6 Hz, 2H), 4.87-4.72 (m, 2H), 4.35-4.15 (m, 4H), 3.85 (s, 6H), 3.79 (s, 3H), 3.73-3.56 (m, 2H), 3.55-3.39 (m, 4H), 3.22-3.02 (m, 2H), 2.39-2.23 (m, 2H), 0.94-0.67 (m, 4H), −0.06 (s, 18H).

(b) (S)-2-(4-(aminomethyl)phenyl)-7-methoxy-8-(3-((S)-7-methoxy-2-(4-methoxyphenyl)-5-oxo-5,11a-dihydro-1H-pyrrolo[2,1-c][1,4]benzodiazepin-8-yloxy)propyloxy)-1H-pyrrolo[2,1-c][1,4]benzodiazepine-5(11aH)-one 32

Compound 31 was deprotected following the method of Example 1, step (c). The crude product was purified by gradient column chromatography (5/95→30/70 MeOH/CHCl$_3$) to afford the product as a mixture of imine and carbinolamine methyl ethers.

LC-MS RT 2.58 mins, 740 (M+H).

Example 10

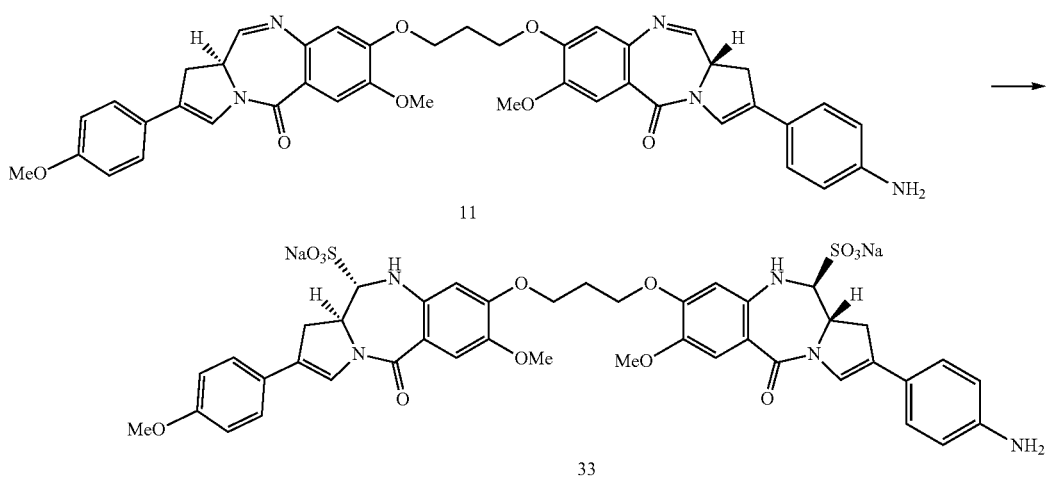

11

33

(S)-2-(4-aminophenyl)-7-methoxy-11(S)-sulpho-8-(3-((S)-7-methoxy-11(S)-sulpho-2-(4-methoxyphenyl)-5-oxo-5,10,11,11a-tetrahydro-1H-pyrrolo[2,1-c][1,4]benzodiazepin-8-yloxy)propyloxy)-1H-pyrrolo[2,1-c][1,4]benzodiazepine-5(11aH)-one disodium salt 33

Sodium bisulphite (8.5 mg, 3.1 eq) was added to a stirred suspension of bis-imine 11 (20 mg, 0.036 mmol) in isopropanol (4 mL) and water (2 mL). The reaction mixture was allowed to stir vigorously and eventually became clear (c, 1 hour). The reaction mixture was transferred to a funnel and filtered through a cotton wall (and then washed with 2 mL water). The filtrate was flash frozen (liquid and to bath) and lyophilized to afford the desired product 33 in quantitative yield.

LC-MS RT 11.77 mins, 727.2 (M+H) (Mass of parent compound, bisulphite adducts unstable in mass spectrometer); $^1$H-NMR (400 MHz, CDCl$_3$) δ 7.66-7.55 (m, 5H), 7.43 (s, 1H), 7.39 (d, J=8.66 Hz, 2H), 7.06 (m, 2H), 6.93 (d, J=8.84 Hz, 2H), 6.54 (m, 2H), 5.29-5.21 (m, 2H), 4.32-4.28 (m, 2H), 4.14-4.20 (m, 4H), 3.96-3.83 (m, 2H), 3.77 (s, 3H), 3.73 (m, 6H), 3.52-3.43 (m, 2H), 3.30-3.08 (m, 2H), 2.24-2.21 (m, 2H).

Example 11 triflate 17 (380 mg), the pinnacol ester of 2-aminophenylboronic acid (124 mg) and sodium carbonate (120 mg) in ethanol (5 mL), toluene (5 mL) and water (5 mL). The reaction mixture was allowed to stir over night at room temperature and at 40° C. until the reaction was complete (c, 2 hr). The reaction mixture was diluted with ethyl acetate and the organic layer was washed with water and brine. The ethyl acetate solution was dried over magnesium sulphate and filtered under vacuum. Removal of ethyl acetate by rotary evaporation under reduced pressure afforded the crude product which was subjected to flash chromatography (silica gel, ethyl acetate/hexane). Pure fractions were collected and combined. Removal of excess eluent by rotary evaporation under reduced pressure afforded the pure product 103 (330 mg, 86% yield). LC/MS RT: 4.17 min, ES$^+$1018.48.

(b) (S)-2-(2-aminophenyl)-7-methoxy-8-(3-(((S)-7-methoxy-2-(4-methoxyphenyl)-5-oxo-5,11a-dihydro-pyrrolo[2,1-c][1,4]benzodiazepin-8-yl)oxy)propoxy)-pyrrolo[2,1-c][1,4]benzodiazepin-5(11aH)-one (104)

A solution of Superhydride in dry tetrahydrofuran (1.0 M, 4.4 eq.) was added to a solution of the 2-analino compound 103 (300 mg) in dry tetrahydrofuran (5 mL) at −78° C. under

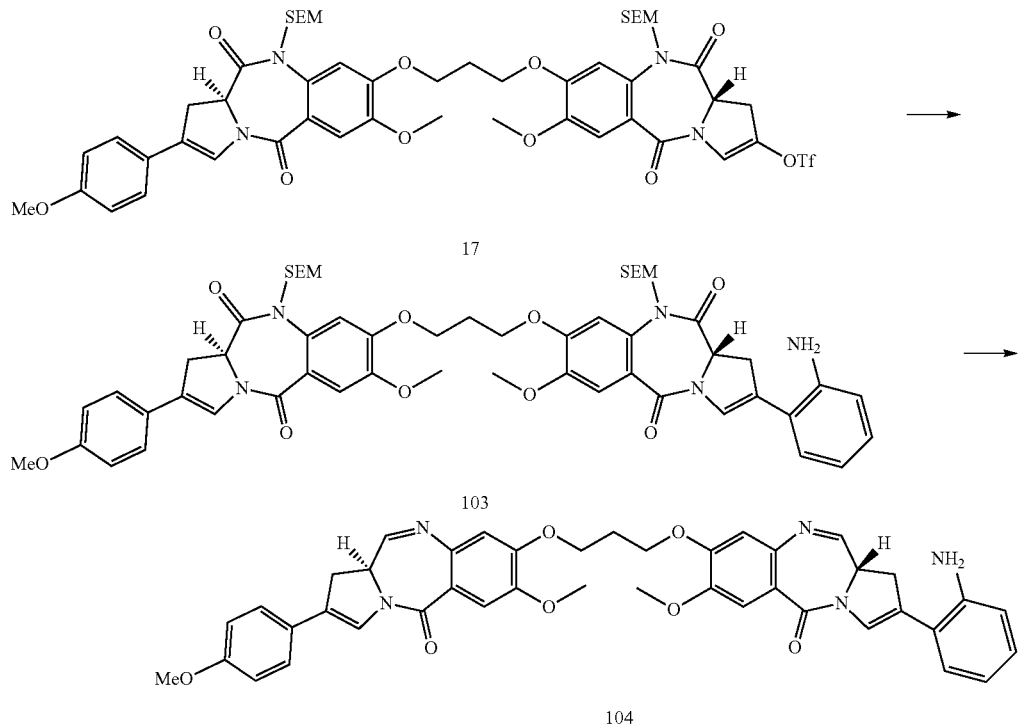

(a) (S)-2-(2-aminophenyl)-7-methoxy-8-(3-(((S)-7-methoxy-2-(4-methoxyphenyl)-5,11-dioxo-10-((2-(trimethylsilyl)ethoxy)methyl)-5,10,11,11a-tetrahydro-pyrrolo[2,1-c][1,4]benzodiazepin-8-yl)oxy)propoxy)-10-((2-(trimethylsilyl)ethoxy)methyl)-pyrrolo[2,1-c][1,4]benzodiazepine-5,11(10H,11aH)-dione (103)

A catalytic amount of tetrakistriphenylphosphinepalladium (0) (11.2 mg) was added to a mixture of the mono an inert atmosphere. As reduction was proceeding slowly an aliquot of lithium borohydride (20 eq.) was added and the reaction mixture was allowed to return to room temperature. Water/ice was added to the reaction mixture to quench unreacted hydrides and the reaction was diluted with dichloromethane. The organic layer was washed sequentially with water (twice), citric acid and brine. Excess dichloromethane was removed by rotary evaporation under reduced pressure and the residue was redissolve in ethanol and water and treated with silica gel for 96 hours. The reaction mixture was vacuum filtered and the filtrate evaporated to dryness. The residue was subjected to flash column chromatography (silica gel, gradient chloroform/methanol). Pure fractions were collected and combined and excess eluent was removed by rotary evaporation under educed pressure to afford the pure product 104 (30 mg, 14% yield). LC/MS RT: 2.90 min, ES+726.09.

Example 12: Determination of In Vitro Cytotoxicity of Representative PBD Compounds K562 Assay K562 human chronic myeloid leukaemia cells were maintained in RPM1 1640 medium supplemented with 10% fetal calf serum and 2 mM glutamine at 37° C. in a humidified atmosphere containing 5% $CO_2$ and were incubated with a specified dose of drug for 1 hour or 96 hours at 37° C. in the dark. The incubation was terminated by centrifugation (5 min, 300 g) and the cells were washed once with drug-free medium. Following the appropriate drug treatment, the cells were transferred to 96-well microtiter plates ($10^4$ cells per well, 8 wells per sample). Plates were then kept in the dark at 37° C. in a humidified atmosphere containing 5% $CO_2$. The assay is based on the ability of viable cells to reduce a yellow soluble tetrazolium salt, 3-(4,5-dimethylthiazol-2-yl)-2,5-diphenyl-2H-tetrazolium bromide (MTT, Aldrich-Sigma), to an insoluble purple formazan precipitate. Following incubation of the plates for 4 days (to allow control cells to increase in number by approximately 10 fold), 20 µL of MTT solution (5 mg/mL in phosphate-buffered saline) was added to each well and the plates further incubated for 5 h. The plates were then centrifuged for 5 min at 300 g and the bulk of the medium pipetted from the cell pellet leaving 10-20 µL per well. DMSO (200 µL) was added to each well and the samples agitated to ensure complete mixing. The optical density was then read at a wavelength of 550 nm on a Titertek Multiscan ELISA plate reader, and a dose-response curve was constructed. For each curve, an $IC_{50}$ value was read as the dose required to reduce the final optical density to 50% of the control value.

Compound 13 has an $IC_{50}$ of 30 pM in this assay.

A2780 Assay

The A2780 parental cell line was grown in Dulbecco's Modified Eagles' Media (DMEM) containing ~10% Foetal Calf Serum (FCS) and ~1% 200 mM L-Glutamine solution and grown in Corning Cellbind 75 cm² flasks.

A 190 µl cell suspension was added (at $1\times10^4$) to each well of columns 2 to 11 of a 96 well plate (Nunc 96F flat bottom TC plate), 190 µl of media was added to each well of columns 1 and 12. The media was Dulbecco's Modified Eagles' Media (DMEM) (which included ~10% Foetal Calf Serum (FCS) and ~1% 200 mM L-Glutamine solution).

Plates were incubated overnight at 37° C. before addition of drug if cells were adherent, 200 µM of the test compound solutions (in 100% DMSO) were serially diluted across a 96 well plate. Each resulting point was then further diluted 1/10 into sterile distilled water (SDW).

To the cell negative blanks and compound negative control wells, 10% DMSO was added at 5% v/v. Assay plates were incubated for the following durations at 37° C. in 5% $CO_2$ in a humidified incubator for 72 hours. Following incubation, MTT solution to a final concentration of 1.5 µM was added to each well. The plates were then incubated for a further 4 hours at 37° C. in 5% $CO_2$ in a humidified incubator. The media was then removed, and the dye was solubilised in 200 µl DMSO (99.99%).

Plates were read at 540 nm absorbance using an Envision plate reader. Data was analysed using Microsoft Excel and GraphPad Prism and $IC_{50}$ values obtained.

Compound 11 has an $IC_{50}$ of 11.7 µM in this assay.

Renal Cell and AML Cell Lines Assays

The cytotoxicity of various free drug compounds was tested on a renal cell cancer cell line, 786-O, a Hodgkin lymphoma cell line, L428 and two AML cell lines, HL60 and HEL.

For a 96-hour assay, cells cultured in log-phase growth were seeded for 24 h in 96-well plates containing 150 µL RPMI 1640 supplemented with 20% FBS. Serial dilutions of test article (i.e., free drug) in cell culture media were prepared at 4× working concentration; 50 µL of each dilution was added to the 96-well plates. Following addition of test article, the cells were incubated with test articles for 4 days at 37° C. Resazurin was then added to each well to achieve a 50 µM final concentration, and the plates were incubated for an additional 4 h at 37° C. The plates were then read for the extent of dye reduction on a Fusion HT plate reader (Packard Instruments, Meridien, Conn., USA) with excitation and emission wavelengths of 530 and 590 nm, respectively. The $IC_{50}$ value, determined in triplicate, is defined here as the concentration that results in a 50% reduction in cell growth relative to untreated controls.

Referring to the following Table 1, the para-aniline compound 11 showed markedly increased activity on these cell lines as compared to the meta-aniline compound 19 in this assay.

TABLE 1

| | $IC_{50}$ Summary for Free Drugs [nM] | | | |
|---|---|---|---|---|
| Free Drug | L428 | 786-O | HL60 | HEL |
| Compound 11 | <0.00001 | <0.00001 | <0.00001 | <0.00001 |
| Compound 19 | 1 | 0.5 | 0.6 | 0.2 |

Referring to the following Table 2, the activity of compounds 28, 30 and 32 is shown on L428, 786-O, HEL, HL-60 and MCF-7 cells, as well as the activity for compound 19 on MCF-7 cells.

TABLE 2

| | $IC_{50}$ Summary for Free Drugs [nM] | | | | |
|---|---|---|---|---|---|
| Free Drug | L428 | 786-O | HEL | HL-60 | MCF-7 |
| Compound 28 | <0.00001 | <0.00001 | <0.00001 | <0.00001 | <0.00001 |
| Compound 30 | <0.00001 | <0.00001 | <0.00001 | <0.00001 | 0.01 |
| Compound 32 | <0.00001 | <0.00001 | <0.00001 | <0.00001 | 1.0 |
| Compound 19 | | | | | 5 |

Referring to the following Table 3, the activities of compounds 23, 25, are compared to that of compound 11 on 786-O, Caki-1, MCF-7, HL-60, THP-1, HEL, and TF1 cells. Cells were plated in 150 µL growth media per well into black-sided clear-bottom 96-well plates (Costar, Corning) and allowed to settle for 1 hour in the biological cabinet before placing in the incubator at 37° C., 5% $CO_2$. The following day, 4× concentration of drug stocks were prepared, and then titrated as 10-fold serial dilutions producing 8-point dose curves and added at 50 µl per well in duplicate. Cells were then incubated for 48 hours at 37° C., 5% $CO_2$. Cytotoxicity was measure by incubating with 100 µL Cell Titer Glo (Promega) solution for 1 hour, and then luminescence was measured on a Fusion HT plate reader (Perkin Elmer). Data was processed with Excel (Microsoft) and GraphPad (Prism) to produce dose response curves and IC50 values were generated and data collected.

TABLE 3

$IC_{50}$ Summary for Free Drugs [nM]

| Free Drug | 786-O | Caki-1 | MCF-7 | HL-60 | THP-1 | HEL | TF1a |
|---|---|---|---|---|---|---|---|
| Compound 11 | 0.4 | 0.2 | 1 | 0.01 | 1 | 0.03 | 1 |
| Compound 23 | 0.06 | 0.02 | 0.7 | 0.005 | 0.4 | 0.009 | 0.2 |
| Compound 25 | 0.09 | 0.06 | 0.8 | 0.01 | 0.9 | 0.02 | 0.9 |

In Examples 13 to 16, the following compounds are referred to by the compound numbers as show below:

| Compound | Alternative Designation |
|---|---|
| 11 | 37 |
| 13 | 57 |
| 19 | 42 |
| 25 | 95 |
| 28 | 50 |
| 30 | 49 |
| 104 | 66 |

Example 13: Synthesis of PBD Drug Linker Compounds

General Information. In the following examples, all commercially available anhydrous solvents were used without further purification. Analytical thin layer chromatography was performed on silica gel 60 F254 aluminum sheets (EMD Chemicals, Gibbstown, N.J.). Radial chromatography was performed on Chromatotron apparatus (Harris Research, Palo Alto, Calif.). Analytical HPLC was performed on a Varian ProStar 210 solvent delivery system configured with a Varian ProStar 330 PDA detector. Samples were eluted over a C12 Phenomenex Synergi 2.0×150 mm, 4 µm, 80 Å reverse-phase column. The acidic mobile phase consisted of acetonitrile and water both containing either 0.05% trifluoroacetic acid or 0.1% formic acid (denoted for each compound). Compounds were eluted with a linear gradient of acidic acetonitrile from 5% at 1 min post injection, to 95% at 11 min, followed by isocratic 95% acetonitrile to 15 min (flow rate=1.0 mL/min). LC-MS was performed on a ZMD Micromass mass spectrometer interfaced to an HP Agilent 1100 HPLC instrument equipped with a C12 Phenomenex Synergi 2.0×150 mm, 4 µm, 80 Å reverse phase column. The acidic eluent consisted of a linear gradient of acetonitrile from 5% to 95% in 0.1% aqueous formic acid over 10 min, followed by isocratic 95% acetonitrile for 5 min (flow rate=0.4 mL/min). Preparative HPLC was carried out on a Varian ProStar 210 solvent delivery system configured with a Varian ProStar 330 PDA detector. Products were purified over a C12 Phenomenex Synergi 10.0×250 mm, 4 µm, 80 Å reverse phase column eluting with 0.1% formic acid in water (solvent A) and 0.1% formic acid in acetonitrile (solvent B). The purification method consisted of the following gradient of solvent A to solvent B: 90:10 from 0 to 5 min; 90:10 to 10:90 from 5 min to 80 min; followed by isocratic 10:90 for 5 min. The flow rate was 4.6 mL/min with monitoring at 254 nm. NMR spectral data were collected on a Varian Mercury 400 MHz spectrometer. Coupling constants (J) are reported in hertz.

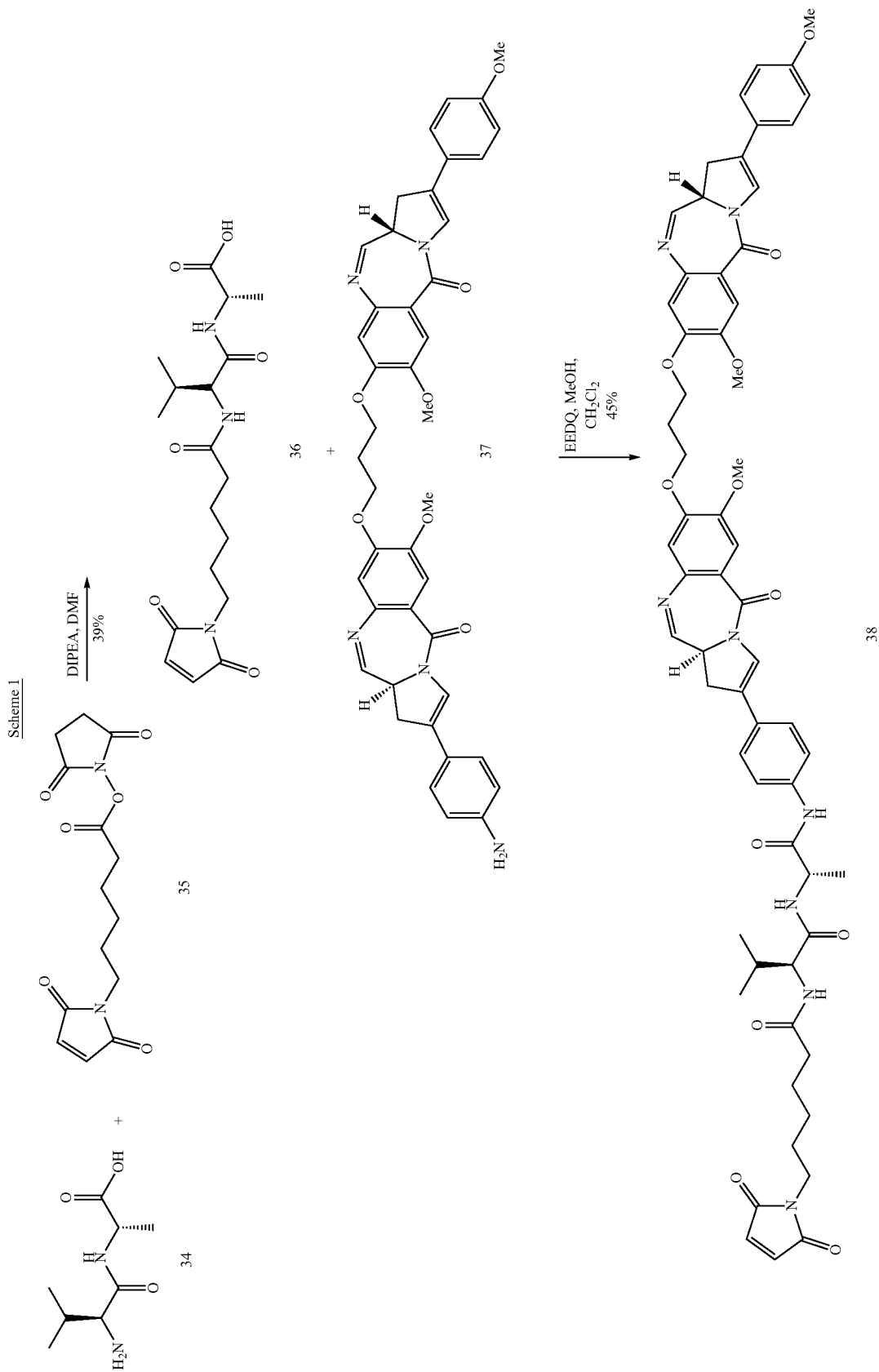

(S)-2-((S)-2-(6-(2,5-dioxo-2,5-dihydro-1H-pyrrol-1-yl)hexanamido)-3-methylbutanamido)propanoic acid (36)

To a solution of Val-Ala dipeptide 34 (200 mg, 1.06 mmol) dissolved in 10.6 mL anhydrous DMF was added maleimidocaproyl NHS ester 35 (327 mg, 1.06 mmol). Diisopropylethyamine (0.92 mL, 5.3 mmol) was then added and the reaction was stirred under nitrogen at an ambient temperature for 18 h, at which time TLC and analytical HPLC revealed consumption of the starting material. The reaction was diluted with 0.1 M HCl (100 mL), and the aqueous layer was extracted with ethyl acetate (100 mL, 3×). The combined organic layer was washed with water and brine, then dried over sodium sulfate, filtered and concentrated. The crude product was dissolved in minimal methylene chloride and purified by radial chromatography on a 2 mm chromatotron plate eluted with $CH_2Cl_2$/MeOH mixtures (95:5 to 90:10 $CH_2Cl_2$/MeOH) to provide 36 (158 mg, 39%) as an oily residue. TLC: Rt=0.26, 10% MeOH in $CH_2Cl_2$. $^1$H NMR (CDCl$_3$) δ (ppm) 0.95 (d, J=17 Hz, 3H), 0.98 (d, J=17 Hz, 3H), 1.30 (m, 2H), 1.40 (d, J=17 Hz, 3H), 1.61 (m, 4H), 2.06 (m, 1H), 2.25 (dt, J=4, 19 Hz, 2H), 3.35 (s, 1H), 3.49 (t, J=17 Hz, 2H), 4.20 (d, J=18 Hz, 1H), 4.38 (m, 1H), 6.80 (s, 2H). Analytical HPLC (0.1% formic acid): $t_R$ 9.05 min. LC-MS: $t_R$ 11.17 min, m/z (ES$^+$) found 381.9 (M+H)$^+$, m/z (ES$^-$) found 379.9 (M−H)$^-$.

6-(2,5-dioxo-2,5-dihydro-1H-pyrrol-1-yl)-N—((S)-1-(((S)-1-((4((S)-7-methoxy-8-(3-(((S)-7-methoxy-2-(4-methoxyphenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)amino)-1-oxopropan-2-yl)amino)-3-methyl-1-oxobutan-2-yl)hexanamide (38)

A flame-dried 10 mL flask was charged with acid 36 (3.6 mg, 9.5 μmol), EEDQ (2.8 mg, 11.4 μmol), and 0.33 mL anhydrous $CH_2Cl_2$. Methanol (four drops, ~80 μL) was added to facilitate dissolution and the mixture was stirred under nitrogen for 1 h. PBD dimer 37 (5.7 mg, 7.9 μmol) was then added and the reaction was stirred at room temperature for 6 h, at which time LC-MS revealed conversion to product. The reaction was concentrated, dissolved in minimal $CH_2Cl_2$, and purified by radial chromatography on a 1 mm chromatotron plate eluted with $CH_2Cl_2$/MeOH mixtures (100:0 to 90:10 $CH_2Cl_2$/MeOH) to provide the drug linker 38 (3.9 mg, 45%). TLC: $R_f$=0.06, 5% MeOH in $CH_2Cl_2$. Analytical HPLC (0.1% formic acid): $t_R$ 11.51 min. LC-MS: $t_R$ 12.73 min, m/z (ES$^+$) found 1089.6 (M+H)$^+$, m/z (ES$^-$) found 1087.3 (M−H)$^-$.

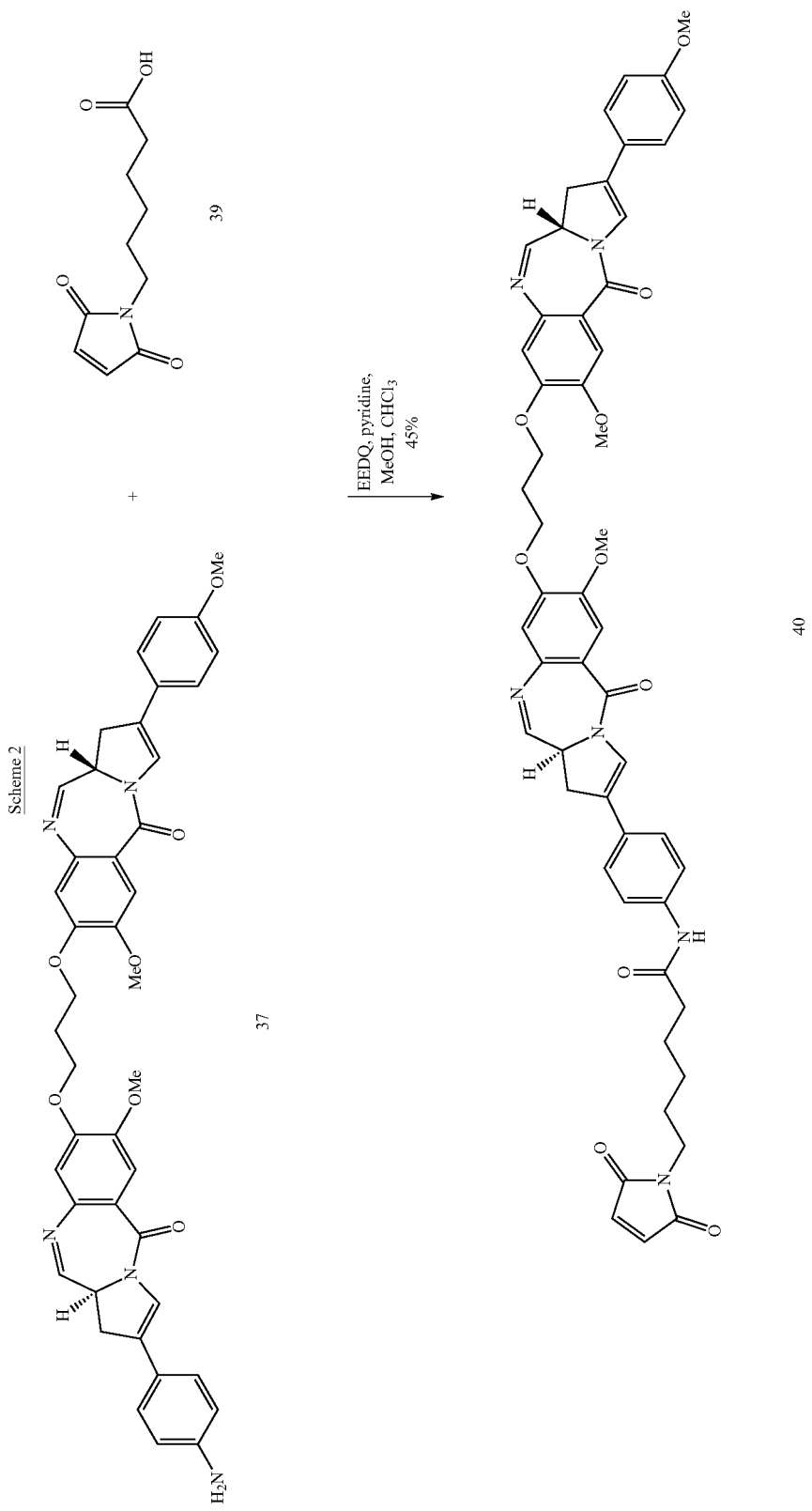

6-(2,5-dioxo-2,5-dihydro-1H-pyrrol-1-yl)-N-(4-((S)-7-methoxy-8-(((S)-7-methoxy-2-(4-methoxyphenyl)-5-oxo-5,11a-dihydro-1H-pyrrolo[2,1-c][1,4]benzodi-azepin-8-yl)oxy)propoxy)-5-oxo-5,11a-dihydro-1H-pyrrolo[2,1-c][1,4]benzodiazepin-2-yl)phenyl) hexanamide (40)

To a flame-dried 10 mL flask was added PBD dimer 37 (25 mg, 34.4 μmol), which was dissolved in 1.4 mL of a 10% MeOH in CHCl₃ solvent mixture. Maleimidocaproic acid (39) was added (7.3 mg, 34.4 μmol), followed by EEDQ (10.2 mg, 41.3 μmol) and pyridine (6 μL, 68.8 μmol). The reaction was stirred at room temperature under a nitrogen atmosphere for 14 h, at which time LC-MS revealed conversion to product. The reaction was concentrated, dissolved in minimal CH₂Cl₂, and purified by radial chromatography on a 1 mm chromatotron plate eluted with CH₂Cl₂/MeOH mixtures (100:0 to 90:10 CH₂Cl₂/MeOH) to provide drug linker 40 (14.1 mg, 45%). LC-MS: $t_R$ 12.81 min, m/z (ES⁺) found 918.9 (M+H)⁺, m/z (ES⁻) found 917.0 (M−H)⁻.

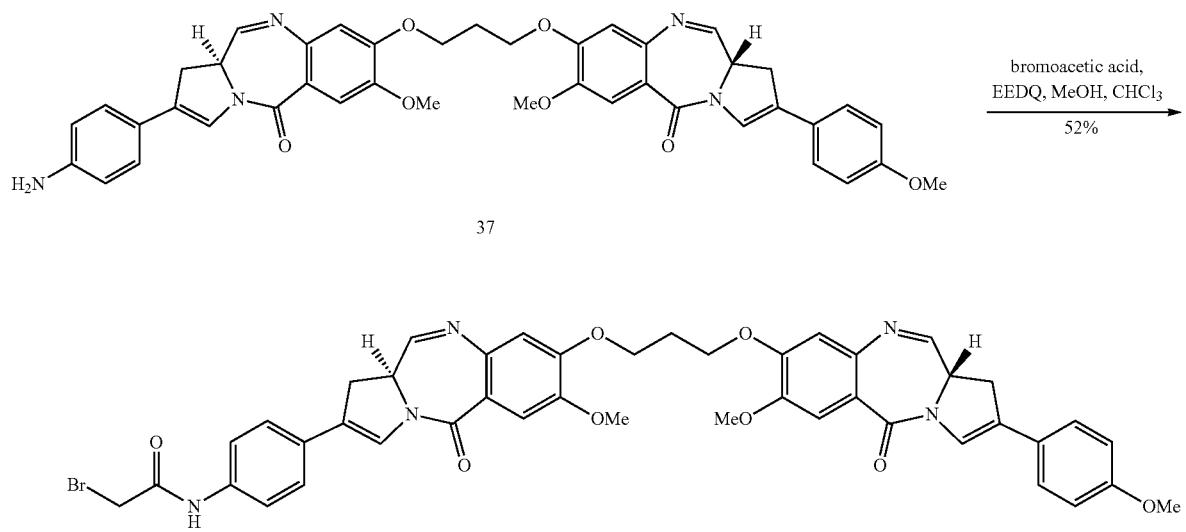

Scheme 3

2-bromo-N-(4-((S)-7-methoxy-8-(3((S)-7-methoxy-2-(4-methoxyphenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)acetamide (41)

To a flame-dried 10 mL flask was added PBD dimer 37 (16.5 mg, 22.7 μmol), which was dissolved in 0.9 mL of a 10% MeOH in CHCl₃ solvent mixture. Bromoacetic acid was added (3.2 mg, 22.7 μmol), followed by EEDQ (6.8 mg, 27.2 μmol). The reaction was stirred at room temperature under a nitrogen atmosphere for 4 h, at which time LC-MS revealed conversion to product. The reaction was concentrated, dissolved in minimal CH₂Cl₂, and purified by radial chromatography on a 1 mm chromatotron plate eluted with CH₂Cl₂/MeOH mixtures (100:0 to 95:5 CH₂Cl₂/MeOH) to provide drug linker 41 (9.9 mg, 52%). TLC: $R_f$=0.09, 5% MeOH in CH₂Cl₂. LC-MS: $t_R$ 12.44 min, m/z (ES⁺) found 848.1 (M+H)⁺, m/z (ES⁻) found 845.7 (M−H).

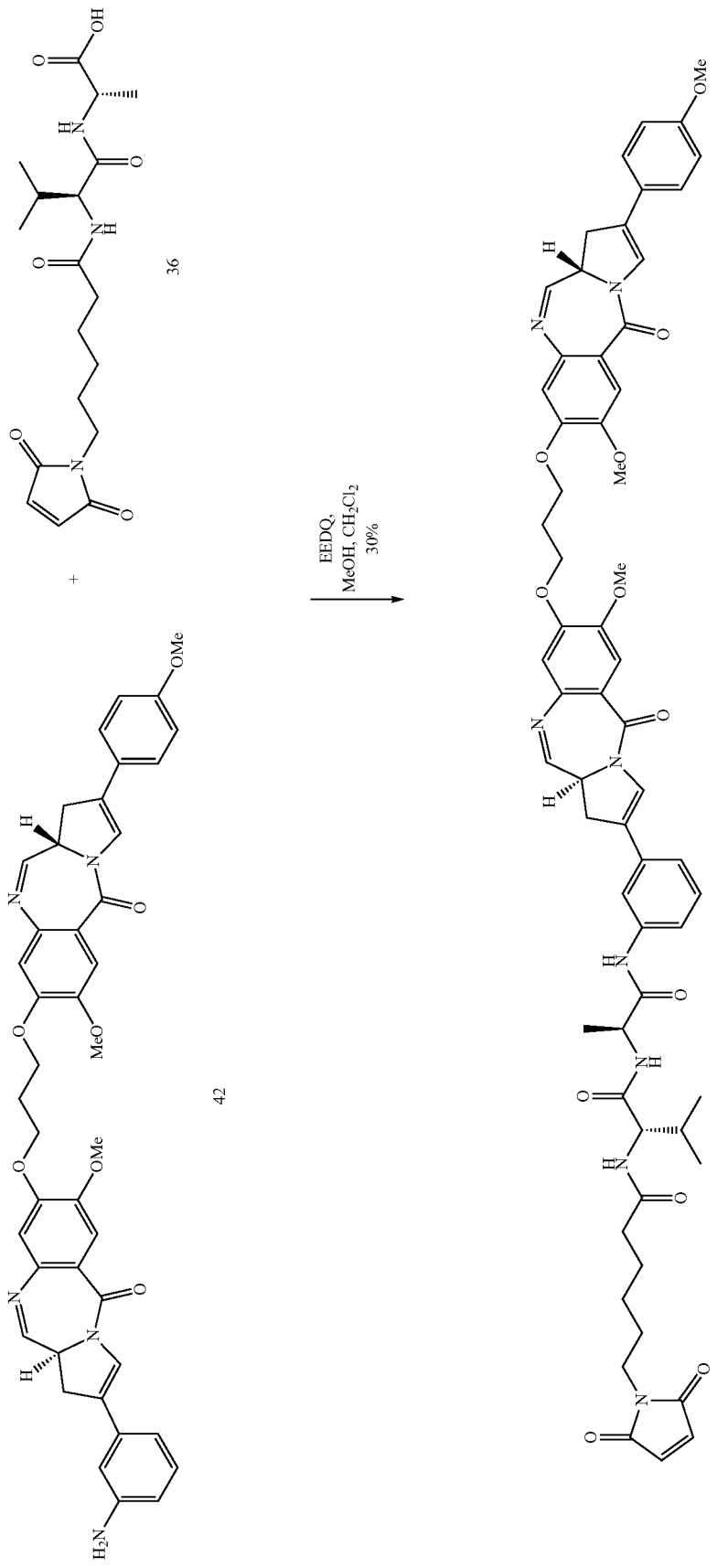

6-(2,5-dioxo-2,5-dihydro-1H-pyrrol-1-yl)-N—((S)-1-(((S)-1((3-((S)-7-methoxy-8-(3-(((S)-7-methoxy-2-(4-methoxyphenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)amino)-1-oxopropan-2-yl)amino)-3-methyl-1-oxobutan-2-yl)hexanamide (43)

A flame-dried 10 mL flask was charged with acid 36 (3.6 mg, 9.4 µmol), EEDQ (2.8 mg, 11.3 µmol), and 0.38 mL anhydrous $CH_2Cl_2$ containing 1% methanol. The reaction was stirred under nitrogen for 1 h; PBD dimer 42 (6.8 mg, 9.4 µmol) was then added and the reaction was stirred at room temperature for 2 h, at which time LC-MS revealed conversion to product. The reaction was concentrated, dissolved in minimal $CH_2Cl_2$, and purified by radial chromatography on a 1 mm chromatotron plate eluted with $CH_2Cl_2$/MeOH mixtures (100:0 to 90:10 $CH_2Cl_2$/MeOH) to provide drug linker 43 (3.1 mg, 30%). TLC: $R_f$=0.31, 10% MeOH in $CH_2Cl_2$. Analytical HPLC (0.1% formic acid): $t_R$ 11.49 min. LC-MS: $t_R$ 12.28 min, m/z (ES$^+$) found 1089.5 (M+H)$^+$, m/z (ES$^-$) found 1087.3 (M−H)$^-$.

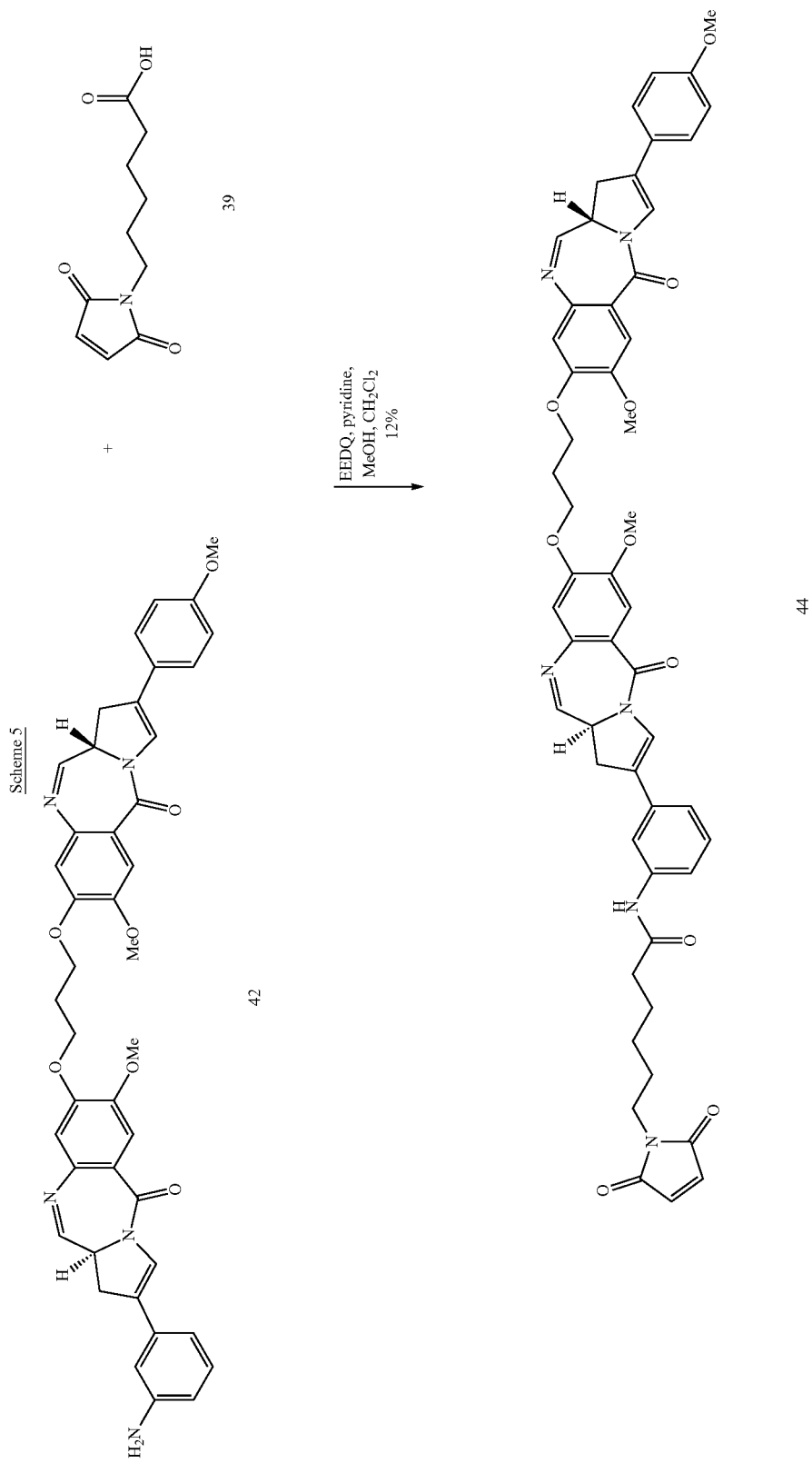

6-(2,5-dioxo-2,5-dihydro-1H-pyrrol-1-yl)-N-(3-((S)-7-methoxy-8-(3-(((S)-7-methoxy-2-(4-methoxyphenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)hexanamide (44)

To a flame-dried 10 mL flask was added PBD dimer 42 (8.0 mg, 11 µmol), which was dissolved in 0.44 mL of a 10% MeOH in $CH_2Cl_2$ solvent mixture. Maleimidocaproic acid (39) was added (2.3 mg, 11 µmol), followed by EEDQ (3.3 mg, 13.2 µmol) and pyridine (1.8 µL, 22 µmol). The reaction was stirred at room temperature under a nitrogen atmosphere for 3 h, at which time LC-MS revealed conversion to product. The reaction was purified by radial chromatography on a 1 mm chromatotron plate eluted with $CH_2Cl_2$/MeOH mixtures (100:0 to 90:10 $CH_2Cl_2$/MeOH) to provide drug linker compound 44 (1.2 mg, 12%). TLC: $R_f$=0.45, 10% MeOH in $CH_2Cl_2$. Analytical HPLC (0.05% trifluoroacetic acid): $t_R$ 11.71 min. LC-MS: $t_R$ 12.63 min, m/z (ES$^+$) found 919.1 (M+H)$^+$, m/z (ES$^-$) found 917.1 (M–H)$^-$.

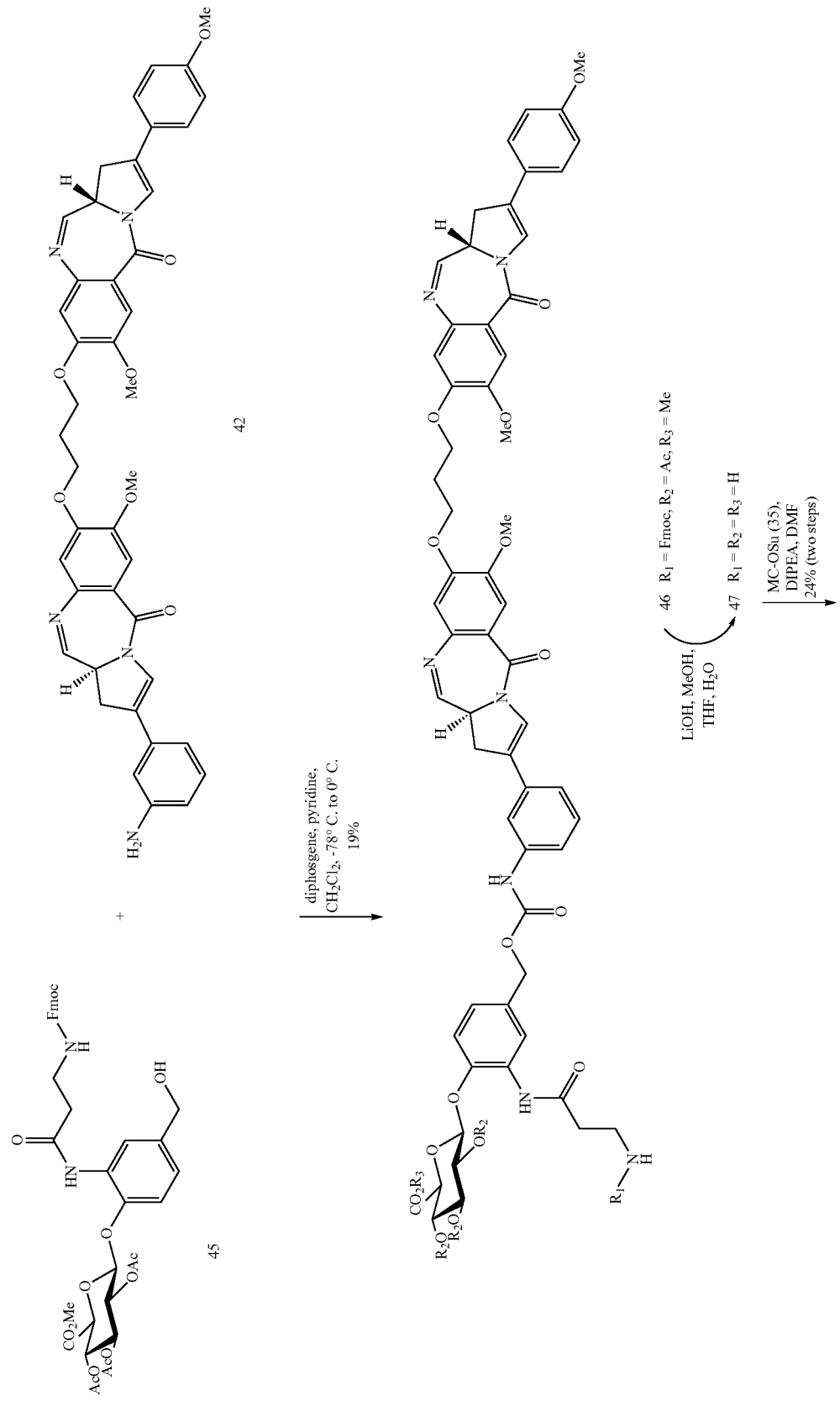
Scheme 6

-continued
48
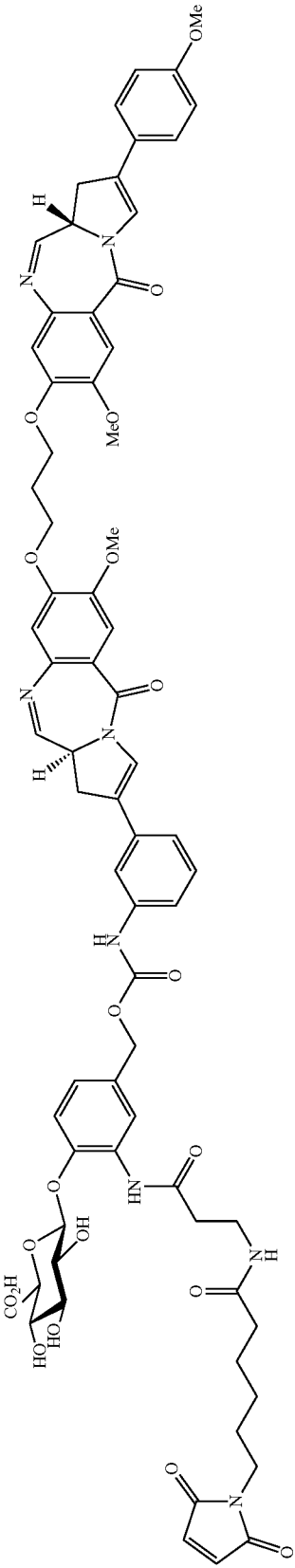

(2S,3R,4S,5R,6R)-2-(2-(3-(((99H-fluoren-9-yl)
methoxy)carbonyl)amino)propanamido)-4-((((3-((S)-
7-methoxy-8-(3-(((S)-7-methoxy-2-(4-methoxyphe-
nyl)-5-oxo-5,11a-dihydro-1H-pyrrolo[2,1-c][1,4]
benzodiazepin-8-yl)oxy)propoxy)-5-oxo-5,11a-
dihydro-1H-pyrrolo[2,1-c][1,4]benzodiazepin-2-yl)
phenyl)carbamoyl)oxy)methyl)phenoxy)-6-
methyltetrahydro-2H-pyran-3,4,5-triyl triacetate
(46)

A flame-dried flask was charged with glucuronide linker intermediate 45 (reference: Jeffrey et al., *Bioconjugate Chemistry*, 2006, 17, 831-840) (15 mg, 20 μmol), 1.4 mL anhydrous $CH_2Cl_2$, pyridine (20 μL, 240 μmol), and then cooled to −78° C. under nitrogen. Diphosgene (3.0 μL, 24 μmol) was then added and the reaction was stirred for 2 h at −78° C., after which time a small aliquot was quenched with methanol and analyzed by LC-MS for formation of the methyl carbonate, which confirmed formation of the glucuronide chloroformate. PBD dimer 42 (15 mg, 20 μmol) was then dissolved in 0.7 mL anhydrous $CH_2Cl_2$ and added dropwise to the reaction vessel. The reaction was warmed to 0° C. over 2 h and then diluted with 50 mL $CH_2Cl_2$. The organic layer was washed with water (50 mL), brine (50 mL), dried over sodium sulfate, filtered and concentrated. The crude reaction product was purified by radial chromatography on a 1 mm chromatotron plate eluted 10% MeOH in $CH_2Cl_2$ to provide 46 (5.7 mg, 19%). TLC: $R_f$=0.47, 10% MeOH in $CH_2Cl_2$. Analytical HPLC (0.1% formic acid): $t_R$ 12.09 min. LC-MS: $t_R$ 14.05 min, m/z (ES$^+$) found 1500.3 (M+H)$^+$, (2S,3S,4S,5R,6S)-6-(2-(3-aminopropanamido)-4-
(((3-((S)-7-methoxy-8-(3-(((S)-7-methoxy-2-(4-
methoxyphenyl)-5-oxo-5,11a-dihydro-1H-pyrrolo[2,
1-c][1,4]benzodiazepin-8-yl)oxy)propoxy)-5-oxo-5,
11a-dihydro-1H-pyrrolo[2,1-c][1,4]benzodiazepin-2-
yl)phenyl)carbamoyl)oxy)methyl)phenoxy)-3,4,5-
trihydroxytetrahydro-2H-pyran-2-carboxylic acid
(47)

A flask containing 46 (5.7 mg, 3.8 μmol) dissolved in a solvent mixture of 0.2 mL each of MeOH, tetrahydrofuran, and water was cooled to 0° C. To the stirred solution was added lithium hydroxide monohydrate (0.8 mg, 19 μmol) and the reaction was stirred at room temperature for 4 h, at which time LC-MS indicated conversion to product. Glacial acetic acid (1.1 μL, 19 μmol) was added and the reaction was concentrated to provide 47, which was carried forward without further purification. LC-MS: $t_R$ 11.59 min, m/z (ES$^+$) found 1138.4 (M+H)$^+$.

(2S,3S,4S,5R,6S)-6-(2-(3-(6-(2,5-dioxo-2,5-dihydro-
1H-pyrrol-1-yl)hexanamido)propanamido)-4-((((3-
(S)-7-methoxy-8-(3-(((S)-7-methoxy-2-(4-methoxy-
phenyl)-5-oxo-5,11a-dihydro-1H-pyrrolo[2,1-c][1,4]
benzodiazepin-8-yl)oxy)propoxy)-5-oxo-5,11a-
dihydro-1H-pyrrolo[2,1-c][1,4]benzodiazepin-2-yl)
phenyl)carbamoyl)oxy)methyl)phenoxy)-3,4,5-
trihydroxytetrahydro-2H-pyran-2-carboxylic acid
(48)

To a solution of 47 (4.3 mg, 3.8 umol) dissolved in 0.38 mL anhydrous DMF was added maleimidocaproyl NHS ester 35 (1.2 mg, 3.8 umol), followed by diisopropylethylamine (4.0 uL, 22.8 umol). The reaction was stirred at room temperature under nitrogen for 2 h, at which time LC-MS revealed conversion to product. The reaction was diluted with a mixture of acetonitrile (0.5 mL), DMSO (1 mL), water (0.5 mL), and then purified by preparative HPLC. The mobile phase consisted of A=water and B=acetonitrile, both containing 0.1% formic acid. A linear elution gradient of 90:10 A:B to 10:90 A:B over 75 minutes was employed and fractions containing the desired product were lyophilized to provide drug linker compound 48 (1.2 mg, 24% over two steps). Analytical HPLC (0.1% formic acid): $t_R$ 10.85 min. LC-MS: $t_R$ 12.12 min, m/z (ES$^+$) found 1331.4 (M+H)$^+$, m/z (ES$^-$) found 1329.5 (M−H)$^-$.

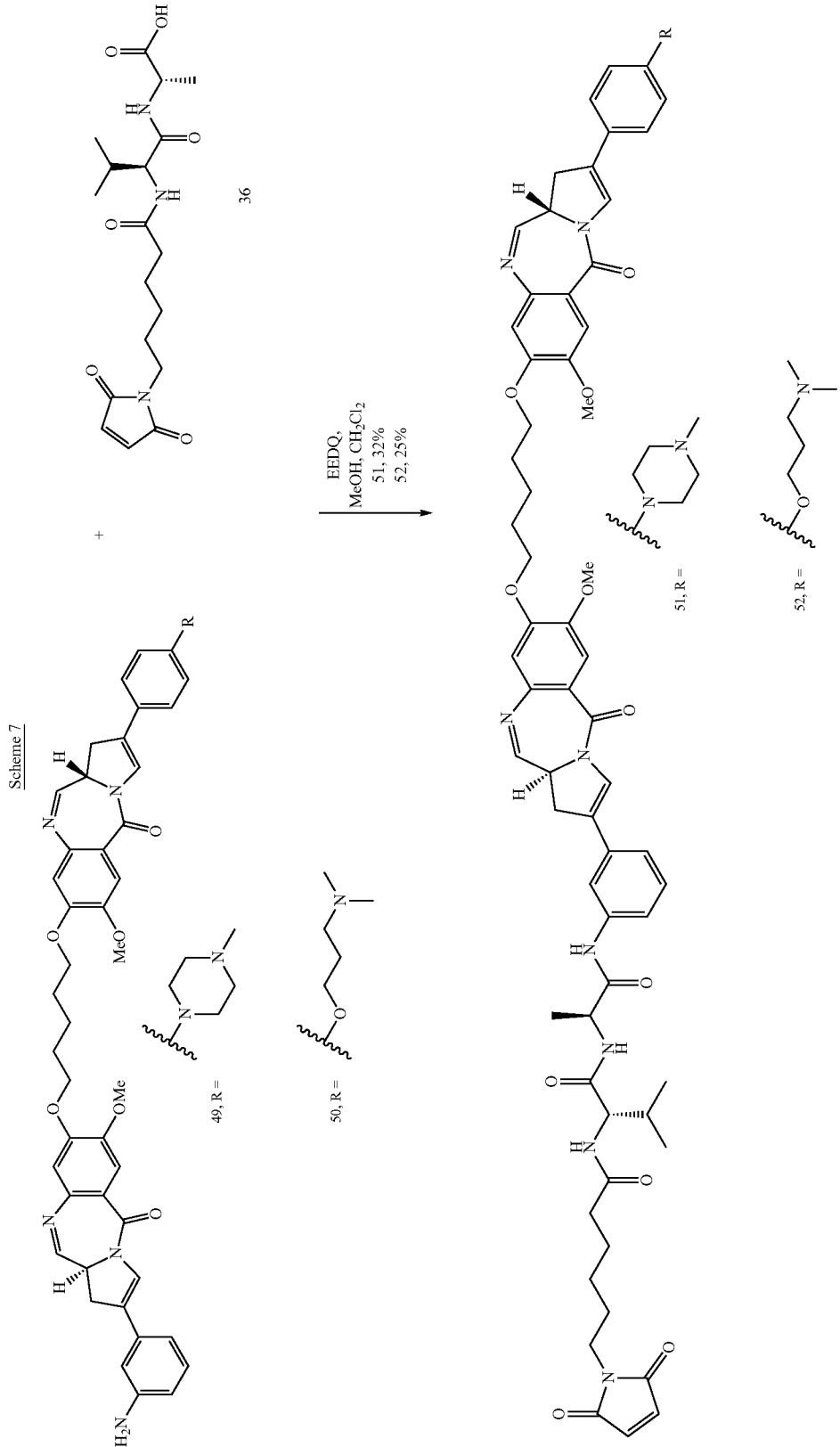

6-(2,5-dioxo-2,5-dihydro-1H-pyrrol-1-yl)-N—((S)-1-(((S)-1-((3-(S)-7-methoxy-8-((5-(((S)-7-methoxy-2-(4-(4-methylpiperazin-1-yl)phenyl)-5-oxo-5,11a-dihydro-1H-pyrrolo[2,1-c][1,4]benzodiazepin-8-yl)oxy)pentyl)oxy)-5-oxo-5,11a-dihydro-1H-pyrrolo[2,1-c][1,4]benzodiazepin-2-yl)phenyl)amino)-1-oxopropan-2-yl)amino)-3-methyl-1-oxobutan-2-yl)hexanamide (51)

A flame-dried 10 mL flask was charged with acid 36 (2.7 mg, 7.1 µmol). EEDQ (2.1 mg, 8.5 µmol), and 0.28 mL anhydrous CH$_2$Cl$_2$ containing 1% methanol. The reaction was stirred under nitrogen for 1 h; PBD dimer 49 (5.8 mg, 7.1 µmol) was then added and the reaction was stirred at room temperature for 20 h, at which time LC-MS revealed conversion to product. The reaction was concentrated then purified by preparative HPLC and fractions containing the desired product were lyophilized to provide drug linker compound 51 (2.7 mg, 32%). Analytical HPLC (0.1% formic acid): $t_R$ 9.17 min. LC-MS: $t_R$ 11.25 min, m/z (ES$^+$) found 1185.3 (M+H)$^+$, m/z (ES$^-$) found 1182.9 (M−H)$^-$.

N—((S)-1-(((S)-1((3-(S)-8-((5-((S)-2-(4-(3(dimethylamino)propoxy)phenyl)-7-meth oxy-5-oxo-5,11a-dihydro-1H-pyrrolo[2,1-c][1,4]benzodiazepin-8-yl)oxy)pentyl)oxy)-7-methoxy-5-oxo-5,11a-dihydro-1H-pyrrolo[2,1-c][1,4]benzodiazepin-2-yl)phenyl)amino)-1-oxopropan-2-yl)amino)-3-methyl-1-oxobutan-2-yl)-6-(2,5-dioxo-2,5-dihydro-1H-pyrrol-1-yl)hexanamide (52)

A flame-dried 10 mL flask was charged with acid 36 (3.7 mg, 9.7 µmol), EEDQ (2.9 mg, 11.6 µmol), and 0.4 mL anhydrous CH$_2$Cl$_2$ containing 1% methanol. The reaction was stirred under nitrogen for 1 h; PBD dimer 50 (8.0 mg, 9.7 µmol) was then added and the reaction was stirred at room temperature for 6 h, at which time LC-MS revealed the presence of product. The reaction was concentrated then purified by preparative HPLC and fractions containing the desired product were lyophilized to provide drug linker compound 52 (3.1 mg, 25%). Analytical HPLC (0.1% formic acid): $t_R$ 9.45 min. LC-MS: $t_R$ 11.75 min, m/z (ES$^+$) found 1188.4 (M+H)$^+$, m/z (ES$^-$) found 1186.0 (M−H)$^-$.

Scheme 8

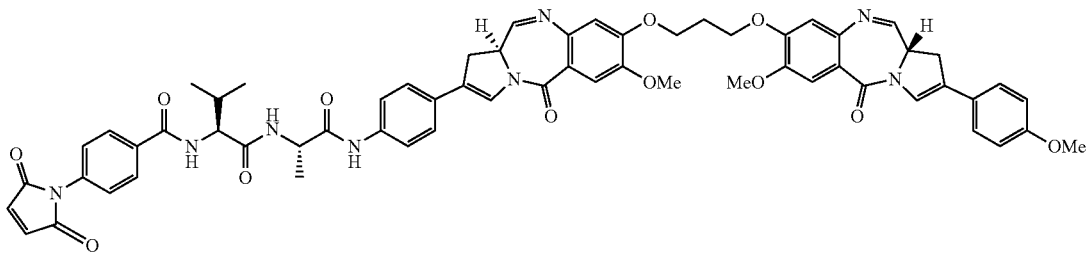

54

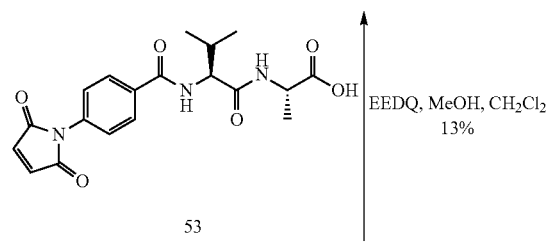

53

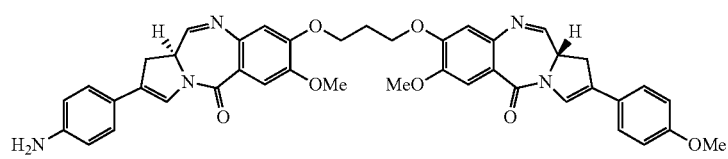

37

-continued

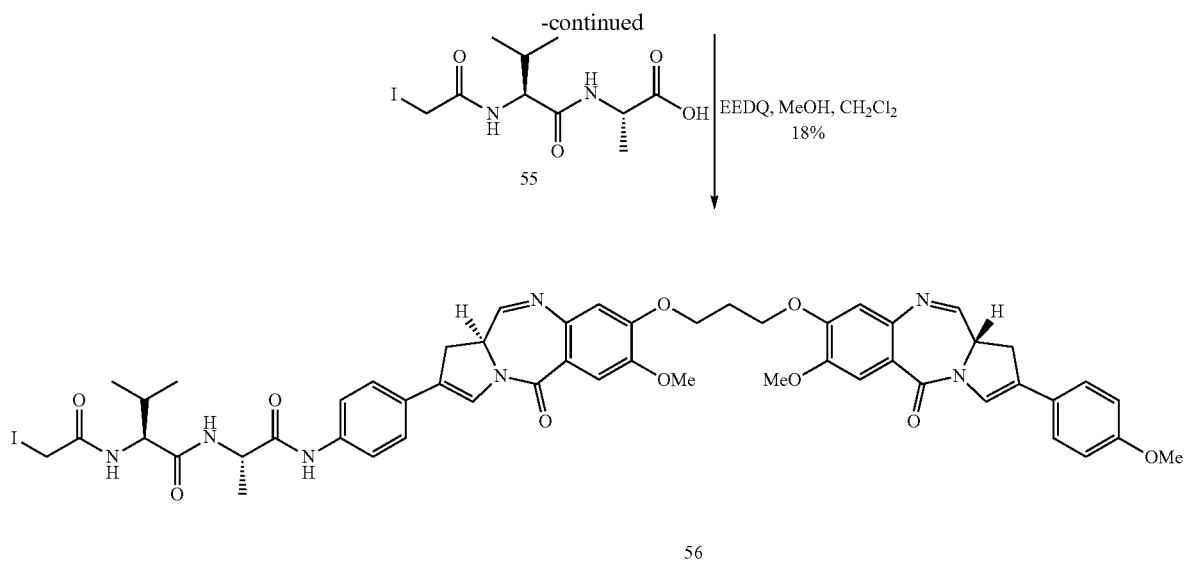

4-(2,5-dioxo-2,5-dihydro-1H-pyrrol-1-yl)-N—((S)-1-(((S)-1-((4-((S)-7-methoxy-8-(3-(((S)-7-methoxy-2-(4-methoxyphenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)amino)-1-oxopropan-2-yl)amino)-3-methyl-1-oxobutan-2-yl)benzamine (54)

To a flame-dried 10 mL flask was added linker fragment 53 (7.7 mg, 20 µmol), which was dissolved in 0.33 mL of a 5% MeOH in CH$_2$Cl$_2$ solvent mixture. EEDQ (6.1 mg, 25 µmol) was added and the reaction was stirred at room temperature under nitrogen for 15 minutes, at which time PBD dimer 37 (12 mg, 16.5 µmol) was added. The reaction was stirred at room temperature under a nitrogen atmosphere for an additional 3 h, at which time LC-MS revealed conversion to product. The reaction was purified by radial chromatography on a 1 mm chromatotron plate eluted with CH$_2$Cl$_2$/MeOH mixtures (100:0 to 90:10 CH$_2$Cl$_2$/MeOH) to provide 54 (2.4 mg, 13%). TLC: R$_f$=0.44, 10% MeOH in CH$_2$Cl$_2$. Analytical HPLC (0.05% trifluoroacetic acid): t$_R$ 11.53 min. LC-MS: t$_R$ 12.61 min, m/z (ES$^+$) found 1095.4 (M+H)$^+$, m/z (ES$^-$) found 1093.9 (M−H)$^-$.

(S)-2-(2-iodoacetamido)-N—((S)-1-((4-((S)-7-methoxy-8(3-((S)-7-methoxy-2-(4-methoxyphenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)amino)-1-oxopropan-2-yl)-3-methylbutanamide (56)

A flame-dried flask was charged with linker 55 (7.8 mg, 22 µmol), which was dissolved in 0.37 mL of a 5% MeOH in CH$_2$Cl$_2$ solvent mixture. EEDQ (6.8 mg, 27.5 µmol) was added and the reaction was stirred at room temperature under nitrogen for 15 minutes, at which time PBD dimer 37 (13 mg, 18 µmol) was added. The reaction was stirred at room temperature under a nitrogen atmosphere for an additional 4 h, at which time LC-MS revealed conversion to product.

The reaction was purified by radial chromatography on a 1 mm chromatotron plate eluted with CH$_2$Cl$_2$/MeOH mixtures (100:0 to 80:20 CH$_2$Cl$_2$/MeOH) to provide 56 (3.5 mg, 18%). Analytical HPLC (0.1% formic acid): t$_R$ 11.43 min. LC-MS: t$_R$ 12.49 min, m/z (ES$^+$) found 1064.6 (M+H)$^+$, m/z (ES$^-$) found 1098.9 (M+2H$_2$O—H)$^-$.

Scheme 9

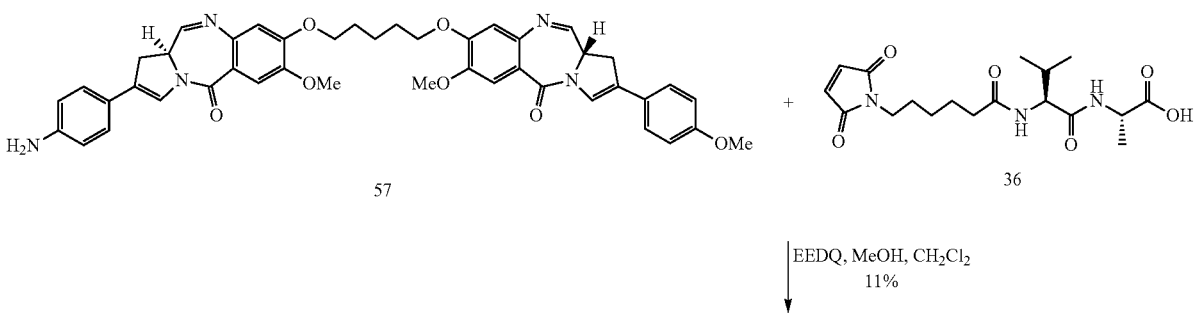

EEDQ, MeOH, CH$_2$Cl$_2$
11%

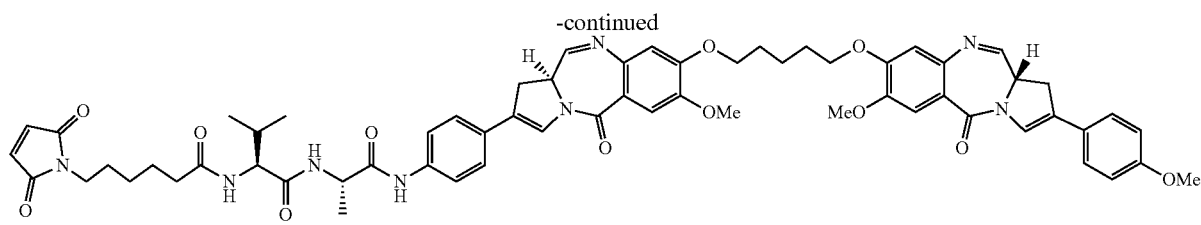

58

6-(2,5-dioxo-2,5-dihydro-1H-pyrrol-1-yl)-N—((S)-1-(((S)-1-((4-((S)-7-methoxy-8-((5-(((S)-7-methoxy-2-(4-methoxyphenyl)-5-oxo-5,11a-dihydro-1H-pyrrolo[2,1-c][1,4]benzodiazepin-8-yl)oxy)pentyl)oxy)-5-oxo-5,11a-dihydro-1H-pyrrolo[2,1-c][1,4]benzodiazepin-2-yl)phenyl)amino)-1-oxopropan-2-yl)amino)-3-methyl-1-oxobutan-2-yl)hexanamide (58)

To a flame-dried 10 mL flask was added linker fragment 36 (19 mg, 50 µmol), which was dissolved in 0.33 mL of a 5% MeOH in CH$_2$Cl$_2$ solvent mixture. EEDQ (12.4 mg, 50 µmol) was added and the reaction was stirred at room temperature under nitrogen for 15 minutes, at which time PBD dimer 57 (12.5 mg, 16.6 µmol) was added. The reaction was stirred at room temperature under a nitrogen atmosphere for an additional 5 h, at which time LC-MS revealed conversion to product. The reaction was purified by radial chromatography on a 1 mm chromatotron plate eluted with CH$_2$Cl$_2$/MeOH mixtures (100:0 to 80:20 CH$_2$Cl$_2$/MeOH) to provide 58 (2.1 mg, 11%). Analytical HPLC (0.1% formic acid): t$_R$ 12.19 min. LC-MS: t$_R$ 12.58 min, m/z (ES$^+$) found 1117.8 (M+H)$^+$, m/z (ES$^-$) found 1133.7 (M+H$_2$O—H)$^-$.

Scheme 10

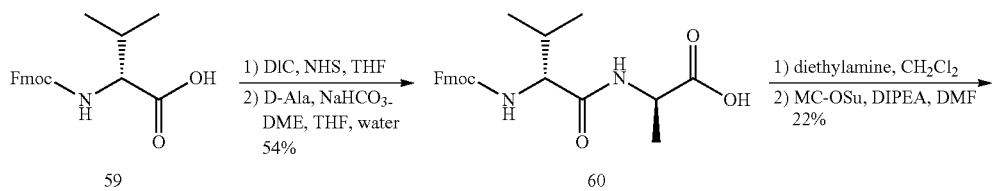

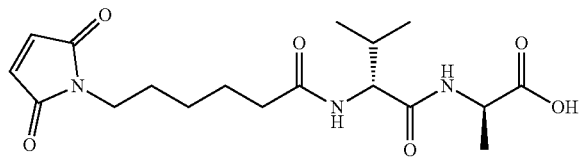

61

+

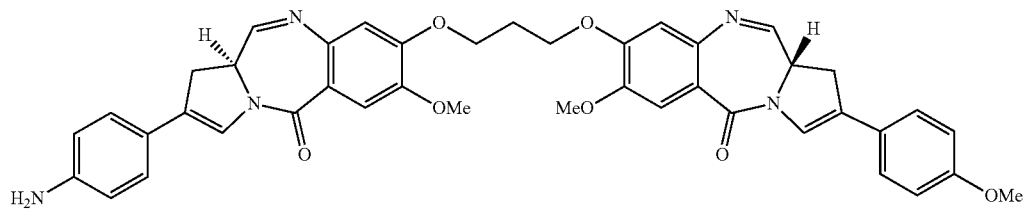

37

EEDQ, MeOH, CH$_2$Cl$_2$
16%

-continued

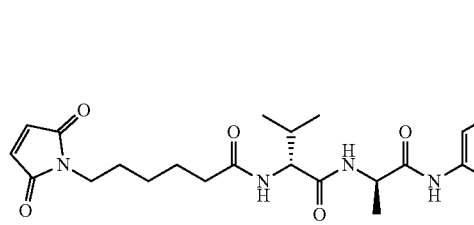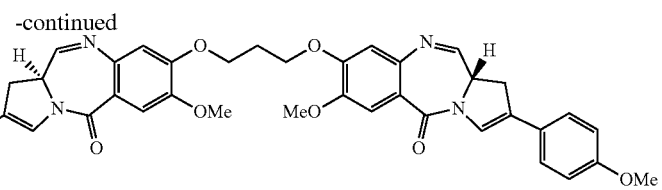

62

(R)-2-((R)-2-(((9H-fluoren-9-yl)methoxy)carbonyl)amino)-3-methylbutanamido)propanoic acid (60)

A flame dried flask was charged with Fmoc-D-Valine (200 mg, 0.59 mmol) and 5.9 mL anhydrous THF. N-hydroxysuccinimide (75 mg, 0.65 mmol) was added, followed by diisopropylcarbodiimide (0.1 mL, 0.65 mmol), and the reaction was stirred at an ambient temperature overnight, at which time LC-MS revealed conversion to product. The reaction mixture was diluted with $CH_2Cl_2$ and washed with water (50 mL), brine (50 mL), dried over sodium sulfate and concentrated to dryness. The material was carried forward without further purification. LC-MS: $t_R$ 13.89 min, m/z ($ES^+$) found 437.0 $(M+H)^+$, Crude Fmoc-D-Val-OSu (0.59 mmol) was dissolved in dimethoxyethane (1.5 mL) and THF (0.8 mL). D-alanine (73 mg, 0.89 mmol) was dissolved in 2.3 mL water and added to the reaction mixture, followed by sodium bicarbonate (99 mg, 1.2 mmol). The resulting slurry was stirred at room temperature overnight, at which time the reaction had clarified and LC-MS revealed completion. The reaction was poured into 50 mL $CH_2Cl_2$ and the organic layer was washed with 50 mL 0.1 M HCl and then brine, dried over sodium sulfate, and then concentrated to dryness. The crude product was purified by radial chromatography on a 1 mm chromatotron plate eluted with $CH_2Cl_2$ to provide 60 (128 mg, 54%). TLC: $R_f$=0.18, 10% MeOH in $CH_2Cl_2$. Analytical HPLC (0.1% formic acid): $t_R$ 9.47 min. LC-MS: $t_R$ 13.09 min, m/z ($ES^+$) found 411.1 $(M+H)^+$, m/z ($ES^-$) found 409.2 $(M-H)^-$.

(R)-2-((R)-2-(6-(2,5-dioxo-2,5-dihydro-1H-pyrrol-1-yl)hexanamido)-3-methylbutanamido)propanoic acid (61)

Protected dipeptide 60 (70 mg, 0.37 mmol) was suspended in 6 mL anhydrous $CH_2Cl_2$, cooled on ice under nitrogen, and 2 mL of diethylamine was added dropwise. The reaction was warmed to room temperature and stirred under nitrogen for 2 h, at which time HPLC revealed consumption of starting material. The reaction was diluted with 6 mL of chloroform and concentrated. The crude reaction residue was re-dissolved in 6 mL chloroform and concentrated twice, followed by drying on a vacuum line for 2 h. The deprotected dipeptide was then dissolved in 3.7 mL anhydrous DMF. MC-OSu (138 mg, 0.44 mmol) was then added, followed by diisopropylethylamine (0.32 mL, 1.9 mmol). The reaction was stirred under a nitrogen atmosphere at room temperature overnight. Workup was achieved by pouring the reaction in to 50 mL 0.1 M HCl and extracting with ethyl acetate (50 mL, 3×). The combined organic layer was washed with water (50 mL) and brine (50 mL), dried over sodium sulfate, and concentrated. The crude product was purified by radial chromatography on a 1 mm chromatotron plate eluted with $CH_2Cl_2$/MeOH mixtures (99:1 to 95:5 $CH_2Cl_2$/MeOH) to provide 61 (14 mg, 22%). $^1$H NMR ($CD_3OD$) δ (ppm) 0.94 (d, J=14 Hz, 3H), 0.98 (d, J=14 Hz, 3H), 1.29 (m, 2H), 1.39 (d, J=7.4 Hz, 3H), 1.61 (m, 4H), 2.05 (m, 1H), 2.25 (dt, J=1.2, 7.4 Hz, 2H), 3.48 (t, J=7 Hz, 2H), 4.19 (m, 1H), 4.37 (m, 1H), 6.78 (s, 2H). Analytical HPLC (0.1% formic acid): $t_R$ 10.04 min. LC-MS: $t_R$ 11.22 min, m/z ($ES^+$) found 382.1 $(M+H)^+$, m/z ($ES^-$) found 380.0 $(M-H)^-$.

6-(2,5-d oxo-2,5-dihydro-1H-pyrrol-1-yl)-N—((R)-1-(((R)-1-((4-((S)-7-methoxy-8-(3-(((S)-7-methoxy-2-(4-methoxyphenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)amino)-1-oxopropan-2-yl)amino)-3-methyl-1-oxobutan-2-yl)hexanamide (62)

To a flame-dried 10 mL flask was added linker 61 (9.5 mg, 25 μmol), which was dissolved in 0.33 mL of a 5% MeOH in $CH_2Cl_2$ solvent mixture. EEDQ (7.3 mg, 30 μmol) was added and the reaction was stirred at room temperature under nitrogen for 15 minutes, at which time PBD dimer 37 (12 mg, 16.5 μmol) was added. The reaction was stirred at room temperature under a nitrogen atmosphere for an additional 3 h, at which time LC-MS revealed conversion to product. The reaction was purified by radial chromatography on a 1 mm chromatotron plate eluted with $CH_2Cl_2$/MeOH mixtures (100:0 to 80:20 $CH_2Cl_2$/MeOH) to provide 62 (2.8 mg, 16%). TLC: R=0.39, 10% MeOH in $CH_2Cl_2$. Analytical HPLC (0.1% formic acid): $t_R$ 11.50 min. LC-MS: $t_R$ 12.50 min, m/z ($ES^+$) found 1089.7 $(M+H)^+$, m/z ($ES^-$) found 1088.0 $(M-H)^-$.

Scheme 11

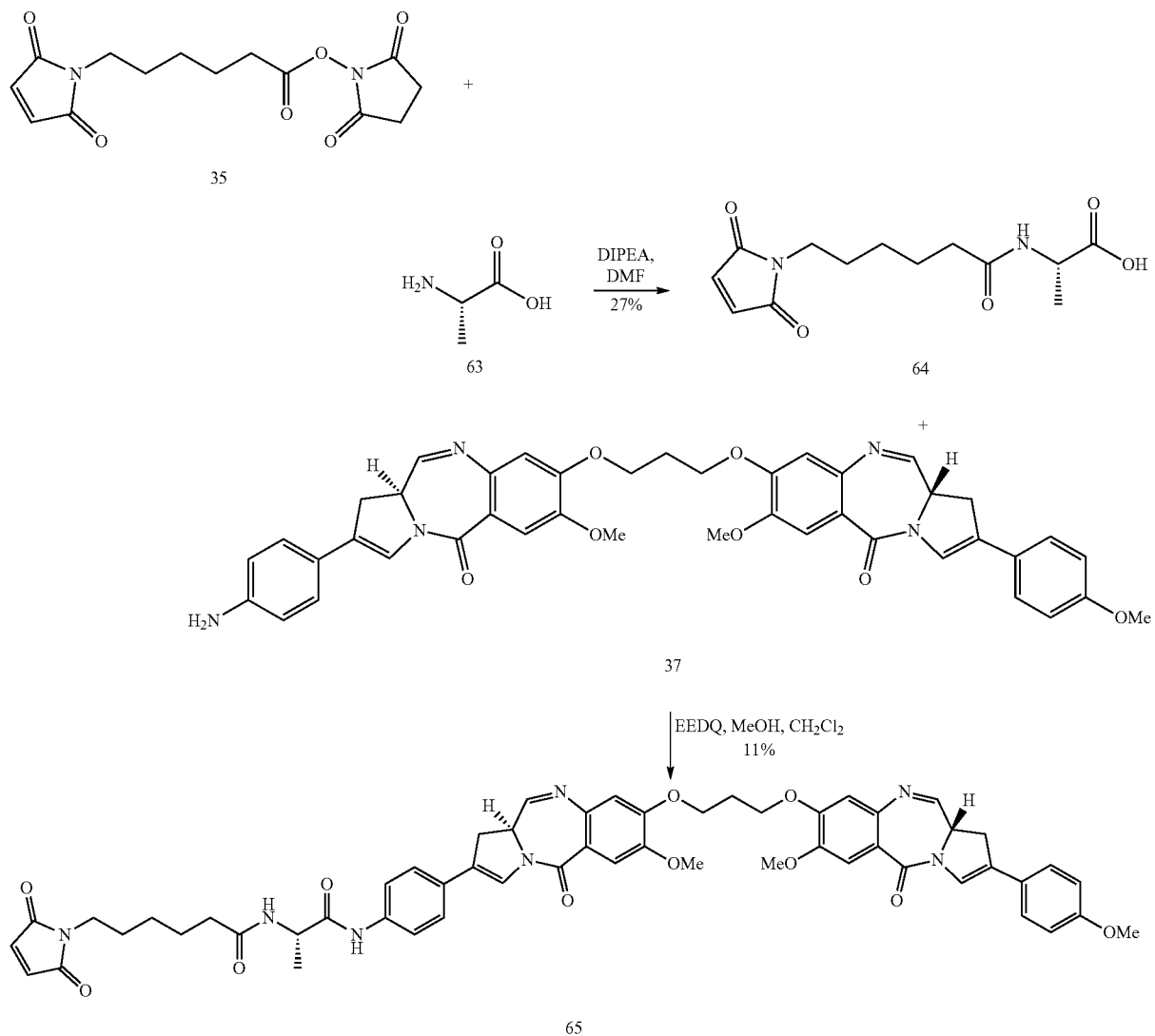

(S)-2-(6-(2,5-dioxo-2,5-dihydro-1H-pyrrol-1-yl)hexanamido)propanoic acid (64)

L-alanine (58 mg, 0.65 mmol) was suspended in 6.5 mL anhydrous DMF and MC-OSu 35 (100 mg, 0.324 mmol) was then added. Diisopropylethylamine (0.28 mL, 1.6 mmol) was added and the reaction was stirred overnight at room temperature under nitrogen. The reaction was then diluted with 50 mL 0.1 M HCl and the aqueous layer was then extracted with ethyl acetate (50 mL, 3×). The combined organic layer was then washed with water (50 mL) and brine (50 mL), dried over sodium sulfate, and then concentrated to dryness.

The reaction was purified by radial chromatography on a 1 mm chromatotron plate eluted with $CH_2Cl_2$/MeOH mixtures (97.5:2.5 to 90:10 $CH_2Cl_2$/MeOH) to provide 64 (25 mg, 27%). TLC: $R_f$=0.25, 10% MeOH in $CH_2Cl_2$. $^1$H NMR ($CD_3OD$) δ (ppm) 1.30 (m, 2H), 1.37 (d, J=7.4 Hz, 3H), 1.60 (m, 4H), 2.21 (t, J=7.4 Hz, 2H), 3.48 (t, J=7 Hz, 2H), 4.35 (q, J=7.4 Hz, 1H), 6.78 (s, 2H). Analytical HPLC (0.1% formic acid): $t_R$ 9.06 min.

6-(2,5-dioxo-2,5-dihydro-1H-pyrrol-1-yl)-N—((S)-1-((4-((S)-7-methoxy-8-(3-((S)-7-methoxy-2-(4-methoxyphenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)amino)-1-oxopropan-2-yl)hexanamide (65)

To a flame-dried 10 mL flask was added linker 64 (14 mg, 50 µmol), which was dissolved in 0.66 mL of a 5% MeOH in $CH_2Cl_2$ solvent mixture. EEDQ (15 mg, 60 µmol) was added and the reaction was stirred at room temperature under nitrogen for 15 minutes, at which time PBD dimer 37 (24 mg, 33 µmol) was added. The reaction was stirred at room temperature under a nitrogen atmosphere for an additional 4 h. The reaction was purified by radial chromatography on a 1 mm chromatotron plate eluted with $CH_2Cl_2$/MeOH mixtures (100:0 to 90:10 $CH_2Cl_2$/MeOH) to provide 65 (3.5 mg, 11%). Analytical HPLC (0.1% formic acid): $t_R$ 11.40 min. LC-MS: $t_R$ 12.39 min, m/z (ES$^+$) found 990.6 (M+H)$^+$, m/z (ES$^-$) found 989.0 (M−H)$^-$.

Scheme 12

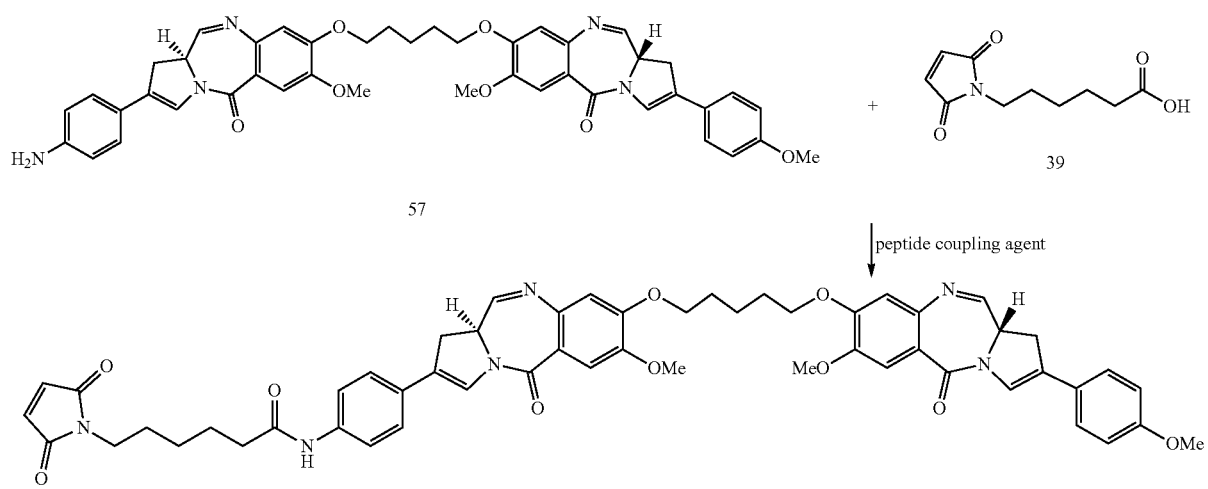

PBD Dimer 57 Linked Directly Through Maleimido-caproyl Spacer (Scheme 14):

PBD dimer 57 is coupled to maleimidocaproic acid 39 employing the chemistry described in Scheme 2.

Scheme 13

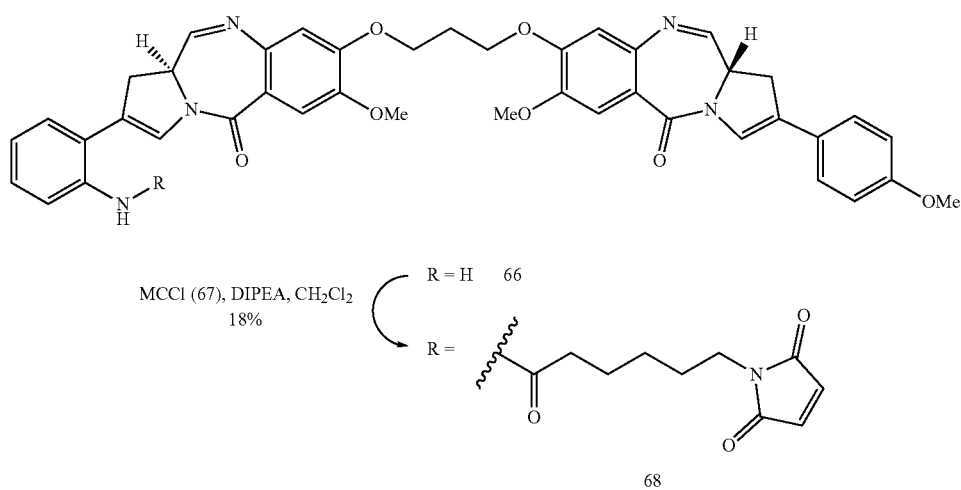

6-(2,5-dioxo-2,5-dihydro-1H-pyrrol-hydro-1H-yl)-N-(2-((S)-7-methoxy-8-(3-(((S)-7-methoxy-2-(4-methoxyphenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4] benzodiazepin-2-yl)phenyl)hexanamide (68)

To a mixture of the 66 (10 mg, 0.013 mmol) in $CH_2Cl_2$ (300 L) was added DIPEA and MC-Cl (67) (3 mg, 0.013 mmol). After 1 h, an additional 3 equiv. of DIPEA (7 μL) and 2 equiv. of the acid chloride (6 mg, 0.026 mmol) were added. After 1 h, an additional quantity of DIPEA (7 μL) and acid chloride (6 mg, 0.026 mmol) were added. After an additional 3 h, the reaction mixture was aspirated directly onto a 1 mm radial chromatotron plate and eluted with dichloromethane followed by a gradient of methanol (1% to 5%) in dichloromethane. Product containing fractions, as a mixture with the starting aniline, were concentrated to a residue and dissolved in a mixture of 0.5 mL DMSO, 0.5 mL acetonitrile and 0.5 mL deionized water and was further purified by preparative HPLC. The major peak was collected and the fractions were combined, frozen and lyophilized to give 2.1 mg (18%): MS (ES$^+$) m/z 919.2 [M+H]$^+$.

Note: Acid chloride 67 was prepared by dissolving 100 mg of 39 in oxalyl chloride (5 mL). A drop of DMF was added and the mixture was stirred at an ambient temperature for several hours before being concentrated under reduced pressure. Dichloromethane was added and the mixture was concentrated a second time to afford an off-white solid which was used directly: $^1$H-NMR (400 MHz, CDCl$_3$) δ 6.70 (s, 2H), 3.46 (t, J=7 Hz, 2H), 2.82 (t, J=7.2 Hz, 2H), 1.72 (pent, J=7.6 Hz, 2H), 1.61 (pent, J=7.4 Hz, 2H), 1.35 (pent, J=7.6 Hz, 2H).

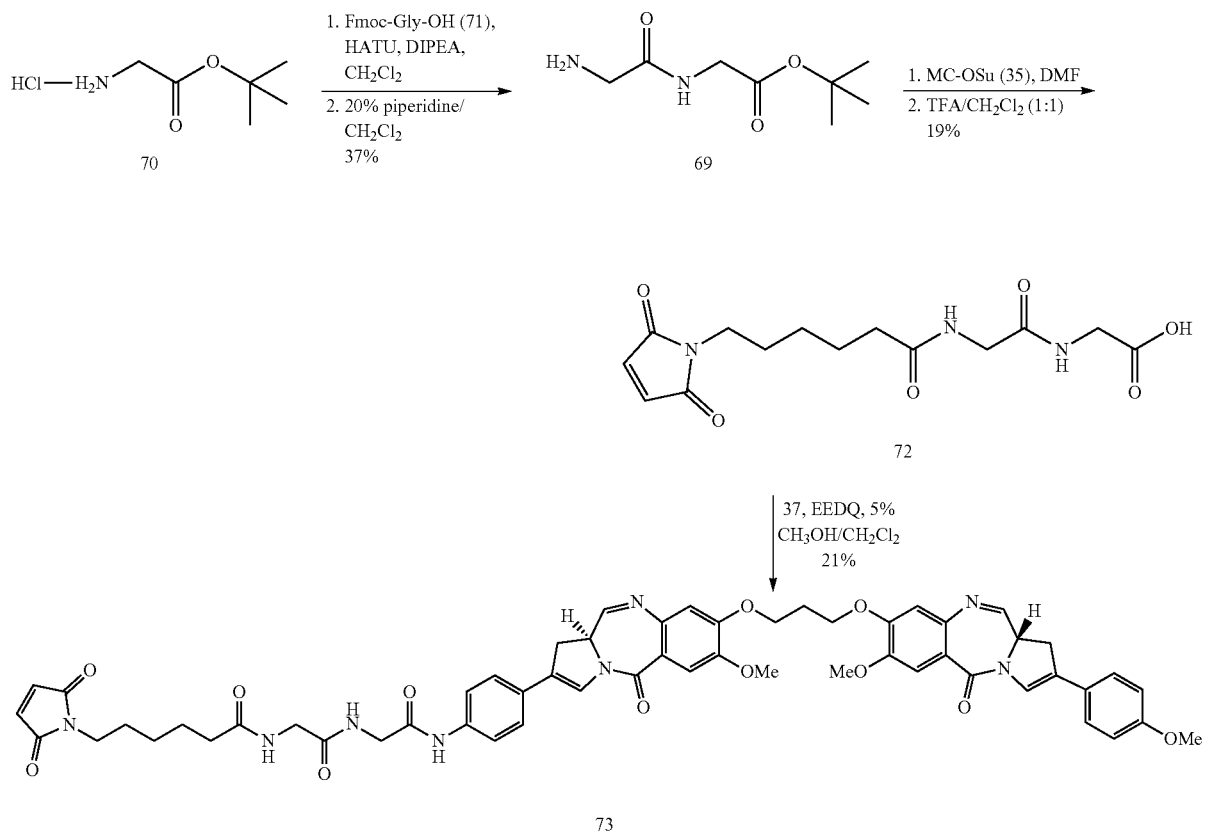

Scheme 14 tert-butyl 2-(2-aminoacetamido)acetate (69)

To a mixture of the glycine tert-butyl ester hydrogen chloride salt (70) (484 mg, 2.9 mmol) in dichloromethane (25 mL) was added Fmoc-Gly-OH (71) (0.861 mg, 2.99 mmol), DIPEA (756 mg, 4.35 mmol) and HATU (1.3 g, 3.5 mmol). The reaction mixture was stirred at an ambient temperature for 16 h and then poured into ethyl acetate and was washed with water (3×) and brine (1×). The organic phase was dried over MgSO4, filtered and concentrated under reduced pressure. The resulting residue was purified via radial chromatography on a 2 mm plate eluting with 5% methanol/dichloromethane. Product containing fractions were concentrated under reduced pressure and treated with 20% piperidine/dichloromethane (10 mL) for 1 h, before being concentrated under reduced pressure and then purified twice via radial chromatography on a 2 mm plate eluting with a gradient of 5 to 10% methanol/dichloromethane to provide (200 mg, 37%): $^1$H-NMR (400 MHz, CDCl$_3$) δ 7.62 (s, 1H), 4.00 (s, 2H), 3.39 (s, 2H), 1.47 (s, 9H).

2-(2-(6-(2,5-dioxo-2,5-dihydro-1H-pyrrol-1-yl)hexanamido)acetamido)acetic acid (72)

To a solution of the amine 69 (200 mg, 0.11 mmol) in DMF (1 mL) was added 35 (350 mg, 0.11 mmol) and the reaction mixture was allowed to stir at an ambient temperature for 2 h.

The mixture was concentrated under reduced pressure and was purify by radial chromatography on a 1 mm plate eluting with dichloromethane and a gradient of methanol (1 to 5%) in dichloromethane. Product containing fractions were concentrated under reduced pressure, dissolved in dichloromethane (4 mL) and treated with trifluoroacetic acid (4 mL). After 40 min the mixture was concentrated under reduced pressure and the resulting residue was dissolved in dichloromethane and concentrated to give 22.5 mg (19%) of 72 as white solid: $^1$H-NMR (400 MHz, CD$_3$OD) δ 6.79 (s, 2H), 3.93 (s, 2H), 3.89 (s, 2H), 3.49 (t, J=6.8 Hz, 2H), 2.26 (t, J=6.8 Hz, 2H), 1.61 (m, 4H), 1.34 (m, 2H); MS (ES$^+$) m/z 326.21 [M+H]$^+$.

6-(2,5-dioxo-2,5-dihydro-1H-pyrrol-1-yl)-N-(2-(2-(((4-(S)-7-methoxy-8-(3-(((S)-7-methoxy-2-(4-methoxyphenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)amino)-2-oxoethyl)amino)-2-oxoethyl)hexanamide (73)

To a mixture of 72 (15 mg, 0.046 mmol) in 5% methanol/dichloromethane (0.5 mL) was added EEDQ (11 mg, 0.046 mmol) and the mixture was stirred for 30 min at an ambient temperature, at which time 37 (16 mg, 0.023 mmol) was added. The reaction mixture was stirred for 3 h and was purified directly on a 1 mm radial chromatotron plate eluting with a 1% to 4% methanol/dichloromethane gradient to give 6.8 mg (29%) of 73 as a yellow solid: MS (ES$^+$) m/z 1033.57 [M+H]$^+$.

Scheme 15

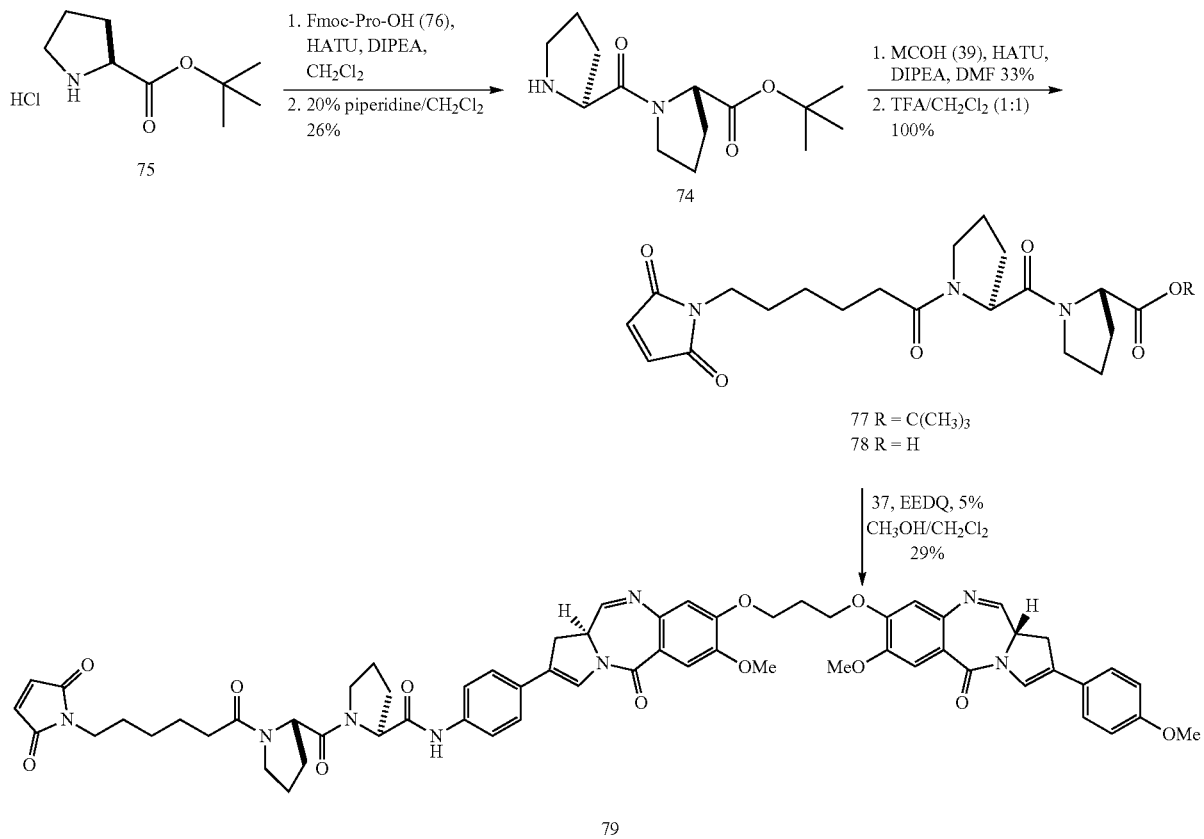

(S)-tert-butyl 1-((S)-pyrrolidine-2-carbonyl)pyrrolidine-2-carboxylate (74)

To a mixture of L-proline-tert-butyl ester hydrogen chloride salt 75 (0.5 g, 2.9 mmol) in dichloromethane (50 mL) was added 76 (0.98 g, 2.99 mmol), DIPEA (756 mg, 4.35 mmol) and HATU (1.3 g, 3.5 mmol). The reaction mixture was allowed to stir at an ambient temperature for 16 h. The mixture was poured into ethyl acetate (100 mL) and was washed with 0.2 N HCl (50 mL), water (50 mL), brine (50 mL) and dried over MgSO$_4$. Chromatography was conducted on a 2 mm radial chromatotron plate eluting with 10% ethyl acetate in hexanes. Product-containing fractions were concentrated under reduced pressure, dissolved in dichloromethane (8 mL) and treated with piperidine (2 mL). The mixture was stirred for 1 h, concentrated under reduced pressure and purified on a 2 mm radial chromatotron plate eluting with 5% methanol/dichloromethane. This gave 200 mg (26%) of the dipeptide 74: $^1$H-NMR (400 MHz, CDCl$_3$) δ 4.41 (m, 1H), 4.17 (m, 1H), 3.82 (m, 1H), 3.57 (m, 4H), 3.2 (m, 1H), 2.82 (m, 1H), 2.83-1.65 (m, 5H), 1.44 (m, 9H).

(S)-tert-butyl 1-((S)-1-(6-(2,5-dioxo-2,5-dihydro-1H-pyrrol-1-yl)hexanoyl)pyrrolidine-2-carbonyl)pyrrolidine-2-carboxylate (77)

To a mixture of the amine 74 (200 mg, 0.75 mmol), 39 (190 mg, 0.9 mmol) and DIPEA (0.32 mL, 1.8 mmol) was added HATU (342 mg, 0.9 mmol) and the mixture was allowed to stir at an ambient temperature for 5 h. The mixture was poured into ethyl acetate (100 mL) and washed with water (3×100 mL) and brine (1×100 mL). The organic phase was dried over magnesium sulfate, filtered and concentrated. The resulting residue was subjected to radial chromatography on a 2 mm radial chromatotron plate eluting with dichloromethane followed by an increasing gradient of 1 to 5% methanol in dichloromethane. Two additional purifications, both eluting with a gradient of 1 to 5% methanol in dichloromethane, first on a 2 mm plate and then on a 1 mm plate afforded 113 mg (33%) of 77 as an white solid: $^1$H-NMR (400 MHz, CDCl$_3$) δ 4.63 (m, 1H), 4.41 (m, 1H), 3.82 (m, 1H), 3.63 (m, 1H), 3.55 (m, 1H), 3.45 (m, 3H), 2.38-1.83 (m, 10H), 1.70-1.50 (m, 5H), 1.45 (m, 9H), 1.35 (m, 2H); MS (ES$^+$) m/z 462.33 [M+H]$^+$.

(S)-1-((S)-1-(6-(2,5-dioxo-2,5-dihydro-1H-pyrrol-1-yl)hexanoyl)pyrrolidine-2-carbonyl)pyrrolidine-2-carboxylic acid (78)

To a mixture of the tert-butyl ester 77 in dichloromethane (4 mL) was added trifluoroacetic acid (4 mL). After 40 min the reaction was determined to be complete by HPLC analysis. The mixture was concentrated under reduced pressure and the resulting residue was dissolved in dichloromethane and concentrated a second time to give 37 mg (100%) of 78 as a white solid: $^1$H-NMR (400 MHz, CDCl$_3$) δ 6.68 (s, 2H), 4.62 (m, 2H), 3.81 (m, 1H), 3.70 (m, 1H), 3.57 (m, 2H), 3.45 (m, 2H), 2.40-1.91 (m, 10H), 1.70-1.45 (m, 4H), 1.33 (m, 2H); MS (ES$^+$) m/z 406.2 [M+H]$^+$.

1-(1-(6-(2,5-dioxo-2,5-dihydro-1H-pyrrol-1-yl)hexanoyl)pyrrolidine-2-carbonyl)-N-(4-((S)-7-methoxy-8-(3-((S)-7-methoxy-2-(4-methoxyphenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)pyrrolidine-2-carboxamide (79)

To a mixture of the 78 (9.3 mg, 0.023 mmol) in 5% methanol/dichloromethane (0.4 mL) was added EEDQ (7 mg, 0.027 mmol). The mixture was stirred for 15 min at an ambient temperature and then 37 (15 mg, 0.021 mmol) was added. The mixture was stirred for 4 h, the reaction mixture was diluted with dichloromethane (2 mL) and was aspirated directly onto a 1 mm radial chromatotron plate. The product was eluted with a gradient of 1 to 5% methanol in dichloromethane to provide 6.8 mg (29%) of 79 as a yellow solid: MS (ES$^+$) m/z 1113.51 [M+H]$^+$.

Scheme 16

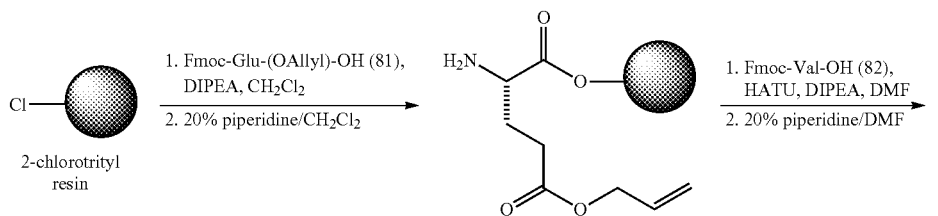

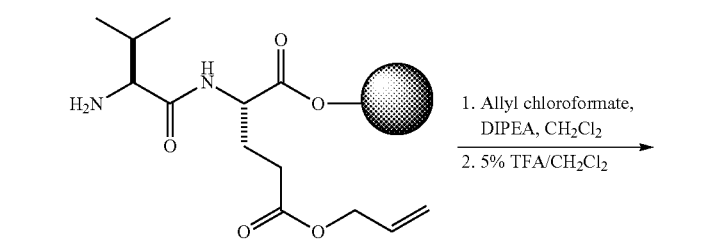

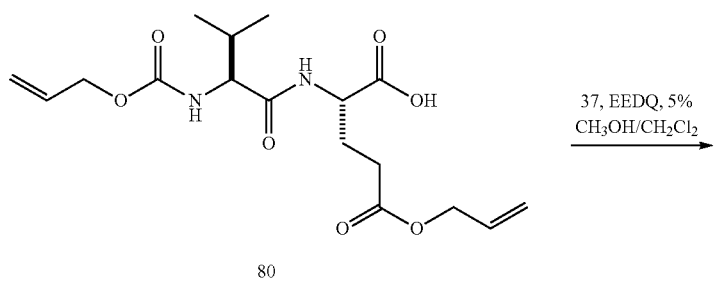

80

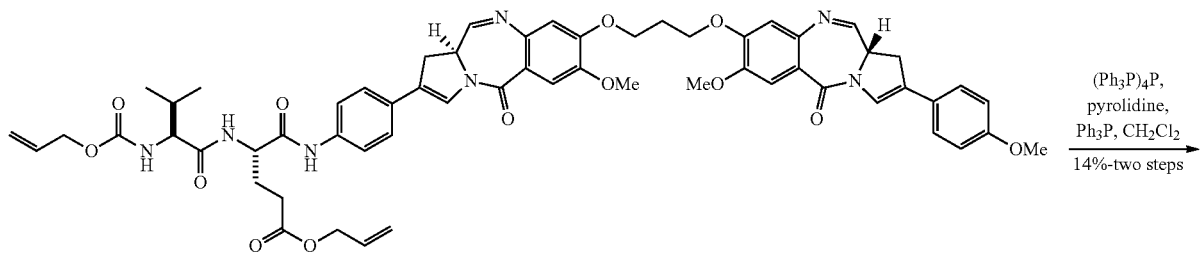

83(+37)

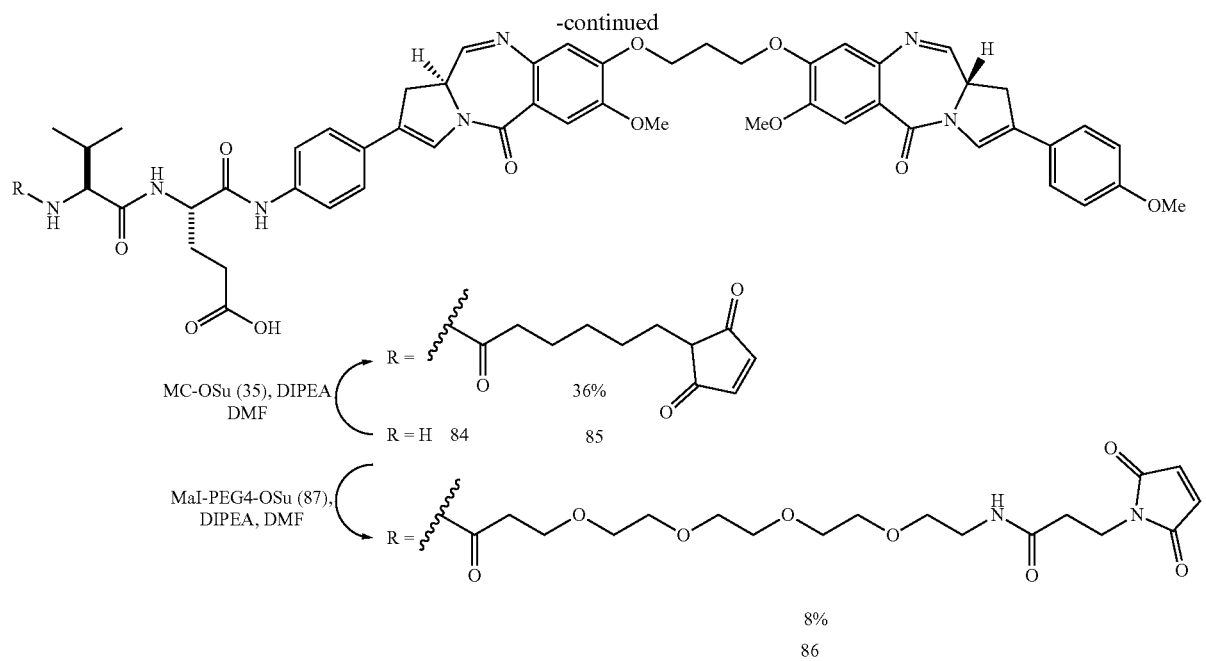

(S)-5-(allyloxy)-2-((S)-2-(((allyloxy)carbonyl)amino)-3-methylbutanamido)-5-oxopentanoic acid (80)

To a mixture of the 2-chlorotrityl resin (1.0 g, 1.01 mmol) suspended in dichloromethane (10 ml) was added Fmoc-Glu-(OAllyl)-OH (81) (409 mg, 1.0 mmol) and DIPEA (173 µL, 1.0 mmol). The reaction mixture was shaken for 5 min, and an additional portion of DIPEA (260 µL, 1.5 mmol) was added and the mixture was shaken for 1 h. Methanol (0.8 mL) was added and the mixture was shaken for 5 min, before being filtered and washed with DMF (6×), dichloromethane (6×), diethyl ether (6×) and dried under reduced pressure. The resulting resin was subjected to 20% piperidine in dichloromethane (10 mL) for 1 h, before being filtered and washed with DMF (6×), dichloromethane (6×), diethyl ether (6×) and dried under reduced pressure.

To a mixture of the Fmoc-Val-OH (82) (1.03 g, 3.30 mmol)) in DMF (7 mL) was added DIPEA (1.0 mL) and HATU (1.1 g, 3.03 mmol). After thorough mixing, the solution as aspirated into a 10 mL syringe containing the resin prepared above. The mixture was capped and shaken for 16 h. The resin was washed with DMF (6×), dichloromethane (6×) and ether (6×). A small portion (10 mg) was isolated and treated with 20% TFA/Dichloromethane and the resulting solution analyzed by LC-MS which revealed one high purity peak which displayed the correct mass (MS (ES+) m/z 509.28 [M+H]+). The remaining resin was then treated with 20% piperidine/DMF (8 mL) for 2 h, before being washed with DMF (6×), dichloromethane (6×), diethyl ether (6×) and dried under reduced pressure.

A mixture of allyl chloroformate (529 µL, 5.05 mmol), DIPEA (1.7 mL, 10 mmol) in dichloromethane (10 mL) was prepared and aspirated into a syringe containing the resin above. The mixture was capped and shaken. After approximately 2 h, the reaction mixture was drained, and washed with dichloromethane (6×). A small portion of the resin (~10 mg) was cleaved with 20% TFA/dichloromethane and analyzed by LC-MS for masses of starting material and product. The main component was still the unreacted amine, so the resin was again subjected to the conditions described above. After 4 h, the resin was washed with dichloromethane (6×), and then treated repeatedly with 5% TFA in dichloromethane (4×7 mL). The resulting solution was concentrated under reduced pressure. The mixture was purified on a 2 mm radial chromatotron plate eluting with 5% methanol/dichloromethane to give 107 mg of 80: $^1$H-NMR (400 MHz, CDCl$_3$) δ 7.05 (s, 1H), 5.90 (m, 2H), 5.57 (d, 1H), 5.29 (d, J=14.7 Hz, 2H), 5.22 (t, J=10.9 Hz, 2H), 4.59 (m, 5H), 4.02 (m, 1H), 2.60-2.40 (m, 2H), 2.37-2.18 (m, 1H), 2.17-2.02 (m, 2H), 0.96 (d, J=6.4 Hz, 3H), 0.93 (d, J=6.6 Hz, 3H); MS (ES+) m/z 371.12 [M+H]+.

(S)-allyl 4-((S)-2-(((allyloxy)carbonyl)amino)-3-methylbutanamido)-5-(4-((S)-7-methoxy-8-(3-(((S)-7-methoxy-2-(4-methoxyphenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)amino)-5-oxopentanoate (83)

To a mixture of the acid 80 (30, 0.04 mmol) in 5% methanol/dichloromethane (1 mL) was added EEDQ (20 mg, 0.082 mmol). The mixture was stirred for 30 min at an ambient temperature and then 37 (30 mg, 0.04 mmol) was added and the mixture was stirred for approximately 5 h. Partially purification by aspirating directly onto a 1 mm radial chromatotron plate and eluting with a gradient of 1% to 5% methanol/dichloromethane afforded a mixture of desired product and 37 (26 mg; ~3:1 respectively) which was carried forward without further purification.

(S)-4-((S)-2-amino-3-methylbutanamido)-5-((4-((S)-7-methoxy-8-(3-(((S)-7-methoxy-2-(4-methoxyphenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)amino)-5-oxopentanoic acid (84)

To the mixture of 83 and 37 (26 mg) in anhydrous dichloromethane (3 mL) was added Ph$_3$P (0.3 mg, 0.0012 mmol), pyrrolidine (4 μL, 0.048 mmol) and tetrakis palladium (0.7 mg, 0.6 μmol). After 2 h, an additional quantity (0.7 mg, 0.6 μmol) of tetrakis palladium was added and the reaction was allowed to stir for an additional 1 hr before being concentrated under reduced pressure. The residue was dissolved in DMSO (1 mL), acetonitrile with 0.05% formic acid (1 mL) and water with 0.05% formic acid (1 mL) and purified by preparative reverse phase HPLC. A single fraction of product was collected and lyophilized to give 6 mg (14% for two steps) of 84: MS (ES+) m/z 1078.6 [M+H]+.

(S)-4-((S)-2-(6-(2,5-dioxo-2,5-dihydro-1H-pyrrol-1-yl)hexanamido)-3-methylbutanamido)-5-((4-((S)-7-methoxy-83-((S)-7-methoxy-2-(4-methoxyphenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)amino)-5-oxopentanoic acid (85)

To a mixture of the 84 (6 mg, 6 μmol), and 35 (2 mg, 6 μmol) in DMF (200 μL) was added DIPEA (3 μL, 18 μmol) and the reaction mixture was stirred at an ambient temperature. After 1 h, an additional equivalent of 35 (2 mg, 6 μmol) was added and the reaction was allowed to continue to stir at an ambient temperature for 3 h. A third equivalent of 35 (2 mg, 6 μmol) was added and the mixture was stirred for approximately 1 h, concentrated under reduced pressure, dissolved in dichloromethane and aspirated directly onto a 1 mm radial chromatotron plate and eluted with 5% methanol in dichloromethane. This gave 2.5 mg (36%) of high purity 85: MS (ES+) m/z 1147.49 [M+H]+.

(21 S,24S)-1-(2,5-dioxo-2,5-dihydro-1H-pyrrol-1-yl)-21-isopropyl-24-((4-((S)-7-methoxy-8-(3-(((S)-7-methoxy-2-(4-methoxyphenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)carbamoyl)-3,19,22-trioxo-7,10,13,16-tetraoxa-4,20,23-triazaheptacosan-27-oic acid (86)

To a mixture of the 84 (8 mg, 8.4 μmol) and Mal-PEG4-NHS (87) (6.5 mg, 12.6 μmol) in DMF (200 μL) was added DIPEA (4.3 μL, 25 μmol). The reaction mixture was stirred at an ambient temperature for 2 h, and was concentrated under reduced pressure. The resulting residue was dissolved in dichloromethane and aspirated onto a 1 mm radial chromatotron plate. The material was polar and did not chromatograph on the silica gel-based chromatotron plate. The plate was eluted with methanol to recover the mixture which was isolated under reduced pressure. The residual material was purified via preparative reverse phase HPLC. A single main peak eluted and the fractions were combined, frozen and lyophilized to a residue of 0.9 mg (8%) of 86: MS (ES+) m/z 1353.04 [M+H]+.

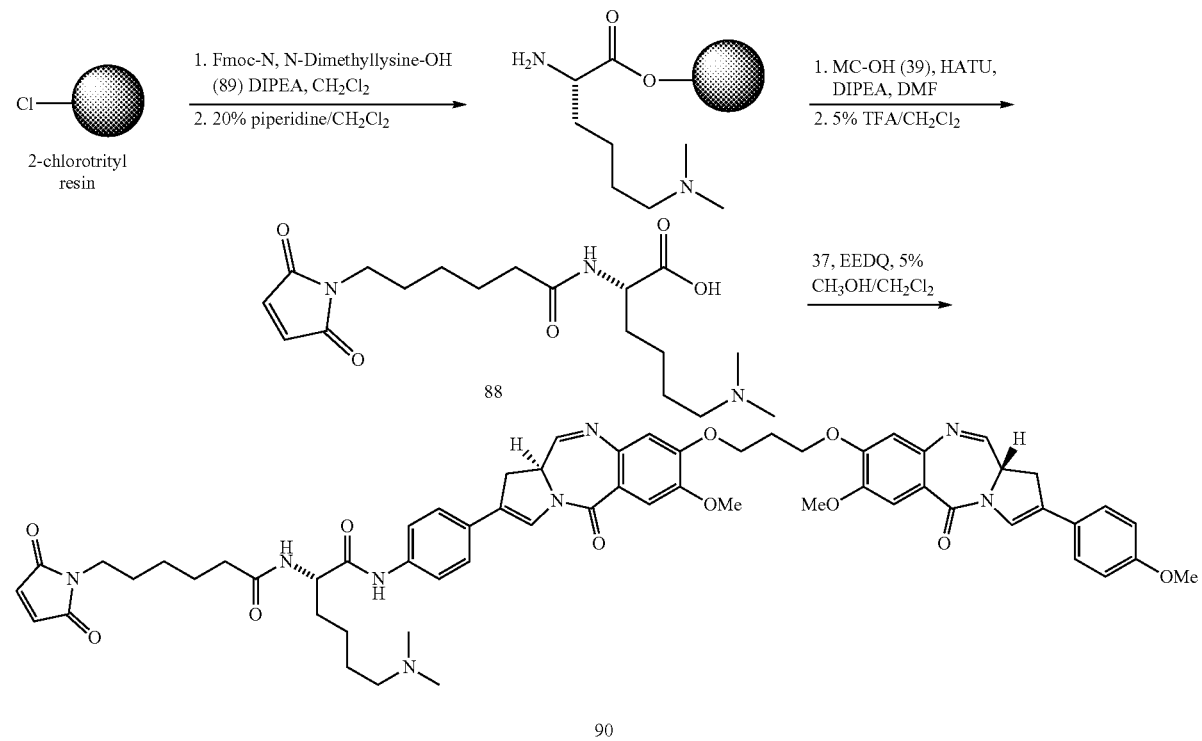

(S)-6-(dimethylamino)-2-(6-(2,5-dioxo-2,5-dihydro-1H-pyrrol-1-yl)hexanamido)hexanoic acid (88)

To a mixture of the 2-chlorotrityl resin (1 g, 1.01 mmol) in CH2Cl2 (10 ml) was added Fmoc-Lys(Me)2-OH (89) (432 mg, 1.0 mmol) and DIPEA (433 μL, 2.5 mmol). The reaction mixture was shaken for 1 h. Methanol (0.8 mL) was added and the mixture was shaken for an additional 5 min, before being filtered and washed with DMF (6×), dichloromethane (6×), diethyl ether (6×) and dried under reduced pressure. The dried resin was subjected to 20% piperidine in DMF (10 mL) for 1 h. before being filtered and washed with DMF (6×), dichloromethane (6×), diethyl ether (6×).

To a mixture of the 39 (3.0 mmol, 633 mg) in DMF (7 mL) was added DIPEA (1.0 mL) and HATU (1.1 g, 3.03 mmol). After thorough mixing, the solution as aspirated into a 10 mL syringe containing the resin above. The mixture was capped, shaken for 16 h, filtered and the resin washed with DMF (6×), dichloromethane (6×), and ethyl ether (6×). The resin was by repeatedly treating with 5% TFA/dichloromethane (6 mL×5), shaking for 1 min, and then filtering. The resulting solution was concentrated under reduced pressure and under high vacuum. The material was purified by preparatory reverse phase HPLC to give 208 mg of 88: $^1$H-NMR (400 MHz, CD$_3$OH/CDCl$_3$ 1:1 mixture) δ 6.73 (s, 2H), 4.41 (m, 1H), 3.48 (t, 2H), 3.31 (s, 1H), 3.03 (m, 2H), 2.84 (s, 6H), 2.22 (m, 2H), 1.87 (m, 2H), 1.78-1.52 (m, 6H), 1.43 (m, 2H), 1.31 (pent, 2H); MS (ES$^+$) m/z 386.28 [M+H]$^+$.

(S)-6-(dimethylamino)-2-(6-(2,5-dioxo-2,5-dihydro-1H-pyrrol-1-yl)hexanamido)-N-(4-((S)-7-methoxy-8-(3-(((S)-7-methoxy-2-(4-methoxyphenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)hexanamide (90)

To a mixture of the 88 (9.3 mg, 0.023 mmol) in 5% methanol/dichloromethane (400 μL) was added EEDQ (7 mg, 0.027 mmol). The mixture was stirred for 30 min at an ambient temperature and then 37 (15 mg, 0.021 mmol) was added. After 4 h, the mixture was concentrated under reduced pressure, dissolved in a mixture of DMSO (1 mL), acetonitrile (2 mL containing 0.05% formic acid) and water (1 mL containing 0.05% formic acid) and purified by reverse-phase HPLC (method A). Product containing fractions were contaminated with 37, so the fractions were lyophilized to a residue and repurified as described above to give 0.5 mg (2%) of pure 90: MS (ES$^+$) m/z 537.46 [M+H]/2$^+$.

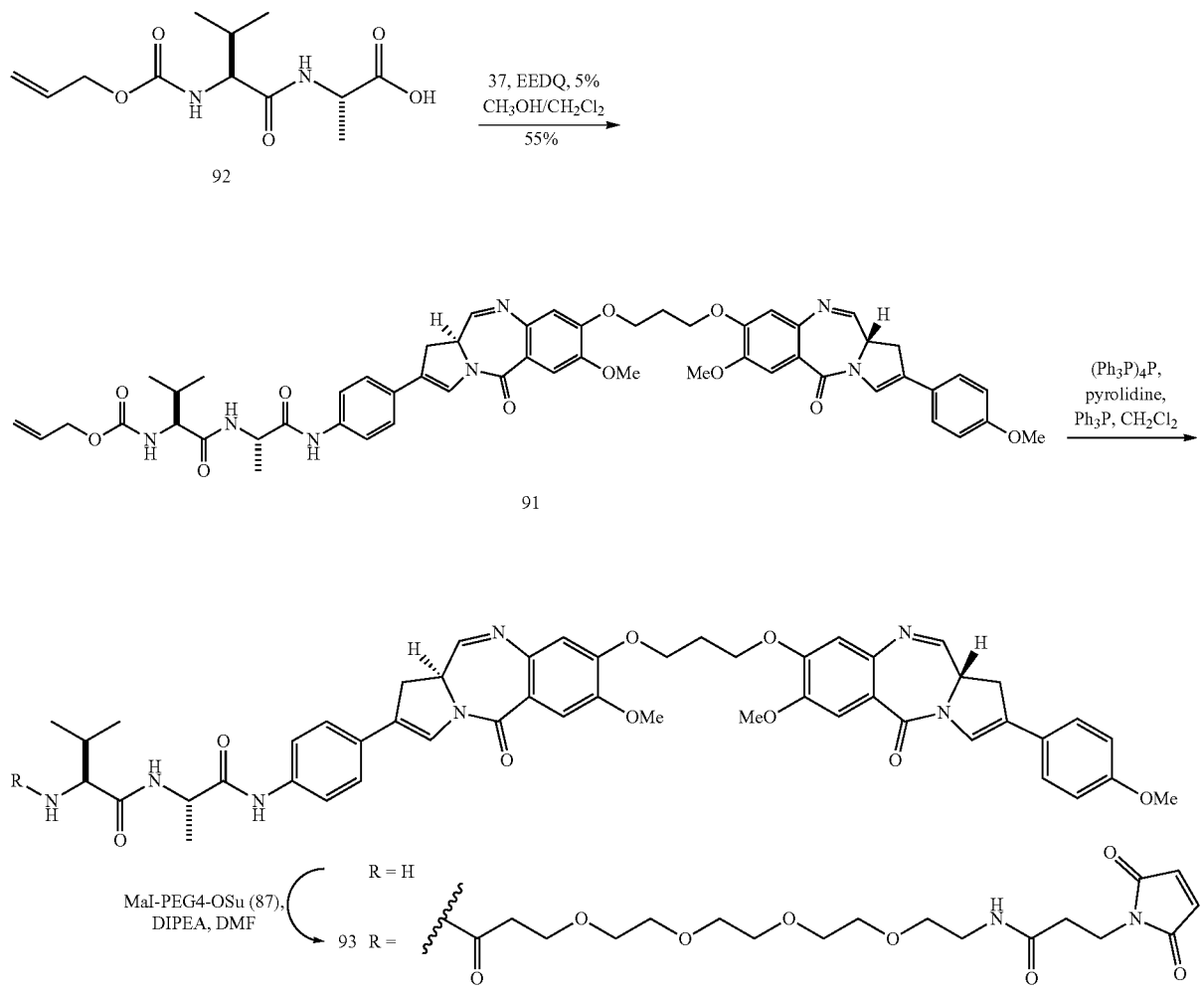

Scheme 18

135

Allyl ((S)-1-((4-((S)-7-methoxy-8-(3-(((S)-7-methoxy-2-(4-methoxyphenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)amino)-1-oxopropan-2-yl)amino)-3-methyl-1-oxobutan-2-yl)carbamate (91)

To a mixture of the 92 (45 mg, 0.123 mmol) in 5% methanol/dichloromethane (1 mL) was added EEDQ (30.4 mg, 0.123 mmol). The mixture was stirred for 30 min at an ambient temperature and then 37 (30 mg, 0.041 mmol) was added. The reaction mixture was stirred for approximately 5 h and then purified on a 1 mm radial chromatotron plate eluting with 5% methanol/dichloromethane to give 22 mg (55%) of 91 which was not characterized but carried on directly.

136

1-(3-(2,5-dioxo-2,5-dihydro-1H-pyrrol-1-yl)propanamido)-N—((S)-1-(((S)-1-((4-((S)-7-methoxy-8-(3-((S)-7-methoxy-2-(4-methoxyphenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)amino)-1-oxopropan-2-yl)amino)-3-methyl-1-oxobutan-2-yl)-3,6,9,12-tetraoxapentadecan-15-amide (93)

To a solution of the 91 (22 mg, 0.022 mmol) in anhydrous dichloromethane (3 mL) was added Ph$_3$P (0.3 mg, 0.0012 mmol), pyrrolidine (4 µL, 0.048 mmol) and tetrakis palladium (0.7 mg, 6 µmol). After approximately 2 h, the reaction mixture was purified on a 1 mm radial chromatotron plate eluting with 5% to 10% methanol/dichloromethane. The major band was collected and concentrated to a residue which was dissolved in DMF (0.2 mL) and reacted with NHS ester 87 (10 mg, 0.19 mmol). The reaction was allowed to stir for 30 min, concentrated and purified by radial chromatography on a 1 mm plate eluting with 5% methanol/dichloromethane to give 3.2 mg (11%) of 93: MS (ES$^+$) m/z 1294.7 [M+H]$^+$.

Scheme 19

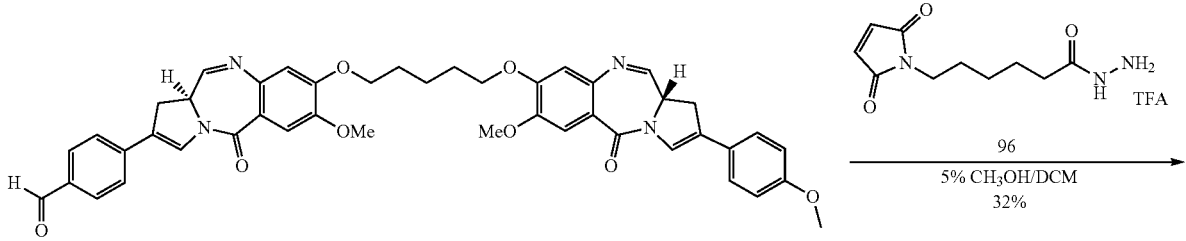

95

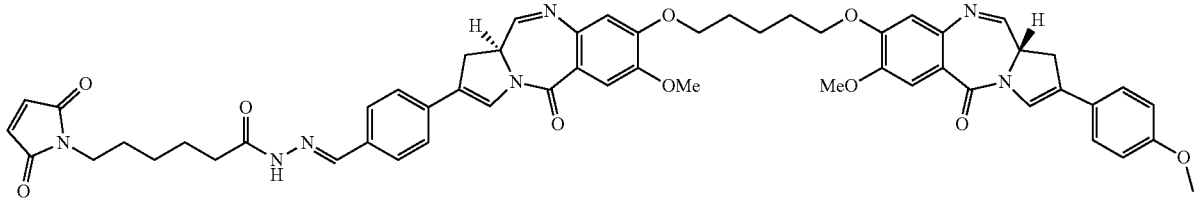

94

(E)-6-(2,5-dioxo-2,5-dihydro-1H-pyrrol-1-yl)-N'-4-((S)-7-methoxy-8-(5-(((S)-7-methoxy-2-(4-methoxyphenyl)-5-oxo-5,11a-dihydro-1H-pyrrolo[2,1-c][1,4]benzodiazepin-8-yl)oxy)pentyl)oxy)-5-oxo-5,11a-dihydro-1H-pyrrolo[2,1-c][1,4]benzodiazepin-2-yl)benzylidene)hexanohydrazide (94)

To a mixture of the aldehyde 95 (5.4 mg, 7 µmol) in 5% methanol/dichloromethane at 0° C. was added the hydrazide-TFA salt 96 (4.5 mg, 14 µmol). The reaction mixture was allowed to warm to an ambient temperature and stir for 5 h before being concentrated under reduced pressure and purified on a silica gel column eluting with 3% methanol/dichloromethane to give 2.2 mg (32%) of 94: MS (ES⁺) m/z 974.49 [M+H]⁺.

DIPEA (0.96 ml, 5.5 mmol) was added and the reaction mixture was allowed to stir at an ambient temperature for 16 h. The mixture was poured into dichloromethane (100 mL) and washed with 1N HCl (50 mL) and water (50 mL) before being dried over magnesium sulfate. The material was chromatographed on a 2 mm radial chromatotron plate eluting with 1 to 5% methanol/dichloromethane gradient and product containing fractions were combined and concentrated. The resulting residue was dissolved in dichloromethane (16 mL) and piperidine (4 mL) was added. The mixture was stirred for 10 min before being concentrated under reduced pressure. The resulting residue was chromatographed on a 2 mm plate eluting first with ammonia-saturated dichloromethane followed by 5% methanol in

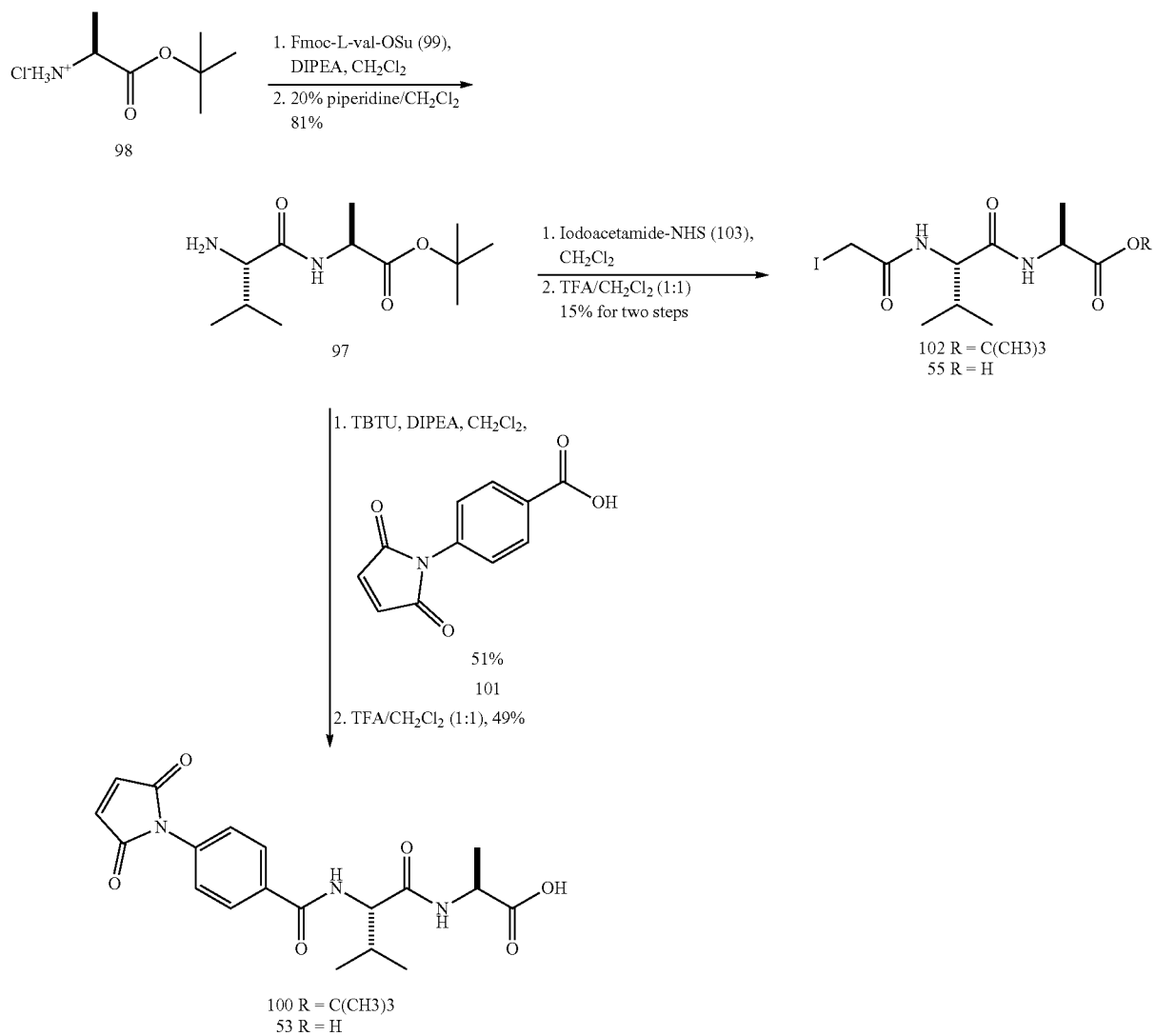

Scheme 20

(S)-tert-butyl 2-((S)-2-amino-3-methylbutanamido)propanoate (97)

To a mixture of the alanine-O-tert-butyl ester hydrogen chloride salt (98) (500 mg, 2.76 mmol) in dichloromethane (5 mL) was added Fmoc-val-OSu (99) (1.09 g, 2.51 mmol).

ammonia-saturated dichloromethane to give 494 mg (2.02 mmol, 81% for two steps) of 97: ¹H-NMR (400 MHz, CDCl₃) δ 7.78 (bs, 1H), 4.47 (m, 1H), 3.30 (d, 1H), 2.30 (m, 1H), 1.38 (d, 3H), 1.47 (s, 9H), 1.00 (d, J=7.0 Hz, 3H), 0.84 (d, J=6.9 Hz, 3H).

(S)-tert-butyl 2-((S)-2-(4-(2,5-dioxo-2,5-dihydro-1H-pyrrol-1-yl)benzamido)-3-methylbutanamido)propanoate (100)

To a mixture of the 97 (100 mg, 0.41 mmol) and 4-maleimidobenzoic acid (101) (98 mg, 0.45 mmol) was added dichloromethane (5 mL), followed by TBTU (157 mg, 0.49 mmol) and DIPEA (212 uL, 1.23 mmol). The mixture was stirred at an ambient temperature for 16 h and then purified on a 2 mm radial chromatotron plate eluting with 50% ethyl acetate in hexanes to give 95 mg (51%) of 100: $^1$H-NMR (400 MHz, CDCl$_3$) δ 7.85 (d, J=6.6 Hz, 2H), 7.42 (d, J=6.6 Hz, 2H), 6.81 (s, 2H), 6.38 (bs, 1H), 4.43 (m, 2H), 2.14 (sept, J=6.6 Hz, 1H), 1.41 (s, 9H), 1.31 (d, J=7.0 Hz, 3H), 0.98 (m, 6H); MS (ES$^-$) m/z 441.90 [M−H].

(R)-2-((S)-2-(4-(2,5-dioxo-2,5-dihydro-1H-pyrrol-1-yl)benzamido)-3-methylbutanamido)propanoic acid (53)

To a mixture of 100 (47 mg, 0.11 mmol) in dichloromethane (5 mL) was added trifluoroacetic acid (5 mL) and the reaction mixture was monitored by TLC (50% ethyl acetate in hexane, after pumping down the TLC plate under high vacuum for 5 min). After 75 min. no starting material could be detected by TLC. The reaction was performed a second time using the same conditions and material from both reactions were combined and purified on a 2 mm radial chromatotron plate eluting with a gradient from 5-10% methanol in dichloromethane. The yield was 42 mg (49%) of 53: $^1$H-NMR (400 MHz, CDCl$_3$) δ 7.92 (d, J=6.6 Hz, 2H), 7.51 (d, J=6.6 Hz, 2H), 7.0 (m, 1H), 6.89 (s, 2H), 6.70 (s, 1H), 4.60 M, 1H), 2.22 (m, 1H), 1.18 (d, J=6.6 Hz, 3H), 1.04 (m, 6H); MS (ES$^+$) m/z 388.02 [M+H]$^+$.

(S)-2-((S)-2-(2-iodoacetamido)-3-methylbutanamido)propanoic acid (102)

To a mixture of the 97 (100 mg, 0.41 mmol) in dichloromethane was added iodoacetamide-NHS ester (103) (115 mg, 0.41 mmol) and the mixture was stirred at an ambient temperature. After 30 min, the mixture was aspirated onto a 1 mm chromototron plate and eluted with ethyl acetate in hexanes (1:1). A single band was collected and the structure was confirmed: $^1$H-NMR (400 MHz, CDCl$_3$) δ 6.70 (d, J=7.8 Hz, 1H), 6.27 (d, J=7.0 Hz, 1H), 4.45 (m, 1H), 4.26 (dd, J=8.6, 6.3 Hz, 1H), 3.72 (quart, J=11.3 Hz, 2H), 2.13 (sept, J=6.5 Hz, 1H), 1.47 (s, 9H), 1.38 (d, J=7.1 Hz, 3H), 0.99 (m, 6H); MS (ES$^+$) m/z 412.87 [M+H]$^+$.

(S)-2-((S)-2-(2-iodoacetamido)-3-methylbutanamido)propanoic acid (55)

See procedure for the synthesis of (R)-2-((S)-2-(4-(2,5-dioxo-2,5-dihydro-1H-pyrrol-1-yl)benzamido)-3-methylbutanamido)propanoic acid (53). This gave 22 mg (15% for two steps): $^1$H-NMR (400 MHz, D$_6$-DMSO) δ 8.27 (d, J=9.4 Hz, 1H), 4.24 (m, 2H), 3.97 (bs, 2H), 3.83 (d, J=9.4 Hz, 1H), 3.71 (d, J=9.6 Hz, 1H), 2.07 (m, 1H), 1.33 (d, J=7.3 Hz, 3H), 0.93 (d, J=6.7 Hz, 3H), 0.89 (d, J=6.9 Hz, 3H); MS (ES$^-$) m/z 354.84 [M−H].

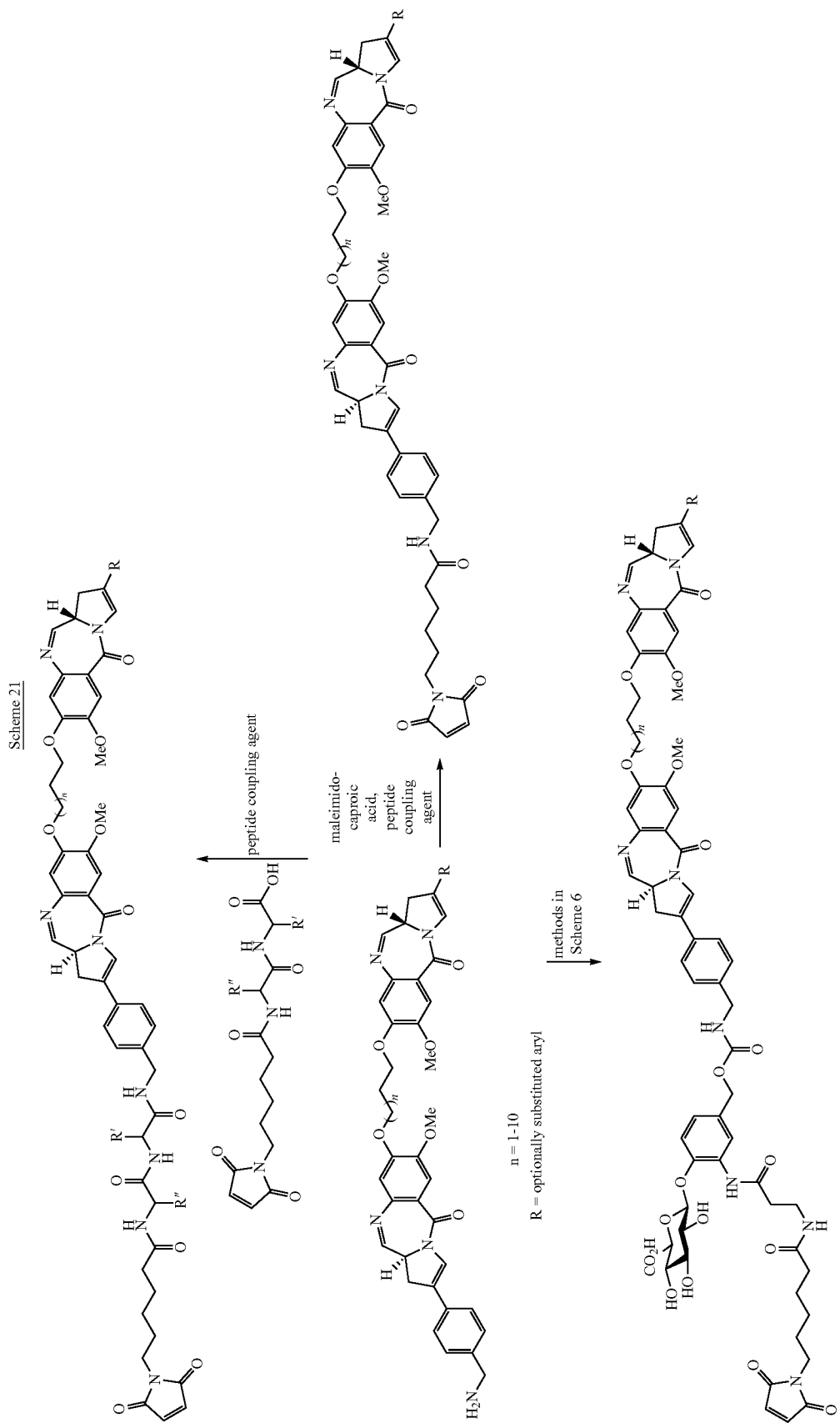

PBD Dimers Linked Through Aliphatic Amines (Scheme 21).

PBD dimers containing aliphatic amines, such as a benzyl amine (Example 9), are synthesized with peptidic linkers, the glucuronide linker, and/or linkers dependent on mAb degradation for release (i.e., non-cleavable linkers). Drug linkers conjugated through a benzyl amine will include: (1) a cleavable peptide employing chemistry similar to Scheme 1; (2) direct attachment with a maleimidocaproyl group (a noncleavable linker) (Scheme 2); (3) a glucuronide linker, prepared as described in Scheme 6.

gel filtration over a PD-10 column. The ADC was then sterile-filtered through a 0.22 μm syringe filter. Protein concentration was determined by spectral analysis at 280 nm and 329 nm, respectively, with correction for the contribution of drug absorbance at 280 nm. Size exclusion chromatography was used to determine the extent of antibody aggregation and RP-HPLC confirmed the absence of remaining NAC-quenched drug-linker.

For halo acetamide-based drug linkers, conjugation was performed generally as follows: To a 10 mg/mL solution of reduced and reoxidized antibody (having introduced cyste-

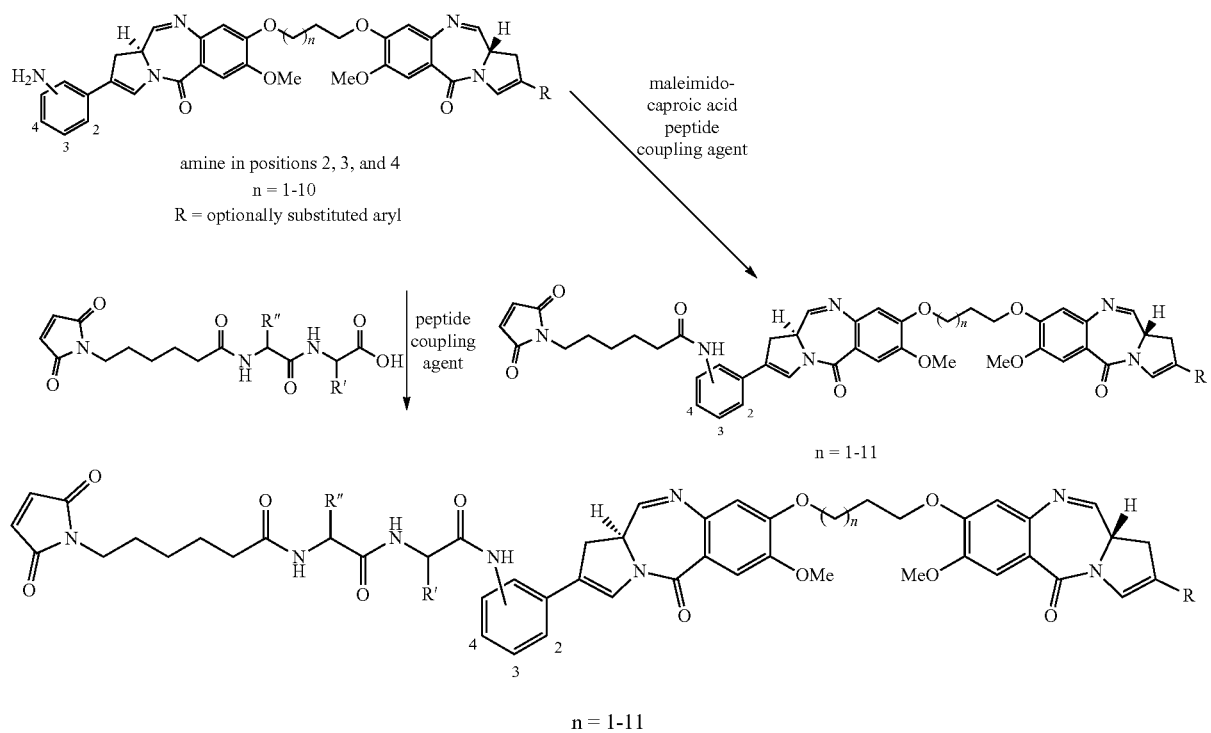

n = 1-11

Generic Peptide Linked 2-, 3-, and 4-Aniline PBD Dimers (Scheme 22).

PBD dimers with anilines at the 2-, 3-, and 4-positions will be conjugated to peptide-based linkers, employing the chemistry described in Scheme 1, or attached directly with maleimidocaproic acid, as exemplified in Scheme 2.

Example 14: Preparation of PDB Dimer Conjugates

Antibody-drug conjugates were prepared as previously described (see Doronina et al., Nature Biotechnology, 21, 778-784 (2003)) or as described below. Briefly, for maleimide drug-linker the mAbs (4-5 mg/mL) in PBS containing 50 mM sodium borate at pH 7.4 were reduced with tris(carboxyethyl)phosphine hydrochloride (TCEP) at 37° C. The progress of the reaction, which reduces interchain disulfides, was monitored by reaction with 5,5'-dithiobis(2-nitrobenzoic acid) and allowed to proceed until the desired level of thiols/mAb was achieved. The reduced antibody was then cooled to 0° C. and alkylated with 1.5 equivalents of maleimide drug-linker per antibody thiol. After 1 h, the reaction was quenched by the addition of 5 equivalents of N-acetyl cysteine. Quenched drug-linker was removed by ines by substitution of S239C in the heavy chains (see infra)) in 10 mM Tris (pH 7.4), 50 mM NaCl, and 2 mM DTPA was added 0.5 volumes of propylene glycol. A 10 mM solution of acetamide-based drug linker in dimethylacetamide was prepared immediately prior to conjugation. An equivalent amount of propylene glycol as added to the antibody solution was added to a 6-fold molar excess of the drug linker. The dilute drug-linker solution was added to the antibody solution and the pH was adjusted to 8.0-8.5 using 1 M Tris (pH 9). The conjugation reaction was allowed to proceed for 45 minutes at 37° C. The conjugation was verified by reducing and denaturing reversed phase PLRP-S chromatography. Excess drug linker was removed with Quadrasil MP resin (Sigma Aldrich; Product #679526) and the buffer was exchanged into 10 mM Tris (pH 7.4), 50 mM NaCl, and 5% propylene glycol using a PD-10 desalting column (GE Heathcare; Product #17-0851-01).

Engineered hIgG1 antibodies with introduced cysteines: CD70 antibodies containing a cysteine residue at position 239 of the heavy chain (h1F6d) were fully reduced by adding 10 equivalents of TCEP and 1 mM EDTA and adjusting the pH to 7.4 with 1M Tris buffer (pH 9.0). Following a 1 hour incubation at 37° C., the reaction was cooled to 22° C. and 30 equivalents of dehydroascorbic acid were added to selectively reoxidize the native disulfides, while leaving cysteine 239 in the reduced state. The pH was adjusted to 6.5 with 1M Tris buffer (pH 3.7) and the reaction was allowed to proceed for 1 hour at 22° C. The pH of the solution was then raised again to 7.4 by addition of 1 M Tris buffer (pH 9.0), 3.5 equivalents of the PBD drug linker in DMSO were placed in a suitable container for dilution with propylene glycol prior to addition to the reaction. To maintain solubility of the PBD drug linker, the antibody itself was first diluted with propylene glycol to a final concentration of 33% (e.g., if the antibody solution was in a 60 mL reaction volume, 30 mL of propylene glycol was added). This same volume of propylene glycol (30 mL in this example) was then added to the PBD drug linker as a diluent. After mixing, the solution of PBD drug linker in propylene glycol was added to the antibody solution to effect the conjugation; the final concentration of propylene glycol is 50%. The reaction was allowed to proceed for 30 minutes and then quenched by addition of 5 equivalents of N-acetyl cysteine. The ADC was then purified by ultrafiltration through a 30 kD membrane. (Note that the concentration of propylene glycol used in the reaction can be reduced for any particular PBD, as its sole purpose is to maintain solubility of the drug linker in the aqueous media.)

Example 15: Determination of In Vitro Activity of Selected Conjugates

The in vitro cytotoxic activity of the selected antibody drug conjugates was assessed using a resazurin (Sigma, St. Louis, Mo., USA) reduction assay (reference: Doronina et al., *Nature Biotechnology*, 2003, 21, 778-784). The antibody drug conjugates were prepared as described above in Example 13.

For the 96-hour assay, cells cultured in log-phase growth were seeded for 24 h in 96-well plates containing 150 μL RPMI 1640 supplemented with 20% FBS. Serial dilutions of ADC in cell culture media were prepared at 4× working concentration; 50 μL of each dilution was added to the 96-well plates. Following addition of ADC, the cells were incubated with test articles for 4 days at 37° C. Resazurin was then added to each well to achieve a 50 μM final concentration, and the plates were incubated for an additional 4 h at 37° C. The plates were then read for the extent of dye reduction on a Fusion HT plate reader (Packard Instruments, Meridien, Conn., USA) with excitation and emission wavelengths of 530 and 590 nm, respectively. The $IC_{50}$ value, determined in triplicate, is defined here as the concentration that results in a 50% reduction in cell growth relative to untreated controls.

Referring to Table 4 (infra), the in vitro cytotoxicity of ADCs having para-aniline PBD dimers using the 96 hour assay is shown. The ADCs were tested against CD70 CD30 cell lines and a control CD70 CD30 cell line. The antibodies used were a CD70 antibody, humanized 1F6 (see Published U.S. Application No. 2009-148942), a CD30 antibody, chimeric AC10 (see Published U.S. Application No. 2008-0213289) and a CD70 antibody (humanized 1F6) having introduced cysteine residues at amino acid heavy chain position 239 (according to the EU numbering system) (indicated as h1F6d). Conjugates having a maleimidyl-peptide linker (drug linker compound 38) had a lower $IC_{50}$ than conjugates with a maleimidyl or acetamide-based linker (compounds 40 and 41, respectively).

In vitro cytotoxic activity of ADCs bearing drug linkers derived from para-aniline PBD dimer 37:

TABLE 4

In vitro cytotoxic activity on CD70+ cell lines (ng/mL), all ADCs 2 drugs/mAb

| | renal cell carcinoma CD70+/30− | | | | AML CD70−/30− |
|---|---|---|---|---|---|
| | 786-O | Caki-1 | 769-P | ACHN | HEL9217 |
| h1F6d-38 | 30 | 5 | | | 1378 |
| h1F6-38 | 4 | | 118 | 26 | |
| cAC10-38 | 1052 | | 4005 | 508 | |
| h1F6-40 | 7113 | | | 1764 | |
| cAC10-40 | 2644 | | | 1264 | |
| h1F6-41 | 580 | | | 1243 | |
| cAC10-41 | 1153 | | | 1121 | |

Referring to Table 5, the in vitro cytotoxicity of ADCs conjugate to PBD dimers on CD30+ cell lines using the 96 hour assay is shown. The ADCs were tested against CD30+ CD70+ cell lines and a CD70+ CD30+ cell line. The antibodies used were a CD70 antibody, humanized 1F6 (see Published U.S. Application No. 2009-148942) and a CD30 antibody, chimeric AC10 (see Published U.S. Application No. 2008-0213289). Conjugates having a maleimidyl-peptide linker (drug linker compound 38) generally had a lower $IC_{50}$ than conjugates with a maleimidyl or acetamide-based linker (compounds 40 and 41, respectively).

TABLE 5

In vitro cytotoxic activity on CD30+ cell lines (ng/mL), all ADCs 2 drugs/mAb

| | ALCL CD70−/30+ | Hodgkin lymphoma CD70+/30+ | | | |
|---|---|---|---|---|---|
| | Karpas 299 | L428 | L540cy | L1236 | Hs445 |
| h1F6-38 | 1165 | 59 | 4 | >10,000 | 5 |
| cAC10-38 | 0.8 | 7 | 3 | 2012 | 0.2 |
| h1F6-40 | 2195 | 7867 | 2557 | | |
| cAC10-40 | 621 | 3172 | 134 | | |
| h1F6-41 | 1330 | 3549 | 755 | | |
| cAC10-41 | 340 | 957 | 13 | | |

In vitro cytotoxic activity of ADCs bearing drug linkers derived from meta-aniline PBD dimer 42:

Referring to Table 6, the in vitro cytotoxicity of ADCs containing PBD dimers on CD30+ cell lines using the 96 hour assay is shown. The activity was tested against CD30+ CD70+ cell lines and a CD70− CD30+ cell line. The antibodies used were a CD70 antibody, humanized 1F6 (see Published U.S. Application No. 2009-148942) and a CD70 antibody (humanized 1F6) having introduced cysteine residues at amino acid heavy chain position 239 (according to the EU numbering system) (indicated as h1F6d). Conjugates having a maleimidyl-peptide linker (drug linker compound 43) and a glucuronide linker (48) generally had a lower $IC_{50}$ than conjugates with a maleimidyl-based linker (compound 44).

TABLE 6

In vitro cytotoxic activity on CD70+ cell lines (ng/mL)

| | renal cell carcinoma | | Hodgkin lymphoma |
|---|---|---|---|
| | Caki-1 | 786-O | L428 |
| h1F6d-43 (2 dr/mAb) | 7 | 39 | >10,000 |
| IgG-43 (2 dr/mAb) | | >10,000 | >10,000 |

TABLE 6-continued

In vitro cytotoxic activity on CD70+ cell lines (ng/mL)

|  | renal cell carcinoma | | Hodgkin lymphoma |
|---|---|---|---|
|  | Caki-1 | 786-O | L428 |
| h1F6-44 (3.5 dr/mAb) |  | 1124 | 2142 |
| IgG-44 (3.5 dr/mAb) |  | 1491 | 1242 |
| h1F6d-48 (2 dr/mAb) |  | 89 | 4093 |
| IgG-48 (2 dr/mAb) |  | 2939 | 6376 |

In vitro cytotoxic activity of ADCs bearing drug linkers derived from para- and meta-aniline PBD dimers 38 and 42 (respectively):

Referring to Table 7, the in vitro cytotoxicity of ADCs containing PBD dimers on CD70$^+$ cell lines using the 96 hour assay is shown. The activity was tested against CD70$^+$ cell lines L428 and 786O and a CD70 AML cell line. The antibodies used were a CD70 antibody, humanized 1F6 (see Published U.S. Application No. 2009-148942) and a CD70 antibody (humanized 1F6) having introduced cysteine residues at amino acid heavy chain position 239 (according to the EU numbering system) (indicated as h1F6d). Conjugates having a maleimidyl-peptide linker with a meta-aniline (drug linker compound 43) were somewhat less active than those having a maleimidyl-peptide linker with a para-aniline (drug linker compound 38). Reducing the drug loading of the meta-aniline compound to 2 per antibody reduced the activity. Conjugates with a glucuronide linker of the para-aniline compound (48) generally had a lower IC$_{50}$ than conjugates with a maleimidyl-based linker (compound 39). Further, an aryl maleimide of the para-aniline compound (54) has no activity on these cell lines. Further, a conjugate having a maleimidyl linker conjugated directly to compound 42 has reduced activity as compared with conjugate h1F6-43 (data not shown).

TABLE 7

In vitro cytotoxic activity on CD70+ cell lines (ng/mL)

|  | Hodgkin lymphoma L428 | Renal cell carcinina 786O | control |
|---|---|---|---|
| h1F6- 43(4 dr/mAb) | 404 | 11 | 1205 |
| h1F6d- 43 (2 dr/mAb) | Max inhib. = 40% | 200 | 1625 |
| h1F6d-48 (2 dr/mAb) | 4093 | 89 | 1964 |
| h1F6 54 (4 dr/mAb) | No effect | No effect | No effect |
| h1F6- 38 (2 dr/mAb) | 230 (n = 2) | 25 (n =3) | 503 |

In Vitro Cytotoxic Activity of ADCs Bearing Drug Linkers Derived from Aniline-Linked PBD Dimers Referring to Table 8, the in vitro cytotoxicity of ADCs containing PBD dimers on CD70$^+$ cell lines using the 96 hour assay is shown. The activity was tested against CD70$^+$ cell lines Caki-1 and L428 and a CD70$^-$ cell line. The antibody used was a CD70 antibody (humanized 1F6) having introduced cysteine residues at amino acid heavy chain position 239 (according to the EU numbering system) (indicated as h F6d). Linkage of a PBD through an amine at the ortho position via a non-cleavable linker (compound 68) markedly reduced activity, as compared with an ADC linked via a para-aniline-linked cleavable linker (compound 54). Compounds 73 and 85, having a cleavable linker, showed comparable activity to compound 54; both of these compounds are linked via a para-aniline. Compounds with cleavable linkers requiring more stringeng cleavage, compounds 79 and 90, showed somewhat reduced activity, as compared to compound 54.

TABLE 8

In vitro cytotoxic activity on CD70+ cell lines (ng/mL)

|  | renal cell carcinoma | | |
|---|---|---|---|
|  | Caki-1 | 786-0 | Control |
| h1F6d- 68 (2 dr/mAb) | 3236 | 3486 | 5501 |
| h1F6d- 73 (2 dr/mAb) | 2 | 7 | 482 |
| h1F6d- 79 (2 dr/mAb) | 24 | 348 | 5385 |
| h1F6d- 54 (2 dr/mAb) | 6 | 17 | 4665 |
| h1F6d- 85 (2 dr/mAb) | 3 | 5 | 4700 |
| h1F6d- 90 (1.4 dr/mAb) | . . . 12 | 47 | 678 |

In Vitro Cytotoxic Activity of ADCs Bearing Drug Linkers Derived from Aniline-Linked PBD Dimers Referring to Table 9, the in vitro cytotoxicity of ADCs containing PBD dimers on CD70$^+$ cell lines using the 96 hour assay is shown. The activity was tested against CD70$^+$ cell lines Caki-1 and L428 and two CD70$^-$ leukemia cell lines. The antibodies used were a CD70 antibody, humanized 1F6 (see Published U.S. Application No. 2009-148942) and a CD70 antibody (humanized 1F6) having introduced cysteine residues at amino acid heavy chain position 239 (according to the EU numbering system) (indicated as h1F6d). Compound 56, having a cleavable linker linked to the antibody via an acetamide showed comparable activity to compound 38. A glucuronide-linked version of the meta-aniline linked PBD dimer, compound 48, demonstrated little activity in this assay. Compound 58, having five methylene groups in the PBD bridge, demonstrated comparable activity to compound 38, having three methylene groups in the PBD bridge.

TABLE 9

In vitro cytotoxic activity on CD70+ cell lines (ng/mL)

|  | Renal Cell | | Leukemia | |
|---|---|---|---|---|
|  | Caki-1 | 786-O | | |
| ADCs | (CD70 #135,000) | (CD70 #190,000) | CD70$^-$ Line 1 | CD70$^-$ Line 2 |
| h1F6d-56 (1.8 dr/Ab) | 3 | 6 | 1672 | Max Inh = 50% |
| h1F6d-48 (0.6 dr/Ab) | Max Inh = 45% | Max Inh = 35% | No Effect | No Effect |
| h1F6d-58 (1.9 dr/Ab) | 0.5 | 2 | 1750 | 4847 |
| h1F6d-38 (2 dr/Ab) | 5 (3-5, n = 4) | 15 (5-30, n = 4) | 2082 | 7188 |

Example 16: Determination of In Vivo Cytotoxicity of Selected Conjugates

All studies were conducted in concordance with the Animal Care and Use Committee in a facility fully accredited by the Association for Assessment and Accreditation of Laboratory Animal Care. In vivo tolerability was first assessed to ensure that the conjugates were tolerated at clinically relevant doses. BALB/c mice were treated with escalating doses of ADC formulated in PBS with 0.01% Tween 20. Mice were monitored for weight loss following drug treatment; those that experienced 20% weight loss or other signs of morbidity were euthanized. The antibodies used were a CD70 antibody, humanized 1 F6 (see Published U.S. Application No. 2009-148942) and a CD30 antibody, chimeric AC10 (see Published U.S. Application No. 2008-0213289).

Referring to FIG. 1, the results of a weight loss study are shown using cAC10-val-ala-SG3132(2) (cAC10-compound 38). A single dose of the conjugate administered at 5 mg administered either IP or IV resulted in little weight loss. A higher dose of the conjugate (15 mg/kg) caused weight loss in the mice.

Figure 2:
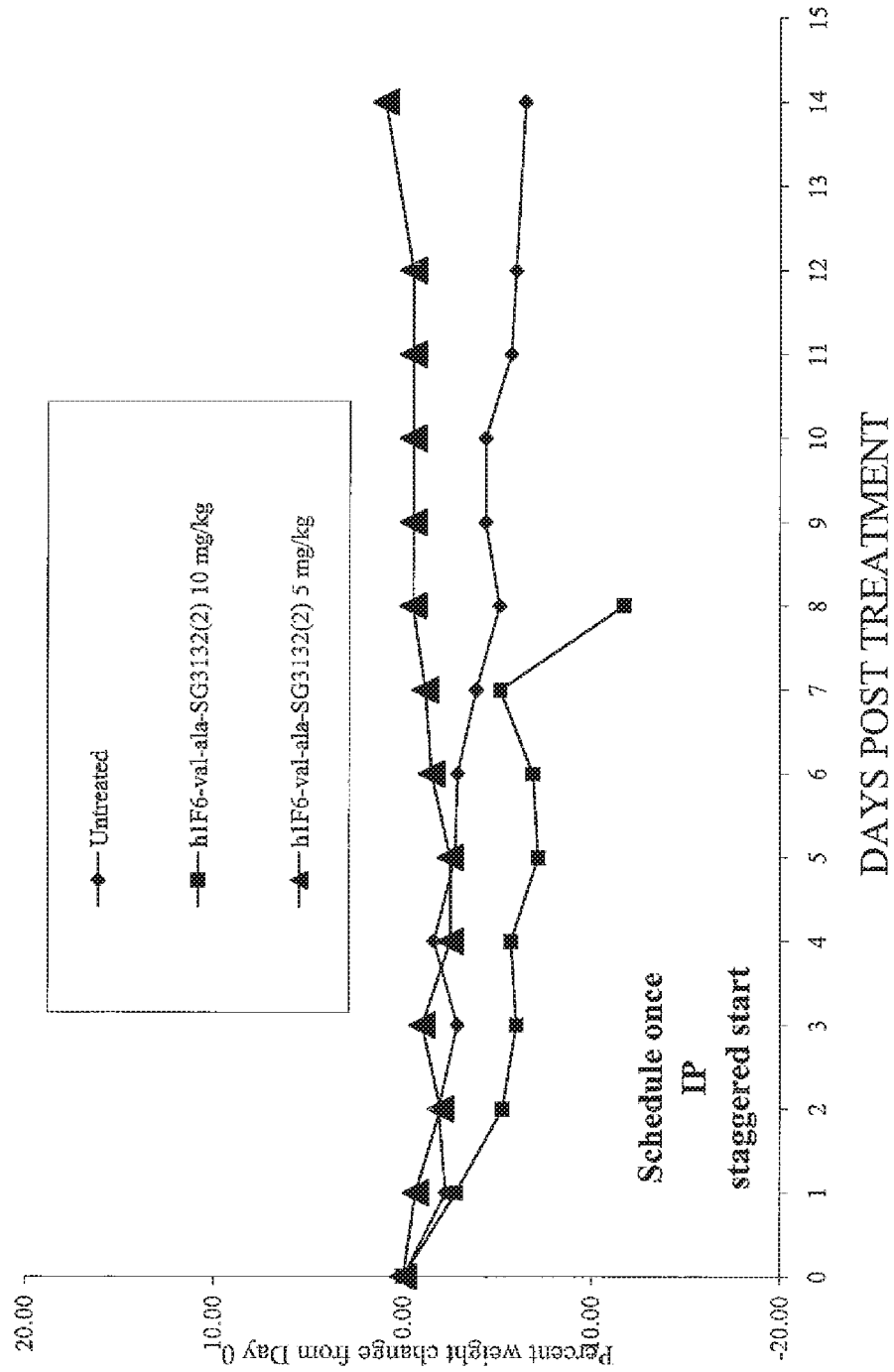

Referring to FIG. 2, the results of a weight loss study are shown using h1F6-val-ala-SG3132(2) (h1F6-compound 38). A single dose of the conjugate administered at 5 mg administered IP resulted in some weight loss. A higher dose of the conjugate (10 mg/kg) caused significant weight loss in the mice.

Treatment studies were conducted in two CD70+ renal cell carcinoma xenograft models. Tumor (786-O and Caki-1) fragments were implanted into the right flank of Nude mice. Mice were randomized to study groups (n=5) on day eight (786-O) or nine (Caki-1) with each group averaging around 100 mm³. The ADC or controls were dosed ip according to a q4dx4 schedule. Tumor volume as a function of time was determined using the formula (L×W²)/2. Animals were euthanized when tumor volumes reached 1000 mm³. Mice showing durable regressions were terminated around day 100 post implant.

Figure 3:
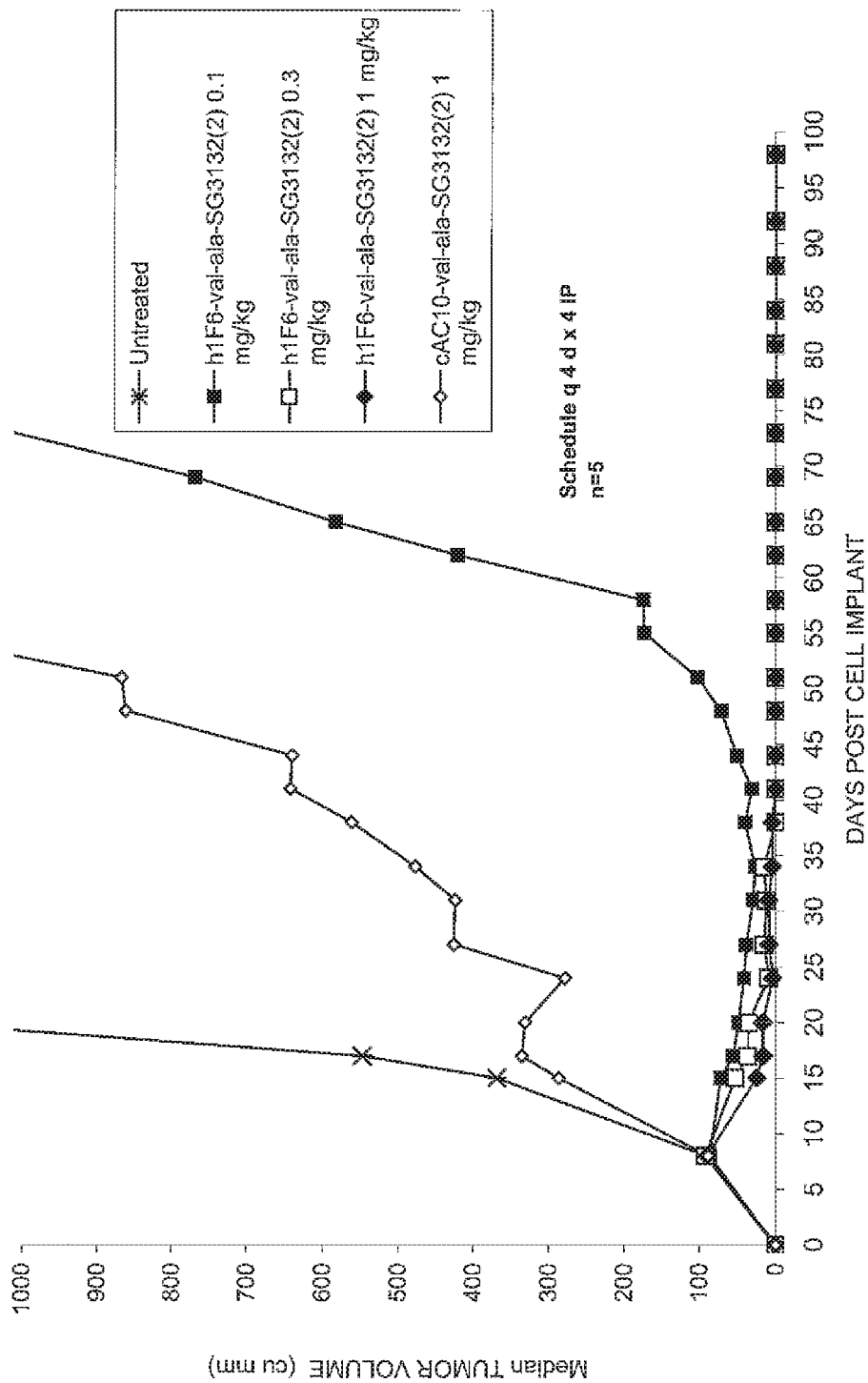

Referring to FIG. 3, the results of a treatment study using an h1F6-val-ala-SG3132(2) (h1F6-compound 38) conjugate are shown. A control conjugate, cAC10-val-ala-SG3132(2) (cAC10-compound 38), was also used. Mice administered doses of the h1F6 conjugate at 0.1 mg/kg exhibited some tumor reduction, while higher doses at 0.3 mg/kg and 1 mg/kg appeared to exhibit complete tumor reduction. The control conjugate (non-binding) was less active the h1F6 conjugates.

Figure 4:
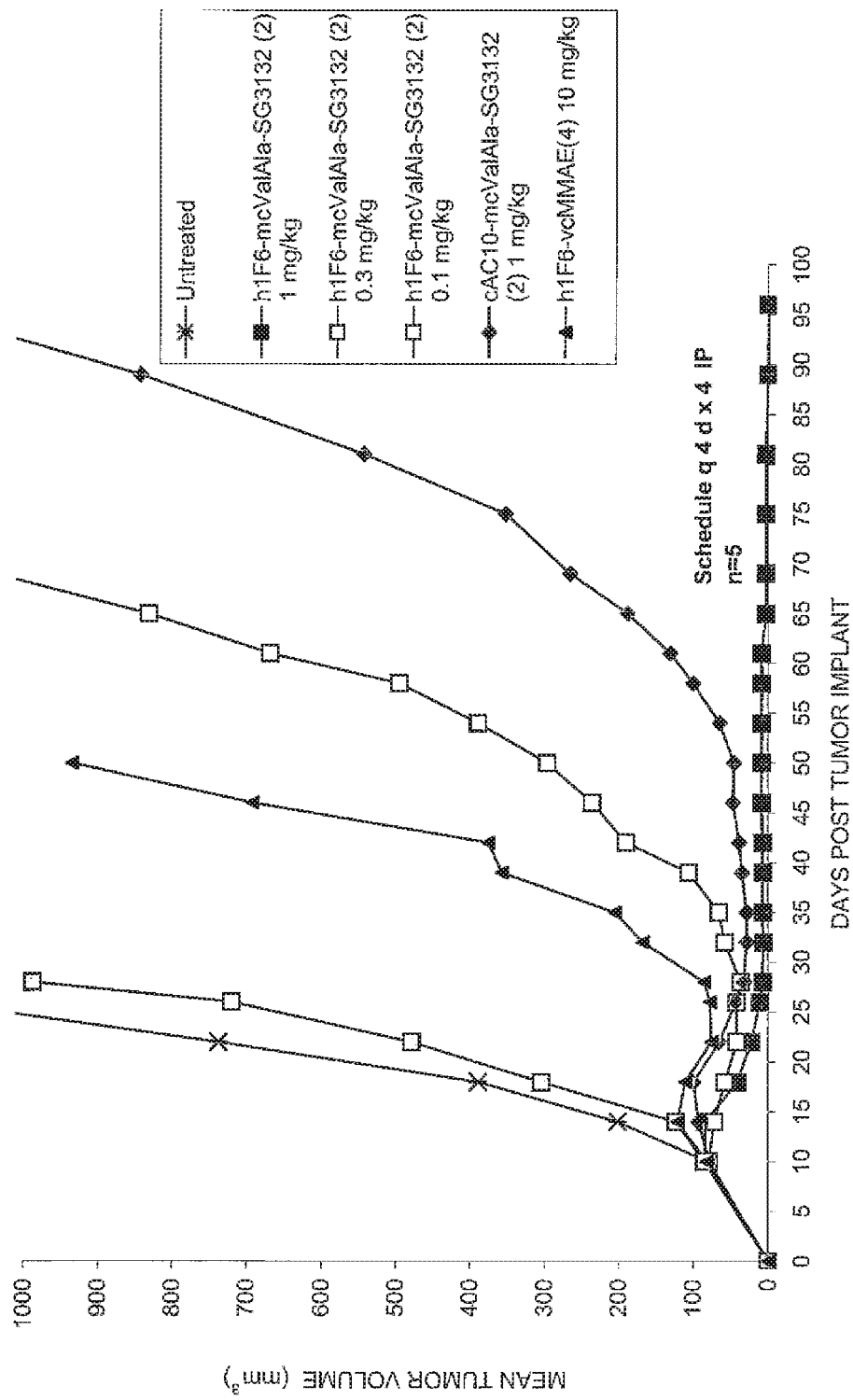

Referring to FIG. 4, the results of a treatment study using an h1F6-mc-val-ala-SG3132(2) (h1F6-compound 38) conjugate are shown. A control conjugate, cAC10-mc-val-ala-SG3132(2) (cAC10-compound 38), was also used. Mice administered doses of the h1F6 conjugate at 1 mg/kg appeared to exhibit complete tumor reduction. Mice administered lower doses at 0.3 mg/kg and 0.1 mg/kg exhibited lesser tumor reduction, respectively. The control conjugate (non-binding) was less active the h1F6 conjugate administered at a similar dose, although it exhibited more activity than the h1F6 conjugate administered at lower doses. The h1F6 conjugate was also more active than an h1F6-vc-MMAE conjugate (Published U.S. Application No. 2009-0148942) administered at higher doses.

Figure 5:
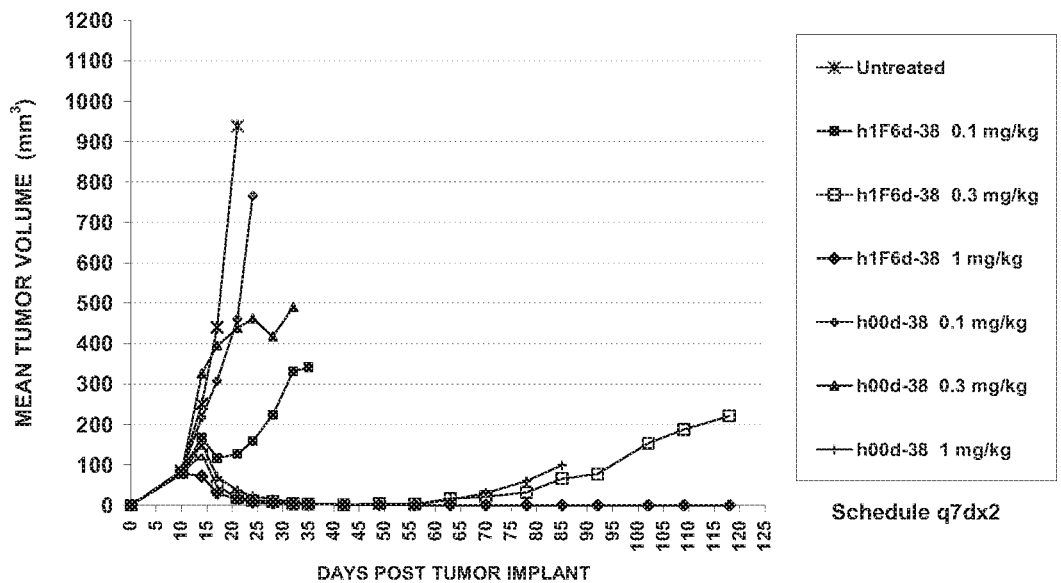

Referring to FIG. 5, the results of a treatment study using a two loaded antibody h1F6d-linked to compound 38 (h1F6d-38) compared to a two-loaded non-binding control, H00d conjugated to the same compound (h00d-38). The model was a Caki subcutaneous model in Nude mice. Doses were 0.1, 0.3 and 1 mg/kg q7dx2. The highest two doses of the h1F6 conjugate demonstrated complete regressions as 1 mg/kg and substantial tumor delay at 0.3 mg/kg. The non-binding control demonstated tumor delay at the 1 mg/kg dose.

Figure 6:
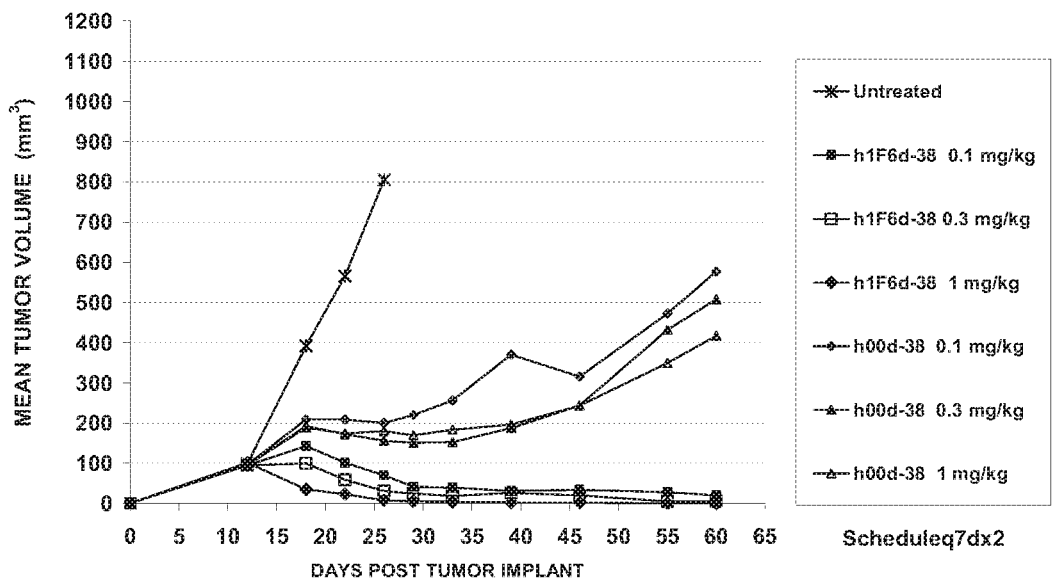

Referring to FIG. 6, the results of a treatment study using a two loaded antibody h1F6d-linked to compound 38 (h1F6d-38) compared to a two-loaded non-binding control, H00d conjugated to the same compound (h00d-38). The model was a 786-O subcutaneous model in Nude mice. Doses were 0.1, 0.3 and 1 mg/kg q7dx2. All three doses of the h1F6 conjugate demonstrated complete regressions or tumor delay, while the non-binding control demonstated tumor delay.

The invention claimed is:

1. A method for preparing a Drug linker compound, or a salt thereof, the method comprising the steps of:
a) contacting a PBD compound having the formula of:

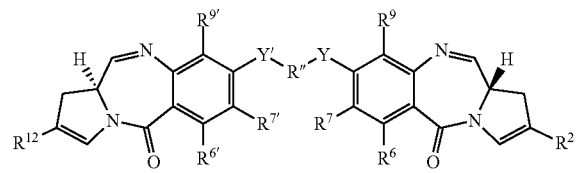

wherein —R² has the formula of:

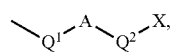

wherein A is a $C_{5-7}$ aryl group and X is

wherein $R^N$ is selected from the group consisting of H and $C_{1-4}$ alkyl;
the asterisk indicates the point of attachment to $Q^2$, and either:
(i) $Q^1$ is a single bond and $Q^2$ is a single bond or —Z—$(CH_2)_n$—, wherein Z is selected from the group consisting of a single bond, O, S and NH; and subscript n is from 1 to 3, or
(ii) $Q^1$ is —CH=CH— and $Q^2$ is a single bond;
and
$R^{12}$ is a $C_{5-10}$ aryl group, substituted by a group selected from the group consisting of —OH, —$CO_2H$, and —$C_2R^O$, where $R^O$ is $C_{1-4}$ alkyl;
$R^6$ and $R^9$ are independently selected from the group consisting of H, R, OH, OR, SH, SR, $NH_2$, NHR, NRR', nitro, $Me_3Sn$ and halo, wherein R and R' are independently selected from the group consisting of optionally substituted $C_{1-12}$ alkyl, $C_{3-20}$ heterocyclyl and $C_{5-20}$ aryl groups, wherein $C_{3-20}$ heterocyclyl is a monovalent moiety derived from removing a hydrogen atom of a heterocyclic compound which has 3 to 20 ring atoms, of which 1 to 10 are heteroatoms selected from the group consisting of N, O and S;
$R^7$ is selected from the group consisting of H, R, OH, OR, SH, SR, $NH_2$, NHR, NRR', nitro, $Me_3Sn$ and halo,
R" is a $C_{3-12}$ alkylene group, which chain is optionally interrupted by one or more heteroatoms selected from the group consisting of O, S, and $NR^{N2}$, wherein $R^{N2}$ is H or $C_{1-4}$ alkyl, and/or by an aromatic ring;
Y and Y' are independently selected from the group consisting of O, S, and NH;
$R^{6'}$, $R^{7'}$, $R^{9'}$ are selected from the same groups as $R^6$, $R^7$ and $R^9$, respectively, with a peptide coupling agent and a compound of formula $G^1$-$L^1$, wherein
$L^1$ is a dipeptide of formula —NH—$X_1$—$X_2$—$CO_2H$, wherein —NH— is the amino group of $X_1$, and $CO_2H$ is the carboxylic acid functional group of $X_2$ for peptide coupling by the peptide coupling agent to the nitrogen atom of X of the PBD compound and wherein the peptide is cleavable by the action of an enzyme for release of the PBD compound; and $G^1$ is a Stretcher Unit for connection to an antibody or antigen-binding fragment thereof, wherein $G^1$ is comprised of a maleimide group for reaction with a reactive thiol functional group provided by the antibody or antigen-binding fragment for said connection, and wherein $G^1$ further comprises the functionality —CO— connected directly to the amino terminus of $X_1$, thereby forming an amide link with —$X_1$—, wherein said contacting provides the Drug Linker compound having the formula of $G^1$-$L^1$-D, wherein $G^1$ is the Stretcher Unit and $L^1$ and D correspond in structure to the dipeptide and PBD compound, respectively.

2. The method of claim 1, wherein $G^1$ is selected from the group consisting of:

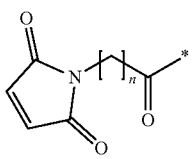

wherein the asterisk indicates the point of attachment to the amino group of $X_1$ and subscript n is an integer ranging from 0 to 6,

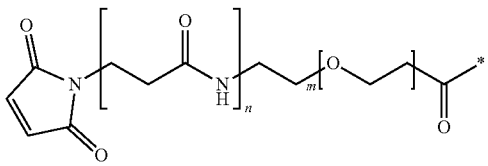

wherein the asterisk indicates the point of attachment to the amino group of $X_1$, subscript n is 0 or 1, and subscript m is an integer ranging from 0 to 30,

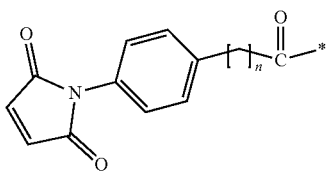

wherein the asterisk indicates the point of attachment to the amino group of $X_1$ and subscript n is an integer ranging from 0 to 6, and

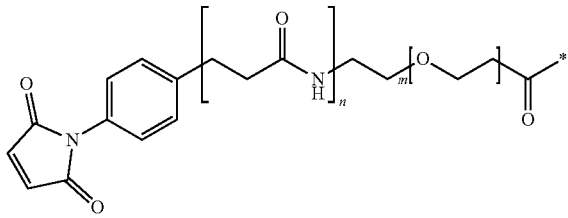

wherein the asterisk indicates the point of attachment to the amino group of $X_1$, subscript n is 0 or 1, and subscript m is an integer ranging from 0 to 30.

3. The method of claim 1, wherein $R^7$ is selected from the group consisting of H, OH and OR.

4. The method of claim 2, wherein $R^7$ is a $C_{1-4}$ alkyloxy group.

5. The method of claim 2, wherein Y and Y' are O.

6. The method of claim 5, wherein R" is $C_{3-7}$ alkylene.

7. The method of claim 6, wherein $R^9$ is H.

8. The conjugate according to claim 7, wherein $R^6$ is selected from the group consisting of H and halo.

9. The conjugate according to claim 1, wherein A is phenyl, X is —$NH_2$, and $Q^1$ is a single bond.

10. The conjugate according to claim 9, wherein $Q^1$ is a single bond and $Q^2$ is a single bond.

11. The method of claim 1, wherein $R^{12}$ is a $C_{5-7}$ aryl group optionally substituted by one or more substituents selected from the group consisting of halo, nitro, cyano, $C_{1-7}$ alkoxy, $C_{5-20}$ aryloxy, $C_{3-20}$ heterocyclyoxy, $C_{1-7}$ alkyl, $C_{3-7}$ heterocyclyl and bis-oxy-$C_{1-3}$ alkylene, wherein the $C_{1-7}$ alkoxy group is optionally substituted by an amino group, and if the $C_{3-7}$ heterocyclyl group is a $C_6$ nitrogen containing heterocyclyl group, it is optionally substituted by a $C_{1-4}$ alkyl group.

12. The method of claim 11, wherein the $C_{5-7}$ aryl group is an optionally substituted phenyl group.

13. The method of claim 12, wherein $R^{12}$ bears one to three substituent groups.

14. The method of claim 1, wherein $R^{6'}$, $R^{7'}$, $R^{9'}$, and Y' are the same as $R^6$, $R^7$, $R^9$, and Y, respectively.

15. The method of claim 1, wherein G is:

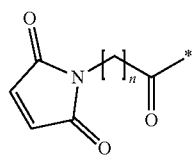

wherein the asterisk indicates the point of attachment to $L^1$; and subscript n is an integer ranging from 0 to 6.

16. The method of claim 15, wherein subscript n is 5.

17. The method of claim 16, wherein the dipeptide is selected from the group consisting of valine-alanine, valine-citrulline and phenylalanine-lysine.

18. The conjugate of claim 1, wherein the PBD compound has the formula:

153 154
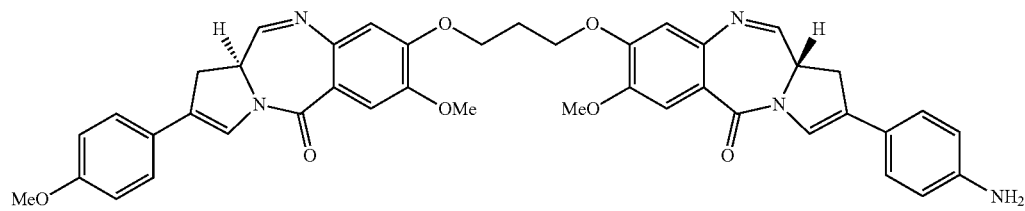
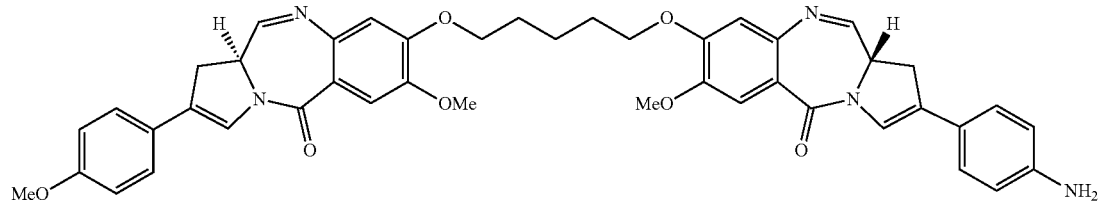
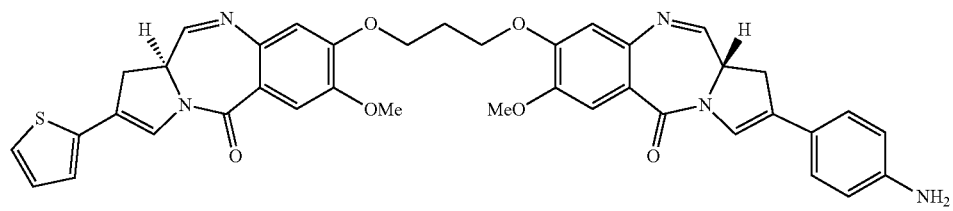
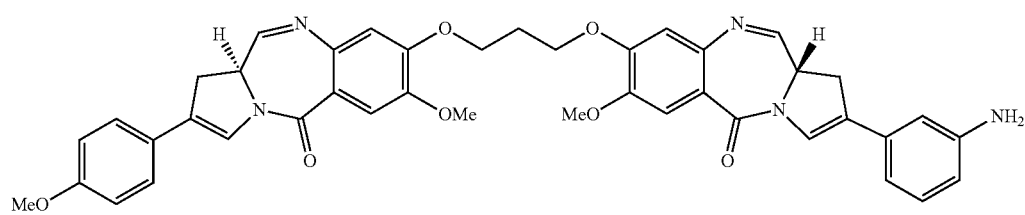
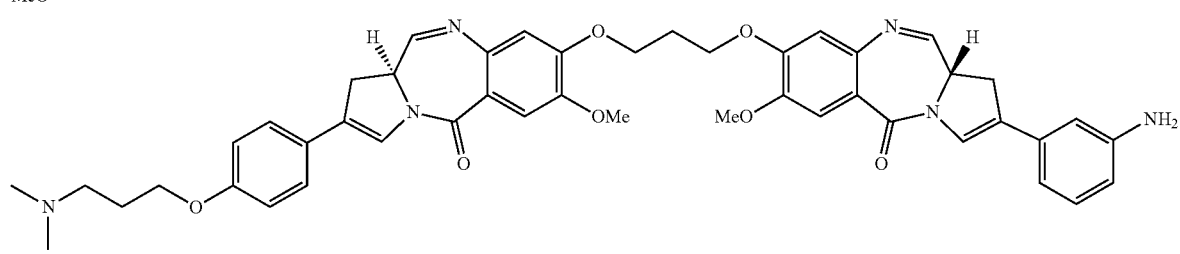
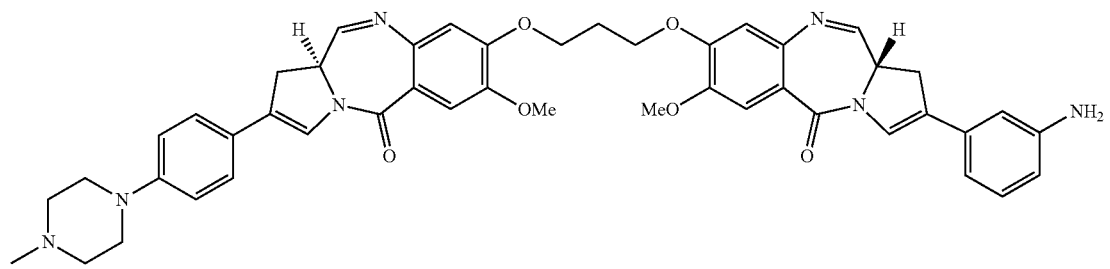
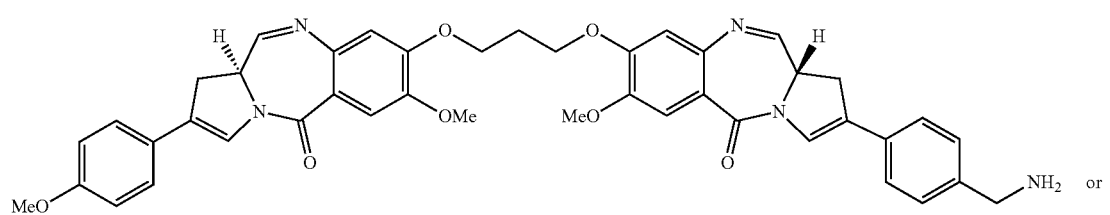
or

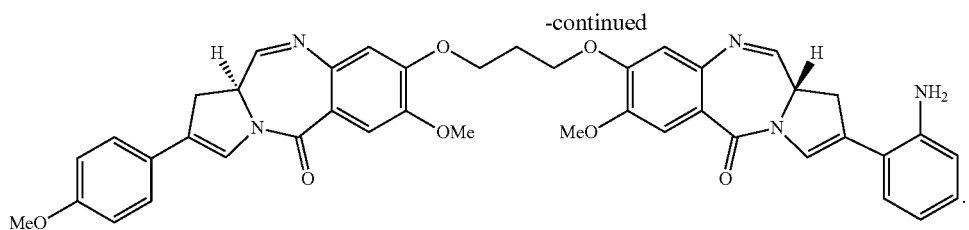
19. The method of claim 1, wherein $G^1$-$L^1$-D has the formula:
wherein subscript n is an integer ranging from 1 to 11; R' is —CH$_3$ and R" is CH(CH$_3$)$_2$.
20. The method of claim 1, wherein $G^1$-$L^1$-D has the formula:
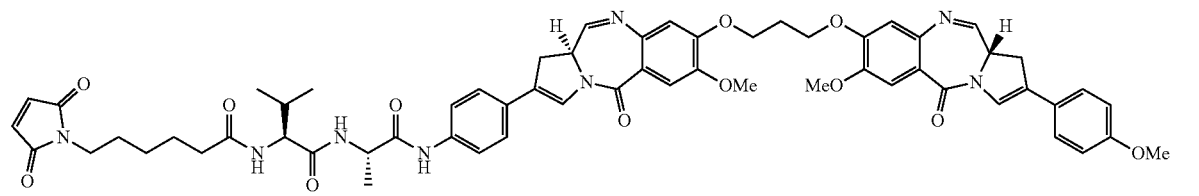
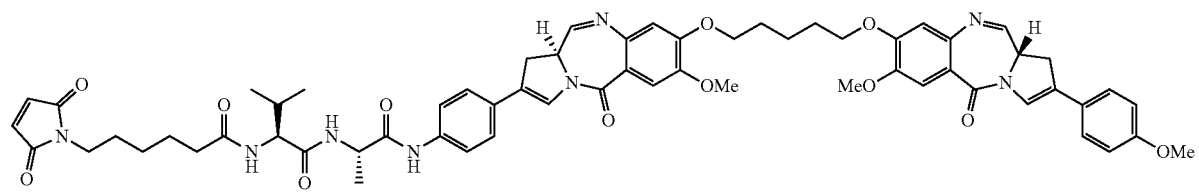
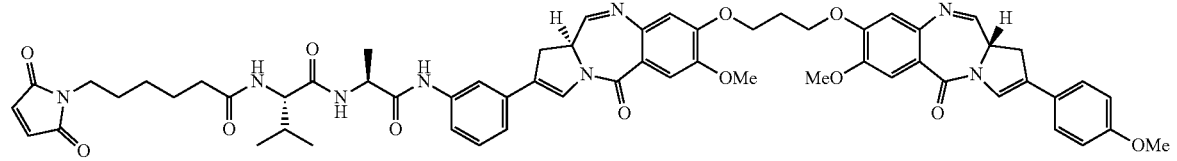
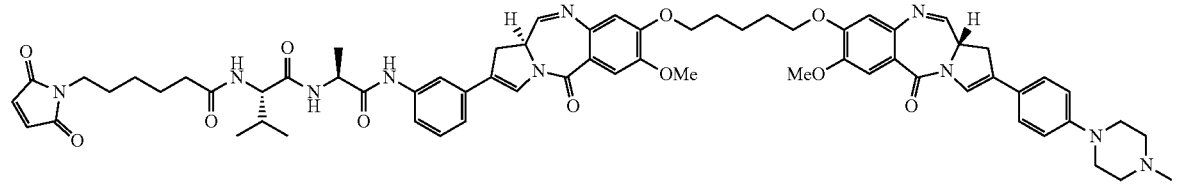
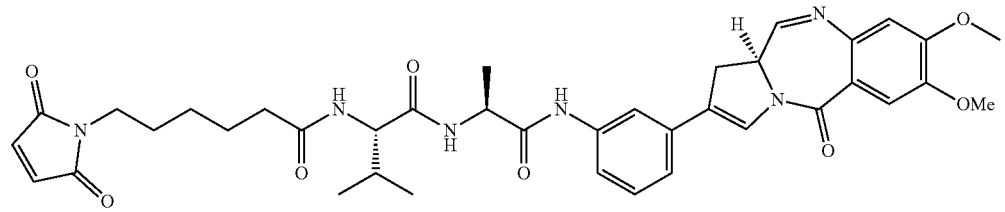

-continued
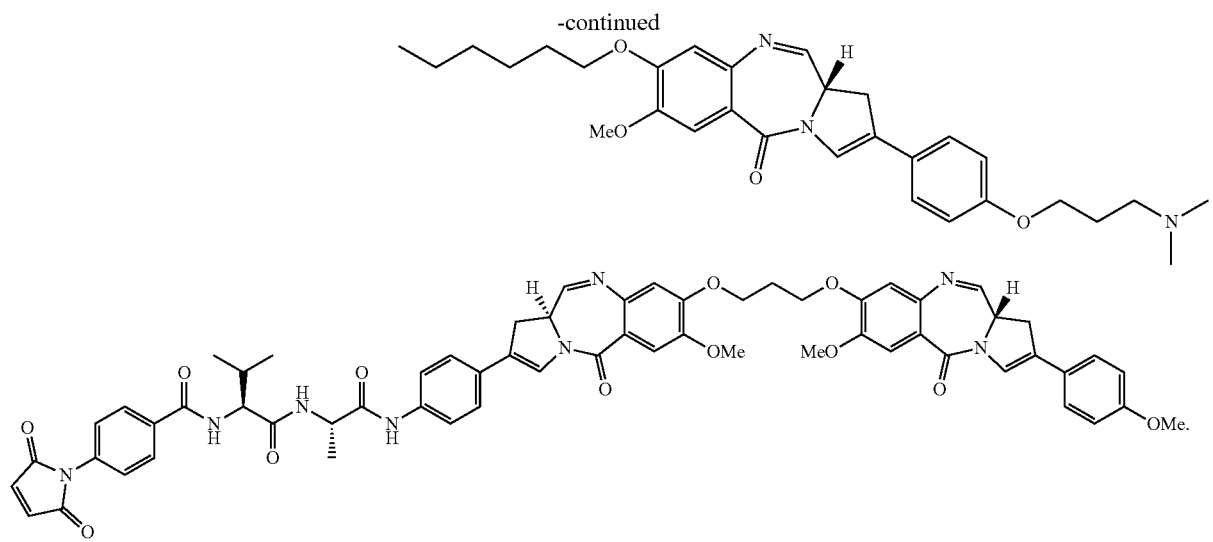
21. The method of claim 1, wherein the peptide coupling agent is N-ethoxylcarbonyl-2-ethoxy-1,2-dihydroquinoline (EEDQ).
22. The method of claim 21, wherein $G^1$-$L^1$-D has the formula of:
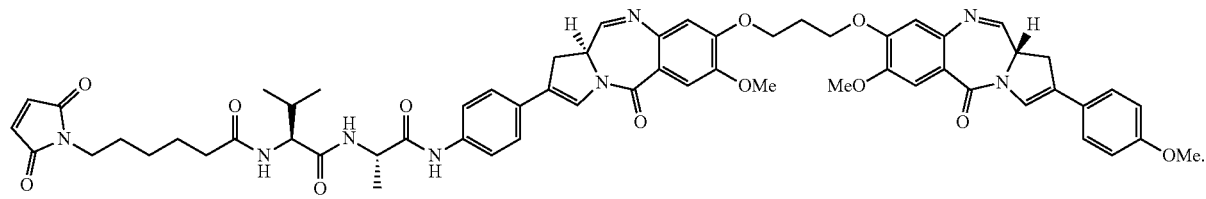 [SMILES: COc1ccc(C2=CN3C(=O)c4cc(OC)c(OCCCOc5cc6c(cc5OC)C(=O)N5C=C(c7ccc(NC(=O)[C@H](C)NC(=O)[C@@H](NC(=O)CCCCCN8C(=O)C=CC8=O)C(C)C)cc7)C[C@H]5C=N6)cc4N=C[C@@H]3C2)cc1]
* * * * *